United States Patent
Andrews et al.

(10) Patent No.: US 10,688,100 B2
(45) Date of Patent: Jun. 23, 2020

(54) MACROCYLIC COMPOUNDS AS ROS1 KINASE INHIBITORS

(71) Applicant: Array BioPharma Inc., Boulder, CO (US)

(72) Inventors: Steven W. Andrews, Boulder, CO (US); James F. Blake, Boulder, CO (US); Julia Haas, Boulder, CO (US); Gabrielle R. Kolakowski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 16/199,875

(22) Filed: Nov. 26, 2018

(65) Prior Publication Data

US 2019/0076437 A1    Mar. 14, 2019

Related U.S. Application Data

(63) Continuation of application No. PCT/US2018/022833, filed on Mar. 16, 2018.

(60) Provisional application No. 62/472,185, filed on Mar. 16, 2017.

(51) Int. Cl.
| | | |
|---|---|---|
| A61K 31/529 | (2006.01) | |
| A61K 31/519 | (2006.01) | |
| A61K 45/06 | (2006.01) | |
| G01N 33/574 | (2006.01) | |
| A61P 35/00 | (2006.01) | |
| A61K 31/4545 | (2006.01) | |
| A61K 31/496 | (2006.01) | |
| A61K 31/675 | (2006.01) | |

(52) U.S. Cl.
CPC ........ *A61K 31/529* (2013.01); *A61K 31/4545* (2013.01); *A61K 31/496* (2013.01); *A61K 31/519* (2013.01); *A61K 31/675* (2013.01); *A61K 45/06* (2013.01); *A61P 35/00* (2018.01); *G01N 33/57484* (2013.01); *G01N 2333/912* (2013.01); *G01N 2800/52* (2013.01)

(58) Field of Classification Search
CPC .............................. A61K 31/529; A61P 35/00
See application file for complete search history.

(56) References Cited

U.S. PATENT DOCUMENTS

| | | |
|---|---|---|
| 5,430,021 A | 7/1995 | Rudnic et al. |
| 5,760,068 A | 6/1998 | Talley et al. |
| 5,844,092 A | 12/1998 | Presta et al. |
| 5,877,016 A | 3/1999 | Presta et al. |
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 6,534,085 B1 | 3/2003 | Zeligs |
| 7,384,632 B2 | 6/2008 | Devaux et al. |
| 7,491,794 B2 | 2/2009 | Blatt et al. |
| 7,514,446 B2 | 4/2009 | Davis-Ward et al. |
| 7,550,470 B2 | 6/2009 | Fraley |
| 7,612,067 B2 | 11/2009 | Barbosa et al. |
| 7,615,383 B2 | 11/2009 | Devaux et al. |
| 7,863,289 B2 | 1/2011 | Spevak et al. |
| 8,026,247 B2 | 9/2011 | Bold et al. |
| 8,106,167 B2 | 1/2012 | Wild, Jr. et al. |
| 8,114,989 B2 | 2/2012 | Wang et al. |
| 8,119,592 B2 | 2/2012 | Beigelman et al. |
| 8,148,107 B2 | 4/2012 | Macdonald et al. |
| 8,299,021 B2 | 10/2012 | Blatt et al. |
| 8,299,057 B2 | 10/2012 | Lombardi Borgia et al. |
| 8,338,417 B2 | 12/2012 | Li et al. |
| 8,399,442 B2 | 3/2013 | Berdini et al. |

(Continued)

FOREIGN PATENT DOCUMENTS

| | | |
|---|---|---|
| AU | 2015/101722 | 5/2016 |
| CN | 1938311 | 3/2007 |

(Continued)

OTHER PUBLICATIONS

Farago et al. ("Durable Clinical Response to Entrectinib in NTRK1-Rearranged Non-Small Cell Lung Cancer," Journal of Thoracic Oncology, 2015, vol. 10, No. 12, 1670-1674).*

(Continued)

*Primary Examiner* — Yong S. Chong
(74) *Attorney, Agent, or Firm* — Meunier Carlin & Curfman LLC

(57) ABSTRACT

Methods for inhibiting a ROS1 kinase with compounds of Formula I:

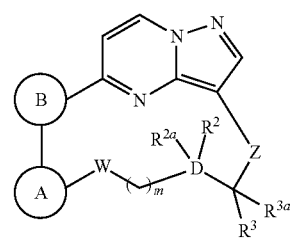

and pharmaceutically acceptable salts thereof, wherein ring A, ring B, W, m, D, $R^2$, $R^{2a}$, $R^3$, $R^{3a}$, and Z are as defined herein. The compounds and methods provided herein are useful in the treatment of cancer (e.g., ROS1-associated cancers as defined herein).

3 Claims, No Drawings
Specification includes a Sequence Listing.

(56) References Cited

U.S. PATENT DOCUMENTS

| | | |
|---|---|---|
| 8,450,322 B2 | 5/2013 | Andrews et al. |
| 8,501,756 B2 | 8/2013 | Artman, III et al. |
| 8,513,263 B2 | 8/2013 | Haas et al. |
| 8,552,002 B2 | 10/2013 | Ding et al. |
| 8,568,998 B2 | 10/2013 | Mani |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,691,221 B2 | 4/2014 | Pavone et al. |
| 8,791,123 B2 | 7/2014 | Allen et al. |
| 8,815,901 B2 | 8/2014 | Furet et al. |
| 8,865,698 B2 | 10/2014 | Haas et al. |
| 8,911,734 B2 | 12/2014 | Latham et al. |
| 8,912,194 B2 | 12/2014 | Ciomei |
| 8,912,204 B2 | 12/2014 | Ibrahim et al. |
| 8,933,084 B2 | 1/2015 | Andrews |
| 8,937,071 B2 | 1/2015 | Eidam et al. |
| 8,946,226 B2 | 2/2015 | Ciomei et al. |
| 9,006,256 B2 | 4/2015 | Matsui |
| 9,035,063 B2 | 5/2015 | Eidam et al. |
| 9,102,671 B2 | 8/2015 | Molteni et al. |
| 9,127,013 B2 | 9/2015 | Haas et al. |
| 9,187,489 B2 | 11/2015 | Takeda et al. |
| 9,227,975 B2 | 1/2016 | Andrews et al. |
| 9,242,977 B2 | 1/2016 | Takeuchi et al. |
| 9,260,437 B2 | 2/2016 | Ibrahim et al. |
| 9,273,051 B2 | 3/2016 | Chen et al. |
| 9,346,788 B2 | 5/2016 | Wu et al. |
| 9,447,135 B2 | 9/2016 | Rohr et al. |
| 9,469,876 B2 | 10/2016 | Kuslich |
| 9,493,476 B2 | 11/2016 | Andrews et al. |
| 9,511,050 B2 | 12/2016 | Toretsky et al. |
| 9,670,207 B2 | 6/2017 | Sasmal et al. |
| 9,682,979 B2 | 6/2017 | Allen et al. |
| 9,701,681 B2 | 6/2017 | Kim et al. |
| 9,782,400 B2 | 10/2017 | Yao et al. |
| 1,013,712 A1 | 11/2018 | Reynolds et al. |
| 1,017,286 A1 | 1/2019 | Arrigo et al. |
| 2005/0209195 A1 | 9/2005 | Menta et al. |
| 2006/0089362 A1 | 4/2006 | Seno et al. |
| 2006/0094699 A1 | 5/2006 | Kampen et al. |
| 2006/0128725 A1 | 6/2006 | Guzi |
| 2006/0211696 A1 | 9/2006 | Hibi et al. |
| 2007/0025540 A1 | 2/2007 | Travis |
| 2007/0042941 A1 | 2/2007 | Hirashima et al. |
| 2007/0082900 A1 | 4/2007 | Guzi et al. |
| 2007/0082902 A1 | 4/2007 | Paruch et al. |
| 2007/0184117 A1 | 8/2007 | Gregory et al. |
| 2007/0225270 A1 | 9/2007 | Guzi et al. |
| 2007/0281951 A1 | 12/2007 | Guzi et al. |
| 2009/0041717 A1 | 2/2009 | Macdonald et al. |
| 2009/0099167 A1 | 4/2009 | Bold et al. |
| 2009/0130229 A1 | 5/2009 | Lanzi et al. |
| 2009/0227556 A1 | 9/2009 | Obaishi |
| 2010/0029633 A1 | 2/2010 | Allen et al. |
| 2010/0152219 A1 | 6/2010 | Block et al. |
| 2010/0297115 A1 | 11/2010 | Blaustein |
| 2010/0324065 A1 | 12/2010 | Ibrahim et al. |
| 2011/0053934 A1 | 3/2011 | Angell et al. |
| 2011/0166122 A1 | 7/2011 | Andrews et al. |
| 2011/0195948 A1 | 8/2011 | Haas et al. |
| 2011/0268725 A1 | 11/2011 | Shelton |
| 2011/0301157 A1 | 12/2011 | Bold et al. |
| 2012/0108568 A1 | 5/2012 | Allen et al. |
| 2013/0029925 A1 | 1/2013 | Vandier et al. |
| 2013/0217662 A1 | 8/2013 | Andrews et al. |
| 2014/0121239 A1 | 5/2014 | Aftab |
| 2014/0194403 A1 | 7/2014 | Haas et al. |
| 2014/0227287 A1 | 8/2014 | Kamohara et al. |
| 2014/0243332 A1* | 8/2014 | Davare ............... A61K 31/47 514/235.2 |
| 2014/0315199 A1 | 10/2014 | Rhodes et al. |
| 2014/0336236 A1 | 11/2014 | Cronin et al. |
| 2015/0005499 A1 | 1/2015 | Haas et al. |
| 2015/0018336 A1 | 1/2015 | Chen et al. |
| 2015/0031667 A1 | 1/2015 | Allen et al. |
| 2015/0051222 A1 | 2/2015 | Barbugian et al. |
| 2015/0073036 A1 | 3/2015 | Hawryluk et al. |
| 2015/0166564 A1 | 6/2015 | Allen et al. |
| 2015/0218132 A1 | 8/2015 | Wu |
| 2015/0218652 A1* | 8/2015 | Doebele ............... C12Q 1/6886 514/253.07 |
| 2015/0283132 A1 | 10/2015 | Lim et al. |
| 2015/0306086 A1 | 10/2015 | Wilcoxen |
| 2015/0315657 A1 | 11/2015 | Rhodes et al. |
| 2016/0000783 A1 | 1/2016 | Takeuchi et al. |
| 2016/0009785 A1 | 1/2016 | Lipson et al. |
| 2016/0010068 A1 | 1/2016 | Bastian |
| 2016/0032396 A1 | 2/2016 | Diehn |
| 2016/0032402 A1 | 2/2016 | Jagani et al. |
| 2016/0032404 A1 | 2/2016 | Schweighofer et al. |
| 2016/0108123 A1 | 4/2016 | Freeman et al. |
| 2016/0108380 A1 | 4/2016 | Iavarone et al. |
| 2016/0137654 A1 | 5/2016 | Arrigo et al. |
| 2016/0145237 A1 | 5/2016 | Hu et al. |
| 2016/0251357 A1 | 9/2016 | Andrews et al. |
| 2016/0263086 A1 | 9/2016 | Toretsky |
| 2016/0272725 A1 | 9/2016 | Stransky et al. |
| 2016/0305943 A1 | 10/2016 | Takeuchi et al. |
| 2016/0367547 A1 | 12/2016 | Yao et al. |
| 2017/0107232 A1 | 4/2017 | Andrews et al. |
| 2017/0112842 A1 | 4/2017 | Andrews et al. |
| 2017/0112849 A1 | 4/2017 | Andrews et al. |
| 2017/0114059 A1 | 4/2017 | Andrews et al. |
| 2017/0114067 A1 | 4/2017 | Haas et al. |
| 2017/0114068 A1 | 4/2017 | Andrews et al. |
| 2017/0114069 A1 | 4/2017 | Allen et al. |
| 2017/0114415 A1 | 4/2017 | Doebele et al. |
| 2017/0119770 A1 | 5/2017 | Allen et al. |
| 2017/0165267 A1 | 6/2017 | Arrigo et al. |
| 2017/0224662 A1 | 8/2017 | Motheram et al. |
| 2017/0260589 A1 | 9/2017 | Nanda et al. |
| 2017/0281632 A1 | 10/2017 | Cox et al. |
| 2017/0283435 A1 | 10/2017 | Andrews et al. |
| 2017/0296544 A1 | 10/2017 | Reynolds et al. |
| 2018/0021342 A1 | 1/2018 | Arrigo et al. |
| 2018/0030548 A1 | 2/2018 | Nanda et al. |
| 2018/0030549 A1 | 2/2018 | Nanda et al. |
| 2018/0119228 A1 | 5/2018 | Nanda et al. |
| 2018/0127427 A1 | 5/2018 | Haas et al. |
| 2018/0133222 A1 | 5/2018 | Cox et al. |
| 2018/0140604 A1 | 5/2018 | Tuch et al. |
| 2018/0142306 A1 | 5/2018 | Nanda et al. |
| 2018/0207162 A1 | 7/2018 | Arrigo et al. |
| 2018/0263984 A1 | 9/2018 | Allen et al. |
| 2019/0031684 A1 | 1/2019 | Andrews |
| 2019/0076436 A1 | 3/2019 | Andrews |
| 2019/0151322 A1 | 5/2019 | Andrews |
| 2019/0169193 A1 | 6/2019 | Andrews et al. |
| 2019/0211017 A1 | 7/2019 | Haas et al. |
| 2019/0216814 A1 | 7/2019 | Reynolds et al. |
| 2019/0218222 A1 | 7/2019 | Reynolds et al. |
| 2019/0247398 A1 | 8/2019 | Zhao et al. |
| 2019/0365763 A1 | 12/2019 | Allen et al. |
| 2020/0000807 A1 | 1/2020 | Arrigo et al. |

FOREIGN PATENT DOCUMENTS

| | | |
|---|---|---|
| CN | 101119996 | 2/2008 |
| CN | 101208093 | 6/2008 |
| EA | 009517 | 2/2008 |
| EP | 0810217 | 12/1997 |
| EP | 1873157 | 1/2008 |
| EP | 1948633 | 8/2011 |
| EP | 2986736 | 2/2016 |
| EP | 2558490 | 12/2016 |
| EP | 3266795 | 10/2018 |
| JP | H10120683 | 5/1998 |
| JP | 2004-087707 | 3/2004 |
| JP | 2004-277337 | 10/2004 |
| JP | 2005-008581 | 1/2005 |
| JP | 2006-518364 | 8/2006 |
| JP | 2007-504276 | 3/2007 |

(56) References Cited

FOREIGN PATENT DOCUMENTS

| | | |
|---|---|---|
| JP | 2007-514712 | 6/2007 |
| JP | 2008-523034 | 7/2008 |
| JP | 2008-285464 | 11/2008 |
| JP | 2009-502734 | 1/2009 |
| JP | 2009-511487 | 3/2009 |
| JP | 2009-541242 | 11/2009 |
| JP | 2010-508315 | 3/2010 |
| JP | 2011-520887 | 7/2011 |
| JP | 2012-506446 | 3/2012 |
| JP | 2012-507569 | 3/2012 |
| JP | 2013-226108 | 11/2013 |
| JP | 2014-082984 | 5/2014 |
| WO | WO 1998/49167 | 11/1998 |
| WO | WO 2003/080064 | 10/2003 |
| WO | WO 2004/022561 | 3/2004 |
| WO | WO 2004/052286 | 6/2004 |
| WO | WO 2004/052315 | 6/2004 |
| WO | WO 2004/074290 | 9/2004 |
| WO | WO 2004/082458 | 9/2004 |
| WO | WO 2004/087707 | 10/2004 |
| WO | WO 2004/089415 | 10/2004 |
| WO | WO 2004/089471 | 10/2004 |
| WO | WO 2005/044835 | 5/2005 |
| WO | WO 2005/049033 | 6/2005 |
| WO | WO 2005/051366 | 6/2005 |
| WO | 2005/077954 | 8/2005 |
| WO | WO 2006/052913 | 5/2006 |
| WO | WO 2006/087538 | 8/2006 |
| WO | WO 2006/115452 | 11/2006 |
| WO | WO 2006/123113 | 11/2006 |
| WO | WO 2006/131051 | 12/2006 |
| WO | WO 2006/131952 | 12/2006 |
| WO | WO 2007/002325 | 1/2007 |
| WO | WO 2007/002433 | 1/2007 |
| WO | WO 2007/013673 | 2/2007 |
| WO | WO 2007/015824 | 2/2007 |
| WO | WO 2007/022999 | 3/2007 |
| WO | WO 2007/024680 | 3/2007 |
| WO | WO 2007/025090 | 3/2007 |
| WO | WO 2007/025540 | 3/2007 |
| WO | WO 2007/038314 | 4/2007 |
| WO | WO 2007/044410 | 4/2007 |
| WO | WO 2007/044449 | 4/2007 |
| WO | WO 2007/044893 | 4/2007 |
| WO | WO 2007/048066 | 4/2007 |
| WO | WO 2007/057399 | 5/2007 |
| WO | WO 2007/062805 | 6/2007 |
| WO | WO 2007/084815 | 7/2007 |
| WO | WO 2007/087245 | 8/2007 |
| WO | WO 2007/102679 | 9/2007 |
| WO | WO 2007/103308 | 9/2007 |
| WO | WO 2007/110344 | 10/2007 |
| WO | WO 2007/113000 | 10/2007 |
| WO | WO 2007/129161 | 11/2007 |
| WO | WO 2007/136103 | 11/2007 |
| WO | 2007/147647 | 12/2007 |
| WO | WO 2008/016131 | 2/2008 |
| WO | WO 2008/021924 | 2/2008 |
| WO | WO 2008/030579 | 3/2008 |
| WO | WO 2008/031551 | 3/2008 |
| WO | WO 2008/037477 | 4/2008 |
| WO | WO 2008/052734 | 5/2008 |
| WO | WO 2008/058126 | 5/2008 |
| WO | WO 2008/079903 | 7/2008 |
| WO | WO 2008/079906 | 7/2008 |
| WO | WO 2008/079909 | 7/2008 |
| WO | WO 2008/080001 | 7/2008 |
| WO | WO 2008/080015 | 7/2008 |
| WO | WO 2008/115974 | 9/2008 |
| WO | WO 2008/116898 | 10/2008 |
| WO | WO 2008/155421 | 12/2008 |
| WO | WO 2009/007748 | 1/2009 |
| WO | WO 2009/012283 | 1/2009 |
| WO | WO 2009/013126 | 1/2009 |
| WO | WO 2009/014637 | 1/2009 |
| WO | WO 2009/017838 | 2/2009 |
| WO | WO 2009/052145 | 4/2009 |
| WO | WO 2009/053442 | 4/2009 |
| WO | WO 2009/060197 | 5/2009 |
| WO | 2009/070567 | 6/2009 |
| WO | WO 2009/071480 | 6/2009 |
| WO | WO 2009/092049 | 7/2009 |
| WO | WO 2009/118411 | 10/2009 |
| WO | WO 2009/140128 | 11/2009 |
| WO | WO 2009/143018 | 11/2009 |
| WO | WO 2009/143024 | 11/2009 |
| WO | WO 2009/152083 | 12/2009 |
| WO | WO 2010/012733 | 2/2010 |
| WO | WO 2010/031816 | 3/2010 |
| WO | WO 2010/033941 | 4/2010 |
| WO | WO 2010/048314 | 4/2010 |
| WO | WO 2010/051549 | 5/2010 |
| WO | WO 2010/058006 | 5/2010 |
| WO | WO 2010/093928 | 8/2010 |
| WO | WO 2010/111527 | 9/2010 |
| WO | WO 2010/145998 | 12/2010 |
| WO | WO 2011/006074 | 1/2011 |
| WO | WO 2011/092120 | 8/2011 |
| WO | WO 2011/130340 | 10/2011 |
| WO | WO 2011/133637 | 10/2011 |
| WO | WO 2011/146336 | 11/2011 |
| WO | WO 2012/024650 | 2/2012 |
| WO | WO 2012/034091 | 3/2012 |
| WO | WO 2012/034095 | 3/2012 |
| WO | WO 2012/053606 | 4/2012 |
| WO | WO 2012/101029 | 8/2012 |
| WO | WO 2012/101032 | 8/2012 |
| WO | WO 2012/109075 | 8/2012 |
| WO | WO 2012/113774 | 8/2012 |
| WO | WO 2012/116217 | 8/2012 |
| WO | WO 2012/139930 | 10/2012 |
| WO | WO 2012/143248 | 10/2012 |
| WO | WO 2012/152763 | 11/2012 |
| WO | WO 2012/158413 | 11/2012 |
| WO | WO 2013/014039 | 1/2013 |
| WO | WO 2013/050446 | 4/2013 |
| WO | WO 2013/050448 | 4/2013 |
| WO | WO 2013/059740 | 4/2013 |
| WO | WO 2013/074518 | 5/2013 |
| WO | WO 2013/102059 | 7/2013 |
| WO | WO 2013/174876 | 11/2013 |
| WO | WO 2013/183578 | 12/2013 |
| WO | 2014/016433 | 1/2014 |
| WO | WO 2014/011900 | 1/2014 |
| WO | WO 2014/019908 | 2/2014 |
| WO | WO 2014/036387 | 3/2014 |
| WO | WO 2014/047572 | 3/2014 |
| WO | WO 2014/071358 | 5/2014 |
| WO | WO 2014/072220 | 5/2014 |
| WO | WO 2014/078322 | 5/2014 |
| WO | WO 2014/078323 | 5/2014 |
| WO | WO 2014/078325 | 5/2014 |
| WO | WO 2014/078328 | 5/2014 |
| WO | WO 2014/078331 | 5/2014 |
| WO | WO 2014/078372 | 5/2014 |
| WO | WO 2014/078378 | 5/2014 |
| WO | WO 2014/078408 | 5/2014 |
| WO | WO 2014/078417 | 5/2014 |
| WO | WO 2014/078454 | 5/2014 |
| WO | WO 2014/083567 | 6/2014 |
| WO | WO 2014/130975 | 8/2014 |
| WO | WO 2014/134096 | 9/2014 |
| WO | WO 2014/152777 | 9/2014 |
| WO | WO 2014/160521 | 10/2014 |
| WO | WO 2014/184069 | 11/2014 |
| WO | WO 2014/194127 | 12/2014 |
| WO | WO 2015/017528 | 2/2015 |
| WO | WO 2015/017533 | 2/2015 |
| WO | WO 2015/039006 | 3/2015 |
| WO | WO 2015/057873 | 4/2015 |
| WO | WO 2015/058129 | 4/2015 |
| WO | WO 2015/061572 | 4/2015 |
| WO | WO 2015/064621 | 5/2015 |
| WO | WO 2015/108992 | 7/2015 |

(56) References Cited

FOREIGN PATENT DOCUMENTS

| | | |
|---|---|---|
| WO | WO 2015/112806 | 7/2015 |
| WO | WO 2015/124697 | 8/2015 |
| WO | WO 2015/161274 | 10/2015 |
| WO | WO 2015/161277 | 10/2015 |
| WO | WO 2015/175788 | 11/2015 |
| WO | WO 2015/183836 | 12/2015 |
| WO | WO 2015/183837 | 12/2015 |
| WO | WO 2015/184443 | 12/2015 |
| WO | WO 2015/191666 | 12/2015 |
| WO | WO 2015/191667 | 12/2015 |
| WO | WO 2016/011141 | 1/2016 |
| WO | WO 2016/011144 | 1/2016 |
| WO | WO 2016/011147 | 1/2016 |
| WO | WO 2016/022569 | 2/2016 |
| WO | WO 2016/027754 | 2/2016 |
| WO | WO 2016/075224 | 5/2016 |
| WO | WO 2016/077841 | 5/2016 |
| WO | WO 2016/081450 | 5/2016 |
| WO | WO 2016/097869 | 6/2016 |
| WO | WO 2016/187508 | 11/2016 |
| WO | WO 2016/196141 | 12/2016 |
| WO | WO 2016/196671 | 12/2016 |
| WO | WO 2017/001491 | 1/2017 |
| WO | WO 2017/004342 | 1/2017 |
| WO | WO 2017/075107 | 5/2017 |
| WO | WO 2017/155018 | 9/2017 |
| WO | WO 2017/184597 | 10/2017 |
| WO | WO 2017/201156 | 11/2017 |
| WO | WO 2017/201241 | 11/2017 |
| WO | WO 2018/081417 | 5/2018 |
| WO | WO 2018/170381 | 9/2018 |
| WO | WO 2019/005796 | 1/2019 |
| WO | WO 2019/084285 | 5/2019 |

OTHER PUBLICATIONS

Adriaenssens et al., "Nerve Growth Factor Is a Potential Therapeutic Target in Breast Cancer," Cancer Res., 2008, 68(2):346-351.
Agaram et al., "Recurrent NTRK1 gene fusions define a novel subset of locally aggressive hpofibromatosis-like neural tumors," Am. J. Surg. Pathol, Oct. 2016, 40(10): 1407-1416.
Agaram, et al., "Abstract 33: NTRK1 Associated Gene Fusions in Pediatric Fibroblastic Myofibroglastic Neoplasms: A Molecular Study of 58 Cases," 105th Annual Meeting of the United States and Canadian Academy of Pathology, 2016, 12A.
Aisner et al., "ROS1 and ALK fusions in colorectal cancer, with evidence of intratumoral heterogeneity for molecular drivers.", Mal. Cancer Res., 12(1): 111-8, 2014.
Alassiri et al., "ETV6-NTRK3 Is Expressed in a Subset of ALK-Negative Inflammatory Myofibroblastic Tumors," Am J Surg Pathol., Aug. 2016;40(8):1051-1061.
Albaugh et al., "Discovery of GNF-5837, a Selective TRK Inhibitor with Efficacy in Rodent Cancer Tumor Models," ACS Medicinal Chemistry Letters, 2012, 3(2):140-145.
Ali et al., "Comprehensive Genomic Profiling Identifies a Subset of Crizotinib-Responsive ALK-Rearranged Non-Small Cell Lung Cancer Not Detected by Fluorescence In Situ Hybridization.", Oncologist, 21(6): 762-70, 2016.
Alvarez-Breckenridge et al., "Clinical and radiographic response following targeting of BCAN-NTRK1 fusion in glioneuronal tumor," NPJ Precision Oncology, Mar. 2017, 5 pages.
Amatu et al., "NTRK gene fusions as novel targets of cancer therapy across multiple tumour types", ESMD Open, 1-9, 2016.
American Cancer Society, "Sarcoma: Adult Soft Tissue Cancer," Jun. 2014, retrieved on Apr. 27, 2015, http://www.cancer.org/cancer/sarcoma-adultsofttissuecancer/detailedguide/sarcoma-adult-soft-tissue-cancer-key-statistics, 45 pages.
Andreason et al., "ETV6 Gene Rearrangements Characterize a Morphologically Distinct Subset of Sinonasal Low-grade Non-intestinal-type Adenocarcinoma," Am. J. Surg. Pathol, Nov. 2017, 41(11):1552-1560.

Arce et al., "Secretory cacinoma of the breast containing the ETV6-NTRK3 fusion gene in a male: case report and review of the literature," World J. Surg. Oncol, Jun. 2005, 3:35.
Ardini et al., "The TPM3-NTRK1 rearrangement is a recurring event in colorectal carcinoma and is associated with tumor sensitivity to TRKA kinase inhibition," Mol. Oncol. 8(8): 1495-1507, 2014.
Asaumi et al., "Expression of neurotrophins and their receptors (TRK) during fracture healing," Bone, 2000, 26(6):625-633.
Awad et al., "Acquired resistance to crizotinib from a mutation in CD74-ROS1.", N Engl. J Med, 368(25): 2395-401, 2013.
Bardelli et al., "Mutational Analysis of the Tyrosine Kinome in Colorectal Cancers," Science, May 2003, 300(5621):949.
Bartenstein et al., "Lipofibromatosis-like neural tumor: Case report of a unique infantile presentation," JAAD Case Reports, 4(2):185-188, 2018.
Baughn et al., "Abstract 5115: Whole-Genome Mate Pair Sequencing Reflex Test to Characterize Chromosome Rearrangements in Hematologic Neoplasia," Blood, 2017, 130: 5115.
Bavle et al., "Abstract GENE-04: Pediatric Malignant Epithelioid Glioneuronal Tumor: Pathological, Clinical, and Molecular Characterization of a Rare and Deadly Malignancy," Neuro-Oncology, Jun. 2017, iv18-iv19.
Behrens et al., "Gö 6976 is a potent inhibitor of neurotrophin-receptor intrinsic tyrosine kinase," J Neurochem., Mar. 1999, 72(3):919-924.
Beimfohr et al., "NTRK1 re-arrangement in papillary thyroid carcinomas of children after the Chernobyl reactor accident," Int. J Cancer, Mar. 15, 1999;80(6):842-847.
Bender et al., Abstract HG-024: Multiple Novel Fusion Genes with the RTK-RAS-PI3K Signalling Axis Highlight its Central Role in the Turmorigenesis of Pediatric Gioblastoma, Neuro-oncology, Jun. 2014, 145.
Bensinger et al., "Transplantation of allogeneic peripheral blood stem cells mobilized by recombinant human granulocyte colony stimulating factor," Stem Cells, Jan. 1996;14(1):90-105.
Bensinger et al., "Transplantation of allogeneic peripheral blood stem cells mobilized by recombinant human granulocyte colony-stimulating factor [see comments].," Blood, Mar. 15, 1995;85(6):1655-8.
Bertrand et al., "The crystal structures of TrkA and TrkB suggest key regions for achieving selective inhibition," Journal of molecular biology, Oct. 26, 2012;423(3):439-53.
Birch et al., "Chromosome 3 anomalies investigated by genome wide SNP analysis of benign, low malignant potential and low grade ovarian serous tumours.", PLoS One, 6(12): e28250, 2011.
Bonanno et al., Journal of Thoracic Oncology, vol. 11, No. 4, Supp. Suppl. 1, pp. S67. Abstract No. 28P; 6th European Lung Cancer Conference, ELCC 2016, Geneva, Switzerland.
Bongarzone et al., "Age-related activation of the tyrosine kinase receptor protooncogenes RET and NTRK1 in papillary thyroid carcinoma," J Clin. Endocrinol. Metab., May 1996, 81(5):2006-2009.
Bouhana et al., "Abstract #1798: Identification of Pan-Trk Inhibitors for the Treatment of Trk-Driven Cancers," Poster, Presented at Proceedings of the AACR 103rd Annual Meeting, Apr. 15, 2012.
Bourgeois et al., "Molecular Detection of the ETV6-NTRK3 Gene Fusion Differentiates Congenital Fibrosarcoma From Other Childhood Spindle Cell Tumors," Am. J Surg. Pathol., Jul. 2000 24(7):937-946.
Branford, S., et al. "High frequency of point mutations clustered within the adenosine triphosphate-binding region of BCR/ABL in patients with chronic myeloid leukemia or Ph-positive acute lymphoblastic leukemia who develop imatinib (STI571) resistance," Blood, May 2002, 99, 3472-3475.
Brastianos et al., "Abstract OS06.4: Identification of Novel NTRK Fusion in Glioneuronal Tumors and Radiographic Response Following Therapy with an NTRK Inhibitor," Neuro-Oncology, May 2017, iii11, 1 pageMeeting Info: 5th Quadrennial Meeting of the World Federation of Neuro-Oncology Societies, WFNOS. Zurich, Switzerland, 2017.
Brenca et al., "Transcriptome sequencing identifies ETV6-NTRK3 as a gene fusion involved in GIST," J. Pathol. 238(4):543-549, 2016.

(56) References Cited

OTHER PUBLICATIONS

Brinner et al., "A rapid and general method for asymmetric syntesis of 2-substituted pyrrolidines using ter-butanesulfinamide," Organic & Biomolecular Chemistry, Jan. 2005, 3(11): 2109.
Brodeur, "Neuroblastoma: biological insights into a clinical enigma," Nat. Rev. Cancer, 2003, 3:203-216.
Bruse et al., "Improvements to Bead Based Oligonucleotide Ligation SNP Genotyping Assays," Biotechniques, Nov. 2008, 45:559-571.
Brzezianska et al., "Rearrangements of NTRK1 oncogene in papillary thyroid carcinoma," Neuroendocrinology Letters, 2007, 28(3):221-229.
Burris et al., "Pharmacokinetics (PK) of LOXO-101 During the First-in-Human Phase I Study in Patients with Advanced Solid Tumors," Interim Update AACR Annual Meeting, Mar. 2015, Philadelphia, PA., 1 page.
Butti et al., "A sequence analysis of the genomic regions involved in the rearrangements between TPM3 and NTRK1 genes producing TRK oncogenes in papillary thyroid carcinomas," Genomics. 28(1):15-24, 1995.
Cajaiba et al., "Expanding the spectrum of ALK-rearranged renal cell carcinomas in children: Identification of a novel HOOK1-ALK fusion transcript.", Genes Chromosomes Cancer, 55(10): 814-7, 2016.
Calabresi and Chabner, Goodman & Gilnnan's The Pharmacological Basis of Therapeutics, 10th ed., 2001, p. 1388, para 2, lines 4-5.
Calero et al., "Sunitinib suppress neuroblastoma growth through degradation of MYCN and inhibition of angiogenesis," PLoS One, Apr. 23, 2014;9(4):e95628. doi: 10.1371/journal.pone.0095628. eCollection 2014.
Camoratto et al., "CEP-751 inhibits trk receptor tyrosine kinase activity in vitro and exhibits anti-tumor activity." International Journal of cancer. 72(4): 673-9, 1997.
Campos et al., "Enantioselective, palladium-catalyzed alpha-arylation of N-Boc-pyrrolidine," J. Am. Chem Soc., 2006, 128:3538-3539.
Cancer.gov'[online]. "National Cancer Institute: Oral TRK Inhibitor LOXO-101 (Larotrectinib) for Treatment of Advanced Pediatric Solid or Primary Central Nervous System Tumors," ClinicalTrials.gov Identifier: NCT02637687, [retrieved on Jul. 17, 2017] Retrived from the Internet: URL<https://www.cancer.gov/about-cancer/treatment/clinical-trials/search/view?cdrid=781000>, 5 pages.
Cancer.sanger.ac.uk' [online]. "COSMIC, Catalog of Somatic Mutations in Cancer: Cosmic » Mutation » Overview » NTRK1 p.V321M / c.961G>A," Catalog of Somatic Mutations in Cancer (COSMIC) database, [retrieved on Jul. 17, 2017] Retrived from the Internet: URL<cancer.sanger.ac.uk/cosmic/mutation/ overview?id=1259646>, 1 page.
Cancer.sanger.ac.uk' [online]. "COSMIC, Catalog of Somatic Mutations in Cancer: Cosmic » Mutation » Overview » NTRK1 p.D679N / c.2035G>A," Catalog of Somatic Mutations in Cancer (COSMIC) database, [retrieved on Jul. 17, 2017] Retrived from the Internet: URL<cancer.sanger.ac.uk/cosmic/mutation/overview?id=897427>, 1 page.
Cancer.sanger.ac.uk' [online]. "COSMIC, Catalog of Somatic Mutations in Cancer: Cosmic » Mutation » Overview » NTRK3 p.D537Y / c.1609G>T," Catalog of Somatic Mutations in Cancer (COSMIC) database, [retrieved on Jul. 17, 2017] Retrived from the Internet: URL<cancer.sanger.ac.uk/cosmic/mutation/ overview?id=966118>, 1 page.
Cancer.sanger.ac.uk' [online]. "Cosmic, Catalog of Somatic Mutations in Cancer: Cosmic » Mutation » Overview » NTRK3 p.D609V / c.1826A>T," Catalog of Somatic Mutations in Cancer (COSMIC) database, [retrieved on Jul. 17, 2017] Retrived from the Internet: URL:<cancer.sanger.ac.uk/cosmic/mutation/ overview?id=124878>, 1 page.
Cancer.sanger.ac.uk' [online]. "COSMIC, Catalog of Somatic Mutations in Cancer: Cosmic » Mutation » Overview » NTRK3 p.G608S / c.1822G>A," Catalog of Somatic Mutations in Cancer (COSMIC) database, [retrieved on Jul. 17, 2017] Retrived from the Internet: URL<cancer.sanger.ac.uk/cosmic/mutation/ overview?id=88799>, 1 page.
Cancer.sanger.ac.uk' [online]. "COSMIC, Catalog of Somatic Mutations in Cancer: Cosmic » Mutation » Overview » NTRK3 p.L282M / c.844C>A," Catalog of Somatic Mutations in Cancer (COSMIC) database, [retrieved on Jul. 17, 2017] Retrived from the Internet: URL<cancer.sanger.ac.uk/cosmic/mutation/ overview?id=401588>, 1 page.
Cancer.sanger.ac.uk' [online]. "COSMIC, Catalog of Somatic Mutations in Cancer: Cosmic » Mutation » Overview » NTRK3 p.V539M / c.1615G>A," Catalog of Somatic Mutations in Cancer (COSMIC) database, [retrieved on Jul. 17, 2017] Retrived from the Internet: URL<cancer.sanger.ac.uk/cosmic/mutation/ overview?id=1708512>, 1 page.
Capparelli et al., "Stromal neuregulin-1 modulates the response to MEK inhibitors in WT BRAF/WT NRAS (WT/WT) melanomas", Pigment Cell Melanoma. Res. vol. 30, No. 5, pp. e61, 2017.
Caria et al., "Cytogenetic and molecular events in adenoma and well-differentiated thyroid follicular-cell neoplasia," Cancer Genet. Cytogenet., 2010, 203:21-29.
Carpinelli et al., "PHA-739358, a potent inhibitor of Aurora kinases with a selective target inhibition profile relevant to cancer," Mol Cancer Ther, Dec. 2007;6(12 Pt 1):3158-3168.
Carvalho et al., Abstract No. HG-09, 3rd Biennial Conference on Pediatric Neuro-Oncology Basic and Translational Research. San Diego, CA, United States, 2015, 1 page.
Catalog of Somatic Mutations in Cancer (COSMIC) database, cancer.sanger.ac.uk/cosmic/mutation/ overview?id=1517968, downloaded on May 31, 2016, 2 pages.
Catalog of Somatic Mutations in Cancer (COSMIC) database, cancer.sanger.ac.uk/cosmic/mutation/ overview?id=1636266, downloaded on May 31, 2016, 2 pages.
Catalog of Somatic Mutations in Cancer (COSMIC) database, cancer.sanger.ac.uk/cosmic/mutation/ overview?id=1688778, downloaded on May 31, 2016, 2 pages.
Catalog of Somatic Mutations in Cancer (COSMIC) database, cancer.sanger.ac.uk/cosmic/mutation/ overview?id=3711772, downloaded on May 31, 2016, 2 pages.
Catalog of Somatic Mutations in Cancer (COSMIC) database, cancer.sanger.ac.uk/cosmic/mutation/ overview?id=471203, downloaded on May 31, 2016, 2 pages.
Catalog of Somatic Mutations in Cancer (COSMIC) database, cancer.sanger.ac.uk/cosmic/mutation/ overview?id=48622, downloaded on May 31, 2016, 2 pages.
Catic et al., "Abstract 1537: The frequency of a novel KANK1 and NTRK3translocation and BRAFV600E mutation in patients diagnosed with metanephric adenoma utilizing molecular mechanisms," 2017 Annual Meeting of the American Society of Clinical Oncology, 2017, 1 page.
Catic et al., "A novel cytogenetic and molecular characterization of renal metanephric adenoma, identification of partner genes involved in translocation t(9;15)(p24;q24)," Cancer Genet. 214-215:9-15, doi: 10.1016/j.cancergen.2017.03.001, 2017.
Chang-Qi et al., "Brain derived neurotrophic factor (BDNF) contributes to the pain hypersensitivity following surgical incision in the rats," Molecular Pain, 2008, 4:27.
Chaudhuri et al., "Early Detection of Molecular Residual Disease in Localized Lung Cancer by Circulating Tumor DNA Profiling," Cancer Discov, Dec. 2017, 7(12):1394-1403.
Chen et al., "40: The landscape of kinase fusions in 445 Chinese NSCLC patients," Annals of Oncology, Oct. 2017, 28(7): vii16, 1 page.
Cherry et al., "Recent kinase and kinase inhibitor X-ray structures: mechanisms of inhibition and selectivity insights," Curr Med Chem. Mar. 2004;11(6):663-73.
Chiang et al., "NTRK Fusions Define a Novel Uterine Sarcoma Subtype with Features of Fibrosarcoma," Am. J. Surg. Pathol. doi: 10.1097/PAS.0000000000001055, 2018.
Chinese Office Action in Chinese Patent Application No. CN 201180025013.9, dated Apr. 28, 2014, 11 pages.

(56) References Cited

OTHER PUBLICATIONS

Chinese Office Action in Chinese Patent Application No. CN201080040095.X, dated Feb. 27, 2015, 8 pages (English translation).
Chintakuntlawar et al., "High-grade transformation of acinic cell carcinoma: an inadequately treated entity?" Oral Surg Oral Med Oral Pathol Oral Radiol. May 2016;121(5):542-549.e1.
Chmielecki et al., "Abstract LB-178: Genomic profiling of 1239 diverse pediatric cancers identifies novel discoveries across tumors", Cancer Research, vol. 76, No. 14, Supp. Supplement. Abstract No. LB-178. 107th Annual meeting of the American Association for Cancer Research, AACR. New Orleans, LA Apr. 16-20, 2016.
Chmielecki et al., "Genomic Profiling of a Large Set of Diverse Pediatric Cancers Identifies Known and Novel Mutations across Tumor Spectra.", Cancer Research, 77(2): 509-519, 2017.
Cho et al., "Expression of mRNA for brain-derived neurotrophic factor in the dorsal root ganglion following peripheral inflammation," Brain Research, 1997, 749:358-362.
Choi et al., "(R)-2-Phenylpyrrolidine Substituted Imidazopyridazines: A New Class of Potent and Selective Pan-TRK Inhibitors," ACS medicinal chemistry letters, Mar. 19, 2015;6(5):562-567.
Chung et al., "Infantile fibrosarcoma," Cancer, Aug. 1976, 38(2):729-739.
Church et al., "Abstract ST16: A Novel EML4-NTRK3 Translocation in Infantile Fibrosarcoma and Congenital Mesoblastic Nephroma Requires a New Approach to Conventional Diagnostic Algorithms," J Molecular Diag, 2015, 816.
Church et al., "Recurrent EML4—NTRK3 fusions in infantile fibrosarcoma and congenital mesoblastic nephroma suggest a revised testing strategy," Mod. Pathol. 31(3), 463-473, 2018.
Cocce et al., "Identification of ZCCHC8 as fusion partner of ROS1 in a case of congenital glioblastoma multiforme with a t(6;12)(q21;q24.3)", Genes Chromosomes Cancer, 55(9): 677-87, 2016.
Coebergh et al., "Abstract 490: Identification of oncogenic gene fusions in primary colon cancers," Cancer Research, Jul. 2017, DOI: 10.1158/1538-7445.AM2017-490, 2 page.
Colombian Office Action in Colombian Application No. CO 12-022-116-4, dated Feb. 14, 2014, 8 pages.
Colombian Office Action in Colombian Application No. CO 12-229421-4, dated Jan. 21, 2014, 6 pages.
Comina-Mendez and Turner, "Predicting Relapse with Circulating Tumor DNA Analysis in Lung Cancer," Cancer Discov, Dec. 2017, 7(12): 1368-1370.
Cook et al., "Somatic chromosomal engineering identifies BCAN-NTRK1 as a potent glioma driver and therapeutic target," Nat. Comm. 8(15987). DOI 10.1038/ncomms15987, 2017.
Créancier et al., "Chromosomal rearrangements involving the NTRK1 gene in colorectal carcinoma," Cancer Lett., Aug. 2015, 365(1):107-111.
Crescenzo et al., "Convergent mutations and kinase fusions lead to oncogenic STAT3 activation in anaplastic large cell lymphoma.", Cancer Cell., 27(4): 516-32, 2015.
Croucher et al., "TrkB inhibition by GNF-4256 slows growth and enhances chemotherapeutic efficacy in neuroblastoma xenografts," Cancer Chemother Pharmacol. Jan. 2015;75(1):131-41. doi: 10.1007/s00280-014-2627-1. Epub Nov. 14, 2014.
Cruz, "Lung cancer: epidemiology, etiology and prevention," Clinics in Chest Medicine, 2011, 32(4): 1-61.
Cui et al., "Abstract #MA 07.09: ALK/ROS1/Inhibitor TPX-0005 Effectively Overcomes Clinical Resistance Solvent Front Mutations," Abstracts, Nov. 2017, p. S1829.
Cui et al., "Use of capture-based next-generation sequencing to detect ALK fusion in plasma cell-free DNA of patients with non-small-cell lung cancer", Oncotarget, 2771-2780, 2016.
Dacic et al., "ALK FISH patterns and the detection of ALK fusions by next generation sequencing in lung adenocarcinoma", Oncotarget, vol. 7, No. 50, pp. 82943-82952, 2016.
Dang et al., "Expression of nerve growth factor receptors is correlated with progression and prognosis of human pancreatic cancer," J. Gastroenterology and Hepatology, 2006, 21(5): 850-858.

Das et al., "Synergistic Effects of Crizotinib and Temozolomide in Experimental FIG-ROS1 Fusion-Positive Glioblastoma.", Cancer Growth Metastasis, 8:51-60, 2015.
Davare et al., "Foretinib is a potent inhibitor of oncogenic ROS1 fusion proteins.", Proc. Natl. Acad Sci. USA., 110(48): 19519-24, 2013.
Davare et al., "Structural insight into selectivity and resistance profiles of ROS1 tyrosine kinase inhibitors.", Proc. Natl. Acad Sci. USA., 1 12(39): E5381-90, 2015.
Davidson et al., "Expression and activation of the nerve growth factor receptor TrkA in serous ovarian carcinoma," Clin. Cancer Res., 2003, 9(6):2248-2259.
Davies and Dobele, "Molecular pathways: ROS1 fusion proteins in cancer.", Clin. Cancer Res, 19(15): 4040-4045, 2013.
Davies et al., "Identifying and targeting ROS1 gene fusions in non-small cell lung cancer.", Clin Cancer Res 18: 4570-4579, 2012.
Davies et al., "Resistance to ROS1 inhibition mediated by EGFR pathway activation in non-small cell lung cell," PLoS One, 2013, 8(12):e82236, 13 pages.
Davis et al., "Infantile NTRK-associated Mesenchymal Tumors," Pediatr. Dev. Pathol. 21(1):68-78, 2018.
De Smith et al., "Clonal and microclonal mutational heterogeneity in high hyperdiploid acute lymphoblastic leukemia", Oneatarget., 7(45) 72733-72745, 2016.
Deihimi et al., "BRCA2, EGFR, and NTRK mutations in mismatch repair-deficient colorectal cancers with MSH2 or MLH1 mutations," Oncotarget. Jun. 20;8(25):39945-39962, 2017.
Delafoy et al., "Role of nerve growth factor in the trinitrobenzene sulfonic acid-induced colonic hypersensitivity," Pain, 2003, 105:489-497.
Demaria et al., "Development of tumor-infiltrating lymphocytes in breast cancer after neoadjuvant paclitaxel chemotherapy," Clin Cancer Res, Oct. 2001;7(10):3025-30.
Di Mola et al., "Nerve growth factor and Trk high affinity receptor (TrkA) gene expression in inflammatory bowel disease," Gut, 2000, 46(5):670-678.
Dinér et al., "Preparation of 3-substituted-1-isopropyl-1H-pyrazolo[3,4-d]pyrimidin-4-amines as RET kinase inhibitors," J. Med. Chem., May 2012, 55 (10), 4872-4876.
Dionne et al., "Cell cycle-independent death of prostate adenocarcinoma is induced by the trk tyrosine kinase inhibitor CEP-751 (KT6587)," Clin. Cancer Research, 1998, 4(8):1887-1898.
Doebele et al., "Abstract 8023: NTRK1 gene fusions as a novel oncogene target in lung cancer," 2013 Annual Meeting of the American Society of Clinical Oncology, Chicago, IL, 2013, 1 page.
Doebele et al., "An oncogenic NTRK fusion in a soft tissue sarcoma patient with response to the tropomysin-related kinase (TRK) inhibitor LOXO-101," Cancer Discovery, Jul. 2015, 5(10):1049-1057.
Doebele et al., "Phase II Trial of Stereotactic Body Radiation Therapy Combined with Erlotinib for Patients with Limited but Progressive Metastatic Non-Small-Cell Lung Cancer," J. Clin. Oncol., 2014, 32:9 pages.
Dolle et al., "Nerve growth factor-induced migration of endothelial cells," J. Pharmacol Exp Ther, 2005, 315(3):1220-1227.
Dolomanov et al., "OLEX2: a complete structure solution, refinement and analysis program," J Appl. Cryst. 2009, 42, 339-341.
Dou et al., "Increased nerve growth factor and its receptors in atopic dermatitis: an immunohistochemical study," Archives of Dermatological Research, 2006, 298(1):31-37.
Drexler et al., "Pathobiology of NPM-ALK and variant fusion genes in anaplastic large cell lymphoma and other lymphomas," Leukemia, Sep. 2000, 14:1533-1559.
Drilon et al., "A Novel Crizotinib-Resistant Solvent-Front Mutation Responsive to Cabozantinib Therapy in a Patient with ROS1-Rearranged Lung Cancer.", Clin. Cancer Res., 22(10): 2351-8, 2016.
Drilon et al., "A phase 1 study of oral LOXO 292 in adult patients with advanced solid tumors, including RET-fusion non-small cell lung cancer, medullary thyroid cancer and other tumors with increased RET activity," Annals of oncology Developmental Therapeutics, Sep. 2017, 28(5):138.

(56) References Cited

OTHER PUBLICATIONS

Drilon et al., "Abstract CT007: Entrectinib, an oral pan-Trk, ROS1, and ALK inhibitor in TKI-naïve patients with advanced solid tumors harboring gene rearrangements: Updated phase I results," Cancer research, 76(14), AACR 107th Annual Meeting, Apr. 2016, URL <http://cancerres.aacrjournals.org/content/76/14_Supplement/CT007.short>, 5 pages.

Drilon et al., "Entrectinib, an oral pan-Trk, ROS1, and ALK inhibitor in TKI-naïve patients with advanced solid tumors harboring gene rearrangements," Cancer research, vol. 76, No. 14, Supp. Supplement., Abstract No. 15 CT007; Presented at the 107th Annual Meeting of the American Association for Cancer Research, AACR 2016. New Orleans, LA; Apr. 16-20, 2016, 35 pages.

Drilon et al., "What hides behind the MASC: clinical response and acquired resistance to entrectinib after ETV6-NTRK3 identification in a mammary analogue secretory carcinoma (MASC)," Annals of Oncology., Feb. 15, 2016, 27(5):920-926.

Du et al., "Expression of NGF family and their receptors in gastric carcinoma: a cDNA microarray study," World Journal of Gastroenterology, http://www.wjgnet.com/1007-9327/full/v9/i7/1431.htm, Jul. 2003, 9(7):1431-1434.

Duranti et al., "Homologation of Mexiletine alkyl chanin and stereoselective blockade of skeletal muscle sodium channels," Euro. J. Med. Chem., 2000, 35:147-156.

Durham et al. "Diverse and Targetable Kinase Alterations Drive Histiocytic Neoplasms," Blood. 126(23):481, 2015.

Edgren et al., "Abstract 4793: Rapid pan-cancer identification of previously unidentified fusion genes to enable novel targeted therapeutics", Cancer Res. 75(15 Supplement): 4793, 2015.

Eguchi et al., "Absence of t(12;15) associated ETV6-NTRK3 fusion transcripts in pediatric acute leukemias," Afed Pediatr. Oneal., Oct. 2001, 37:417.

Eguchi et al., "Fusion of ETV6 to neurotrophin-3 receptor TRKC in acute myeloid leukemia with t(12;15)(p13;q25)," Blood, 1999, 93(4):1355-1363.

Eisenhauer et al., "New response evaluation criteria in solid tumours: revised RECIST guideline (version 1.1)," Eur J Cancer, Jan. 2009, 45(2):228-247.

Ellison et al., "Abstract O13: Genetic alterations in uncommon low-grade neural tumors—BRAF, FGFR1, and MYB/MYBL1 mutations occur frequently and align with morphology," Neuropathology and Applied Neurobiology, 2016, 42(S1): 18.

Elvin et al., "319:Genomic profiling of uterine leiomyosarcomas reveal frequent alterations in Akt/mammalian target of rapamycin (mTOR) pathway genes and other actionable genomic abnormalties linked to targeted therapies," Poseter Session—Molecular Targeted Agents I, Nov. 2014, 1 page.

Endometrial Cancer Gene Database, ecgene.bioinfominzhao.org/gene_mutation.cgi?gene=4915, downloaded on May 31, 2016, 13 pages.

Engman et al., "Syngeneic transplant in mantle cell lymphoma: a rare event and review of the literature," Clin Adv Hematol Oncol. May 2009;7(5):321-3.

ESMO, "TRK Cancer-Causing Mutation Discovered in 1982 Finally Target of Clinical Trials: Matching drugs to long-overlooked oncogene," European Society of Medical Oncology, Jan. 2015, 2 pages.

Essand et al., "Genetically engineered T cells for the treatment of cancer," J Intern Med. Feb. 2013;273(2):166-81. doi: 10.1111/joim.12020.

Estrada-Bernal et al., "Abstract #: C65: TRK kinase domain mutations that induce resistance to a pan-TRK inhibitor," Poster, Presented at Proceedings of the AACR-NCI-EORTC International Conference: Molecular Targets and Cancer Therapeutics, Boston MA, Nov. 5-9, 2015; Mol Cancer Ther, Dec. 2015, 14(12)(Suppl. 2): 1 page.

Estrada-Bernal et al., "Abstract #: LB-118: Identification of TRKA and TRKB kinase domain mutations that induce resistance to a pan-TRK inhibitor," Poster, Presented at Proceedings of the 107th Annual Meeting of the American Association for Cancer Research, New Orleans LA, Apr. 16-20, 2016; Cancer Res, Jul. 2016, 76(14): 1 page.

European Office Action in Application No. 15808300.6, dated Nov. 20, 2018.

European Search Report in European Application No. 13197815.7, dated Apr. 1, 2014, 5 pages.

Euthus et al., "ETV6-NTRK3—Trk-ing the primary event in human secretory breast cancer," Cancer Cell, 2002, 2(5):347-348.

Evans et al., "Antitumor activity of CEP-751 (KT-6587) on human neuroblastoma and medulloblastoma xenografts," Clin. Cancer Res., Nov. 1999, 5(11):3594-3602.

Extended European Search Report in European Application No. 16166461.0, dated Sep. 28, 2016, 5 pages.

Extended European Search Report in European Application No. 17163978.4, dated Jul. 17, 2017, 5 pages.

Extended European Search Report in European Application No. 17199899.0, dated Feb. 26, 2018, 7 pages.

Extended European Search Report in European Application No. 18151233.6, dated Jun. 26, 2018, 6 pages.

Facchinetti et al., "Crizotinib-Resistant ROS1 Mutations Reveal a Predictive Kinase Inhibitor Sensitivity Model for ROS1- and ALK-Rearranged Lung Cancers.", Clin. Cancer Res., 22(24): 5983-5991, 2016.

Farago et al., "Abstract MINI30.09: Clinical Response to Entrectinib in a Patient with NTRK1-Rearranged Non-small cell Lung Cancer," J Thoracic Oncol, Sep. 2015, 10(9-S2): S374-S375.

Farago et al., "Durable clinical response to entrectinib in NTRK1-rearranged non-small cell lung cancer," J. Thorac Oncol. 10(12):1670-1674, 2015.

Farhat et al., "Primary benign and malignant thyroid neoplasms with signet ring cells: cytologic, histologic, and molecular features," Am. J. Clin. Pathol., 148(3):251-258, 2017.

Femandez-Cuesta et al., "Abstract 1531: Cross-entity mutation analysis of lung neuroendocrine tumors sheds light into their molecular origin and identifies new therapeutic targets," AACR Annual Meeting 2014, Apr. 2014, URL <http://cancerres.aacrjournals.org/content/74/19_Supplement/1531.short>, 5 pages.

Flannery et al., "Immunomodulation: NK cells activated by interferon-conjugated monoclonal antibody against human osteosarcoma," Eur J Cancer Clin Oncol. Jun. 1984;20(6):791-8.

Forghieri et al., Abstract P137: Chronic Eosinophilic Leukemia with ETV6-NTRK3 Fusion Transcript in an Elderly Patient Affected with Pancreatic Carcinoma, Haemologica, 2010, 95(s3): S125-S126.

Frattini et al., "The integrated landscape of driver genomic alterations in glioblastoma," Nature Genet., 2013, 45:1141-1149.

Freund-Michel and Frossard, "The nerve growth factor and its receptors in airway inflammatory diseases," Pharmacology & Therapeutics, 2008, 117(1):52-76.

Frey et al., "7-Aminopyrazolo [1,5-a]pyrimidines as potent multitargeted receptor tyrosine kinase inhibitors," J. Med. Chem, Jul. 2008, 51(13):3777-3787.

Fu et al., "The Frequency and Clinical Implication of ROS1 and RET Rearrangements in Resected Stage IIIA-N2 Non-Small Cell Lung Cancer Patients.", PLoS One, 10(4):e0124354, 2015.

Fuse et al., "Mechanisms of Resistance to NTRK Inhibitors and Therapeutic Stategies in NTRK1-Rearranged Cancers," Mol. Cancer Ther.,. Jan.;6(1):36-44, 2016.

Gainor et al., "Patterns of Metastatic Spread and Mechanisms of Resistance to Crizotinib in ROS1-Positive Non-Small-Cell Lung Cancer", JCO Precis Oneal. 10.1200/PO.1 7.00063, 2017.

Gang et al., "The landscape of fusion transcripts in spitzoid melanoma and biologically indeterminate spitzoid tumors by RNA sequencing.", Mod Pathol., 29(4): 359-69, 2016.

Gao et al., "Driver fusions and their implications in the development and treatment of human cancers," Cell Rep. 23(1):227-238.e3, 2018.

Gatalica et al., "Abstract A047: Molecular characterization of the malignancies with targetable NTRK gene fusions," American Association for Cancer Research, Jan. 2018, 2 pages.

Gaudet et al., "Allele-specific PCR in SNP genotyping," Methods Mol Biol. 2009;578:415-24. doi: 10.1007/978-1-60327-411-1_26.

(56) References Cited

OTHER PUBLICATIONS

Gavrin et al., "Synthesis of Pyrazolo[1,5-[alpha]]pyrimidoinone Regioisomers," J Org Chem, Feb. 2007, 72(3): 1043-1046.
Geiger et al., "Functional Characterization of Human Cancer-Derived TRKB Mutations," PLoS ONE, Feb. 17, 2011, 6(2):e16871.
Geiger et al., "The neurotrophic receptor TrkB in anoikis resistance and metastasis: a perspective," J Cancer Res., Aug. 2005, 65(16):7033-7036.
GenBank Accession No. AAB33109.1, "trkB [*Homo sapiens*]," Jul. 27, 1995, 1 page.
GenBank Accession No. AAB33111.1, "trkC [*Homo sapiens*]," Jul. 27, 1995, 1 page.
GenBank Accession No. NM_002529, "high affinity nerve growth factor receptor isoform 2 precursor [*Homo sapiens*]," May 11, 2014, 4 pages.
GenBank Accession No. NM_001007792 "*Homo sapiens* neurotrophic tyrosine kinase, receptor type 1(NTRK1), transcript variant 3, mRNA," May 10, 2014, 5 pages.
GenBank Accession No. NM_001012339, "*Homo sapiens* neurotrophic tyrosine kinase, receptor, type 3 (NTRK3), transcript variant 1, mRNA," May 10, 2014, 6 pages.
GenBank Accession No. NM_006180, "*Homo sapiens* neurotrophic tyrosine kinase, receptor, type 2 (NTRK2), transcript variant a, mRNA," May 12, 2014, 9 pages.
GenBank Accession No. NP 001007793, "high affinity nerve growth factor receptor isoform 3 [*Homo sapiens*]," May 10, 2014, 3 pages.
GenBank Accession No. NP_002520 "high affinity nerve growth factor receptor isoform 2 precursor [*Homo sapiens*]," May 11, 2014, 4 pages.
GenBank Accession No. NP_001007157, "NT-3 growth factor receptor isoform c precursor [*Homo sapiens*]," May 10, 2014, 3 pages.
GenBank Accession No. NP_001012331.1, "high affinity nerve growth factor receptor isoform 1 precursor [*Homo sapiens*]," May 10, 2014, 4 pages.
GenBank Accession No. NP_001012338, "NT-3 growth factor receptor isoform a precursor [*Homo sapiens*]," May 10, 2014, 3 pages.
GenBank Accession No. NP_006171, "BDNF/NT-3 growth factors receptor isoform a precursor [*Homo sapiens*]," May 12, 2014, 4 pages.
GenBank Accession No. S76473.1, "trkB [human, brain, mRNA, 3194 nt]," Jul. 27, 1995, 2 pages.
GenBank Accession No. S76475.1, "trkC [human, brain, mRNA, 2715 nt]," Jul. 27, 1995, 2 pages.
Genevois et al., "Dependence receptor TrkC is a putative colon cancer tumor suppressor," Proc. Nat. Acad. Sci. U.S.A. Feb. 19, 2013, 110(8):3017-3022.
Giacomini et al., "Breakpoint Analysis of Transcriptional and Genomic Profiles Uncovers Novel Gene Fusions Spanning Multiple Human Cancer Types", PLoS Gene.t, 9(4):e1003464, 2013.
Gimm et al., "Mutation analysis of NTRK2 and NTRK3, encoding 2 tyrosine kinase receptors, in sporadic human medullary thyroid carcinoma reveals novel sequence variants," International Journal of Cancer, Apr. 1, 2001, 92(1):70-74.
Greco et al., "Chromosome I rearrangements involving the genes TPR and NTRK1 produce structurally different thyroid-specific TRK oncogenes,"Genes Chromosomes Cancer. 19(2):112-23, 1997.
Greco et al., "Rearrangements of NTRK1 gene in papillary thyroid carcinoma," Molecular and Cellular Endocrinology, 2010, 321(1):44-49.
Greco et al., "The DNA rearrangement that generates the TRK-T3 oncogene involves a novel gene on chromosome 3 whose product has a potential coiled-coil domain," Mol. Cell. Biol. 15(11):6118-6127, 1995.
Greco et al., "TRK-T1 is a novel oncogene formed by the fusion of TPR and TRK genes in human papillary thyroid carcinomas," Oncogene. 7(2):237-42, 1992.
Green & Wuts, eds, "Protective Groups in Organic Synthesis," John Wiley & Sons Inc, May 8, 1999.

Groisberg et al., "Clinical next-generation sequencing in sarcomas", Journal of Clinical Oncology, vol. 34, Supp. Supplement 15; Abstract No. 11046; 2016 Annual Meeting of the American Society of Clinical Oncology, ASCO 2016, Chicago, IL. Jun. 3-7, 2016.
Gruber-Olipitz et al., "Neurotrophin 3/TrkC-regulated proteins in the human medulloblastoma cell line DAOY," J. Proteome Research, 2008, 7(5):1932-1944.
Gu et al., "Lung adenocarcinoma harboring concomitant SPTBN1-ALK fusion, c-Met overexpression, and HER-2 amplification with inherent resistance to crizotinib, chemotherapy, and radiotherapy.", J Hematol Oneal, 9(1): 66, 2016.
Gwak et al., "Attenuation of mechanical hyperalgesia following spinal cord injury by administration of antibodies to nerve growth factor in the rat." Neurosci. Lett., 2003, 336:117-120.
Hainsworth et al., "Lung Adenocarcinoma with Anaplastic Lymphoma Kinase (ALK) Rearrangement Presenting as Carcinoma of Unknown Primary Site: Recognition and Treatment Implications.", Drugs Real World Outcomes, 3:115-120, 2016.
Hakinni et al., "Minimally invasive approaches to prostate cancer: a review of the current literature.", Urol. J., 4: 130-137, 2007.
Hallberg and Palmer, "The role of the ALK receptor in cancer biology.", Ann. Oncology, 27 (Suppl 3):iii4-iii15. doi: 10.1093/annonc/mdw301, 2016.
Haller et al., "Paediatric and adult soft tissue sarcomas with NTRK1 gene fusions: a subset of spindle cell sarcomas unified by a prominent myopericytic/haemangiopericytic pattern," J Pathol, Apr. 2016, 238(5):700-710.
Hamdouchi et a 1 "Imidazo[1,2-b]pyridazines, novel nucleus with potent and broad spectrum activity against human picornaviruses: design, synthesis, and biological evaluation" J Med Chem., Sep. 25, 2003;46(20):4333-4341.
Hansen et al., "Autophagic cell death induced by TrkA receptor activation in human glioblastoma cells," J. of Neurochemistry, 2007, 103:259-275.
Harada et al., "Role and Relevance of TrkB Mutations and Expression in Non-Small Cell Lung Cancer," Clinical Cancer Research, Jan. 17, 2011, 17(9):2638-2645.
Harris et al., "Multicenter Feasibility Study of Tumor Molecular Profiling to Inform Therapeutic Decisions in Advanced Pediatric Solid Tumors: The Individualized Cancer Therapy (iCat) Study," JAMA Oncol, Jan. 2016; 10.1001/jamaoncol.2015.5689, 8 pages.
Harwood et al., "Experimental organic chemistry—Principles and practice," Experimental Chemistry—Organic Chemistry and Reaction, Jan. 1, 1989, 127-132.
Hayashi et al., "Crizotinib treatment for refractory pediatric acute myeloid leukemia with RAN-binding protein 2-anaplastic lymphoma kinase fusion gene.", Blood Cancer J, 6(8): e456, 2016.
Hechtman et al., "Identification of targetable kinase alterations in patients with colorectal carcinoma that are preferentially associated with wild-type RAS/RAF," Mol. Cancer Res. 14(3):296-301, 2016.
Hechtman et al., Abstract 1837: Pan-TRK IHC Is an Efficient and Reliable Screening Assay for Targetable NTRK Fusions, Annual Meeting Abstracts, 2017, 457A.
Herzberg et al., "NGF involvement in pain induced by chronic constriction injury of the rat sciatic nerve," Neuroreport, 1997, 8:1613-1618.
Hinrichs et al., "Exploiting the curative potential of adoptive T-cell therapy for cancer," Immunol Rev. Jan. 2014;257(1):56-71. doi: 10.1111/imr.12132.
Hobbs et al., "Effects of T-Cell Depletion on Allogeneic Hematopoietic Stem Cell Transplantation Outcomes in AML Patients," J Clin Med. Mar. 19, 2015;4(3):488-503. doi: 10.3390/jcm4030488.
Holla et al., "ALK: a tyrosine kinase target for cancer therapy", Cold Spring Harb Mol Case Study, 3(1):a001115. doi: 10.1101/mcs.a001115, 20 pages, 2017.
Hong et al., "Clinical Safety and activity from a Phase 1 study of LOXO-101, a selective TRKA/B/C inhibitor, in solid-tumor patients with NTRK gene fusions," 2016 AACR Annual Meeting, Apr. 17, 2016, 32 pages.
Hong et al., Abstract PR13: Clinical safety and activity from a phase 1 study of LOXO-101, a selective TRKA/B/C inhibitor, in solid-tumor patients with NTRK gene fusions, Molecular Cancer Therapeutics 2015:14(12 Supplement 2):PR13.; Abstract only, 4 pages.

(56) References Cited

OTHER PUBLICATIONS

Hornick et al., "Expression of ROS1 predicts ROS1 gene rearrangement in inflammatory myofibroblastic tumors.", Mod Pathol., 28(5): 732-9, 2015.
Hover et al., "Abstract TMOD-07: NTRK3 Gene Fusions Drive Tumorigenesis in Novel Models of Pediatric High Grade Glioma," Neuro-Oncology, Jun. 2017, iv49.
Howell et al., "Dynamic allele-specific hybridization. A new method for scoring single nucleotide polymorphisms," Nat Biotechnol. Jan. 1999;17(1):87-8.
Hu et al., "Decrease in bladder overactivity with REN1820 in rats with cyclophosphamide induced cystitis," J. Urology, 2005, 173(3):1016-1021.
Hu et al., "Identification of brain-derived neurotrophic factor as a novel angiogenic protein in multiple myeloma" Cancer Genetics and Cytogenetics, 2007, 178:1-10.
Huehls et al., "Bispecific T-cell engagers for cancer immunotherapy," Immunol Cell Biol. Mar. 2015 ;93(3):290-6. doi: 10.1038/icb.2014.93. Epub Nov. 4, 2014.
Hyrcza et al., "Abstract OFP-06-007: Comparison of ultrastructural features between pediatric Mammary Analogue Secretory Carcinoma (MASC) of the salivary glands and Pediatric Secretory Breast Carcinoma (SBC) reveals similar pathological features," Virchows Arch, Sep. 2016, 469(S1): S17.
Hyrcza et al., vol. 469, Supp. Supplement 1, pp. S17. Abstract No. OFP-1997-7; 31st International Congress of the International Academy of Pathology and the 28th Congress of the European Society of Pathology, Cologne, Germany. Sep. 25-29, 2016.
Igaz et al., "Biological and clinical significance of the JAK-STAT pathway; lessons from knockout mice," Inflamm Res., 2001, 50:435-441.
Ihle et al., "The Roles of Jaks and Stats in Cytokine Signaling," Canc. J. Sci. Am., 1998, 4(1):84-91.
Ihuegbu et al., "Non-invasive detection of crizotinib resistance in ALK-rearranged lung adenocarcinoma directs treatment with next-generation ALK inhibitors", J Clin. Oncology, vol. 34, Supp. Supplement 15, Abstract No. e20643, 2016 Annual Meeting of the American Society of Clinical Oncology, Chicago, IL, 2016.
Ikeda et al., "Basic Sciene", Annals of Oncology. vol. 28 (suppl_10): xl x6.10.1093/annonc/mdx652, 2017.
Imamura et al., "Allogeneic hematopoietic stem cell transplantation in adult acute lymphoblastic leukemia: potential benefit of medium-dose etoposide conditioning," Exp Hematol Oncol, Jul. 16, 2015;4:20. doi: 10.1186/s40164-015-0015-0. eCollection 2015.
Iniguez-Ariza et al., "Abstract 6087: NTRK1-3 point mutations in poor prognosis thyroid cancers," J Clinical Oncology, May 2017, 35(15): 6087.
Isdori et al., "Advancement in high dose therapy and autologous stem cell rescue in lymphoma," World J Stem Cells, Aug. 2015, 7(7):1039-1046.
Iyama et al., "Identification of Three Novel Fusion Oncogenes, SQSTM1/NTRK3, AFAP1L2/RET, and PPFIBP2/RET, in Thyroid Cancers of Young Patients in Fukushima," Thyroid. 27(6):811-818, 2017.
Iyer et al., "AZ64 inhibits TrkB and enhances the efficacy of chemotherapy and local radiation in neuroblastoma xenografts," Cancer Chemother Pharmacol. Sep. 2012;70(3):477-86. doi: 10.1007/s00280-012-1879-x. Epub May 24, 2012.
Iyer, R., "Entrectinib is a potent inhibitor of Trk-driven neuroblastomas in a xenograft mouse model." Cancer letters 372.2 (2016): 179-186. (Year: 2016).
Jaggar et al "Inflammation of the rat urinary bladder is associated with a referred thermal hyperalgesia which is nerve growth factor dependent," Br. J. Anaesth, 1999, 83:442-448.
Japanese Office Action in Japanese Application No. JP 2013-511239, dated Mar. 4, 2015, 2 pages (English translation).
Jencks and Regenstein, "Ionization Constatns fo Acids and Bases," Handbook of Biochemistry and Molecular Biology, 3rd ed., G. D. Fassman, CRC Press, 1976, 1: 305-347.
Jin et al., "TrkC plays an essential role in breast tumor growth and metastasis," Carcinogenesis, 2010, 31(11):1939-1947.
Johnson et al., "Comprehensive Genomic Profiling of 282 Pediatric Low- and High-Grade Gliomas Reveals Genomic Drivers, Tumor Mutational Burden, and Hypermutation Signatures.", Oncologist. 22(12): 1478-1490, 2017.
Jones et al., "Recurrent somatic alterations of FGFR1 and NTRK2 in pilocytic astrocytoma," Nature Genetics, 2013, 45:927-932.
Kao et al., "Recurrent BRAF Gene Fusions in a Subset of Pediatric Spindle Cell Sarcomas," Am. J. Surg. Pathol. 42(1):28-38, 2018.
Karachialiou et al., "Real-time liquid biopsies become a reality in cancer treatment", Ann. Transl. Med, 3(3):36, 2016.
Katayama et al., "Cabozantinib Overcomes Crizotinib Resistance in ROS1 Fusion-Positive Cancer", Clin. Cancer Res., 21 (I): 166-7 4, 2015.
Katayama et al., "Mechanisms of Acquired Crizotinib Resistance in ALK Rearranged Lung Cancers," Sci Transl Med, Feb. 2012, 4(120): 120ra17.
Katayama et al., "Therapeutic targeting of anaplastic lymphoma kinase in lung cancer: a paradigm for precision cancer medicine.", Clin Cancer Res, 21(10): 2227-35, 2015.
Keysar et al., "A patient tumor transplant model of Squamous cell cancer identifies PI3K inhibitors as candidate therapeutics in defined molecular bins," Molecular Oncology, 2013, 7(4):776-790.
Kim et al., "Mammaglobin-A is a target for breast cancer vaccination", OncoImmunology 5(2): e1069940, 2016.
Kim et al., "NTRK1 fusion in glioblastoma multiforme," PloS ONE, 2014, 9(3):e91940.
Kim et al., "SEC31A-ALK Fusion Gene in Lung Adenocarcinoma", Cancer Res Treat, 48(1): 398-402, 2016.
Klijn et al., "A comprehensive transcriptional portrait of human cancer cell lines," Nat Biotechnol.,.2015, 33(3):306-312.
Knezevich et al., "A novel ETV6-NTRK3 gene fusion in congenital fibrosarcoma," Nat Genet, Feb. 1998 :18(2):184-187.
Knezevich et al., "ETV6-NTRK3 gene fusions and trisomy 11 establish a histogenetic link between mesoblastic nephroma and congenital fibrosarcoma," Cancer Res, Nov. 1998:58(22):5046-5048.
Koboldt et al., "The next-generation sequencing revolution and its impact on genomics," Cell, Sep. 26, 2013;155(1):27-38. doi: 10.1016/j.cell.2013.09.006.
Kohsaka et al., "Refractory and metastatic infantile fibrosarcoma harboring LMNA—NTRK1 fusion shows complete and durable response to crizotinib," Hum. Pathol. 72:167-173, 2017.
Kolokythas et al., "Nerve growth factor and tyrosine kinase a receptor in oral squamous cell carcinoma: is there an association with perineural invasion?" J. Oral Maxillofacial Surgery, 2010, 68(6):1290-1295.
Konicek et al., Cancer research, vol. 76, No. 14, Supp. Supplement. Abstract No. 2647; 107th Annual Meeting of the American Association for Cancer Research, AACR 2016. New Orleans, LA; Apr. 16-20, 2016; Abstract only, 3 pages.
Kralik et al., "Characterization of a newly identified ETV6-NTRK3 fusion transcript in acute myeloid leukemia," Diagn. Pathol. 6:19, 2011.
Kremer et al., "The safety and efficacy of a JAK inhibitor in patients with active rheumatoid arthritis: Results of a double-blind, placebo-controlled phase IIa trial of three dosage levels of CP-690,550 versus placebo," Arth. & Rheum., 2009, 60:1895-1905.
Kruettgen et al., "The dark side of the NGF family: neurotrophins in neoplasias," Brain Pathology, 2006, 16:304-310.
Kubler et al., "Self-adjuvanted mRNA vaccination in advanced prostate cancer patients: a first-in-man phase I/IIa study.", J. Immunother Cancer 3 :26, 2015.
Kusano et al., "Two Cases of Renal Cell Carcinoma Harboring a Novel STRN-ALK Fusion Gene.", Am J Surg Pathol. 40(6): 761-9, 2016.
Lamb et al., "Nerve growth factor and gastric hyperalgesia in the rat," Neurogastrenterol. Motil., 2003, 15:355-361.
Lannon et al., "ETV6-NTRK3: a chimeric protein tyrosine kinase with transformation activity in.multiple cell lineages," Semin Cancer Biol, Jun. 2005:15(3):215-223.

(56) References Cited

OTHER PUBLICATIONS

Lansky et al., "The measurement of performance in childhood cancer patients," Cancer, 1987, 60(7):1651-1651.
Lecht et al., "Angiostatic effects of K252a, a Trk inhibitor, in murine brain capillary endothelial cells," Mol Cell Biochem, Jun. 2010;339(1-2):201-13. doi: 10.1007/s11010-010-0386-9. Epub Feb. 11, 2010.
Lee et al., "Identification of ROS1 rearrangement in gastric adenocarcinoma.", Cancer, 119(9): 1627-1635, 2013.
Leeman-Neill et al., "ETV6-NTRK3 is a common chromosomal rearrangement in radiation-associated thyroid cancer," Cancer, 2014, 120(6):799-807.
Leukemia, Wikipedia The Free Encyclopedia, Dec. 8, 2001, https://en.wikipedia.org/wiki/Leukemia, 15 pages.
Leyvraz et al., Abstract No. 897. Meeting Info: 33. Deutscher Krebskongress, DKK. Berlin, Germany, 2018.
Lezcano et al., "Regular transfusion lowers plasma free hemoglobin in children with sickle-cell disease at risk for stroke," Am. J. Surg. Pathol. doi: 10.1097/PAS.0000000000001070, 2018.
Li et al., "Brain derived neurotrophic factor (BDNF) contributes to the pain hypersensitivity following surgical incision in the rats," Molecular Pain, 2008, 4(28):1-11.
Li et al., "Combinational Analysis of FISH and Immunohistochemistry Reveals Rare Genomic Events in ALK Fusion Patterns in NSCLC that Responds to Crizotinib Treatment", J Thorac. Oneal., 12(1):94-101. doi: 10.1016/j .jtho.2016.08.145, 2017.
Li et al., "Correlation of expressions of GFAP, NT-3, Trk and NCAM with neurotropic molecular mechanism and clinical factors in adenoid cystic carcinoma of salivary gland," Chinese Journal of Cancer Prevention and Treatment, 2009, 16(6): 428-430 (with English abstract).
Li et al., "In vivo sensitized and in vitro activated B cells mediate tumor regression in cancer adoptive immunotherapy," J Immunol, Sep. 1, 2009;183(5):3195-203. doi: 10.4049/jimmunol.0803773. Epub Aug. 10, 2009.
Li et al., "Lumbar 5 ventral root transection-induced upregulation of nerve growth factor in sensory neurons and their target tissues: a mechanism in neuropathic pain," Mol. Cell. Neurosci., 2003, 23:232-250.
Li et al., "Trk inhibitor attenuates the BDNF/TrkB-induced protection of neuroblastoma cells from etoposide in vitro and in vivo," Cancer Biol. Ther., Feb. 2015, 16(3):477-483.
Lin et al., "HG-48. Integrated Sequencing of Pediatric Pilocytic Astrocytomawith Anaplasia Reveals Molecular Features of Both Lowand High-Grade Glial Tumors", Neuro-Oneol, vol. 18, Supp. Supplement 3, pp. iii58, Abstract No. HG-48; 17th International Symposium on Pediatric Neuro-Oncology, ISPNO 2016. Liverpool, UK, Jun. 12, 2016-Jun. 15, 2016.
Lin et al., Neuro-Oncol, vol. 18, Supp. Supplement 3, pp. iii58, Abstract No. HG-48; 17th International Symposium on Pediatric Neuro-Oncology, ISPNO 2016. Liverpool, UK, Jun. 12, 2016-Jun. 15, 2016.
Linch et al., "Systemic treatment of soft-tissue sarcoma [mdash] gold standard and novel therapies," Nature Reviews Clinical Oncology, 2014, 11(4):187-202.
Loh et al., "Treatment of infantile fibrosarcoma with chemotherapy and surgery: results from the Dana-Farber Cancer Institute and Children's Hospital, Boston," J Pediatr Hematol Oncol, Dec. 2002:24(9):722-726.
Lorigan et al., "Phase III trial of two investigational schedules of ifosfamide compared with standard-dose doxorubicin in advanced or metastatic soft tissue sarcoma: a European Organisation for Research and Treatment of Cancer Soft Tissue and Bone Sarcoma Group Study," J. Clin Oncol., 2007, 25(21):3144-3150.
Lovly et al "Inflammatory myofibroblastic tumors harbor multiple potentially actionable kinase fusions," Cancer Discov., 2014, 4(8):889-895.
Lu et al., "Targeted next generation sequencing identifies somatic mutations and gene fusions in papillary thyroid carcinoma," Oncotarget. 8(28):45784-45792, 2017.

Ma and Woolf, "The progressive tactile hyperalgesia induced by peripheral inflammation is nerve growth factor dependent," Neuroreport, 1997, 8:807-810.
Ma et al., "Responses to crizotinib in patients with ALK-positive lung adenocarcinoma who tested immunohistochemistry (IHC)-positive and fluorescence in situ hybridization (FISH)-negative", Oncotarget, 7(39), 64410-64420, 2016.
Macleod, et al., "Abstract 0294: Gene Targets of ETV6-NTRK3 Fusion," Haematologica, 14th Congress of the European Hematology Association,2009, 94(s2): 116.
Majweska et al., Cancer Research, vol. 76, No. 14, Supp. Supplement. Abstract No. 3190. 107th Annual meeting of the American Association for Cancer Research, AACR. New Orleans, LA Apr. 16-20, 2016.
Makretsov et al., "A fluorescence in situ hybridization study of ETV6-NTRK3 fusion gene in secretory breast carcinoma," Genes, Chromosomes and Cancer, Jun. 2004:40(2):152-157.
Marchetti et al., "Frequent mutations in the neurotrophic tyrosine receptor kinase gene family in large cell neuroendocrine carcinoma of the lung," Human Mutation, 2008, 29(5):609-616.
Marras et al., "Genotyping SNPs with molecular beacons," Methods Mol Biol, 2003;212:111-28.
Marras et al., Single Nucleotide Polymorphism: Methods and Protocols. Methods in Molecular Biology, Kwok, P.-Y., Ed., Totowa, NJ, Humana Press, vol. 212, pp. 111-128, 2003.
Martin-Zanca et al., "A human oncogene formed by the fusion of truncated tropomyosin and protein tyrosine kinase sequences," Nature, 1986, 319:743-748.
Matayoshi, "Actions of brain-derived neurotrophic factor on spinal nociceptive transmission during inflammation in the rat," J. Physiol., 2005, 569:685-695.
McCahon et al., "Non-Resectable Congenital Tumors with the ETV6-NTRK3 Gene Fusion Are Highly Responsive to Chemotherapy," Med. Pediatr. Oncol., May 2003, 40(5):288-292.
McCarthy et al., "Tropomyosin receptor kinase inhibitors: a patent update 2009-2013," Expert Opin Ther Pat. Jul. 2014;24(7):731-44. doi: 10.1517/13543776.2014.910195. Epub May 8, 2014.
McMahon et al., "The biological effects of endogenous nerve growth factor on adult sensory neurons revealed by a trkA-IgG fusion molecule," Nat. Med., 1995, 1:774-780.
McMahon., "VEGF Receptor Signaling in Tumor Angiogenesis," The Oncologist, 2000, 5(1): 3-10.
Mekinist, Highlights of Prescribing Information, Initial Approval 2013, revised Nov. 2015, Novartis Pharmaceuticals Corp., 27 pages.
Melo-Jorge et al., The Chagas' disease parasite Trypanosoma cruzi exploits nerve growth factor receptor TrkA to infect mammalian hosts Cell Host & Microbe, 2007, 1(4):251-261.
Meyer et al., "Remarkable leukemogenic potency and quality of a constitutively active neurotrophin receptor, deltaTrkA," Leukemia, 2007, 21:2171-2180.
Milione et al., "Identification and characterization of a novel SCYL3-NTRK1 rearrangement in a colorectal cancer patient," Oncotarget, 8(33):55353-55360, 2017.
Miranda et al., "Functional characterization of NTRK1 mutations Identified in melanoma," Genes Chromosomes & Cancer, Jun. 26, 2014, 53(10):875-880.
Montagnoli et al., "Anti-proliferative effects of GW441756, a novel inhibitor of NGFreceptor tyrosine kinase a (TRKA), in human sarcoma," Italian Journal of Anatomy and Embryology, Nov. 11, 2010, 115:117.
Montalli et al., "Mammaglobin and DOG-1 expression in polymorphous low-grade adenocarcinoma: an appraisal of its origin and morphology," J Oral Pathol Med., Mar. 2017, 46(3):182-187.
Morissette et al., "High-throughput crystallization: polymorphs, salts, co-crystals and solvates of pharmaceutical solids," Adv. Drug Deliv Rev, 2004, 56: 375-300.
Mulligan, "RET revisited: expanding the oncogenic portfolio.", Nature Reviews Cancer, 14, 173-186, 2014.
Murakami et al., "Integrated molecular profiling of juvenile myelomonocytic leukemia", Blood, blood-2017-07-798157, DOI: 10.1182/blood-2017-07-798157, 2018.
Myers, "Synthesis of Chiral Amines by Asymmetric Additions to tert-Butylsulfinimines (Ellman Auxiliary)," Chem 115, retrieved on

(56) References Cited

OTHER PUBLICATIONS

May 18, 2016, retreived from the Internet. URL: <faculty.chemist.harvard.edu/files/myers/files/15-e11man_auxiliary.pdf>, 6 pages.
Nagasubramanian et al., "Infantile Fibrosarcoma With NTRK3-ETV6 Fusion Successfully Treated With the Tropomyosin-Related Kinase Inhibitor LOXO-101," Pediatr Blood Cancer., Aug. 2016, 63(8):1468-70.
Nagasubruamanian et al., "Brief Report: Infantile Fibrsarcoma With NTRK3-ETV6 Fusion Successfully Treated With the Tropomyosin-Related Kinase Inhibitor LOXO-101," Pediatric Blood & Cancer, 2016, DOI 10.1002, 3 pages.
Nakagawa, "Trk receptor tyrosine kinases: a bridge between cancer and neural development," Cancer Letters, 2001, 169(2):107-114.
Nakano et al., "Novel Oncogenic KLC1-ROS1 Fusion in Pediatric Low Grade Glioma", Pediatr Blood Cancer. vol. 64, S54-S55 Suppe. 4. 013-1-7, 2017.
Narayanan et al., "Discovery and preclinical characterization of novel small molecule TRK and ROS1 tryosine kinase inhibitors for the treatment of cancer and inflammation," PLoS One, Dec. 26, 2013;8(12):e83380. doi: 10.1371/journal.pone.0083380. eCollection 2013.
National Cancer Institute at the National Institutes of Health, posted on or before Jan. 5, 2000, retrieved on Jan. 13, 2015, http://www.cancer.gov/, 2 pages.
National Comprehensive Cancer Network, posted on or before Dec. 3, 1998, retrieved on Jan. 13, 2015, http://www.nccn.org/, 1 page.
NCT02050919, "Sorafenib Tosylate, Combination Chemotherapy, Radiation Therapy, and Surgery in Treating Patients With High-Risk Stage IIB-IV Soft Tissue Sarcoma," ClinicalTrials.gov, First received Jan. 29, 2014, Last Updated Dec. 16, 2015, https://www.clinicaltrials.gov/ct2/show/NCT02050919, 5 pages.
NCT02122913, "Oral TRK Inhibitor LOXO-101 for Treatment of Advanced Adult Solid Tumors," ClinicalTrials.gov, Last Updated Dec. 7, 2015, https://clinicaltrials.gov/ct2/show/NCT02122913.
Ni et al., "siRNA interference with a proliferation-inducing ligand gene in the Sgr-7901 gastric carcinoma cell line," Asian Pacific Journal of Cancer Prevention, 2012, 13:1511-1514.
Ni et al., "Tyrosine receptor kinase B is a drug target in astrocytomas," Neuro Oncol., Jan. 2017, 19(1):22-30.
NIH National Cancer Institute [online], "recurrence (ree-KER-ents)," NCI Dictionary of Cancer Terms, retrieved on Sep. 21, 2018, URL: <https://www.cancer.gov/publications/dictionaries/cancer-terms/def/recurrence>, 1 page.
NIH National Cancer Institute [online], "relapse (REE-laps)," NCI Dictionary of Cancer Terms, retrieved on Sep. 17, 2019, URL: <https://www.cancer.gov/publications/dictionaries/cancer-terms/def/relapse>, 1 page.
NIH National Cancer Institute [online], "progression (pru-GREH-shun)," NCI Dictionary of Cancer Terms, retrieved on Sep. 17, 2018, URL: <https://www.cancer.gov/publications/dictionaries/cancer-terms/def/progression>, 1 page.
Nikiforova et al., Abstract No. 5. Meeting Info: 84th Annual Meeting of the American Thyroid Association. Coronado, CA, United States, 2014.
Nollau et al., "Methods for detection of point mutations: performance and quality assessment. IFCC Scientific Division, Committee on Molecular Biology Techniques," Clin Chem. Jul. 1997;43(7):1114-28.
Obianyo et al., "Novel small molecule activators of the Trk family of receptor tyrosine kinases. Biochim Biophys Acta, 1834:2214-2218," Biochim Biophys Acta, Oct. 2013, 1834(10):2213-2218.
Ocgene.bioinfo-minzhao.org' [online]. "Ovarian Cancer Gene Database, Gene ID: 4914," [retrieved on Jul. 17, 2017] Retrived from the Internet: URL<ocgene.bioinfominzhao.org/gene_mutation.cgi?gene=4914>, 13 pages.
Oken et al., "Toxicity and response criteria of th Eastern Cooperative Oncology Group," Am J Clin Oncol, 1982, 5:649-655.
Olivier, "The Invader assay for SNP genotyping," Mutat Res, Jun. 3, 2005;573(1-2):103-10.
Orbach et al., "Conservative strategy in infantile fibrosarcoma is possible: The European paediatric Soft tissue sarcoma Study Group experience," Eur J Cancer, Apr. 2016, 57:1-9.
Orbach et al., "Infantile fibrosarcoma: management based on the European experience," J Clin Oncol, Jan. 2010, 28(2):318-323.
O'Shea, "Jaks, STATs, cytokine signal transduction, and immunoregulation: are we there yet?" Immunity, 1997, 7:1-11.
Otsubo et al., "Sporadic pediatric papillary thyroid carcinoma harboring the ETV6/NTRK3 fusion in oncogene in a 7-year-old Japanese girl: a case report and review of literature," J. Pediatr. Endocrinol. Metab. 28;31(4):461-467, 201.
Ott et al., "An immunogenic personal neoantigen vaccine for patients with melanoma.", Nature 547: 217-221, 2017.
Ou et al., "Emergence of novel and dominant acquired EGFR solvent-front mutations at Gly796 (G796S/R) together with C797S/R and L792F/H EGFR (L858R/T790M) NSCLC patient who progressed on osimertinib," Lung Cancer, 2017, 108: 228-231.
Ou et al., "Identification of a novel TMEM106B-ROS1 fusion variant in lung adenocarcinoma by comprehensive genomic profiling.", Lung Cancer, 88(3):352-4, 2015.
Ou et al., "Next-Generation Sequencing Reveals a Novel NSCLC ALK F1174V Mutation and Confirms ALK G1202R Mutation Confers High-Level Resistance to Alectinib (CH5424802/R05424802) in ALK-Rearranged NSCLC Patients Who Progressed on Crizotinib," Journal of Thoracic Oncology, Apr. 2014, 9: 549-553.
Ovanan Cancer Gene Database, ocgene.bioinfo-minzhao.org/gene_mutation.cgi?gene=4914, downloaded on May 31, 2016, 14 pages.
Ovarian Cancer Gene Database, ocgene.bioinfo-minzhao.org/gene_mutation.cgi?gene=4916, downloaded on May 31, 2016, 21 pages.
Pan et al., Laboratory Investigation, vol. 96, Supp. SUPPL. 1, pp. 367A, Abstract No. 1450, 105th Annual Meeting of the United States and Canadian Academy of Pathology, Seattle, WA, 2016.
Panagopoulos et al., "Recurrent fusion of the genes FN1 and ALK in gastrointestinal leiomyomas", Modern Pathology 29: 1415-1423, 2016.
Pao, W. et al."Acquired resistance of lung adenocarcinomas to gefitinib or erlotinib is associated with a second mutation in the EGFR kinase domain," PLoS Med, Feb. 2005, 2(3), e73.
Papatsoris et al., "Manipulation of the nerve growth factor network in prostate cancer," Exper Opin Invest Drugs, 2007, 16(3):303-309.
Park et al., "Genomic alterations in BCL2L1 and DLC1 contribute to drug sensitivity in gastric cancer," Proc. Natl. Acad. Sci. U.S.A., Oct. 2015, 112(40):12492-12497.
Park et al., "NTRK1 fusions for the therapeutic intervention of Korean patients with colon cancer," Oncotarget. 7(7):8399-412, 2016.
Patani et al., "Bioisosterism: A rational approach in Drug Design," Chem Rev., Dec. 1996, 96(8):3147-3176.
Patapoutian et al., "Trk receptors: mediators of neurotrophin action," Current Opinion in Neurobiology, 2001, 11:272-280.
Pavlick et al., "Identification of NTRK fusions in pediatric mesenchymal tumors," Pediatr Blood Cancer, Aug. 2017, 64(8). doi: 10.1002/pbc.26433. Epub Jan. 18, 2017.
PCT International Preliminary Report on Patentability in International Application No. PCT/US2009/057729, dated Mar. 22, 2011, 7 pages.
PCT International Preliminary Report on Patentability in International Application No. PCT/US2009/061519, dated Apr. 26, 2011, 6 pages.
PCT International Preliminary Report on Patentability in International Application No. PCT/US2010/041538, dated Jan. 10, 2012, 7 pages.
PCT International Preliminary Report on Patentability in International Application No. PCT/US2011/036452, dated Nov. 29, 2012, 6 pages.
PCT International Preliminary Report on Patentability in International Application No. PCT/US2015/060953, dated May 16, 2017, 7 pages.
PCT International Preliminary Report on Patentability in International Application No. PCT/US2016/035327, dated Dec. 14, 2017, 9 pages.

(56) References Cited

OTHER PUBLICATIONS

PCT International Preliminary Report on Patentability in International Application No. PCT/US2016/058951, dated May 11, 2018, 11 pages.
PCT International Preliminary Report on Patentability in International Application No. PCT/US2017/033257, dated Nov. 20, 2018, 8 pages.
PCT International Seach Report and Written Opinion for International Application No. PCT/US2016/035327, dated Aug. 18, 2016, 15 pages.
PCT International Seach Report and Written Opinion in International Application No. PCT/US2009/0161519, dated Feb. 2, 2010, 8 pages.
PCT International Seach Report and Written Opinion in International Application No. PCT/US2009/057729, dated Feb. 4, 2010, 10 pages.
PCT International Seach Report and Written Opinion in International Application No. PCT/US2010/041538, dated Oct. 1, 2010, 10 pages.
PCT International Seach Report and Written Opinion in International Application No. PCT/US2011/036452, dated Aug. 18, 2011, 9 pages.
PCT International Seach Report and Written Opinion in International Application No. PCT/US2015/060953, dated Feb. 8, 2016, 12 pages.
PCT International Seach Report and Written Opinion in International Application No. PCT/US2016/058951, dated Feb. 7, 2017, 20 pages.
PCT International Seach Report and Written Opinion in International Application No. PCT/US2017/025932, dated May 31, 2017, 16 pages.
PCT International Seach Report and Written Opinion in International Application No. PCT/US2017/025939, dated May 31, 2017, 16 pages.
PCT International Seach Report and Written Opinion in International Application No. PCT/US2017/033257, dated Jul. 24, 2017, 13 pages.
PCT International Seach Report and Written Opinion in International Application No. PCT/US2018/022833, dated Aug. 13, 2018.
PCT International Search Report and Written Opinion in International Application No. PCT/US2017/058518, dated May 2, 2018, 17 pages.
PCT International Search Report and Written Opinion in International Application No. PCT/US2018/039502, dated Apr. 16, 2018, 16 pages.
PCT International Search Report and Written Opinion in International Application No. PCT/US2018/057542, dated Mar. 6, 2019, 19 pages.
Pediatric Cancer Gene Database, pedican.bioinfominzhao.org/gene_mutation.cgi?gene=4914, downloaded on May 31, 2016, 6 pages.
Pediatric Cancer Gene Database, pedican.bioinfominzhao.org/gene_mutation.cgi?gene=4915, downloaded on May 31, 2016, 5 pages.
Pediatric Cancer Gene Database, pedican.bioinfominzhao.org/gene_mutation.cgi?gene=4916, downloaded on May 31, 2016, 9 pages.
Perales et al., "Fast Cars and No Brakes: Autologous Stem Cell Transplantation as a Platform for Novel Immunotherapies," Biol Blood Marrow Transplant, Jan. 2016;22(1):17-22. doi: 10.1016/j.bbmt.2015.10.014. Epub Oct. 17, 2015.
Perez-Pinera et al., "The Trk tyrosine kinase inhibitor K252a regulates growth of lung.adenocarcinomas," Molecular and Cellular Biochemistry, 2007, 295(1&2):19-26.
Perrault et al., "The Synthesis of N-Aryl-5(S)-aminomethyl-2-oxazolidinone Antibacterials and Derivatives in One Step from Aryl Carbamates," Org. Process Res. Dev., 2003, 7:533-546.
Peus et al., "Appraisal of the Karnofsky Performance Status and proposal of simple algorithmic system for its evaluation," BMC Med Infomr Decis Mak, 2013, 13:72.
Philippines Office Action in Philippines Application No. PH 1/2012/500048, dated May 30, 2014, 2 pages.

Picarsic et al., "Molecular characterization of sporadic pediatric thyroid carcinoma with the DNA/RNA ThyroSeq v2 next-generation sequencing assay," Pediatr. Dev. Pathol, Mar. 2016, 19(2): 115-122.
Pierottia and Greco, "Oncogenic rearrangements of the NTRK1/NGF receptor," Cancer Letters, 2006, 232:90-98.
Pinedo et al., "Translational Research: The Role of VEGF in Tumor Angiogenesis," The Oncologist, 2000, 5(1): 1-2.
Pinski et al., "Trk receptor inhibition induces apoptosis of proliferating but not quiescent human osteoblasts," Cancer Res, 2002, 62:986-989.
Plosker, "Sipuleucel-T: in metastatic castration-resistant prostate cancer.", Drugs 71(1): 101-108, 2011.
Ponsaerts et al., "Cancer immunotherapy using RNA-loaded dendritic cells," Clin. Exp. Immunol., Dec. 2003, 134:378-384.
Prabhakaran et al., "Novel TLE4-NTRK2 fusion in a ganglioglioma identified by array-CGH and confirmed by NGS: Potential for a gene targeted therapy," Neuropathology, Mar. 2018, doi:10.1111/neup.12458.
Prasad et al., "NTRK fusion oncogenes in pediatric papillary thyroid carcinoma in northeast United States," Cancer, Apr. 2016, 122(7):1097-1107.
Pulciani et al., "Oncogenes in solid human tumours," Nature, 1982, 300(5892):539-542.
Qaddoumi et al., "Genetic alterations in uncommon low-grade neuroepithelial tumors: BRAF, FGFR1, and MYB mutations occur at high frequency and align with morphology,"Acta Neuropathol, Jun. 2016, 131(6):833-845.
Qiu et al., "Next generation sequencing (NGS) in wild type GISTs", J Clin. Oneal. 35: 15 _suppl, e22507-e22507, 2017.
Ramer and Bisby, "Adrenergic innervation of rat sensory ganglia following proximal or distal painful sciatic neuropathy: distinct mechanisms revealed by anti-NGF treatment," Eur. J. Neurosci., 1999, 11:837-846.
Rausch et al., "mRNA vaccine CV9103 and CV9104 for the treatment of prostate cancer.", Human Vaccin Immunother 10(11): 3146-52, 2014.
Raychaudhuri et al., K252a, a high-affinity nerve growth factor receptor blocker, improves psoriasis: an in vivo study using the severe combined immunodeficient mouse-human skin model, J. Investigative Dermatology, 2004, 122(3):812-819.
Reshmi et al., "Abstract 477: Genomic and Outcome Analyses of Philadelphia Chromosome like (Ph-like) NCI Standard Risk B-Acute Lymphoblastic Leukemia (SR B-ALL) Patients Treated on Children's Oncology Group (COG) AALL0331," Blood, 2017, 130(S1): 477.
Reungwetwattana et al., "Targeted therapies in development for non-small cell lung cancer," J Carcinog, Dec. 2013, 12:22, doi: 10.4103/1477-3163.123972. eCollection 2013.
Reuther et al., "Identification and characterization of an activating TrkA deletion mutation in acute myeloid leukemia," Mol. Cell. Biol. 2000, 20:8655-8666.
Ricarte-Filho et al., "Identification of kinase fusion oncogenes in post-Chernobyl radiation-induced thyroid cancers," J. Clin. Invest, Nov. 2013, 123(11): 4935-4944.
Ricci et al., Neurotrophins and neurotrophin receptors in human lung cancer, Am. J. Respiratory Cell and Molecular Biology, Oct. 2001, 25(4): 439-446.
Richard et al., "Syngeneic stem cell transplant for spent-phase polycythaemia vera: eradication of myelofibrosis and restoration of normal haematopoiesis," Br. J Haematol., Apr. 2002, 117(1):245-246.
Rimkunas et al., "Analysis of receptor tyrosine kinase ROS1-positive tumors in non-small cell lung.cancer: identification of a FIG-ROS1 fusion.", Clin. Cancer Res., 18: 4449-58, 2012.
Ritterhouse et al., "ROS1 Rearrangement in Thyroid Cancer.", Thyroid, 26(6): 794-7, 2016.
Ro et al., "Effect of NGF and anti-NGF on neuropathic pain in rats following chronic constriction injury of the sciatic nerve," Pain, 1999, 79:265-274.
Roberts et al., "Targetable kinase-activating lesions in Ph-like acute lymphoblastic leukemia," N Engl J Med, Sep. 2014, 371(11):1005-1015.

(56) References Cited

OTHER PUBLICATIONS

Roberts et al., Blood, vol. 128, No. 22. Abstract No. 278, 58th Annual Meeting of the American Society of Hematology, ASH 2016. San Diego, CA, United States. Dec. 3, 2016-Dec. 6, 2016, 2 pages.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis," Acta Derm. Venereal., 2015, 95:542-548.
Rosenbaum et al., "Next Generation Sequencing Reveals Genomic Heterogenity of ALK Fusion Breakpoints in Non-Small Cell Lung Cancer", Laboratory Investigation, vol. 96, Supp. SUPPL. 1, pp. 481A-482A, Abstract No. 1914, 105th Annual Meeting of the United States and Canadian Academy of Pathology, Seattle, WA, 2016.
Roskoski, Jr. et al., "Classification of small molecule protein kinase inhibitors based upon the structures of their drug-enzyme complexes," Pharmacological Research, 2016, 103: 26-48.
Ross et al., "New routes to targeted therapy of intrahepatic cholangiocarcinomas revealed by next-generation sequencing," Oncologist, 2014, 19:235-242.
Rossi et al., "Abstract 84: RNA-Sequencing Identifies ETV6-NTRAK3 as a Gene Fusion Involved in Gastrointestinal Stromal Tumors," Meeting Info: 105th Annual Meeting of the United States and Canadian Academy of Pathology, Seattle, WA, Annual Meeting Abstracts, 24A.
Rubin et al., "Congenital mesoblastic nephroma t(12;15) is associated with ETV6-NTRK3 gene fusion: cytogenic and molecular relationship to congenital (infantile) fibrosarcoma," Am. J. Pathol, Nov. 1998, 153(5):1451-1458.
Rubin et al., "Growth, survival and migration: the Trk to cancer," Cancer Treat Res, 2003, 115:1-18.
Russo et al., "Acquired Resistance to the Trk Inhibitor Entrectinib in Colorectal Cancer," Cancer Discovery, Jan. 1, 2016, 6(1):36-44.
Rutkowski et al., "Treatment of advanced dermatofibrosarcoma protuberans with imatinib mesylate with or without surgical resection," J. Eur. Acad. Dermatol. Vencreol., 2011, 25:264-270.
Saborowski et al., "Mouse model of intrahepatic cholangiocarcinoma validates FIG-ROS as a potent fusion oncogene and therapeutic target.", Proc. Natl. Acad Sci. USA., 110(48): 19513-19518, 2013.
Sahin et al., "Personalized RNA mutanome vaccines mobilize poly-specific therapeutic immunity against cancer.", Nature 547: 222-226, 2017.
Santoro et al., "Doxorubicin versus CYVADIC versus doxorubicin plus ifosfamide in first-line treatment of advanced soft tissue sarcomas: a randomized study of the European Organization for Reasearh and Treatment of Cancer Soft Tissue and Bone Sarcoma Group," J. Clin Oncol., 1995, 13(7): 1537-1545.
Saragovi et al., "A TrkA-selective, fast internalizing nerve growth factor-antibody complex induces trophic but not neuritogenic signals," J Biol Chem, Dec. 25, 1995;273(52):34933-34940.
Sartore-Bianchi et al., "Sensitivity to Entrectinib Associated With a Novel LMNA-NTRK1 Gene Fusion in Metastatic Colorectal Cancer," J. Natl. Cancer Inst, Nov. 2015, 108(1). doi: 10.1093/jnci/djv306.
Sassolas et al., "Oncogenic alterations in papillary thyroid cancers of young patients," Thyroid Jan. 2012, 22(1):17-26.
Scaruffi et al., "Detection of DNA polymorphisms and point mutations of high-affinity nerve growth factor receptor (TrkA) in human neuroblastoma," Int. J. Oneal., May 1999, 14:935-938.
Schmidt et al., "Heilmittelchemische untersuchungen in der Heterocyclischen Rihe. Pyrazolo-(3,4-D)-Pyrimidine (Medicinal chemical studies in the heterocyclic series.Pyrazolo-(3,4-D)-Pyrimidine)," Helvetica Chimica, Verlag Helvetica Chimica Acta, Jan. 1956, 39: 986-991 (with English Abstract).
Schram et al., "Abstract LB-302: Potential role of larotrectinib (LOXO-101), a selective pan-TRK inhibitor, in NTRK fusion-positive recurrent glioblastoma,"Cancer Research, Jul. 2017, DOI: 10.1158/1538-7445.AM2017-LB-302, 2 pages.
Schrock et al., "Gastrointestinal tumours, non-colorectal", Annals of Oncology. vol. 27, Suppl 6, 6130, 2016.
SG Search Report and Written Opinin in Singapore Appln. No. 112017099495, dated Dec. 21, 2018, 11 pages.
Shah et al., "Cardiac metastasis and hypertrophic osteoarthropathy in recurrent infantile fibrosarcoma," Pediatr. Blood Cancer, Jul. 2012, 59(1):179-181.
Shaver et al., "Diverse, Biologically Relevant, and Targetable Gene Rearrangements in Triple-Negative Breast Cancer and Other Malignancies.", Cancer Res, 76(16): 4850-60, 2016.
Shaw et al., "Ceritinib in ALK-rearranged non-small-cell lung cancer.", New Engl. J Med 370: 1189-1197, 2014.
Shaw et al., "Crizotinib in ROS1-rearranged non-small-cell lung cancer.", New Engl. J Med 371: 1963-1971, 2014.
Shaw et al., "Tyrosine kinase gene rearrangements in epithelial malignancies," Nat Rev Cancer, Nov. 2013, 13(11):772-787.
Sheldrick, "A short history of SHELX," Acta Crystallogr A, Jan. 2008, 64(Pt1): 112-122.
Shelton et al., "Nerve growth factor mediates hyperalgesia and cachexia in auto-immune arthritis," Pain, 2005, 116:8-16.
Sheng et al., "Congenital-infantile fibrosarcoma. A clinicopathologic study of 10 cases and molecular detection of the ETV6-NTRK3 fusion transcripts using paraffin-embedded tissues," Am. J Clin. Pathol., Mar. 2001, 115:348-355.
Sigal, et al., "Activity of Entrectinib in a Patient With the First Reported NTRK Fusion in Neuroendocrine Cancer," J. Natl. Compr. Canc. Netw, Nov. 2017, 15(11): 1317-1322.
Silverman, The Organic Chemistry of Drug Design and Drug Action, Second Edition, 2007, 20-21.
Sims et al., Abstract P280: Profiling abscopal regression in a pediatric fibrosarcoma with a novel EML4-NTRK3 fusion using immunogenomics and high-dimensional histopathology, J mmunotherapy of Cancer, Nov. 2016, 4(S1): 73.
Sims et al., Journal of Immunotherapy of Cancer, vol. 4, Supp. Supplement 1; Abstract No. P280; 31st Annual Meeting and Associated Programs of the Society for Immunotherapy of Cancer, SITC 2016. National Harbor, MD; Nov. 9-13, 2016.
Skálová et al., "Mammary Analogue Secretory Carcinoma of Salivary Glands. Molecular Analysis of 25 ETV6 Gene Rearranged Tumors With Lack of Detection of Classical ETV6-NTRK3 Fusion Transcript by Standard RT-PCR: Report of 4 Cases Harboring ETV6-X Gene Fusion," Am. J. Surg. Pathol, Jan. 2016, 40(1):3-13.
Skalova et al., "Molecular Profiling of Mammary Analog Secretory Carcinoma Revealed a Subset of Tumors Harboring a Novel ETV6-RET Translocation: Report of 10 Cases," Am. J. Surg. Pathol, Feb. 2018, 42(2):234-246.
Skalova et al., "Newly described salivary gland tumors," Modern Pathology, Jan. 2017, 30(s1): S27-S43.
Sleijfer et al., "Prognastic and predictive factors for outcome to firs-line ifosfamide-containing chemotherapy for adult patients with advanced soft tissue sarcomas:an exploratory, retrospective analysis on large series from the European Organization for Research and Treatment of Cancer—Soft Tissue and Bone Sarcoma Group," Eur J. Cancer, 2010, 46(1):72-83.
Sleijfer et al., "Using single-agent therapy in adult patients with advanced soft tissue sarcoma can still be considered standard care," Oncologist, 2005, 10(10):833-841.
Smith et al., "Annotation of human cancers with EGFT signaling-associated protein complexes using proximity ligation assays," Sci Signal, 2015, 8(359):ra4, 12 pages.
Sohrabji et al., "Estrogen-BDNF interactions: implications for neurodegenerative diseases," Frontiers in Neuroendocrinology, 2006, 27(4):404-414.
Song et al., "Molecular Changes Associated with Acquired Resistance to Crizotinib in ROS1-Rearranged Non-Small Cell Lung Cancer.", Clin. Cancer Res., 21(10): 2379-87, 2015.
Stephens et al., "Trk receptors use redundant signal transduction pathways involving SHC and PLC-gamma 1 to mediate NGF responses," Neuron, Mar. 1994, 12(3):691-705.
Stransky et al., "The landscape of kinase fusions in cancer," Nature comm., 2014, 5:4846.

(56) References Cited

OTHER PUBLICATIONS

Subramaniam et al., Abstract 2019: RNA-Seq analysis of glioma tumors to reveal targetable gene fusions, 2017 Annual Meeting of the American Society of Clinical Oncology,2017, 1 page.
Sun et al., "P-loop conformation governed crizotinib resistance in G2032R-mutated ROS1 tyrosine kinase clues from free energy landscape," PLoS computational biology, Jul. 17, 2014, 10(7): e1003729.
Tacconelli et al., "TrkA alternative splicing: a regulated tumor-promoting switch in human neuroblastoma," Cancer Cell, 2004, 6:347-360.
Tafinlar, Highlights of Prescribing Information, GlaxoSmithKline, Jan. 2014, 41 pages.
Tahira et al., "dbQSNP: a database of SNPs in human promoter regions with allele frequency information determined by single-strand conformation polymorphism-based methods," Hum Mutat, Aug. 2005;26(2):69-77.
Taipale et al., "Chaperones as thermodynamic sensors of drug-target interactions reveal kinase inhibitor specifities in living cells," Nat Biotech, 2013, 31(7):630-637.
Taiwan Office Action in Taiwan Application No. 098135670, dated Jan. 20, 2014, 7 pages (with English Translation).
Taiwan Search Report in Taiwan Application No. 098132033, dated Dec. 13, 2013, 1 page (English translation only).
Taiwan Search Report in Taiwan Application No. 105143120, dated Aug. 10, 2017, 6 pages (with English translation).
Tan et al., "Genetic landscape of ALK+ non-small cell lung cancer (NSCLC) patients (pts) and response to ceritinib in ASCEND-1", J Clin. Oncology, vol. 34, Supp. Supplement 15, Abstract No. 9064, 2016 Annual Meeting of the American Society of Clinical Oncology, Chicago, IL, 2016.
Tanaka et al., "Brain-derived neurotrophic factor (BDNF)-induced tropomyosin-related kinase B (Trk B) signaling is a potential therapeutic target for peritoneal carcinomatosis arising from colorectal cancer," PLoS One May 6, 2014, 9(5):e96410.
Tannenbaum, et al., "Abstract 749: Characterization of a Novel Fusion Gene, EML4-NTRK3, in Infantile Fibrosarcoma," Pediatr Blood Cancer, DOI 10.1002/pbc, 1 page.
Tannenbaum-Dvir et al., "Characterization of a novel fusion gene EML4-NTRK3 in a case of recurrent congenital fibrosarcoma," Cold Spring Harb. Mol. Case Stud., Oct. 2015;1(1):a000471.
Tarate et al., "Oral Solid Self-Emulsifying Formulations: A Patent Review," Recent Patents on Drug Delivery & Formulation, 2014, 8(2):126-143.
Taylor et al., "Abstract 794: Characterization of NTRK fusions and Therapeutic Response to NTRK Inhibition in Hematologic Malignancies," Blood, 2017, 130: 794.
The Cancer Genome Atlas Network, "Comprehensive Molecular Characterization of Human colon and Rectal Cancer," Nature, Jan. 2013, 487(7407): 330-337.
Theodosiou et al., "Hyperalgesia due to nerve damage: role of nerve growth factor," Pain, 1999, 81:245-255.
Thiele, "On Trk—the TrkB signal transduction pathway is an increasingly important target in cancer biology," Clinical Cancer Research, 2009, 105(19):5962-5967.
Thompson et al., "Brain-derived neurotrophic factor is an endogenous modulator of nociceptive responses in the spinal cord," Proc.Natl. Acad. Sci. USA, 1999, 96:7714-7718.
Thress et al., "Identification and preclinical characterization of AZ-23, a novel, selective, and orally bioavailable inhibitor of the Trk kinase pathway," Mol Cancer Ther, Jul. 2009;8(7):1818-27, doi: 10.1158/1535-7163.MCT-09-0036. Epub Jun. 9, 2009.
Tognon et al., "Expression of the ETV6-NTRK3 gene fusion as a primary event in human secretory breast carcinoma," Cancer Cell, Nov. 2002, 2(5):367-376.
Truzzi et al., "Neurotrophins and their receptors stimulate melanoma cell proliferation and migration," J. Investigative Dermatology, 2008, 128(8):2031-2040.
Truzzi et al., "Neurotrophins in healthy and diseased skin ," Dermato-Endrocrinology, 2008, 3(1):32-36.
Turtle et al., "Artificial antigen-presenting cells for use in adoptive immunotherapy," Cancer J, Jul.-Aug. 2010;16(4):374-81. doi: 10.1097/PPO.0b013e3181eb33a6.
UniProtKB/Swiss-Prot: P04629.4, "RecName: Full=High affinity nerve growth factor receptor; AltName: Full=Neurotrophic tyrosine kinase receptor type 1; AltName: Full=TRK1-transforming tyrosine kinase protein; AltName: Full=Tropomyosin-related kinase A; AltName: Full=Tyrosine kinase receptor; AltName: Full=Tyrosine kinase receptor A; Short=Trk-A; AltName: Full=gp140trk; AltName: Full=p140-TrkA; Flags: Precursor," May 14, 2014, 28 pages, available at URL<https://www.ncbi.nlm.nih.gov/protein/94730402?sat=18&satkey=12407077>.
UniProtKB/Swiss-Prot: Q16288.2, "RecName: Full=NT-3 growth factor receptor; AltName: Full=GP145-TrkC; Short=Trk-C; AltName: Full=Neurotrophic tyrosine kinase receptor type 3; AltName: Full=TrkC tyrosine kinase; Flags: Precursor," May 14, 2014, 13 pages, available at URL<www.ncbi.nlm.nih.gov/protein/134035335?report=genbank&log$=protalign&blast_rank=0&RID=0>.
UniProtKB/Swiss-Prot: Q16620.1, "RecName: Full=BDNF/NT-3 growth factors receptor; AltName: Full=GP145-TrkB; Short=Trk-B; AltName: Full=Neurotrophic tyrosine kinase receptor type 2; AltName: Full=TrkB tyrosine kinase; AltName: Full=Tropomyosin-related kinase B; Flags: Precursor," May 14, 2014, 17 pages, available at URL<www.ncbi.nlm.nih.gov/protein/2497560?report=genbank&log$=protalign&blast_rank=0&RID=0>.
Vaishnavi et al., "Oncogenic and drug-sensitive NTRK1 rearrangements in lung cancer.", Nature Med 19: 1469-1472, 2013.
Vaishnavi et al., "TRKing Down an Old Oncogene in a New Era of Targeted Therapy," Cancer Discovery, Jan. 2015, 5(1):25-34.
Van Gurp et al., "Phase 1 dose-escalation preliminary findings of safety, tolerability, study of CP-690 550 in stable renal allograft recipients: effects on lymphocyte subsets and pharmacokinetics," Am. J. Transpl., 2008, 8:1711-1718.
Van Noesel et al., "Pediatric neuroblastomas: genetic and epigenetic 'danse macabre'," Gene, 2004, 325:1-15.
Vanden et al., "endocrine and neuroendocrine tumours", Annals of Oncology, vol. 27, Supp. Supplement 6. Abstract No. 427PD' 4pt European Society for Medical Oncology Congress, ESMO 2016; Copenhagen, Denmark; Oct. 7-11, 2016.
Vippagunta et al., "Crystalline Solids" Advanced Drug Delivery Rev., 2001, 48(1): 3-26.
Vogelstein and Kinzler, The Genetic Basis of Human Cancer, 2nd ed., 2002, p. 3, col. 1, para 2.
Wadhwa et al., "Expression of the neurotrophin receptors Trk A and Trk B in adult human astrocytoma and glioblastoma," Journal of Biosciences, 2003, 28(2):181-188.
Walch et al., "Role of neurotrophins and neurotrophins receptors in the in vitro invasion and heparanase production of human prostate cancer cells," Clin. Exp. Metastasis, 1999, 17:307-314.
Walther et al., "Cytogenetic and single nucleotide polymorphism array findings in soft tissue tumors in infants," Cancer Genet, Jul.-Aug. 2013, 206(7-8): 299-303.
Wang et al., "Identification of NTRK3 fusions in childhood melanocytic neoplasms," J. Mol. Diagn, May 2017, 19(3):387-396.
Wang et al., "Design, synthesis and biological evaluation of novel 4-arylaminopyrimidine derivatives possessing a hydrazone moiety as dual inhibitors of L1196M ALK and ROS1.", Eur. J.Med Chem., 123, 80-99, 2016.
Wang et al., "Identification of 4-aminopyrazolylpyrimidines as potent inhibitors of Trk kinases," J Med Chem, Aug. 14, 2008;51(15):4672-84. doi: 10.1021/jm800343j. Epub Jul. 23, 2008.
Wang et al., "T cells sensitized with breast tumor progenitor cell vaccine have therapeutic activity against spontaneous HER2/neu tumors," Breast Cancer Res Treat, Jul. 2012;134(1):61-70. doi: 10.1007/s10549-011-1912-5. Epub Dec. 16, 2011.
Wang et al., "Trk kinase inhibitors as new treatments for cancer and pain," Expert Opin. Ther Patents, Mar. 2009, 19(3):305-319.
Wang, "Pan-cancer analysis of ROS1 genomic aberrations", University of Hong Kong, Pokfulam, Hong Kong SAR (Thesis), 44 pages, 2015.
Watanbe et al., "Cryptic t(12;15)(p13;q26) producing the ETV6-NTRK3 fusion gene and no loss of IGF2 imprinting in congenital

(56) References Cited

OTHER PUBLICATIONS mesoblastic nephroma with trisomy 11: fluorescence in situ hybridization and IGF2 allelic expression analysis," Cancer Genet. Cytogenet, Jul. 2002, 136(1):10-16.
Wei et al., "Abstract #2136: Entrectinib is Effective Against the Gatekeeper and Other Emerging Resistance Mutations in NTRK-, ROS1- and ALK-Rearranged Cancers," Poster, Presented at Proceedings of the 107th Annual Meeting of the American Association for Cancer Research, New Orleans LA, Apr. 16-20, 2016; Cancer Res, Jul. 2016, 76(14): 1 page.
Wei et al., "Abstract 78: Entrectinib, a highly potent pan-Trk, and ALK inhibitor, has broad-spectrum, histology-agnostic anti-tumor activity in molecularly defined cancers," 28th EORTC-NCI-AACR Symposium on Molecular Targets and Cancer Therapeutics, Munich, Germany, 2016, 1 page.
Weinstein,"Cancer. Addiction to oncogenes—the Achilles heal of cancer," Science, Jul. 2002, 297(5578):63-64.
Wen et al, "Updated response assessment criteria for high-grade gliomas: response assessment in neuro-oncology working group," J Clin Oncol, Apr. 2010, 28(11): 1963-1972.
Wiesner et al., "Kinase fusions are frequent in Spitz tumours and spitzoid melanomas," Nature Comm., 2014, 5:3116.
Winski et al., "LOXO-101, a pan-Trk inhibitor, for the treatment of TRK-driven cancers," 26th EORTC-NCI-AACR Symposium on Molecular Targets and Cancer Therapeutics, Barcelona, Spain, 2014, 175.
Wittwer et al., "High-resolution genotyping by amplicon melting analysis using LCGreen," Clin Chem, Jun. 2003;49(6 Pt 1):853-60.
Wlodarska et al., "ALK-Positive Anaplastic Large Cell Lymphoma with the Variant EEF1G-, RNF213- and Atic-ALK Fusions Is Featured by Copy Number Gain of the Rearranged ALK Gene", Blood, vol. 126(23): 3654, 57th Annual Meeting of the American Society of Hematology, San Diego, CA, 2015.
Won et al., "Post-Crizotinib management of effective ceritinib therapy in a patient with ALK-positive non-small cell lung cancer", BMC Cancer, 16: 568, 2016.
Wong et al., "Evaluation of a Congenital Infantile Fibrosarcoma by Comprehensive Genomic Profiling Reveals an LMNA-NTRK1 Gene Fusion Responsive to Crizotinib," J Natl Cancer Inst, Nov. 2016, 108(1) pii: djv307.
Woodward, "Bi-allelic SNP genotyping using the TaqMan® assay," Methods Mol Biol., 2014;1145:67-74. doi: 10.1007/978-1-4939-0446-4_6.
Woolf et al., "Letter to Neuroscience: Nerve Growth Factor Contributes to the Generation of Inflammatory Sensory Hypersensitivity," Neuroscience, 1994, 62:327-331.
Wu et al., "The genomic landscape of diffuse intrinsic pontine glioma and pediatric non-brainstem high-grade glioma," Nature Genetics, 2014, 444-450.
Wu et al., "The landscape of fusion transcripts in spitzoid melanoma and biologically indeterminate spitzoid tumors by RNA sequencing," Modern Pathol., Apr. 2016, 29(4):359-369.
Xalkori, Highlights of Prescribing Information, Pfizer Labs, Initial approval 2011, revised Mar. 2016, 20 pages.
Yakirevich et al., "Colorectal Adenocarcinoma with ALK Rearrangement: Clinicopathologic and Molecular Characteristics", Laboratory Investigation, vol. 96, Supp. SUPPL. 1, pp. 209A, Abstract No. 827, 105th Annual Meeting of the United States and Canadian Academy of Pathology, Seattle, WA, 2016.
Yakirevich et al., "Oncogenic ALK Fusion in Rare and Aggressive Subtype of Colorectal Adenocarcinoma as a Potential Therapeutic Target.", Clin Cancer Res, 22(15): 3831-40, 2016.
Yamamoto et al., "ALK, ROS1 and NTRK3 gene rearrangements in inflammatory myofibroblastic tumours.", Histopathology, 69(1): 72-83, 2016.
Yamamoto et al., "Anaplastic lymphoma kinase-positive squamous cell carcinoma of the lung: A case report.", Mal Clin. Oneal. 5(1): 61-63, 2016.
Yanai et al., "A rare case of bilateral stage IV adrenal neuroblastoma with multiple skin metastases in a neonate: diagnosis, management, and outcome," J Pediatr. Surg., Dec. 2004, 39(12):1782-1783.
Yeh et al., "NTRK3 kinase fusions in Spitz tumours," J Pathol., Nov. 2016, 240(3): 282-290.
Yilmaz et al., "Theraputic targeting of Trk supresses tumor proliferation and enhances cisplatin activity in HNSCC," Cancer Biology and Therapy, 2010, 10(6):644-653.
Ying et al., "Atypical negative ALK FISH accompanied by immunohistochemistry positivity harbored various ALK rearrangements in NSCLC patients and respond to targeted therapy.", J Clin. Oncology, vol. 34, Supp. Supplement 15, Abstract No. e20506, 2016 Annual Meeting of the American Society of Clinical Oncology, Chicago, IL, 2016.
Yu et al., "Denaturing high performance liquid chromatography: high throughput mutation screening in familial hypertrophic cardiomyopathy and SNP genotyping in motor neurone disease," J Clin Pathol, May 2005;58(5):479-85.
Yu et al., "Detection of ALK rearrangements in lung cancer patients using a homebrew PCR assay", Oncotarget, 8(5): 7722-7728, 2016.
Yuzugullu et al., "NTRK2 activation cooperates with PTEN deficiency in T-ALL through activation of both the PI3K-AKT and JAK-STAT3 pathways.", Cell Diseov. 2: 16030, 2016.
Zage et al., "The selective Trk inhibitor AZ623 inhibits brain-derived neurotrophic factor-mediated neuroblastoma cell proliferation and signaling and is synergistic with topotecan," Cancer, Mar. 2011, 117(6): 1321-1391.
Zahn et al., "Effect of blockade of nerve growth factor and tumor necrosis factor on pain behaviors after plantar incision," J. Pain, 2004, 5:157-163.
Zehir et al., "Mutational landscape of metastatic cancer revealed from prospective clinical sequencing of 10,000 patients," Nat. Med, Jun. 2017, 23(6):703-713.
Zelboraf, Highlights of Prescribing Information, Genentech USA, Initial Approval 2011, revised Aug. 2015, 18 pages.
Zhang et al., "A novel multiplex tetra-primer ARMS-PCR for the simultaneous genotyping of six single nucleotide polymorphisms associated with female cancers," PLoS One, Apr. 17, 2013;8(4):e62126. doi: 10.1371/journal.pone.0062126. Print 2013.
Zhang et al., "Expression of nerve growth factor receptors and their prognostic value in human pancreatic cancer," Oncology Reports, 2005, 14:161-171.
Zhang et al., "Novel Phenotypic and Genetic Analysis of T-Cell Prolymphocytic Leukemia (T-PLL)," Blood, 2014, 124(21):1682.
Zhang et al., "Whole-genome sequencing identifies genetic alterations in pediatric low-grade gliomas," Nat. Genet., Jun. 2013, 45(6): 602-612.
Zheng et al., "Anchored multiplex PCR for targeted next-generation sequencing," Nature Med., Dec. 2014, 20(12):1479-1486.
Zhu et al., "TPD52L1-ROS1, a new ROS1 fusion variant in lung adenosquamous cellcarcinoma identified by comprehensive genomic profiling", Lung Cancer, 97:48-50, doi: 10.1016/j.lungcan.2016.04.013, 2012.
Ziemiecki et al., "Oncogenic activation of the human trk proto-oncogene by recombination with the ribosomal large subunit protein L7a," EMBO J, Jan. 1990, 9(1):191-196.
Zou et al., "PF-06463922 is a potent and selective next-generation ROS1/ALK inhibitor capable of blocking crizotinib-resistant ROS1 mutations.", Proc. Natl. Acad Sci. USA., 112(11): 3493-8, 2015.
U.S. Appl. No. 13/382,858, filed Jan. 6, 2012, Shelley Allen.
U.S. Appl. No. 14/321,246, filed Jul. 1, 2014, Shelley Allen.
U.S. Appl. No. 15/401,895, filed Jan. 9, 2017, Shelley Allen.
U.S. Appl. No. 15/401,913, filed Jan. 9, 2017, Shelley Allen.
U.S. Appl. No. 15/724,601, filed Oct. 4, 2017, Shelley Allen.
U.S. Appl. No. 13/063,894, filed Mar. 14, 2011, Steven W. Andrews.
U.S. Appl. No. 13/614,968, filed Sep. 13, 2012, Steven W. Andrews.
U.S. Appl. No. 14/984,353, filed Dec. 30, 2015, Steven W. Andrews.
U.S. Appl. No. 15/401,792, filed Jan. 9, 2017, Steven W. Andrews.
U.S. Appl. No. 15/401,969, filed Jan. 9, 2017, Steven W. Andrews.
U.S. Appl. No. 16/025,281, filed Jul. 2, 2018, Steven W. Andrews.
U.S. Appl. No. 13/698,922, filed Nov. 19, 2012, Steven W. Andrews.
U.S. Appl. No. 14/575,663, filed Dec. 18, 2014, Steven W. Andrews.
U.S. Appl. No. 15/350,888, filed Nov. 14, 2016, Steven W. Andrews.

(56) References Cited

OTHER PUBLICATIONS

U.S. Appl. No. 15/401,839, filed Jan. 9, 2017, Steven W. Andrews.
U.S. Appl. No. 15/401,952, filed Jan. 9, 2017, Steven W. Andrews.
U.S. Appl. No. 15/632,187, filed Jun. 23, 2017, Steven W. Andrews.
U.S. Appl. No. 15/900,019, filed Feb. 20, 2018, Steven W. Andrews.
U.S. Appl. No. 13/125,263, filed Apr. 20, 2011, Julia Haas.
U.S. Appl. No. 13/943,590, filed Jul. 16, 2013, Julia Haas.
U.S. Appl. No. 14/490,460, filed Sep. 18, 2014, Julia Haas.
U.S. Appl. No. 14/596,611, filed Jan. 14, 2015, Julia Haas.
U.S. Appl. No. 14/846,166, filed Sep. 4, 2015, Julia Haas.
U.S. Appl. No. 15/399,389, filed Jan. 5, 2017, Julia Haas.
U.S. Appl. No. 15/860,948, filed Jan. 3, 2018, Julia Haas.
U.S. Appl. No. 16/044,653, filed Jul. 25, 2018, Julia Haas.
U.S. Appl. No. 14/943,014, filed Nov. 16, 2015, Alisha B. Arrigo.
U.S. Appl. No. 15/399,207, filed Jan. 5, 2017, Alisha B. Arrigo.
U.S. Appl. No. 15/706,062, filed Sep. 15, 2017, Alisha B. Arrigo.
U.S. Appl. No. 15/872,769, filed Jan. 16, 2018, Alisha B. Arrigo.
U.S. Appl. No. 16/199,818, filed Nov. 26, 2018, Steven W. Andrews.
U.S. Appl. No. 16/199,867, filed Nov. 26, 2018, Steven W. Andrews.
U.S. Appl. No. 15/335,378, filed Oct. 26, 2016, Nisha Nanda.
U.S. Appl. No. 15/785,174, filed Oct. 16, 2017, Nisha Nanda.
U.S. Appl. No. 15/785,228, filed Oct. 16, 2017, Nisha Nanda.
U.S. Appl. No. 15/785,218, filed Oct. 16, 2017, Nisha Nanda.
U.S. Appl. No. 15/860,789, filed Jan. 3, 2018, Nisha Nanda.
U.S. Appl. No. 16/302,312, filed Nov. 16, 2018, Mark Reynolds.
U.S. Appl. No. 16/170,976, filed Oct. 25, 2018, Zhao.
U.S. Appl. No. 15/579,007, filed Dec. 1, 2017, Tuch et al.
U.S. Appl. No. 15/622,388, filed Jun. 14, 2017, Michael Cox.
U.S. Appl. No. 15/861,017, filed Jan. 3, 2018, Michael Cox.
U.S. Appl. No. 15/622,544, filed Jun. 14, 2017, Mark Reynolds.
U.S. Appl. No. 16/199,739, filed Nov. 26, 2018, Mark Reynolds.
American Association for Cancer Research, "TRK Inhibitor Shows Early Promise," Cancer Discovery, 6(1), Jan. 1, 2016, XP009194480.
Bailey, Justin J., et al. "Tropomyosin receptor kinase inhibitors: an updated patent review for 2010-2016—Part II." Expert opinion on therapeutic patents 27.7 (2017): 831-849.
Caira, "Crystalline Polymorphism of Organic Compounds," Topics in Current Chemistry, Feb. 1999, 198: 163-208.
Extended European Search Report in European Application No. 18208279.2, dated Jun. 27, 2019, 10 pages.
NIH, "List of Cancer-causing Agents Grows," National Institute of Environmental Health Sciences, https://www.niehs.nih.gov/news/newsroom/releases/2005/january31/index.cfm, 4 pages.
PCT International Preliminary Report on Patentability in International Application. No. PCT/US2017/058518, dated Apr. 30, 2019, 8 pages.
PCT International Search Report and Written Opinion in International Application No. PCT/US2019/024961, dated Jul. 23, 2019, 13 pages.
PubChem, "Larotrectinib," https://pubchem.ncbi.nlm.nih.gov/compound/46188928, retrieved on Apr. 29, 2019, 20 pages.
Schmidt, Charles. "Combinations on trial." Nature 552.7685 (Dec. 21, 2017): S67-S69.
Braga, Dario, et al. "Crystal polymorphism and multiple crystal forms." Struct Bond (2009) 132:25-50. Springer-Verlag Berlin Heidelberg.
Camidge, D. Ross, William Pao, and Lecia V. Sequist. "Acquired resistance to TKIs in solid tumours: learning from lung cancer." Nature reviews Clinical oncology 11.8 (2014): 473.
Center for Drug Evaluation and Research. https://www.accessdata.fda.gov/drugsatfda_docs/nda/2018/210861Orig1s000_211710Orig1s000ChemR.pdf, 2017.
Hilfiker, Rolf, Fritz Blatter, and Markus von Raumer. "Relevance of solid-state properties for pharmaceutical products." Polymorphism in the pharmaceutical industry (2006): 1-19.
PCT International Preliminary Report on Patentability in International Application No. PCT/US2018/022833, dated Sep. 26, 2019, 8 pages.
U.S. Appl. No. 13/125,263, filed Oct. 21, 2009, Issued.
U.S. Appl. No. 13/943,590, filed Jul. 16, 2013, Issued.
U.S. Appl. No. 14/490,460, filed Sep. 18, 2014, Issued.
U.S. Appl. No. 14/596,611, filed Jan. 14, 2015, Issued.
U.S. Appl. No. 14/846,166, filed Sep. 4, 2015, Issued.
U.S. Appl. No. 15/399,389, filed Jan. 5, 2017, Issued.
U.S. Appl. No. 15/860,948, filed Jan. 3, 2018, Issued.
U.S. Appl. No. 16/044,653, filed Jul. 25, 2018, Published.
U.S. Appl. No. 14/943,014, filed Nov. 16, 2015, Published.
U.S. Appl. No. 15/399,207, filed Jan. 5, 2017, Issued.
U.S. Appl. No. 15/706,062, filed Sep. 15, 2017, Issued.
U.S. Appl. No. 15/872,769, filed Jan. 16, 2018, Issued.
U.S. Appl. No. 16/366,368, filed Mar. 27, 2019, Pending.
U.S. Appl. No. 16/302,312, filed May 18, 2017, Published.
U.S. Appl. No. 15/579,007, filed Jun. 1, 2016, Published.
U.S. Appl. No. 15/622,388, filed Apr. 4, 2017, Issued.
U.S. Appl. No. 15/861,017, filed Jan. 3, 2018, Published.
U.S. Appl. No. 15/622,544, filed Apr. 4, 2017, Issued.
U.S. Appl. No. 16/199,739, filed Nov. 26, 2018, Published.
U.S. Appl. No. 13/698,922, filed May 13, 2011, Issued.
U.S. Appl. No. 14/575,663, filed Dec. 18, 2014, Issued.
U.S. Appl. No. 15/350,888, filed Nov. 14, 2016, Issued.
U.S. Appl. No. 15/401,839, filed Jan. 9, 2017, Issued.
U.S. Appl. No. 15/632,187, filed Jun 23, 2017, Issued.
U.S. Appl. No. 15/900,019, filed Feb. 20, 2018, Allowed.
U.S. Appl. No. 15/401,952, filed Jan. 9, 2017, Issued.
U.S. Appl. No. 13/063,894, filed Sep. 21, 2009, Issued.
U.S. Appl. No. 13/614,968, filed Sep. 13, 2012, Issued.
U.S. Appl. No. 14/984,353, filed Dec. 30, 2015, Issued.
U.S. Appl. No. 15/401,792, filed Jan. 9, 2017, Issued.
U.S. Appl. No. 15/401,969, filed Jan. 9, 2017, Issued.
U.S. Appl. No. 16/025,281, filed Jul. 2, 2018, Published.
U.S. Appl. No. 16/170,976, filed Oct. 25, 2018, Pending.
U.S. Appl. No. 15/335,378, filed Oct. 26, 2016, Published.
U.S. Appl. No. 15/785,174, filed Oct. 16, 2017, Allowed.
U.S. Appl. No. 15/785,218, filed Oct. 16, 2017, Published.
U.S. Appl. No. 15/860,789, filed Jan. 3, 2018, Published.
U.S. Appl. No. 15/785,228, filed Oct. 16, 2017, Allowed.
U.S. Appl. No. 16/199,818, filed Mar. 16, 2018, Pending.
U.S. Appl. No. 16/199,867, filed Nov. 26, 2018, Published.
U.S. Appl. No. 13/382,858, filed Jul. 9, 2010, Issued.
U.S. Appl. No. 14/321,246, filed Jul. 1, 2014, Issued.
U.S. Appl. No. 15/401,895, filed Jan. 9, 2017, Issued.
U.S. Appl. No. 15/401,913, filed Jan. 9, 2017, Issued.
U.S. Appl. No. 15/724,601, filed Oct. 4, 2017, Issued.
U.S. Appl. No. 16/377,514, filed Apr. 8, 2019, Pending.
U.S. Appl. No. 16/345,571, filed Oct. 26, 2017, Pending.
U.S. Appl. No. 15/399,339, filed Jan. 5, 2017, Issued.
U.S. Appl. No. 16/366,368, filed Mar. 27, 2019, Published.
U.S. Appl. No. 15/861,017, filed Jan. 3, 2018, Allowed.
U.S. Appl. No. 16/789,845, filed Jan. 10, 2020, Pending.
U.S. Appl. No. 13/068,894, filed Sep. 21, 2009, Issued.
U.S. Appl. No. 16/170,976, filed Oct. 25, 2018, Published.
U.S. Appl. No. 16/677,514, filed Apr. 8, 2019, Pending.
JoVE Science Education Database. Organic Chemistry. Purifying Compounds by Recrystallization. JoVE, Cambridge, MA (2019).

* cited by examiner

MACROCYLIC COMPOUNDS AS ROS1 KINASE INHIBITORS

CROSS-REFERENCE TO RELATED APPLICATIONS

This application is a continuation of International Application No. PCT/US2018/022833, filed Mar. 16, 2018, which claims priority to U.S. Provisional Application No. 62/472,185, filed Mar. 16, 2017, the contents of which are incorporated by reference in their entirety herein.

TECHNICAL FIELD

Provided herein are compounds and pharmaceutical compositions comprising the compounds and the use of the compounds in therapy. More particularly, provided herein are certain macrocyclic compounds which exhibit ROS1 protein kinase inhibition, and which are useful in the treatment of cancer.

BACKGROUND

ROS1 is a receptor tyrosine kinase that is closely related to ALK, and, like ALK, it undergoes genomic rearrangement that creates fusion proteins in various cancers (Davies K D and Doebele R C (2013) *Clin Cancer Res* 19: 4040-4045). It is well established that these fusion proteins act as oncogenic drivers and that ROS1 inhibition is anti-proliferative in cells that express ROS1 fusions (Davies K D, Le A T, Theodoro M F, Skokan M C, Aisner D L, et al. (2012) *Clin Cancer Res* 18: 4570-4579). Thus, it appears that ROS1 targeted therapy will likely soon be the standard of care for this patient population. However, based on the experiences with other kinase inhibitors in various cancers, it is fully expected that acquired resistance to ROS1 inhibition will occur, and this will ultimately limit the treatment options for patients.

SUMMARY

It has now been found that macrocyclic compounds are inhibitors of ROS1 kinase, and are useful for treating various cancers. Compounds which are inhibitors of ROS1 may be useful in the treatment of multiple types of cancer including cancers exhibiting resistance to ROS1 inhibition.

Accordingly, in one aspect of the present disclosure, the methods provided include administration of a ROS1 inhibitor, wherein the ROS1 inhibitor is a compound of Formula I

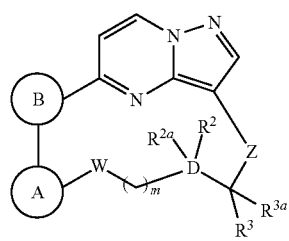

or a pharmaceutically acceptable salt or solvate thereof, wherein ring A, ring B, W, m, D, $R^2$, $R^{2a}$, $R^3$, $R^{3a}$, and Z are as defined herein.

In some embodiments, a compound of Formula I has the general formula:

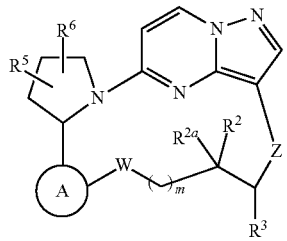

or a pharmaceutically acceptable salt or solvate thereof, wherein ring A, W, m, $R^2$, $R^{2a}$, $R^3$, and Z are as defined herein.

In some embodiments, the compound of Formula I is selected from the compounds of Table 1, or a pharmaceutically acceptable salt or solvate thereof. In some embodiments, the compound of Formula I is selected from the group consisting of Example No. 2, 3, 7, 9, 14, 19, 20, 22, 33-A, 33-B, 35, 36, and 45, or a pharmaceutically acceptable salt or solvate thereof.

Provided herein is a method for treating a cancer in a patient in need thereof, the method comprising:
 (a) determining if the cancer is associated with a dysregulation of a ROS1 gene, a ROS1 kinase, or expression or activity or level of any of the same; and
 (b) if the cancer is determined to be associated with a dysregulation of a ROS1 gene, a ROS1 kinase, or expression or activity or level of any of the same, administering to the patient a therapeutically effective amount of a ROS1 inhibitor, wherein the ROS1 inhibitor is a compound of Formula I or a pharmaceutically acceptable salt or solvate thereof.

Provided herein is a method for treating a cancer in a patient in need thereof, the method comprising:
 (a) detecting that the cancer is associated with a dysregulation of a ROS1 gene, a ROS1 kinase, or expression or activity or level of any of the same; and
 (b) administering to the patient a therapeutically effective amount of a ROS1 inhibitor, wherein the ROS1 inhibitor is a compound of Formula I or a pharmaceutically acceptable salt or solvate thereof.

Also provided herein is a method for treating cancer in a patient in need thereof, the method comprising administering to a patient identified or diagnosed as having a ROS1-associated cancer a therapeutically effective amount of a ROS1 inhibitor, wherein the ROS1 inhibitor is a compound of Formula I or a pharmaceutically acceptable salt or solvate thereof.

In some embodiments of the present disclosure, a method of treating cancer in a patient in need thereof is provided. The method comprising:
 (a) determining if the cancer in a patient is a ROS1-associated cancer; and
 (b) administering to the patient determined to have a ROS1-associated cancer a therapeutically effective amount of a ROS1 inhibitor, wherein the ROS1 inhibitor is a compound of Formula I or a pharmaceutically acceptable salt or solvate thereof.

In some embodiments of the present disclosure, a method of treating cancer in a patient in need thereof is provided. The method comprising:
 (a) detecting that a cancer in a patient is a ROS1-associated cancer; and (b) administering to the patient a therapeutically effective amount of a ROS1 inhibitor, wherein the ROS1 inhibitor is a compound of Formula I or a pharmaceutically acceptable salt or solvate thereof.

Further provided herein is a method of treating a subject having a cancer, wherein the method comprises:
- (a) administering a first ROS1 inhibitor to the subject;
- (b) after (a), determining whether a cancer cell in a sample obtained from the subject has one or more ROS1 inhibitor resistance mutations; and
- (c) administering a second ROS1 inhibitor, wherein the second ROS1 inhibitor is a compound of Formula I or a pharmaceutically acceptable salt or solvate thereof, as a monotherapy or in conjunction with another anticancer agent to the subject if the subject has a cancer cell that has one or more ROS1 inhibitor resistance mutations; or
- (d) administering additional doses of the first ROS1 inhibitor of step (a) to the subject if the subject has a cancer cell that does not have one or more ROS1 inhibitor resistance mutations.

Also provided herein is a method of treating a subject having a cancer, wherein the method comprises:
- (a) administering a first ALK inhibitor to the subject;
- (b) after (a), determining whether a cancer cell in a sample obtained from the subject has one or more ROS1 inhibitor resistance mutations; and
- (c) administering a compound of Formula I, or a pharmaceutically acceptable salt or solvate thereof, as a monotherapy or in conjunction with another anticancer agent to the subject if the subject has a cancer cell that has one or more ROS1 inhibitor resistance mutations; or
- (d) administering additional doses of the first ALK inhibitor of step (a) to the subject if the subject has a cancer cell that does not have one or more ROS1 inhibitor resistance mutations.

In some embodiments, a method of treating a subject having a cancer is provided herein, wherein the method comprises:
- (a) administering a first TRK inhibitor to the subject;
- (b) after (a), determining whether a cancer cell in a sample obtained from the subject has one or more ROS1 inhibitor resistance mutations; and
- (c) administering a compound of Formula I, or a pharmaceutically acceptable salt or solvate thereof, as a monotherapy or in conjunction with another anticancer agent to the subject if the subject has a cancer cell that has one or more ROS1 inhibitor resistance mutations; or
- (d) administering additional doses of the first TRK inhibitor of step (a) to the subject if the subject has a cancer cell that does not have one or more ROS1 inhibitor resistance mutations.

Also provided herein is a method of treating a subject having a cancer, wherein the method comprises:
- (a) determining whether a cancer cell in a sample obtained from a subject having a cancer and previously administered a first ROS1 inhibitor has one or more ROS1 inhibitor resistance mutations that confer increased resistance to a cancer cell or tumor to treatment with the first ROS1 inhibitor that was previously administered to the subject; and
- (b) administering a compound of Formula I, or a pharmaceutically acceptable salt or solvate thereof, as a monotherapy or in conjunction with another anticancer agent to the subject if the subject has a cancer cell that has one or more ROS1 inhibitor resistance mutations that confers increased resistance to a cancer cell or tumor to treatment with the first ROS1 inhibitor that was previously administered to the subject; or
- (c) administering additional doses of the first ROS1 inhibitor to the subject if the subject has a cancer cell that does not have one or more ROS1 inhibitor resistance mutations that confers increased resistance to a cancer cell or tumor to treatment with the first ROS1 inhibitor previously administered to the subject.

Further provided herein is a method of treating a subject having a cancer, wherein the method comprises:
- (a) determining whether a cancer cell in a sample obtained from a subject having a cancer and previously administered a first ALK inhibitor has one or more ROS1 inhibitor resistance mutations; and
- (b) administering a compound of Formula I, or a pharmaceutically acceptable salt or solvate thereof, as a monotherapy or in conjunction with another anticancer agent to the subject if the subject has a cancer cell that has one or more ROS1 inhibitor resistance mutations; or
- (c) administering additional doses of the first ALK inhibitor to the subject if the subject has a cancer cell that does not have one or more ROS1 inhibitor resistance mutations.

In some embodiments, a method of treating a subject having a cancer is provided herein, wherein the method comprises:
- (a) determining whether a cancer cell in a sample obtained from a subject having a cancer and previously administered a first TRK inhibitor has one or more ROS1 inhibitor resistance mutations; and
- (b) administering a compound of Formula I, or a pharmaceutically acceptable salt or solvate thereof, as a monotherapy or in conjunction with another anticancer agent to the subject if the subject has a cancer cell that has one or more ROS1 inhibitor resistance mutations; or
- (c) administering additional doses of the first TRK inhibitor to the subject if the subject has a cancer cell that does not have one or more ROS1 inhibitor resistance mutations.

Also provided herein is a method of treating a subject having a cancer, wherein the method comprises:
- (a) determining whether a cancer cell in a sample obtained from a subject having a cancer and previously administered a first ROS1 inhibitor has one or more ROS1 inhibitor resistance mutations that confer increased resistance to a cancer cell or tumor to treatment with the first ROS1 inhibitor previously administered to the subject; and
- (b) administering a second ROS1 inhibitor to the subject as a monotherapy or in conjunction with another anticancer agent to the subject if the subject has a cancer cell that has one or more ROS1 inhibitor resistance mutations that confers increased resistance to a cancer cell or tumor to treatment with the first ROS1 inhibitor that was previously administered to the subject; or
- (c) administering additional doses of the first ROS1 inhibitor that was previously administered to the subject if the subject has a cancer cell that does not have one or more ROS1 inhibitor resistance mutations that confers increased resistance to a cancer cell or tumor to treatment with the first ROS1 inhibitor that was previously administered to the subject.

Further provided herein is a method of treating a subject having a cancer, wherein the method comprises:
(a) determining whether a cancer cell in a sample obtained from a subject having a cancer and previously administered an ALK inhibitor has one or more ROS1 inhibitor resistance mutations; and
(b) administering a ROS1 inhibitor to the subject as a monotherapy or in conjunction with another anticancer agent to the subject if the subject has a cancer cell that has one or more ROS1 inhibitor resistance mutations; or
(c) administering additional doses of the ALK inhibitor that was previously administered to the subject if the subject has a cancer cell that does not have one or more ROS1 inhibitor resistance mutations.

In some embodiments, a method of treating a subject having a cancer is provided, wherein the method comprises:
(a) determining whether a cancer cell in a sample obtained from a subject having a cancer and previously administered a TRK inhibitor has one or more ROS1 inhibitor resistance mutations; and
(b) administering a ROS1 inhibitor to the subject as a monotherapy or in conjunction with another anticancer agent to the subject if the subject has a cancer cell that has one or more ROS1 inhibitor resistance mutations; or
(c) administering additional doses of the TRK inhibitor that was previously administered to the subject if the subject has a cancer cell that does not have one or more ROS1 inhibitor resistance mutations.

Also provided herein is a method of treating a patient, the method comprising administering a therapeutically effective amount of a compound of Formula I, or a pharmaceutically acceptable salt or solvate thereof, to a patient having a clinical record that indicates that the patient has a dysregulation of a ROS1 gene, a ROS1 kinase, or expression or activity or level of any of the same.

Further provided herein is a method of selecting a treatment for a patient, the method comprising selecting a treatment comprising administration of a compound of Formula I, or a pharmaceutically acceptable salt or solvate thereof, for a patient identified or diagnosed as having a ROS1-associated cancer.

In some embodiments, provided herein is a method of selecting a treatment for a patient having a cancer, the method comprising:
(a) determining if the cancer in the patient is a ROS1-associated cancer; and
(b) selecting a treatment including administration of a therapeutically effective amount of a compound of Formula I, or a pharmaceutically acceptable salt or solvate thereof, for a patient determined to have a ROS1-associated cancer.

Also provided herein is a method of selecting a patient for treatment including administration of a therapeutically effective amount of a compound of Formula I, or a pharmaceutically acceptable salt or solvate thereof, the method comprising:
(a) identifying a patient having a ROS1-associated cancer; and
(b) selecting the patient for treatment including administration of a therapeutically effective amount of a compound of Formula I, or a pharmaceutically acceptable salt or solvate thereof.

Further provided herein is a method of selecting a patient having cancer for treatment including administration of a therapeutically effective amount of a compound of Formula I, or a pharmaceutically acceptable salt or solvate thereof, the method comprising:
(a) determining if the cancer in the patient is a ROS1-associated cancer; and
(b) selecting a patient determined to have a ROS1-associated cancer for treatment including administration of a therapeutically effective amount of a compound of Formula I, or a pharmaceutically acceptable salt or solvate thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Provided herein are methods for using compounds of the general Formula I containing a pyrazolo[1,5-a]pyrimidinyl ring and having the structure:

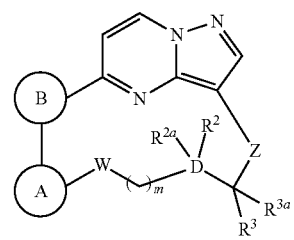

I or pharmaceutically acceptable salts or solvates thereof, wherein:
ring A is selected from rings A-1, A-2 and A-3 having the structures:

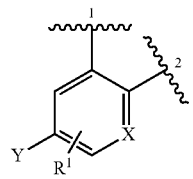

A-1

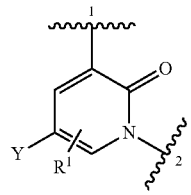

A-2

-continued

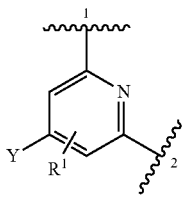
A-3 wherein the wavy line labeled 1 indicates the point of attachment of ring A to ring B and the wavy line labeled 2 indicates the point of attachment of ring A to W;
X is N or CH;
Y is H or F;
$R^1$ is H, (1-3C)alkoxy or halogen;
ring B is selected from rings B-1 and B-2 having the structures:

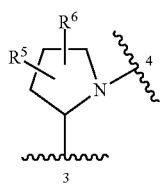
B-1

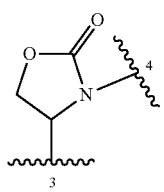
B-2 wherein the wavy line labeled 3 indicates the point of attachment to ring A and the wavy line labeled 4 indicates the point of attachment to the pyrazolo[1,5-a]pyrimidine ring of Formula I;
W is O, NH or $CH_2$, wherein when ring A is A-2, then W is $CH_2$;
m is 0, 1 or 2;
D is carbon;
$R^2$ and $R^{2a}$ are independently H, F, (1-3 C)alkyl or OH, provided that $R^2$ and $R^{2a}$ are not both OH;
$R^3$ and $R^{3a}$ are independently H, (1-3C)alkyl or hydroxy (1-3 C)alkyl;
or D is carbon or nitrogen, $R^2$ and $R^3$ are absent and $R^{2a}$ and $R^{3a}$ together with the atoms to which they are attached form a 5-6 membered heteroaryl ring having 1-2 ring heteroatoms;
Z is *—$NR^{4a}C(=O)$—, *—$ONHC(=O)$—, *—$NR^{4b}CH_2$— or *—$OC(=O)$—, wherein the asterisk indicates the point of attachment of Z to the carbon bearing $R^3$;
$R^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl);
$R^{4b}$ is H, (1-6C)alkyl, fluoro(1-6C)alkyl, difluoro(1-6C)alkyl, trifluoro(1-6C)alkyl, hydroxy(1-6C alkyl), dihydroxy(2-6C alkyl), (1-6C alkyl)C(O)—, (3-6C cycloalkyl)C(O)—, $Ar^1C(O)$—, $HOCH_2C(O)$—, (1-6C alkyl)sulfonyl, (3-6C cycloalkyl)sulfonyl, $Ar^2(SO_2)$—, $HO_2CCH_2$— or (1-6C alkyl)NH(CO)—;

$Ar^1$ is phenyl optionally substituted with one or more substituents independently selected from halogen, (1-6C)alkyl, and (1-6C)alkoxy;
$Ar^2$ is phenyl optionally substituted with one or more substituents independently selected from halogen, (1-6C)alkyl, and (1-6C)alkoxy; and
$R^5$ and $R^6$ are independently H, halogen, OH, (1-6C)alkyl or hydroxy(1-6C)alkyl.
In some embodiments of Formula I, ring B is ring B-2 having the structure:

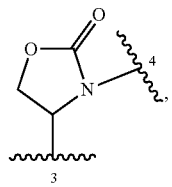
B-2

D is carbon, $R^2$ and $R^{2a}$ are independently (1-3 C)alkyl, and $R^3$ and $R^{3a}$ are independently H, (1-3 C)alkyl or hydroxy (1-3 C)alkyl, or D is carbon or nitrogen, $R^2$ and $R^3$ are absent and $R^{2a}$ and $R^{3a}$ together with the atoms to which they are attached form a 5-6 membered heteroaryl ring having 1-2 ring heteroatoms.
In some embodiments of Formula I, ring A is ring A-1 having the structure

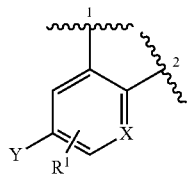
A-1 wherein X, Y and $R^1$ are as defined for Formula I. In some embodiments of Formula I, X is CH. In some embodiments, X is N. In some embodiments of Formula I, Y is F. In some embodiments, Y is H. In some embodiments of Formula I, $R^1$ is H. In some embodiments, $R^1$ is (1-3C)alkoxy. A particular example is methoxy. In some embodiments, $R^1$ is halogen. In some embodiments, $R^1$ is F.
Particular examples of ring A when represented by structure A-1 include the structures:

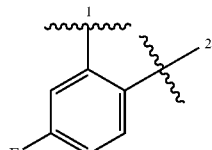

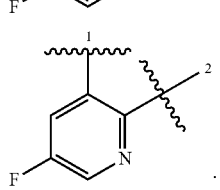

In some embodiments, ring A is ring A-2 having the structure

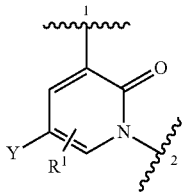

A-2 wherein Y is H or F. In some embodiments, Y is F. In some embodiments, Y is H. In some embodiments, $R^1$ is H. In some embodiments, $R^1$ is (1-3C)alkoxy. A particular example is methoxy. In some embodiments, $R^1$ is halogen. In some embodiments, $R^1$ is F.

Particular examples of ring A when represented by ring A-2 are the structures:

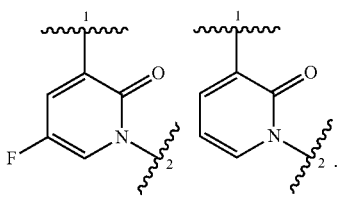

In some embodiments of Formula I, ring A is ring A-3 having the structure

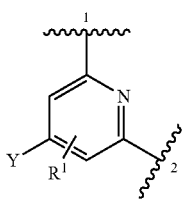

A-3 wherein Y and $R^1$ is as defined for Formula I. In some embodiments, Y is F. In some embodiments, Y is H. In some embodiments, $R^1$ is H. In some embodiments, $R^1$ is (1-3C) alkoxy. A particular example is methoxy. In some embodiments, $R^1$ is halogen. In some embodiments, $R^1$ is F.

Particular examples of ring A when represented by ring A-3 are the structures:

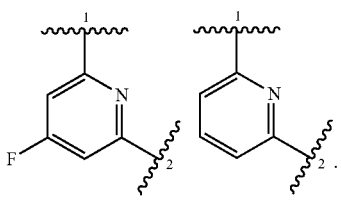

In some embodiments of Formula I, W is O.
In some embodiments, W is NH.
In some embodiments, W is $CH_2$.

In some embodiments of Formula I, D is carbon, $R^2$ and $R^{2a}$ are independently H, F, (1-3 C)alkyl or OH (provided that $R^2$ and $R^{2a}$ are not both OH), and $R^3$ and $R^{3a}$ are independently H, (1-3 C)alkyl or hydroxy(1-3 C)alkyl.

In some embodiments, $R^2$ and $R^{2a}$ are independently H, F, methyl or OH, provided that $R^2$ and $R^{2a}$ are not both OH.

In some embodiments, $R^2$ and $R^{2a}$ are both H.
In some embodiments, $R^2$ is H and $R^{2a}$ is F.
In some embodiments, $R^2$ and $R^{2a}$ are both F.
In some embodiments, $R^2$ is H and $R^{2a}$ is OH.
In some embodiments, $R^2$ is H and $R^{2a}$ is methyl.
In some embodiments, $R^2$ and $R^{2a}$ are both methyl.
In some embodiments, $R^3$ and $R^{3a}$ are independently H, (1-3C)alkyl or hydroxy(1-3 C)alkyl.

In some embodiments, $R^{3a}$ is H. In some embodiments, $R^3$ is H. In some embodiments, both $R^3$ and $R^{3a}$ are H.

In some embodiments, $R^{3a}$ is (1-3C)alkyl. Examples include methyl, ethyl, propyl and isopropyl. In some embodiments, $R^3$ is (1-3C)alkyl. Examples include methyl, ethyl, propyl and isopropyl.

In some embodiments, $R^{3a}$ is (1-3C)alkyl and $R^3$ is H. In some embodiments, $R^{3a}$ is methyl and $R^3$ is H.

In some embodiments, both $R^{3a}$ and $R^3$ are (1-3C)alkyl. In some embodiments, $R^{3a}$ and $R^{3a}$ are both methyl.

In some embodiments, $R^3$ is hydroxy(1-3C)alkyl. Examples include hydroxymethyl, 2-hydroxyethyl, 2-hydroxypropyl, and 3-hydroxypropyl. In some embodiments, $R^3$ is hydroxymethyl, 2-hydroxyethyl, 2-hydroxypropyl, or 3-hydroxypropyl and $R^{3a}$ is H.

In some embodiments of Formula I, D is carbon or nitrogen, $R^2$ and $R^3$ are absent, and $R^{2a}$ and $R^{3a}$ together with the atoms to which they are attached form a 5-6 membered heteroaryl ring having 1-2 ring heteroatoms. In some embodiments, $R^{2a}$ and $R^{3a}$ together with the atoms to which they are attached form a 5-6 membered heteroaryl ring having 1-2 ring nitrogen atoms. Examples of heteroaryl rings include pyridyl and pyrazolyl rings. Specific examples of heteroaryl rings include the structures:

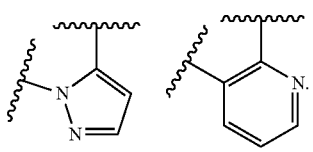 [SMILES: *c1ccnn1* ; *c1cccnc1*]

In some embodiments, Z is *—$NR^{4a}C(=O)$—.
In some embodiments, $R^{4a}$ is H.
In some embodiments, $R^{4a}$ is (1-6C)alkyl. Examples include methyl, ethyl, propyl, isopropyl, butyl, and isobutyl.

In some embodiments, $R^{4a}$ is fluoro(1-6C)alkyl. Examples include fluoromethyl and 2-fluoroethyl.

In some embodiments, $R^{4a}$ is difluoro(1-6C)alkyl. Example include difluoromethyl and 2,2-difluoroethyl.

In some embodiments, $R^{4a}$ is trifluoro(1-6C)alkyl. Examples include trifluoromethyl and 2,2,2-trifluoroethyl.

In some embodiments, $R^{4a}$ is hydroxy(1-6C alkyl). Examples include hydroxymethyl, 2-hydroxyethyl, 2-hydroxypropyl and 3-hydroxypropyl.

In some embodiments, $R^{4a}$ is dihydroxy(2-6C alkyl). An example includes 2,3-dihydroxypropyl.

In some embodiments, $R^{4a}$ is H or (1-6C)alkyl. In some embodiments, $R^{4a}$ is H or Me.

An example of Z when represented by *—$NR^{4a}C(=O)$— is *—$ONHC(=O)$—.

In some embodiments, Z is *—$NR^{4b}CH_2$—.

In some embodiments, $R^{4b}$ is H.

In some embodiments, $R^{4b}$ is selected from (1-6C)alkyl, fluoro(1-6C)alkyl, difluoro(1-6C)alkyl, and trifluoro(1-6C)alkyl.

In some embodiments, $R^{4b}$ is (1-6C)alkyl. Examples include methyl, ethyl, propyl, isopropyl, butyl and tert-butyl. In some embodiments, $R^{4b}$ is methyl.

In some embodiments, $R^{4b}$ is fluoro(1-6C)alkyl. Examples include fluoromethyl and 2-fluoroethyl.

In some embodiments, $R^{4b}$ is difluoro(1-6C)alkyl. Example include difluoromethyl and 2,2-difluoroethyl.

In some embodiments, $R^{4b}$ is trifluoro(1-6C)alkyl. Examples include trifluoromethyl and 2,2,2-trifluoroethyl.

In some embodiments, $R^{4b}$ is selected from (1-6C alkyl)C(O)—, (3-6C cycloalkyl)C(O)—, $Ar^1$C(O)— and $HOCH_2$C(O)—.

In some embodiments, $R^{4b}$ is (1-6C alkyl)C(O)—. Examples include $CH_3$C(O)—, $CH_3CH_2$C(O)—, $CH_3CH_2CH_2$C(O)—, and $(CH_3)_2$CHC(O)—. In some embodiments, $R^4$ is $CH_3$C(O)—.

In some embodiments, $R^{4b}$ is (3-6C cycloalkyl)C(O)—. Examples include cyclopropylC(O)—, cyclobutylC(O)—, cyclopentylC(O)— and cyclohexylC(O)—.

In some embodiments, $R^{4b}$ is $Ar^1$C(O)—. An example is phenylC(O)—.

In some embodiments, $R^{4b}$ is $HOCH_2$C(O)—.

In some embodiments, $R^{4b}$ is selected from (1-6C alkyl)sulfonyl, (3-6C cycloalkyl)sulfonyl, and $Ar^2(SO_2)$—.

In some embodiments, $R^{4b}$ is (1-6C alkyl)sulfonyl. Examples include methylsulfonyl, ethylsulfonyl and propylsulfonyl.

In some embodiments, $R^{4b}$ is (3-6C cycloalkyl)sulfonyl. Examples include cyclopropylsulfonyl, cyclobutylsulfonyl, cyclopentylsulfonyl and cyclohexylsulfonyl. In some embodiments, $R^4$ is methylsulfonyl.

In some embodiments, $R^{4b}$ is $Ar^2(SO_2)$—. An example is phenylsulfonyl.

In some embodiments, $R^{4b}$ is $HO_2CCH_2$—.

In some embodiments, $R^{4b}$ is (1-6C alkyl)NH(CO)—. Examples include $CH_3$NHC(O)—, $CH_3CH_2$NHC(O)—, $CH_3CH_2CH_2$NHC(O)—, and $(CH_3)_2$CHNHC(O)—. In some embodiments, $R^4$ is $CH_3$NHC(O)—.

In some embodiments, $R^{4b}$ is selected from H, methyl, —C(O)$CH_3$, methylsulfonyl, —C(O)$CH_2$OH, —$CH_2$COOH and —C(O)NH$CH_2CH_3$.

In some embodiments, Z is *—OC(═O)—.

In some embodiments of Formula I, ring B is ring B-1:

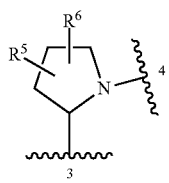

B-1 where $R^5$ and $R^6$ are independently H, halogen, OH, (1-6C)alkyl or hydroxy(1-6C)alkyl.

In some embodiments, $R^5$ and $R^6$ are independently H, F, OH, (1-6C)alkyl or hydroxy(1-6C)alkyl. In some embodiments, $R^5$ is H and $R^6$ is H, F, OH, (1-6C)alkyl or hydroxy(1-6C)alkyl.

In some embodiments, $R^5$ and $R^6$ are independently H, F, OH, (1-3C)alkyl or hydroxy(1-3C)alkyl. In some embodiments, $R^5$ is hydrogen and $R^6$ is H, F, OH, (1-3C)alkyl or hydroxy(1-3C)alkyl.

In some embodiments, $R^5$ and $R^6$ are independently H, F, OH, methyl, ethyl, $HOCH_2$— or $HOCH_2CH_2$—. In some embodiments, $R^5$ is hydrogen and $R^6$ is H, F, OH, methyl, ethyl, $HOCH_2$— or $HOCH_2CH_2$—.

In some embodiments, $R^5$ and $R^6$ are independently H, F, or methyl. In some embodiments, $R^5$ is H and $R^6$ is H, F, or methyl.

In some embodiments, $R^5$ is H and $R^6$ is F.

In some embodiments, $R^5$ is H and $R^6$ is methyl.

In some embodiments, $R^5$ and $R^6$ are both H.

In some embodiments, $R^5$ and $R^6$ are both F.

In some embodiments, $R^5$ and $R^6$ are both methyl.

In some embodiments, ring B is ring B-1 which is optionally substituted with one or two substituents independently selected from OH and F, provided that two OH substituents are not on the same ring carbon atom.

Particular examples of ring B when represented by ring B-1 include the structures:

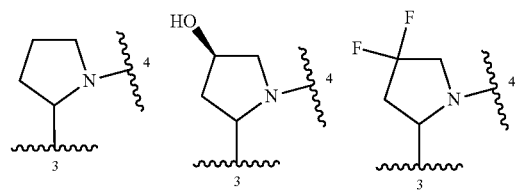

In some embodiments of Formula I, ring B is ring B-2 having the formula:

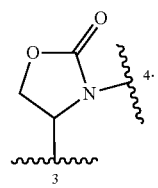

B-2

In some embodiments, m is 0.

In some embodiments, m is 1.

In some embodiments, m is 2.

Provided herein are compounds of the general Formula I or pharmaceutically acceptable salts or solvates thereof, wherein:

ring B is ring B-1:

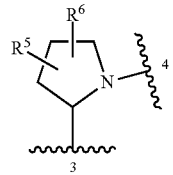

B-1 ring A is selected from rings A-1, A-2 and A-3 having the structures:

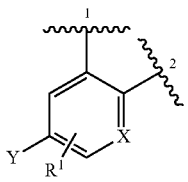

A-1

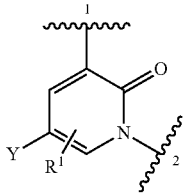

A-2

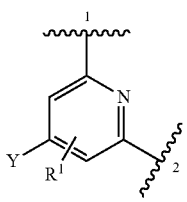

A-3 wherein the wavy line labeled 1 indicates the point of attachment of ring A to the pyrrolidine ring of Formula I and the wavy line labeled 2 indicates the point of attachment of ring A to W;

X is N or CH;
Y is H or F;
$R^1$ is H, (1-3C)alkoxy or halogen;
W is O, NH or $CH_2$, wherein when ring A is A-2, then W is $CH_2$;
m is 0, 1 or 2;
D is carbon;
$R^2$ and $R^{2a}$ are independently H, F, (1-3 C)alkyl or OH, provided that $R^2$ and $R^{2a}$ are not both OH;
$R^3$ and $R^{3a}$ are independently H, (1-3 C)alkyl or hydroxy (1-3 C)alkyl;
or $R^2$ and $R^3$ are absent and $R^{2a}$ and $R^{3a}$ together with the atoms to which they are attached form a bivalent 5-6 membered heteroaryl ring having 1-2 ring nitrogen atoms; Z is *—$NR^{4a}C(=O)$—, *—$ONHC(=O)$—, *—$NR^{4b}CH_2$— or *—$OC(=O)$—, wherein the asterisk indicates the point of attachment of Z to the carbon bearing $R^3$;
$R^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl);
$R^{4b}$ is H, (1-6C)alkyl, fluoro(1-6C)alkyl, difluoro(1-6C)alkyl, trifluoro(1-6C)alkyl, hydroxy(1-6C alkyl), dihydroxy (2-6C alkyl), (1-6C alkyl)C(O)—, (3-6C cycloalkyl)C(O)—, $Ar^1C(O)$—, $HOCH_2C(O)$—, (1-6C alkyl)sulfonyl, (3-6C cycloalkyl)sulfonyl, $Ar^2(SO_2)$—, $HO_2CCH_2$— or (1-6C alkyl)NH(CO)—;
$Ar^1$ is phenyl optionally substituted with one or more substituents independently selected from halogen, (1-6C) alkyl, and (1-6C)alkoxy;
$Ar^2$ is phenyl optionally substituted with one or more substituents independently selected from halogen, (1-6C) alkyl, and (1-6C)alkoxy; and
$R^5$ and $R^6$ are independently H, halogen, OH, (1-6C)alkyl or hydroxy(1-6C)alkyl.

Also provided herein are compounds of the general Formula IA

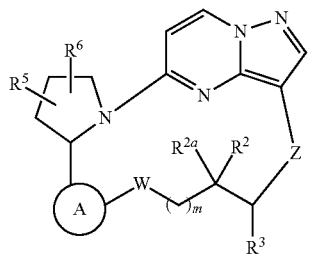

IA or pharmaceutically acceptable salts or solvates thereof, wherein:
ring A is selected from rings A-1, A-2 and A-3 having the structures:

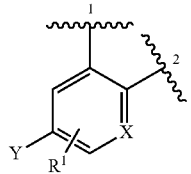

A-1

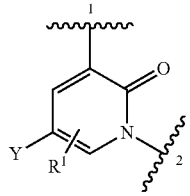

A-2

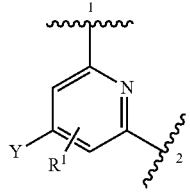

A-3 wherein the wavy line labeled 1 indicates the point of attachment of ring A to the pyrrolidine ring of Formula I and the wavy line labeled 2 indicates the point of attachment of ring A to W;

X is N or CH;
Y is H or F;
$R^1$ is H, (1-3C)alkoxy or halogen;
W is O, NH or $CH_2$, wherein when ring A is A-2, then W is $CH_2$;
m is 0, 1 or 2;
$R^2$ and $R^{2a}$ are independently H, F, or OH, provided that $R^2$ and $R^{2a}$ are not both OH;
$R^3$ is H, (1-3 C)alkyl or hydroxy(1-3 C)alkyl; Z is *—$NR^{4a}C(=O)$—, *—$ONHC(=O)$—, *—$NR^{4b}CH_2$— or *—$OC(=O)$—, wherein the asterisk indicates the point of attachment of Z to the carbon bearing $R^3$;
$R^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl);

R$^{4b}$ is H, (1-6C)alkyl, fluoro(1-6C)alkyl, difluoro(1-6C)alkyl, trifluoro(1-6C)alkyl, hydroxy(1-6C alkyl), dihydroxy(2-6C alkyl), (1-6C alkyl)C(O)—, (3-6C cycloalkyl)C(O)—, Ar$^1$C(O)—, HOCH$_2$C(O)—, (1-6C alkyl)sulfonyl, (3-6C cycloalkyl)sulfonyl, Ar$^2$(SO$_2$)—, HO$_2$CCH$_2$— or (1-6C alkyl)NH(CO)—;

Ar$^1$ is phenyl optionally substituted with one or more substituents independently selected from halogen, (1-6C)alkyl, and (1-6C)alkoxy;

Ar$^2$ is phenyl optionally substituted with one or more substituents independently selected from halogen, (1-6C)alkyl, and (1-6C)alkoxy; and R$^5$ and R$^6$ are independently H, halogen, OH, (1-6C)alkyl or hydroxy(1-6C)alkyl.

In some embodiments, Formula IA includes compounds wherein:

ring A is ring A-1 represented by the structure

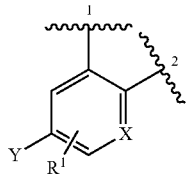

A-1 wherein the wavy line labeled 1 indicates the point of attachment of ring A to the pyrrolidine ring of Formula I and the wavy line labeled 2 indicates the point of attachment of ring A to W;

X is N or CH;
Y is H or F;
R$^1$ is H, (1-3C)alkyl, (1-3C)alkoxy or halogen;
W is O or NH;
m is 0, 1 or 2;
R$^2$ and R$^{2a}$ are independently H, F, or OH, provided that R$^2$ and R$^{2a}$ are not both OH;
R$^3$ is H, (1-3 C)alkyl or hydroxy(1-3 C)alkyl;
Z is *—NR$^{4a}$C(=O)—, *—ONHC(=O)—, or *—OC(=O)—, wherein the asterisk indicates the point of attachment to the carbon bearing R$^3$;
R$^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl); and
R$^5$ and R$^6$ are independently H, halogen, OH, (1-6C)alkyl or hydroxy(1-6C)alkyl.

In some embodiments of Formula IA, X is N. In some embodiments, X is CH.

In some embodiments, Formula IA includes compounds wherein:

ring A is ring A-2 represented by the structure

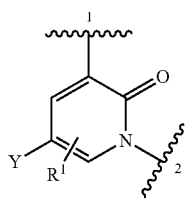

A-2 wherein the wavy line labeled 1 indicates the point of attachment of ring A to the pyrrolidine ring of Formula I and the wavy line labeled 2 indicates the point of attachment of ring A to W;

Y is H or F;
R$^1$ is H, (1-3C)alkyl, (1-3C)alkoxy or halogen;
m is 0, 1 or 2;
W is CH$_2$;
m is 0, 1 or 2;
R$^2$ and R$^{2a}$ are independently H, F, or OH, provided that R$^2$ and R$^{2a}$ are not both OH;
R$^3$ is H, (1-3 C)alkyl or hydroxy(1-3 C)alkyl;
Z is *—NR$^{4a}$C(=O)—, wherein the asterisk indicates the point of attachment to the carbon bearing R$^3$;
R$^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl); and
R$^5$ and R$^6$ are independently H, halogen, OH, (1-6C)alkyl or hydroxy(1-6C)alkyl.

In some embodiments, Formula IA includes compounds wherein:

ring A is ring A-3 represented by the structure

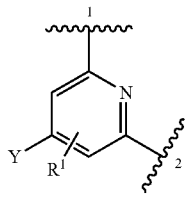

A-3 wherein the wavy line labeled 1 indicates the point of attachment of ring A to the pyrrolidine ring of Formula I and the wavy line labeled 2 indicates the point of attachment of ring A to W;

Y is H or F;
R$^1$ is H, (1-3C)alkyl, (1-3C)alkoxy or halogen;
W is O;
m is 0, 1 or 2;
R$^2$ and R$^{2a}$ are independently H, F, or OH, provided that R$^2$ and R$^{2a}$ are not both OH;
R$^3$ is H, (1-3 C)alkyl or hydroxy(1-3 C)alkyl;
Z is *—OC(=O)— or *—NR$^{4a}$C(=O)—, wherein the asterisk indicates the point of attachment to the carbon bearing R$^3$;
R$^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl); and
R$^5$ and R$^6$ are independently H, halogen, OH, (1-6C)alkyl or hydroxy(1-6C)alkyl.

In some embodiments, Formula IA includes compounds wherein:

ring A is ring A-1 represented by the structure

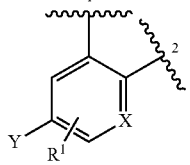

A-1 wherein the wavy line labeled 1 indicates the point of attachment of ring A to the pyrrolidine ring of Formula I and the wavy line labeled 2 indicates the point of attachment of ring A to W;

X is N or CH;
Y is H or F;
$R^1$ is H, (1-3C)alkyl, (1-3C)alkoxy or halogen;
W is O;
m is 0, 1 or 2;
$R^2$ and $R^{2a}$ are independently H, F, or OH, provided that $R^2$ and $R^{2a}$ are not both OH;
$R^3$ is H, (1-3 C)alkyl or hydroxy(1-3 C)alkyl;
Z is *—$NR^{4b}CH_2$—, wherein the asterisk indicates the point of attachment to the carbon bearing $R^3$;
$R^{4b}$ is H, (1-6C)alkyl, fluoro(1-6C)alkyl, difluoro(1-6C)alkyl, trifluoro(1-6C)alkyl (1-6C alkyl)C(O)—, (3-6C cycloalkyl)C(O)—, $Ar^1$C(O)—, $HOCH_2$C(O)—, (1-6C alkyl)sulfonyl, (3-6C cycloalkyl)sulfonyl, $Ar^2(SO_2)$—, $HO_2CCH_2$— or (1-6C alkyl)NH(CO)—;
$Ar^1$ is phenyl optionally substituted with one or more substituents independently selected from halogen, (1-6C)alkyl, and (1-6C)alkoxy;
$Ar^2$ is phenyl optionally substituted with one or more substituents independently selected from halogen, (1-6C)alkyl, and (1-6C)alkoxy; and
$R^5$ and $R^6$ are independently H, halogen, OH, (1-6C)alkyl or hydroxy(1-6C)alkyl.

In some embodiments of general Formula IA,
ring A is selected from rings A-1, A-2 and A-3 having the structures:

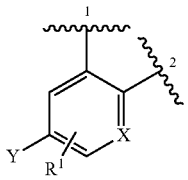

A-1

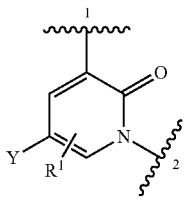

A-2

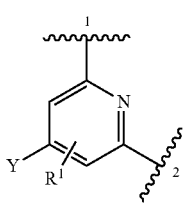

A-3 wherein the wavy line labeled 1 indicates the point of attachment of ring A to the pyrrolidine ring of Formula I and the wavy line labeled 2 indicates the point of attachment of ring A to W;
X is N or CH;
Y is H or F;
$R^1$ is H;
W is O or $CH_2$, wherein when ring A is A-2, then W is $CH_2$;
m is 0 or 1;
$R^2$ and $R^{2a}$ are independently H, F, (1-3 C)alkyl, or OH, provided that $R^2$ and $R^{2a}$ are not both OH;
$R^3$ is H or (1-3 C)alkyl;
Z is *—$NR^{4a}C(=O)$—, *—$NR^{4b}CH_2$— or *—OC(=O)—, wherein the asterisk indicates the point of attachment of Z to the carbon bearing $R^3$;
$R^{4a}$ is H;
$R^{4b}$ is (1-6C alkyl)C(O)—; and
$R^5$ and $R^6$ are independently H or halogen.

In some embodiments, Formula IA includes compounds wherein:
ring A is ring A-1 represented by the structure

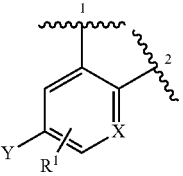

A-1 wherein the wavy line labeled 1 indicates the point of attachment of ring A to the pyrrolidine ring of Formula I and the wavy line labeled 2 indicates the point of attachment of ring A to W;
X is N or CH;
Y is H or F;
$R^1$ is H;
W is O or $CH_2$;
m is 0 or 1;
$R^2$ and $R^{2a}$ are independently H, F, (1-3 C)alkyl, or OH, provided that $R^2$ and $R^{2a}$ are not both OH;
$R^3$ is H or (1-3 C)alkyl;
Z is *—$NR^{4a}C(=O)$—, wherein the asterisk indicates the point of attachment to the carbon bearing $R^3$;
$R^{4a}$ is H; and
$R^5$ and $R^6$ are independently H or halogen.

In some embodiments of Formula IA where ring A is ring A-1, X is N. In some such embodiments of Formula IA where ring A is ring A-1, W is O. In some embodiments of Formula IA where ring A is ring A-1, W is $CH_2$. In some embodiments of Formula IA where ring A is ring A-1, $R^2$ and $R^{2a}$ are H. In some embodiments of Formula IA where ring A is ring A-1, $R^2$ and $R^{2a}$ are independently F, (1-3 C)alkyl, or OH. In some embodiments of Formula IA where ring A is ring A-1, $R^3$ is (1-3 C)alkyl. In some embodiments of Formula IA where ring A is ring A-1, $R^3$ is H. In some embodiments of Formula IA where ring A is ring A-1, Z is *—$NR^{4a}C(=O)$—. In some embodiments of Formula IA where ring A is ring A-1, $R^5$ and $R^6$ are H.

In some embodiments, Formula IA includes compounds wherein:

ring A is ring A-2 represented by the structure

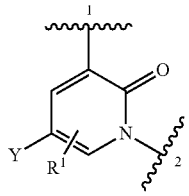

A-2 wherein the wavy line labeled 1 indicates the point of attachment of ring A to the pyrrolidine ring of Formula I and the wavy line labeled 2 indicates the point of attachment of ring A to W;

Y is H or F;
$R^1$ is H;
W is $CH_2$;
m is 0 or 1;
$R^2$ and $R^{2a}$ are independently H, F, (1-3 C)alkyl, or OH, provided that $R^2$ and $R^{2a}$ are not both OH;
$R^3$ is H or (1-3 C)alkyl;
Z is *—$NR^{4a}C(=O)$—, wherein the asterisk indicates the point of attachment to the carbon bearing $R^3$;
$R^{4a}$ is H; and
$R^5$ and $R^6$ are independently H or halogen.

In some embodiments of Formula IA where ring A is ring A-2, Y is F. In some embodiments of Formula IA where ring A is ring A-2, $R^2$ and $R^{2a}$ are H. In some embodiments of Formula IA where ring A is ring A-2, $R^2$ and $R^{2a}$ are independently H or (1-3 C)alkyl. In some embodiments of Formula IA where ring A is ring A-2, $R^3$ is (1-3 C)alkyl. In some embodiments of Formula IA where ring A is ring A-2, $R^3$ is H. In some embodiments of Formula IA where ring A is ring A-2, $R^5$ and $R^6$ are H.

In some embodiments, Formula IA includes compounds wherein:

ring A is ring A-3 represented by the structure

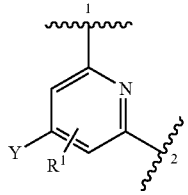

A-3 wherein the wavy line labeled 1 indicates the point of attachment of ring A to the pyrrolidine ring of Formula I and the wavy line labeled 2 indicates the point of attachment of ring A to W;

Y is H or F;
$R^1$ is H;
W is O;
m is 0 or 1;
$R^2$ and $R^{2a}$ are independently H, F, (1-3 C)alkyl, or OH, provided that $R^2$ and $R^{2a}$ are not both OH;
$R^3$ is H or (1-3 C)alkyl;
Z is *—$NR^{4a}C(=O)$—, wherein the asterisk indicates the point of attachment to the carbon bearing $R^3$;
$R^{4a}$ is H; and
$R^5$ and $R^6$ are independently H or halogen.

In some embodiments of Formula IA where ring A is ring A-3, Y is F. In some embodiments of Formula IA where ring A is ring A-3, Y is H. In some embodiments of Formula IA where ring A is ring A-3, $R^2$ and $R^{2a}$ are H. In some embodiments of Formula IA where ring A is ring A-3, $R^2$ and $R^{2a}$ are independently H or (1-3 C)alkyl. In some embodiments of Formula IA where ring A is ring A-3, $R^3$ is (1-3 C)alkyl. In some embodiments of Formula IA where ring A is ring A-3, $R^3$ is H. In some embodiments of Formula IA where ring A is ring A-3, $R^5$ and $R^6$ are H.

It will be appreciated that certain compounds as provided herein may contain one or more centers of asymmetry and may therefore be prepared and isolated as a mixture of isomers such as a racemic or diastereomeric mixture, or in an enantiomerically or diastereomerically pure form. It is intended that all stereoisomeric forms of the compounds provided herein, including but not limited to, diastereomers, enantiomers and atropisomers, as well as mixtures thereof such as racemic mixtures, form part of the present disclosure.

In some embodiments, compounds of the general Formula I wherein Ring B is ring B-1 have the absolute configuration of Formula 1-a:

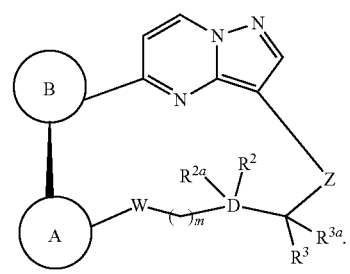

1-a

In some embodiments, compounds of the general Formula I wherein Ring B is ring B-1 have the absolute configuration of Formula 1-b:

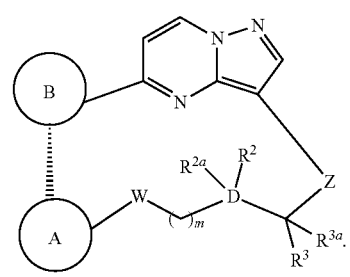

1-b

In the structures shown herein, where the stereochemistry of any particular chiral atom is not specified, then all stereoisomers are contemplated and included as the compounds of the disclosure. Where stereochemistry is specified by a solid wedge or dashed line representing a particular configuration, then that stereoisomer is so specified and defined.

The terms "(1-3C)alkyl" and "(1-6C)alkyl" as used herein refer to saturated linear or branched-chain monovalent hydrocarbon radicals of one to three carbon atoms and one to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, and hexyl.

The term "fluoro(1-6C)alkyl" as used herein refers to saturated linear or branched-chain monovalent hydrocarbon radicals of one to six carbon atoms as defined herein, wherein one of the hydrogens is replaced by a fluorine atom.

The term "difluoro(1-6C)alkyl" as used herein refers to saturated linear or branched-chain monovalent hydrocarbon radicals of one to six carbon atoms as defined herein, wherein two of the hydrogens are replaced by fluorine atoms.

The term "trifluoro(1-6C)alkyl" as used herein refers to saturated linear or branched-chain monovalent hydrocarbon radicals of one to six carbon atoms as defined herein, wherein three of the hydrogens are replaced by fluorine atoms.

The term "hydroxy(1-6Calkyl) as used herein refers to saturated linear or branched-chain monovalent hydrocarbon radicals of one to six carbon atoms, wherein one of the hydrogens is replaced by a hydroxy (OH) group.

The term "dihydroxy(2-6C alkyl) as used herein refers to saturated linear or branched-chain monovalent hydrocarbon radicals of two to six carbon atoms as defined herein, wherein two of the hydrogens are replaced by hydroxy (OH) groups, provided the hydroxy groups are not on the same carbon atom.

The term "(1-6C alkyl)sulfonyl" as used herein refers to a (1-6C alkyl)$SO_2$— group, wherein the radical is on the sulfur atom and the (1-6C alkyl) portion is as defined above. Examples include methylsulfonyl ($CH_3SO_2$—) and ethylsulfonyl ($CH_3CH_2SO_2$—).

The term "(3-6C cycloalkyl)sulfonyl" as used herein refers to a (3-6C cycloalkyl)$SO_2$— group, wherein the radical is on the sulfur atom. An example is cyclopropylsulfonyl.

The terms "(1-3C)alkoxy" and "(1-6C)alkoxy", as used herein refer to saturated linear or branched-chain monovalent alkoxy radicals of one to three carbon atoms or one to six carbon atoms, respectively, wherein the radical is on the oxygen atom. Examples include methoxy, ethoxy, propoxy, isopropoxy, and butoxy.

The term "halogen" includes fluoro, chloro, bromo and iodo.

Non-limiting examples of the compounds of Formula I include those in Table 1.

TABLE 1

| Compound No. | Compound Structure | Compound Name |
|---|---|---|
| 1 | 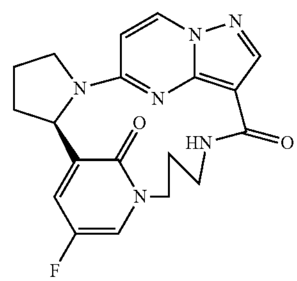 [SMILES: O=C1NCCCn2cc(F)cc(c2=O)[C@H]2CCCN2c2ccn3ncc1c3n2] | (6R)-9-fluoro-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione |
| 2 | 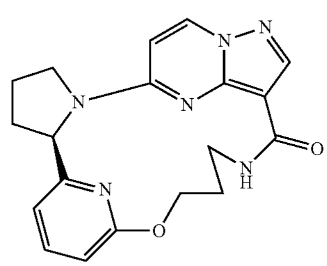 [SMILES: O=C1NCCCOc2cccc(n2)[C@H]2CCCN2c2ccn3ncc1c3n2] | (6R)-12-oxa-2,16,20,21,24,26-hexaazapentacyclo[16.5.2.1$^{7,11}$.0$^{2,6}$.0$^{21,25}$]hexacosa-1(24),7(26),8,10,18(25),19,22-heptaen-17-one |
| 3 | 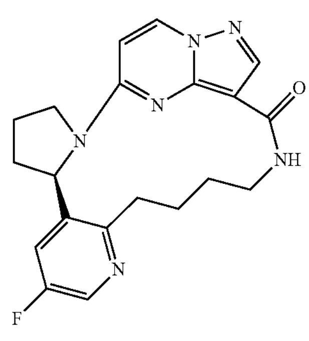 [SMILES: O=C1NCCCCc2ncc(F)cc2[C@H]2CCCN2c2ccn3ncc1c3n2] | (6R)-9-fluoro-13-oxa-2,11,17,21,22,25-hexaazapentacyclo[17.5.2.0$^{2,6}$.0$^{7,12}$.0$^{22,6}$]hexacosa-1(25),7,9,11,19(26),20,23-heptaen-18-one |

TABLE 1-continued

| Compound No. | Compound Structure | Compound Name |
|---|---|---|
| 4 | 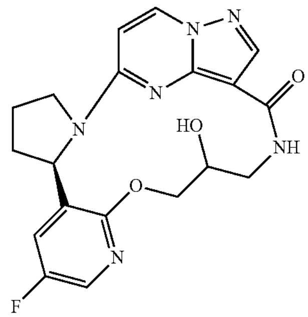 [SMILES: O=C1NCC(O)COc2ncc(F)cc2[C@H]2CCCN2c2ccn3ncc1c3n2] | (6R)-9-fluoro-15-hydroxy-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one |
| 5 | 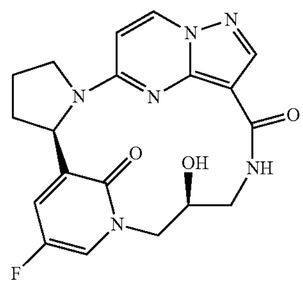 [SMILES: O=C1NC[C@H](O)Cn2cc(F)cc(c2=O)[C@H]2CCCN2c2ccn3ncc1c3n2] | (6R,13S)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione |
| 5-B | 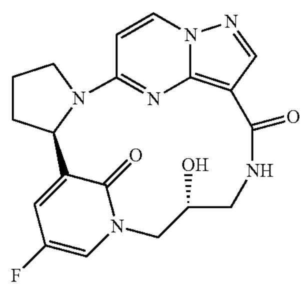 [SMILES: O=C1NC[C@@H](O)Cn2cc(F)cc(c2=O)[C@H]2CCCN2c2ccn3ncc1c3n2] | (6R,13R)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione |
| 6 | 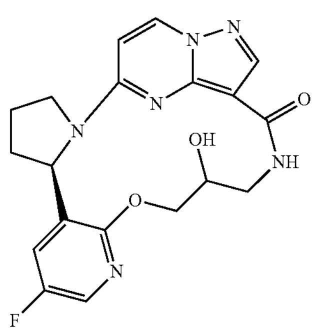 [SMILES: O=C1NCC(O)COc2ncc(F)cc2[C@H]2CCCN2c2ccn3ncc1c3n2] | (6R)-9-fluoro-15-hydroxy-13-oxa-2,11,17,21,22,25-hexaazapentacyclo-[17.5.2.0$^{2,6}$.0$^{7,12}$.0$^{22,26}$]hexacosa-1(25),7,9,11,19(26),20,23-heptaen-18-one |
| 7 | 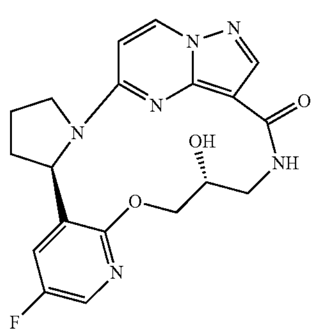 [SMILES: O=C1NC[C@@H](O)COc2ncc(F)cc2[C@H]2CCCN2c2ccn3ncc1c3n2] | (6R,15R)-9-fluoro-15-hydroxy-13-oxa-2,11,17,21,22,25-hexaazapentacyclo-[17.5.2.0$^{2,6}$.0$^{7,12}$.0$^{22,26}$]hexacosa-1(25),7,9,11,19(26),20,23-heptaen-18-one |

TABLE 1-continued

| Compound No. | Compound Structure | Compound Name |
| --- | --- | --- |
| 7-B | 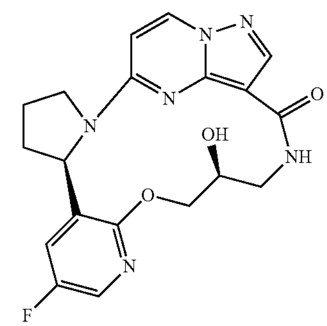 [SMILES: O=C1NC[C@H](O)COc2ncc(F)cc2[C@H]2CCCN2c2ccn3ncc1c3n2] | (6R,15S)-9-fluoro-15-hydroxy-13-oxa-2,11,17,21,22,25-hexaazapentacyclo-[17.5.2.0$^{2,6}$.0$^{7,12}$.0$^{22,26}$]hexacosa-1(25),7,9,11,19(26),20,23-heptaen-18-one |
| 8 | 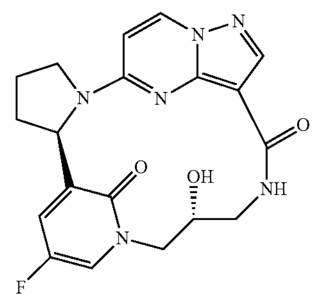 [SMILES: O=C1NC[C@@H](O)Cn2cc(F)cc(c2=O)[C@H]2CCCN2c2ccn3ncc1c3n2] | (6R,13R)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione |
| 8-B | 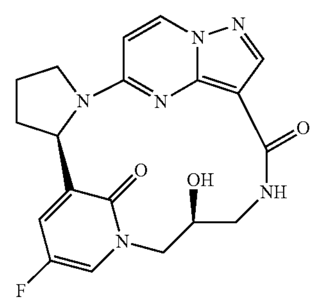 [SMILES: O=C1NC[C@H](O)Cn2cc(F)cc(c2=O)[C@H]2CCCN2c2ccn3ncc1c3n2] | (6R,13S)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione |
| 9 | 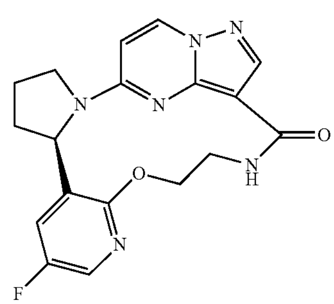 [SMILES: O=C1NCCOc2ncc(F)cc2[C@H]2CCCN2c2ccn3ncc1c3n2] | (6R)-9-fluoro-13-oxa-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one |
| 10 | 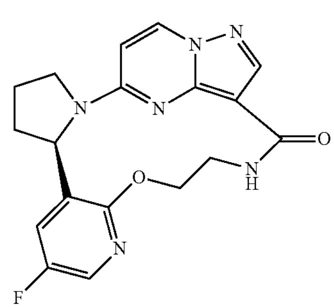 [SMILES: O=C1NCCOc2ncc(F)cc2[C@H]2CCCN2c2ccn3ncc1c3n2] | (6R)-9-fluoro-13-oxa-2,11,18,22,23,26-hexaazapentacyclo[18.5.2.0$^{2,6}$.0$^{7,12}$.0$^{23,27}$]heptacosa-1(26),7,9,11,20(27),21,24-heptaen-19-one |

TABLE 1-continued

| Compound No. | Compound Structure | Compound Name |
|---|---|---|
| 11 | 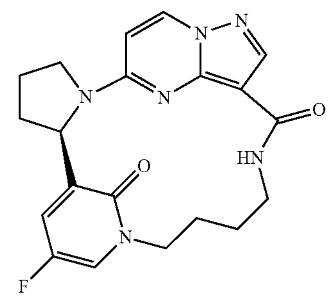 [SMILES: O=C1NCCCCn2cc(F)cc(c2=O)[C@H]2CCCN2c2ccn3ncc1c3n2] | (6R)-9-fluoro-2,11,16,20,21,24-hexaazapentacyclo[16.5.2.1$^{7,11}$.0$^{2,6}$.0$^{21,25}$]hexacosa-1(24),7,9,18(25),19,22-hexaene-17,26-dione |
| 12 | 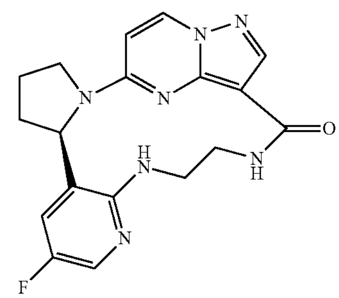 [SMILES: O=C1NCCNc2ncc(F)cc2[C@H]2CCCN2c2ccn3ncc1c3n2] | (6R)-9-fluoro-2,11,13,16,20,21,24-heptaazapentacyclo[16.5.2.0$^{2,6}$.0$^{7,12}$.0$^{21,25}$]pentacosa-1(24),7,9,11,18(25),19,22-heptaen-17-one |
| 13 | 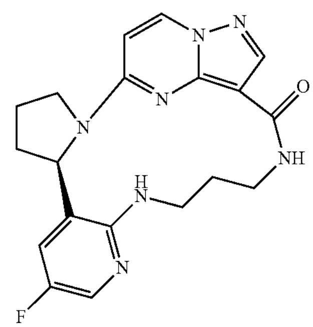 [SMILES: O=C1NCCCNc2ncc(F)cc2[C@H]2CCCN2c2ccn3ncc1c3n2] | (6R)-9-fluoro-2,11,13,17,21,22,25-heptaazapentacyclo[17.5.2.0$^{2,6}$.0$^{7,12}$.0$^{22,26}$]hexacosa-1(25),7,9,11,19(26),20,23-heptaen-18-one |
| 14 | 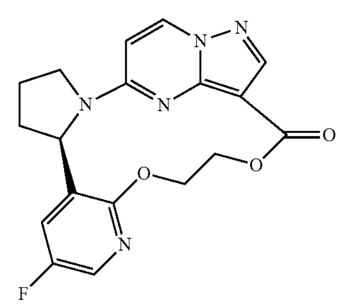 [SMILES: O=C1OCCOc2ncc(F)cc2[C@H]2CCCN2c2ccn3ncc1c3n2] | (6R)-9-fluro-13,16-dioxa-2,11,20,21,24-pentaazapentacyclo[16.5.2.0$^{2,6}$.0$^{7,12}$.0$^{21,25}$]-pentacosa-1(24),7,9,11,18(25),19,22-heptaen-17-one |
| 15 | 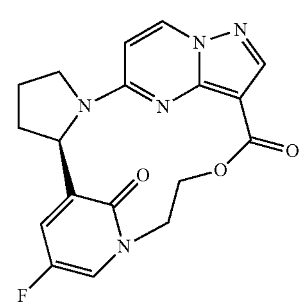 [SMILES: O=C1OCCn2cc(F)cc(c2=O)[C@H]2CCCN2c2ccn3ncc1c3n2] | (6R)-9-fluoro-14-oxa-2,11,18,19,22-pentaazapentacyclo[14.5.2.1$^{7,11}$.0$^{2,6}$.0$^{19,23}$]tetracosa-1(22),7,9,16(23),17,20-hexaene-15,24-dione |

TABLE 1-continued

| Compound No. | Compound Structure | Compound Name |
|---|---|---|
| 16 | 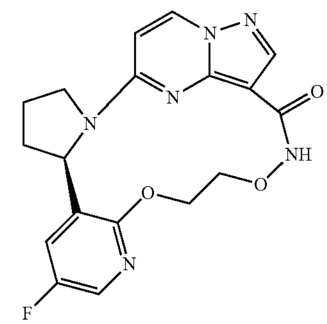 [SMILES: O=C1NOCCOc2ncc(F)cc2[C@H]2CCCN2c2ccn3ncc1c3n2] | (6R)-9-fluoro-13,16-dioxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one |
| 17 | 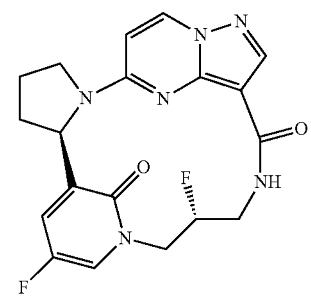 [SMILES: O=C1NC[C@@H](F)Cn2cc(F)cc(c2=O)[C@H]2CCCN2c2ccn3ncc1c3n2] | (6R,13R)-9,13-difluoro-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione |
| 17-B | 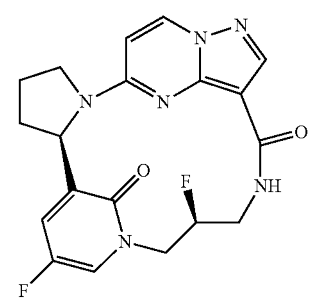 [SMILES: O=C1NC[C@H](F)Cn2cc(F)cc(c2=O)[C@H]2CCCN2c2ccn3ncc1c3n2] | (6R,13S)-9,13-difluoro-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione |
| 18 | 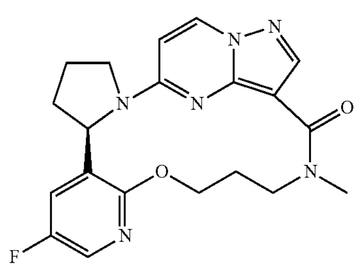 [SMILES: CN1CCCOc2ncc(F)cc2[C@H]2CCCN2c2ccn3ncc(c3n2)C1=O] | (6R)-9-fluoro-17-methyl-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one |
| 19 | 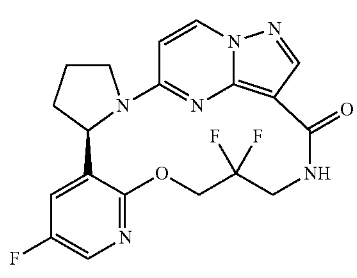 [SMILES: O=C1NCC(F)(F)COc2ncc(F)cc2[C@H]2CCCN2c2ccn3ncc1c3n2] | (6R)-9,15,15-trifluoro-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one |

TABLE 1-continued

| Compound No. | Compound Structure | Compound Name |
|---|---|---|
| 20 | 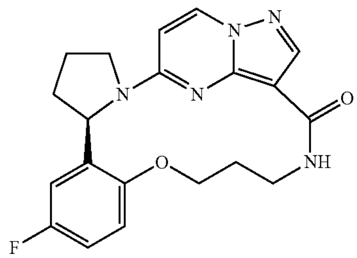 [SMILES: O=C1NCCCOc2ccc(F)cc2[C@H]2CCCN2c2ccn3ncc1c3n2] | (6R)-9-fluoro-13-oxa-2,17,21,22,25-pentaazapentacyclo[17.5.2.0$^{2,6}$.0$^{7,12}$.0$^{22,26}$]hexacosa-1(25),7,9,11,19(26),20,23-heptaen-18-one |
| 21 | 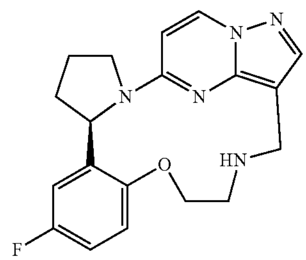 [SMILES: Fc1ccc2c(c1)[C@H]1CCCN1c1ccn3ncc(c3n1)CNCCO2] | (6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaene |
| 22 | 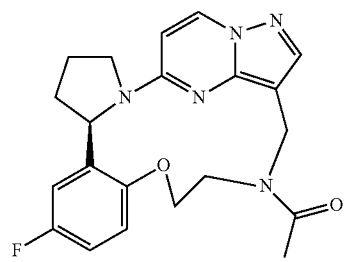 [SMILES: CC(=O)N1CCOc2ccc(F)cc2[C@H]2CCCN2c2ccn3ncc(c3n2)C1] | 1-[(6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-16-yl]ethan-1-one |
| 23 | 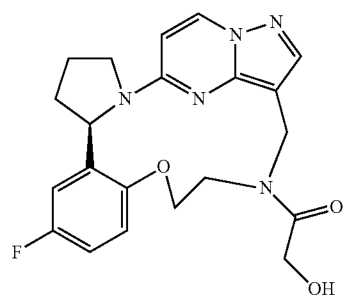 [SMILES: O=C(CO)N1CCOc2ccc(F)cc2[C@H]2CCCN2c2ccn3ncc(c3n2)C1] | 1-[(6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-16-yl]-2-hydroxyethan-1-one |
| 24 | 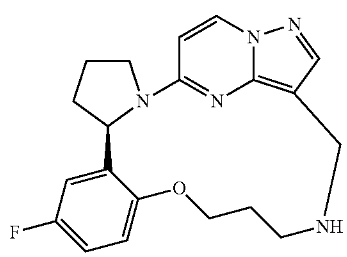 [SMILES: Fc1ccc2c(c1)[C@H]1CCCN1c1ccn3ncc(c3n1)CNCCCO2] | (6R)-9-fluoro-13-oxa-2,17,21,22,25-pentaazapentacyclo[17.5.2.0$^{2,6}$.0$^{7,12}$.0$^{22,26}$]hexacosa-1(25),7,9,11,19(26),20,23-heptaene |
| 25 | 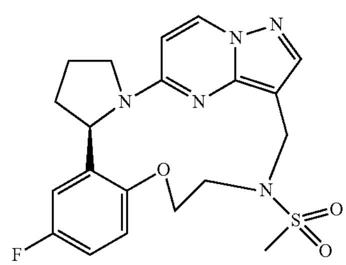 [SMILES: CS(=O)(=O)N1CCOc2ccc(F)cc2[C@H]2CCCN2c2ccn3ncc(c3n2)C1] | (6R)-9-fluoro-16-methanesulfonyl-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaene |

TABLE 1-continued

| Compound No. | Compound Structure | Compound Name |
| --- | --- | --- |
| 26 | 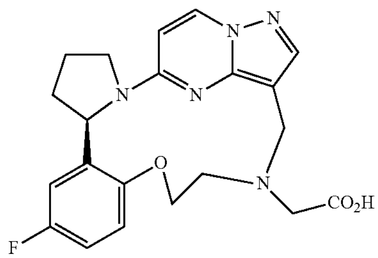 [SMILES: O=C(O)CN1CCOc2ccc(F)cc2[C@H]2CCCN2c2ccn3ncc(c3n2)C1] | 2-[(6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-16-yl]acetic acid |
| 27 | 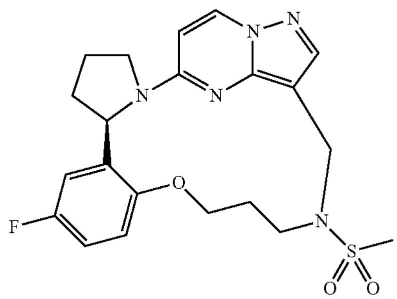 [SMILES: CS(=O)(=O)N1CCCOc2ccc(F)cc2[C@H]2CCCN2c2ccn3ncc(c3n2)C1] | (6R)-9-fluoro-17-methanesulfonyl-13-oxa-2,17,21,22,25-pentaazapentacyclo[17.5.2.0$^{2,6}$.0$^{7,12}$.0$^{22,26}$]hexacosa-1(25),7,9,11,19(26),20,23-heptaene |
| 28 | 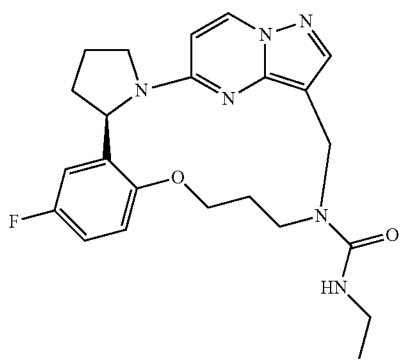 [SMILES: CCNC(=O)N1CCCOc2ccc(F)cc2[C@H]2CCCN2c2ccn3ncc(c3n2)C1] | (6R)-N-ethyl-9-fluoro-13-oxa-2,17,21,22,25-pentaazapentacyclo 17.5.2.0$^{2,6}$.0$^{7,12}$.0$^{22,26}$]hexacosa-1(25),7,9,11,19(26),20,23-heptaene-17-carboxamide |
| 29 | 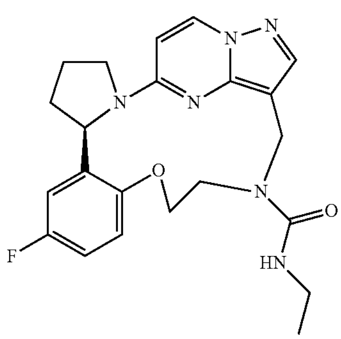 [SMILES: CCNC(=O)N1CCOc2ccc(F)cc2[C@H]2CCCN2c2ccn3ncc(c3n2)C1] | (6R)-N-ethyl-9-fluoro-13-oxa-2,16,20,21,24-pentaazapentacyclo-[16.5.2.0$^{2,6}$.0$^{7,12}$.0$^{21,25}$]pentacosa-1(24),7,9,11,18(25),19,22-heptaene-16-carboxamide |
| 30 | 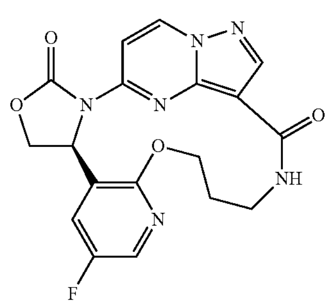 [SMILES: O=C1NCCCOc2ncc(F)cc2[C@H]2COC(=O)N2c2ccn3ncc1c3n2] | (6S)-9-fluoro-4,13-dioxa-2,11,17,21,22,25-hexaazapentacyclo[17.5.2.0$^{2,6}$.0$^{7,12}$.0$^{22,26}$]hexacosa-1(25),7(12),8,10,19(26),20,23-heptaene-3,18-dione |

TABLE 1-continued

| Compound No. | Compound Structure | Compound Name |
|---|---|---|
| 31 | 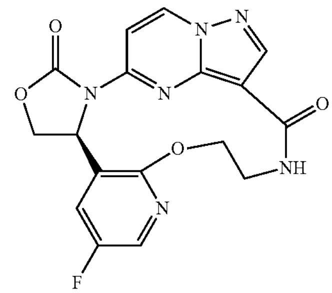 [SMILES: O=C1NCCOc2ncc(F)cc2[C@H]2COC(=O)N2c2ccn3ncc1c3n2] | (6S)-9-fluoro-4,13-dioxa-2,11,16,20,21,24-hexaazapentacyclo[16.5.2.0$^{2,6}$.0$^{7,12}$.0$^{21,25}$]pentacosa-1(24),7(12),8,10,18(25),19,22-heptaene-3,17-dione |
| 32 | 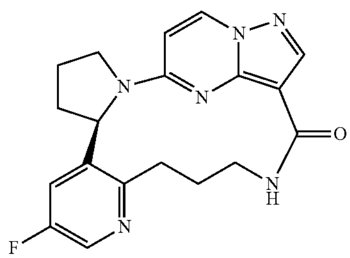 [SMILES: O=C1NCCCc2ncc(F)cc2[C@H]2CCCN2c2ccn3ncc1c3n2] | (6R)-9-fluoro-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one |
| 33 | 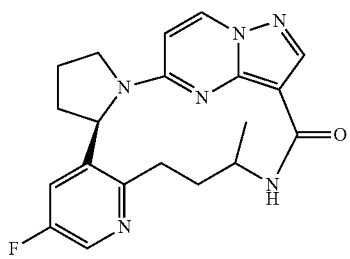 [SMILES: CC1CCc2ncc(F)cc2[C@H]2CCCN2c2ccn3ncc(c3n2)C(=O)N1] | (6R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one |
| 33-A | 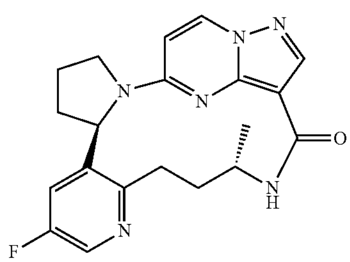 [SMILES: C[C@H]1CCc2ncc(F)cc2[C@H]2CCCN2c2ccn3ncc(c3n2)C(=O)N1] | (6R,15S)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one |
| 33-B | 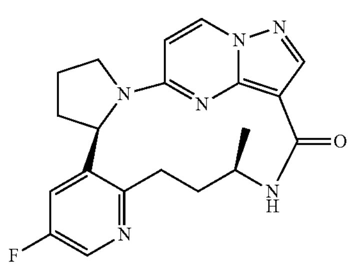 [SMILES: C[C@@H]1CCc2ncc(F)cc2[C@H]2CCCN2c2ccn3ncc(c3n2)C(=O)N1] | (6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one |

TABLE 1-continued

| Compound No. | Compound Structure | Compound Name |
|---|---|---|
| 34 | 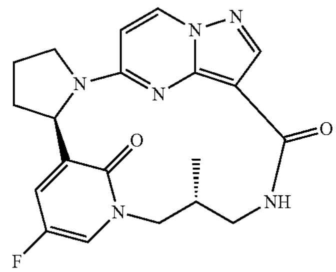 [SMILES: C[C@@H]1CNC(=O)c2cnn3ccc(nc23)N2CCC[C@@H]2c2cc(F)cn(c2=O)C1] | (6R,13R)-9-fluoro-13-methyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione |
| 35 | 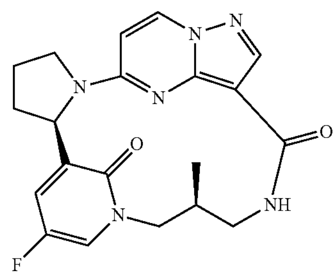 [SMILES: C[C@H]1CNC(=O)c2cnn3ccc(nc23)N2CCC[C@@H]2c2cc(F)cn(c2=O)C1] | (6R,13S)-9-fluoro-13-methyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione |
| 36 | 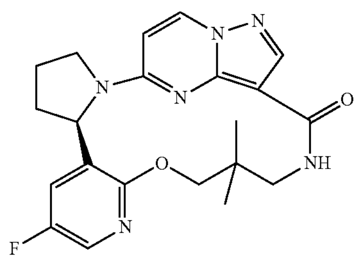 [SMILES: CC1(C)CNC(=O)c2cnn3ccc(nc23)N2CCC[C@@H]2c2cc(F)cnc2OC1] | (6R)-9-fluoro-15,15-dimethyl-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one |
| 37 | 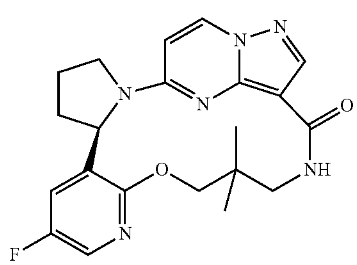 [SMILES: CC1(C)CNC(=O)c2cnn3ccc(nc23)N2CCC[C@@H]2c2cc(F)cnc2OC1] | (6R)-9-fluoro-15,15-dimethyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one |
| 38 | 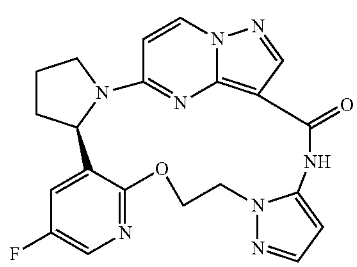 [SMILES: O=C1Nc2ccnn2CCOc2ncc(F)cc2[C@H]2CCCN2c2ccn3ncc1c3n2] | (6R)-9-fluoro-13-oxa-2,11,16,17,21,25,26,29-octaazahexacyclo[21.5.2.0$^{2,6}$.0$^{7,12}$.0$^{16,20}$.0$^{26,30}$]triaconta-1(29),7,9,11,17,19,23(30),24,27-nonaen-22-one |

TABLE 1-continued

| Compound No. | Compound Structure | Compound Name |
|---|---|---|
| 39 | 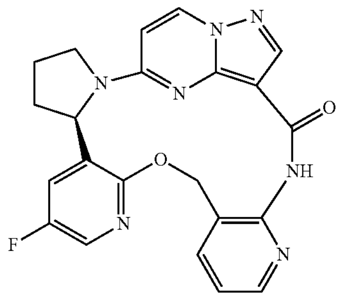 [SMILES: O=C1Nc2ncccc2COc2ncc(F)cc2[C@H]2CCCN2c2ccn3ncc1c3n2] | (6R)-9-fluoro-13-oxa-2,11,19,21,25,26,29-heptaazahexacyclo[21.5.2.0$^{2,6}$.0$^{7,12}$.0$^{15,20}$.0$^{26.30}$]triaconta-1(29),7,9,11,15(20),16,18,23(30),24,27-decaen-22-one |
| 40 | 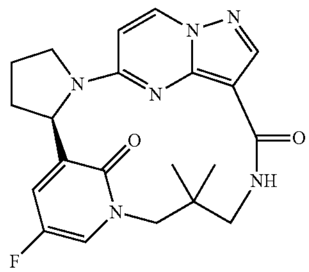 [SMILES: CC1(C)CNC(=O)c2cnn3ccc(nc23)N2CCC[C@@H]2c2cc(F)cn(c2=O)C1] | (6R)-9-fluoro-13,13,-dimethyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione |
| 41 | 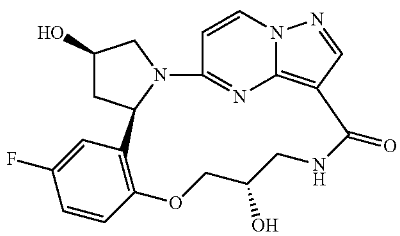 [SMILES: O=C1NC[C@H](O)COc2ccc(F)cc2[C@H]2C[C@@H](O)CN2c2ccn3ncc1c3n2] | (4R,6R,15S)-9-fluoro-4,15-dihydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one |
| 41-B | 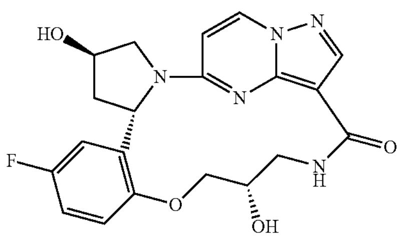 [SMILES: O=C1NC[C@H](O)COc2ccc(F)cc2[C@@H]2C[C@@H](O)CN2c2ccn3ncc1c3n2] | (4R,6S,15S)-9-fluoro-4,15-dihydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one |
| 42 | 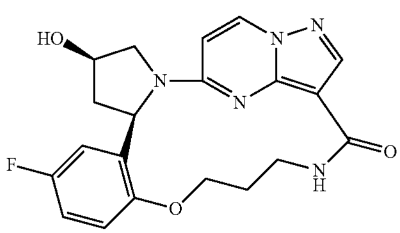 [SMILES: O=C1NCCCOc2ccc(F)cc2[C@H]2C[C@@H](O)CN2c2ccn3ncc1c3n2] | (4R,6R)-9-fluoro-4-hydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one |
| 42-B | 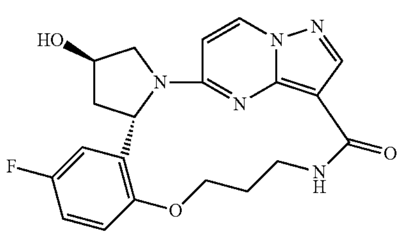 [SMILES: O=C1NCCCOc2ccc(F)cc2[C@@H]2C[C@@H](O)CN2c2ccn3ncc1c3n2] | (4R,6S)-9-fluoro-4-hydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one |

TABLE 1-continued

| Compound No. | Compound Structure | Compound Name |
|---|---|---|
| 43 | 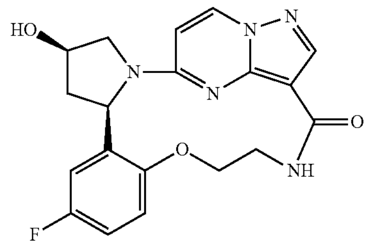 [SMILES: O=C1NCCOc2ccc(F)cc2[C@H]2C[C@@H](O)CN2c2ccn3ncc1c3n2] | (4R,6R)-9-fluoro-4-hydroxy-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-17-one |
| 43-B | 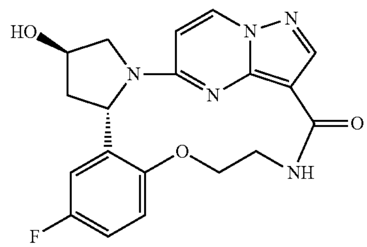 [SMILES: O=C1NCCOc2ccc(F)cc2[C@@H]2C[C@@H](O)CN2c2ccn3ncc1c3n2] | (4R,6S)-9-fluoro-4-hydroxy-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-17-one |
| 44 | 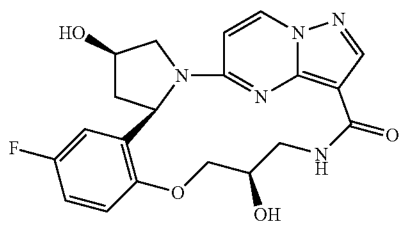 [SMILES: O=C1NC[C@@H](O)COc2ccc(F)cc2[C@H]2C[C@@H](O)CN2c2ccn3ncc1c3n2] | (4R,6R,15R)-9-fluoro-4,15-dihydroxy-13-oxa-2,17,21,22,25-pentaazapentacyclo[17.5.2.0$^{2,6}$.0$^{7,12}$.0$^{22,6}$]hexacosa-1(25),7(12),8,10,19(26),20,23-heptaen-18-one |
| 44-B | 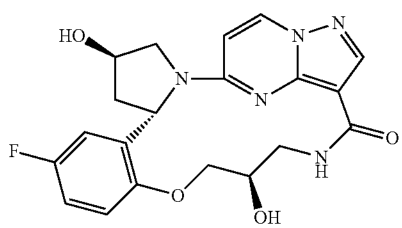 [SMILES: O=C1NC[C@@H](O)COc2ccc(F)cc2[C@@H]2C[C@@H](O)CN2c2ccn3ncc1c3n2] | (4R,6S,15R)-9-fluoro-4,15-dihydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one |
| 45 | 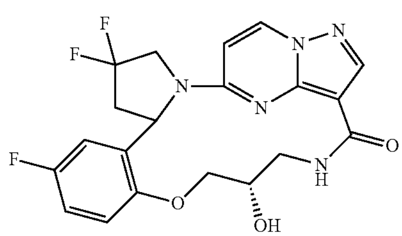 [SMILES: O=C1NC[C@H](O)COc2ccc(F)cc2C2CC(F)(F)CN2c2ccn3ncc1c3n2] | Diasteromer 1 and Diastereomer 2 of (15S)-4,4,9-trifluoro-15-hydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one |

It will also be appreciated that certain compounds of Formula I may be used as intermediates for the preparation of further compounds of Formula I.

The compounds of Formula I include salts thereof. In certain embodiments, the salts are pharmaceutically acceptable salts. In addition, the compounds of Formula I include other salts of such compounds which are not necessarily pharmaceutically acceptable salts, and which may be useful as intermediates for preparing and/or purifying compounds of Formula I and/or for separating enantiomers of compounds of Formula I.

The term "pharmaceutically acceptable" indicates that the substance or composition is compatible chemically and/or toxicologically, with the other ingredients comprising a formulation, and/or the mammal being treated therewith.

It will further be appreciated that the compounds of Formula I and their salts may be isolated in the form of solvates, and accordingly that any such solvate is included within the scope of the present disclosure.

The compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C, $^{14}$C or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds provided herein therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds of the present disclosure, whether radioactive or not, are intended to be encompassed within the scope of the present disclosure.

The compounds of Formula I or a salt thereof as defined herein can be prepared as described in U.S. Pat. No. 8,933,084, which is incorporated by reference in its entirety herein. For example, a process for preparing a compound of Formula I or a salt thereof as defined herein can include:

(a) for a compound of Formula I wherein Z is *—NHC(=O)—, and ring A, ring B, 5 W, D, $R^2$, $R^{2a}$, $R^3$, $R^{3a}$ and m are as defined for Formula I, cyclizing a corresponding compound having the formula II

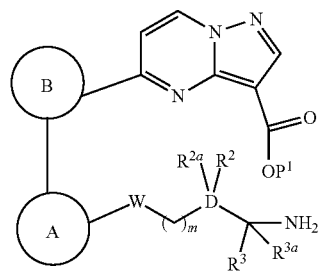

II where $P^1$ is H or a carboxyl protecting group, in the presence of a coupling reagent and a base; or (b) for a compound of Formula I wherein W is O, ring A is formula A-1:

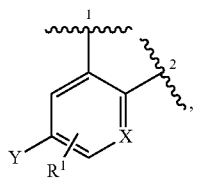

A-1

X is N, and ring B, D, Z, Y, $R^1$, $R^2$, $R^{2a}$, $R^3$, $R^{3a}$ and m are as defined for Formula I, cyclizing a corresponding compound having the formula III

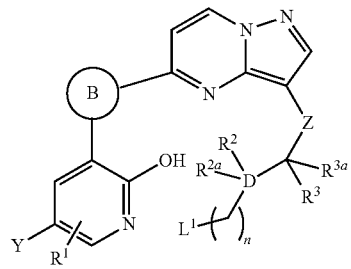

III where n is 1, 2, 3 or 4 and $L^1$ is a leaving group or atom, in the presence of a base; or (c) for a compound of Formula I wherein W is $CH_2$, ring A is formula A-2:

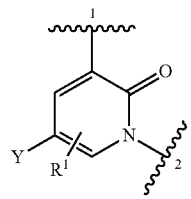

A-2 and ring B, Z, D, Y, $R^1$, $R^2$, $R^{2a}$, $R^3$, $R^{3a}$ and m are as defined for Formula I, cyclizing a corresponding compound having the formula IV

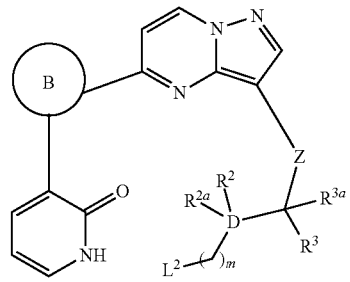

IV where $L^2$ is a leaving group or atom, in the presence of a base; or (d) for a compound of Formula I wherein Z is *—NHC(=O)—, and ring A, ring B, W, D, $R^2$, $R^{2a}$, $R^3$, $R^{3a}$ and m are as defined for Formula I, cyclizing a corresponding compound having the formula V

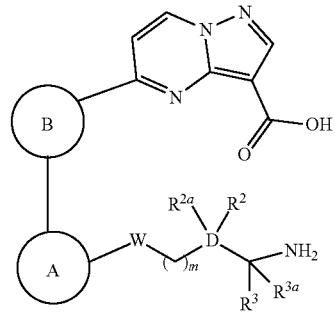

V in the presence of a base and a coupling reagent; or (e) for a compound of Formula I wherein Z is *—NHCH$_2$—, and ring A, ring B, W, D, $R^2$, $R^{2a}$, $R^3$, $R^{3a}$ and m are as defined for Formula I, cyclizing a corresponding compound having the formula VI

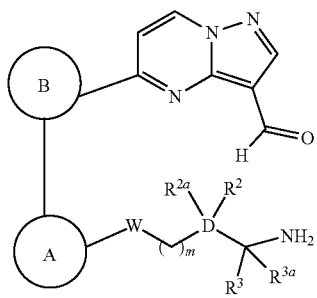

VI in the presence of a reducing agent; or (f) for a compound of Formula I wherein Z is *—NHCH$_2$—, and ring A, ring B, W, D, R$^2$, R$^{2a}$, R$^3$, R$^{3a}$ and m are as defined for Formula I, cyclizing a corresponding compound having the formula VII

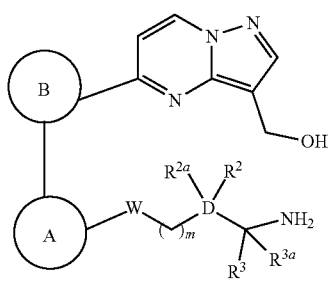

VII in the presence of triphenylphosphine; or (g) for a compound of Formula I wherein ring A, ring B, W, D, m, R$^2$, R$^{2a}$, R$^3$, and R$^{3a}$ are as defined for Formula I, Z is *—NR$^{4b}$CH$_2$—, and R$^{4b}$ is (1-6C alkyl)C(O)—, (3-6C cycloalkyl)C(O)—, Ar$^1$C(O)—, HOCH$_2$C(O)—, (1-6C alkyl)sulfonyl, (3-6C cycloalkyl)sulfonyl, (1-6C alkyl)sulfonyl, (3-6C cycloalkyl)sulfonyl, or Ar$^2$(SO$_2$)—, coupling a corresponding compound having the formula VIII

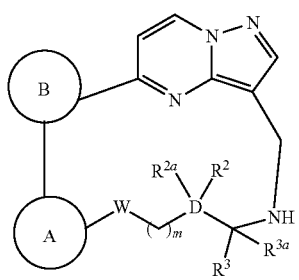

VIII with a reagent having the formula (1-6C alkyl)C(O)-L$^3$, (3-6C cycloalkyl)C(O)-L$^3$, Ar$^1$C(O)-L$^3$, HOCH$_2$C(O)-L$^3$, (1-6C alkyl)(SO$_2$)-L$^3$, (3-6C cycloalkyl)(SO$_2$)-L$^3$, or Ar$^2$(SO$_2$)-L$^3$, respectively, where L$^3$ is a leaving atom, in the presence of a base; or (h) for a compound of Formula I wherein ring A, ring B, W, D, R$^2$, R$^{2a}$, R$^3$, R$^{3a}$ and m are as defined for Formula I, Z is *—NR$^{4b}$CH$_2$—, and R$^{4b}$ is (1-6C alkyl)NH(CO)—, reacting a compound having the formula VIII

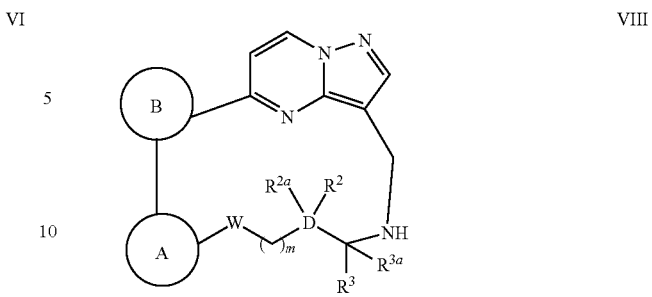

VIII with a reagent having the formula (1-6C alkyl)N=C=O in the presence of a base; or (i) for a compound of Formula I wherein R$^2$ is F, R$^{2a}$ is H, and ring A, ring B, Z, W, D, R$^3$, R$^{3a}$, and m are as defined for Formula I, reacting a corresponding compound having the formula IX

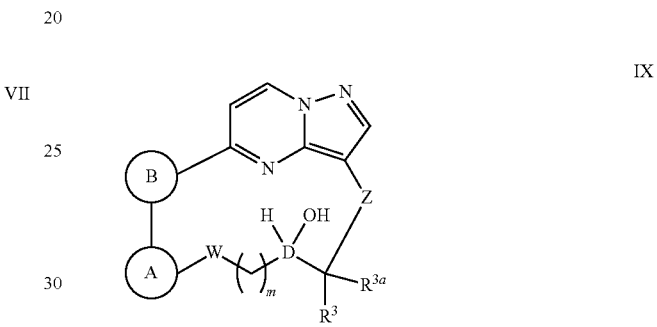

IX with a fluorination reagent;

(j) for a compound of Formula I wherein W is O, ring A is formula A-1,

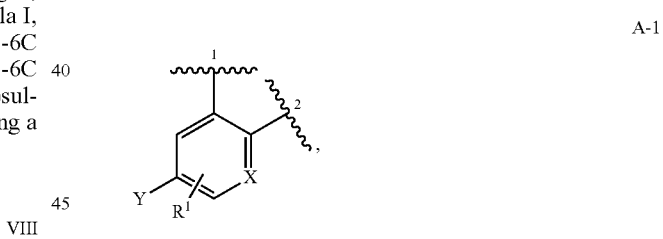

A-1

X is CH, and Y, R$^1$, D, ring B, Z, R$^2$, R$^{2a}$, R$^3$ and m are as defined for Formula I, cyclizing a corresponding compound having the formula X

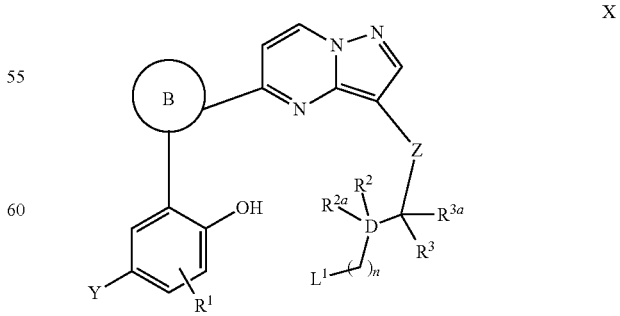

X where n is 1, 2, 3 or 4 and L$^1$ is a leaving group or atom, in the presence of a base; and optionally removing any protecting groups and optionally preparing a salt thereof.

In some embodiments of the above-described methods (a)-(j), ring B is ring B-1 having the structure:

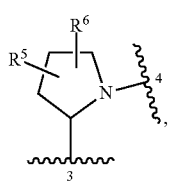

D is carbon, $R^2$ and $R^{2a}$ are independently H, F, (1-3 C)alkyl or OH (provided that $R^2$ and $R^{2a}$ are not both OH), $R^3$ is H, (1-3 C)alkyl or hydroxy(1-3 C)alkyl, and ring A, W, m, Z, Y, $R^{3a}$, $R^5$ and $R^6$ are as defined for Formula I.

Referring to method (a), the cyclization may be performed using conventional amide bond formation conditions, for example by treating the carboxylic acid with an activating agent, followed by addition of the amine in the presence of a base. Suitable activating agents include EDCI, oxalyl chloride, thionyl chloride, HATU, and HOBt. Suitable bases include amine bases, for example triethylamine, diisopropylethylamine, pyridine, or excess ammonia. Suitable solvents include DCM, DCE, THF and DMF.

Referring to methods (b) and (c), the leaving atoms $L^1$ and $L^2$ may be, for example a halogen atom such as Br, Cl or I. Alternatively, $L^1$ and $L^2$ can be a leaving group, for example an arylsulfonyloxy group or an alkylsulfonyloxy group, such as a mesylate or a tosylate group. Suitable bases include alkali metal carbonates, such as sodium carbonate, potassium carbonate or cesium carbonate. Convenient solvents include aprotic solvents such as ethers (for example tetrahydrofuran or p-dioxane), DMF, or acetone. The reaction can be conveniently performed at elevated temperatures, for example 50-150° C., for example at 85° C.

Referring to method (d), suitable coupling reagents include HATU, HBTU, TBTU, DCC, DIEC, and any other amide coupling reagents well known to persons skilled in the art. Suitable bases include tertiary amine bases such as DIEA and triethylamine. Convenient solvents include DMF, THF, DCM and DCE.

Referring to method (e), suitable reducing agents include $Me_4N(OAc)_3BH$, $Na(OAc)_3BH$ and $NaCNBH_3$. Suitable solvents include neutral solvents such as acetonitrile, THF and DCE. The reaction can be conveniently performed at ambient temperature.

Referring to method (f), in certain embodiments the triphenylphosphine reagent is used in the form of a polystyrene-bound $PPh_3$ resin (sold as PS-$PPh_3$ by Biotage Systems). The reaction is conveniently performed at ambient temperature. Suitable solvents include neutral solvents, for example DCM.

Referring to method (g), the leaving atom $L^3$ may be a halogen, for example Cl or Br. Suitable bases include tertiary amine bases such as diisopropylethylamine and triethylamine. The reaction is conveniently performed at ambient temperature.

Referring to method (h), suitable bases include tertiary amine bases such as DIEA and triethylamine. The reaction is conveniently performed at ambient temperature.

Referring to method (i), the fluorination reagent may be, for example, bis(2-methoxyethyl)amino-sulfur trifluoride (Deoxo-Fluor™) or diethylaminosulfur trifluoride (DAST). Suitable solvents include dichloromethane, chloroform, dichloroethane, and toluene. The reaction is conveniently performed at ambient temperature.

Referring to method (j), base may be, for example, an alkali metal carbonate, such as for example sodium carbonate, potassium carbonate or cesium carbonate. Convenient solvents include aprotic solvents such as ethers (for example tetrahydrofuran or p-dioxane) or toluene. The reaction can be conveniently performed at a temperature between ambient temperature and reflux, for example at 85° C.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC), and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The ability of test compounds to act as ROS1 inhibitors may be demonstrated by the assay described in Example A. $IC_{50}$ values are shown in Table 17.

In some embodiments, inhibition of L2026M is similar to, or better than, that observed for wild-type ROS1. For example, inhibition of L2026M is within about 2-fold (e.g., about 5-fold, about 7-fold, about 10-fold) of inhibition of wild-type ROS1 (i.e. the compounds are similarly potent against wild-type ROS1 and L2026M). In some embodiments, inhibition of L2026M is about the same as inhibition of wild-type ROS1. In some embodiments, inhibition of L2026M is about 2-fold, 3-fold, 4-fold, 5-fold, 6-fold, 7-fold, 8-fold, 9-fold, 10-fold, or greater than inhibition of wild-type ROS1. In some embodiments, selectivity for a wildtype or L2026M ROS1 kinase over another kinase is measured in an enzyme assay (e.g., an enzyme assay as provided herein). In some embodiments, the compounds provided herein exhibit selective cytotoxicity to ROS1-mutant cells.

In some embodiments, inhibition of D2033N is similar to, or better than, that observed for wild-type ROS1. In some embodiments, inhibition of D2033N is within about 2-fold (e.g., about 5-fold, about 7-fold, about 10-fold) of inhibition of wild-type ROS1 (i.e. the compounds are similarly potent against wild-type ROS1 and D2033N). In some embodiments, inhibition of D2033N is about the same as inhibition of wild-type ROS1. In some embodiments, inhibition of D2033N is about 2-fold, 3-fold, 4-fold, 5-fold, 6-fold, 7-fold, 8-fold, 9-fold, 10-fold, or greater than inhibition of wild-type ROS1. In some embodiments, selectivity for a wildtype or D2033N ROS1 kinase over another kinase is measured in an enzyme assay (e.g., an enzyme assay as provided herein). In some embodiments, the compounds provided herein exhibit selective cytotoxicity to ROS1-mutant cells.

Compounds of Formula I are useful for treating diseases and disorders which can be treated with a ROS1 kinase inhibitor, such as ROS1-associated diseases and disorders, e.g., proliferative disorders such as cancers, including hematological cancers and solid tumors.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with a dysregulation of a ROS1 gene, a ROS1 protein, or expression or activity, or level of any of the same (a ROS1-associated cancer) (e.g., as determined using a regulatory agency-approved, e.g., FDA-approved, assay or kit). In some embodiments, the assay is a liquid biopsy. In some embodiments, the subject has a tumor that is positive for a dysregulation of a ROS1 gene, a ROS1 protein, or expression or activity, or level of any of the same (e.g., as determined using a regulatory agency-approved assay or kit). The subject can be a subject with a tumor(s) that is positive for a dysregulation of a ROS1 gene, a ROS1 protein, or expression or activity, or level of any of the same (e.g., identified as positive using a regulatory agency-approved, e.g., FDA-approved, assay or kit). In some embodiments, the assay is a liquid biopsy. The subject can be a subject whose tumors have a dysregulation of a ROS1 gene, a ROS1 protein, or expression or activity, or a level of the same (e.g., where the tumor is identified as such using a regulatory agency-approved, e.g., FDA-approved, kit or assay). In some embodiments, the subject is suspected of having a ROS1-associated cancer. In some embodiments, the subject has a clinical record indicating that the subject has a tumor that has a dysregulation of a ROS1 gene, a ROS1 protein, or expression or activity, or level of any of the same (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula I are useful for preventing diseases and disorders as defined herein (for example, cancer). The term "preventing" as used herein means the prevention of the onset, recurrence or spread, in whole or in part, of the disease or condition as described herein, or a symptom thereof.

The term "ROS1-associated disease or disorder" as used herein refers to diseases or disorders associated with or having a dysregulation of a ROS1 gene, a ROS1 kinase (also called herein ROS1 kinase protein), or the expression or activity or level of any (e.g., one or more) of the same (e.g., any of the types of dysregulation of a ROS1 gene, a ROS1 kinase, a ROS1 kinase domain, or the expression or activity or level of any of the same described herein). A non-limiting example of a ROS1-associated disease or disorder includes cancer.

The term "ROS1-associated cancer" as used herein refers to cancers associated with or having a dysregulation of a ROS1 gene, a ROS1 kinase (also called herein ROS1 kinase protein), or expression or activity, or level of any of the same. Non-limiting examples of a ROS1-associated cancer are described herein.

The phrase "dysregulation of a ROS1 gene, a ROS1 kinase, or the expression or activity or level of any of the same" refers to a genetic mutation (e.g., a ROS1 gene translocation that results in the expression of a fusion protein, a deletion in a ROS1 gene that results in the expression of a ROS1 protein that includes a deletion of at least one amino acid as compared to the wild-type ROS1 protein, a mutation in a ROS1 gene that results in the expression of a ROS1 protein with one or more point mutations, or an alternative spliced version of a ROS1 mRNA that results in a ROS1 protein having a deletion of at least one amino acid in the ROS1 protein as compared to the wild-type ROS1 protein) or a ROS1 gene amplification that results in overexpression of a ROS1 protein or an autocrine activity resulting from the overexpression of a ROS1 gene in a cell that results in a pathogenic increase in the activity of a kinase domain of a ROS1 protein (e.g., a constitutively active kinase domain of a ROS1 protein) in a cell. As another example, a dysregulation of a ROS1 gene, a ROS1 protein, or expression or activity, or level of any of the same, can be a mutation in a ROS1 gene that encodes a ROS1 protein that is constitutively active or has increased activity as compared to a protein encoded by a ROS1 gene that does not include the mutation. For example, a dysregulation of a ROS1 gene, a ROS1 protein, or expression or activity, or level of any of the same, can be the result of a gene or chromosome translocation which results in the expression of a fusion protein that contains a first portion of ROS1 that includes a functional kinase domain, and a second portion of a partner protein that is not ROS1. In some examples, dysregulation of a ROS1 gene, a ROS1 protein, or expression or activity or level of any of the same can be a result of a gene translocation of one ROS1 gene with another non-ROS1 gene. Non-limiting examples of fusion proteins are described in Table 2. Non-limiting examples of ROS1 kinase protein point mutations are described in Table 3 and Table 3a. Additional examples of ROS1 kinase protein mutations (e.g., point mutations) are ROS1 inhibitor resistance mutations. Non-limiting examples of ROS1 inhibitor resistance mutations are described in Table 4.

The term "wildtype" or "wild-type" when referring to a ROS1 nucleic acid or protein describes a nucleic acid (e.g., a ROS1 gene or a ROS1 mRNA) or protein (e.g., a ROS1 protein) that is found in a subject that does not have a ROS1-associated disease, e.g., a ROS1-associated cancer (and optionally also does not have an increased risk of developing a ROS1-associated disease and/or is not suspected of having a ROS1-associated disease), or is found in a cell or tissue from a subject that does not have a ROS1-associated disease, e.g., a ROS1-associated cancer (and optionally also does not have an increased risk of developing a ROS1-associated disease and/or is not suspected of having a ROS1-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating cancer (e.g., a ROS1-associated cancer) in a patient in need of such treatment, the method comprising administering to the patient a therapeutically effective amount of a compound of Formula I or a pharmaceutically acceptable salt or solvate thereof or a pharmaceutical composition thereof. For example, provided herein are methods for treating a ROS1-associated cancer in a patient in need of such treatment, the method comprising a) detecting a dysregulation of a ROS1 gene, a ROS1 kinase, or the expression or activity or level of any of the same in a sample from the patient; and b) administering a therapeutically effective amount of a compound of Formula I or a pharmaceutically acceptable salt or solvate thereof. In some embodiments, the dysregulation of a ROS1 gene, a ROS1 kinase, or the expression or activity or level of any of the same includes one or more fusion proteins. Non-limiting examples of ROS1 gene fusion proteins are described in Table 2. In some embodiments, the fusion protein is one of SLC34A2-ROS1, CD74-ROS1, EZR-ROS1, TPM3-ROS1, or SDC4-ROS1. In some embodiments, the dysregulation of a ROS1 gene, a ROS1 kinase, or the expression or activity or level of any of the same includes one or more ROS1 kinase protein point mutations, insertions, and/or deletions. Non-limiting examples of ROS1 kinase protein point mutations are described in Table 3 and Table 3a. In some embodiments, the ROS1 kinase protein point mutations, insertions, and/or deletions are point mutations selected from the group consisting of A15G, R118N, G1025R, T1735M, R1948H, and R2072N. In some embodiments, a compound of Formula I is selected from Example No. 2, 3, 7, 9, 14, 19, 20, 22, 33-A, 33-B, 35, 36, and 45, or a pharmaceutically acceptable salt or solvate thereof.

In some embodiments of any of the methods or uses described herein, the cancer (e.g., ROS1-associated cancer) is a hematological cancer. In some embodiments of any of the methods or uses described herein, the cancer (e.g., ROS1-associated cancer) is a solid tumor. In some embodiments of any of the methods or uses described herein, the cancer (e.g., ROS1-associated cancer) is lung cancer (e.g., small cell lung carcinoma or non-small cell lung carcinoma), papillary thyroid cancer, medullary thyroid cancer, differentiated thyroid cancer, recurrent thyroid cancer, refractory differentiated thyroid cancer, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., ROS1-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are ROS1-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In some embodiments, the hematological cancer (e.g., the hematological cancer that is a RET-associated cancer) is AML or CMML.

In some embodiments, the cancer (e.g., the ROS1-associated cancer) is a solid tumor. Examples of solid tumors (e.g., solid tumors that are ROS1-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer (including, e.g., non-small-cell lung cancer), colorectal cancer, gastric cancer, adenocarcinoma (including, e.g., small bowel adenocarcinoma), cholangiocarcinoma, glioblastoma, ovarian cancer, angiocarcinoma, congenital gliobastoma multiforme, papillary thyroid carcinoma, inflammatory myofibroblastic tumour, a spitzoid neoplasm, anaplastic large cell lymphoma, diffuse large B cell lymphoma, and B-cell acute lymphoblastic leukemia.

In some embodiments, the patient is a human.

Compounds of Formula I and pharmaceutically acceptable salts and solvates thereof are also useful for treating a ROS1-associated cancer.

Accordingly, also provided herein is a method for treating a patient diagnosed with or identified as having a ROS1-associated cancer, e.g., any of the exemplary ROS1-associated cancers disclosed herein, comprising administering to the patient a therapeutically effective amount of a compound of Formula I or a pharmaceutically acceptable salt or solvate thereof, or a pharmaceutical composition thereof as defined herein.

Dysregulation of a ROS1 kinase, a ROS1 gene, or the expression or activity or level of any (e.g., one or more) of the same can contribute to tumorigenesis. For example, a dysregulation of a ROS1 kinase, a ROS1 gene, or expression or activity or level of any of the same can be a translocation, overexpression, activation, amplification, or mutation of a ROS1 kinase, a ROS1 gene, or a ROS1 kinase domain. A translocation can include a translocation involving the ROS1 kinase domain, a mutation can include a mutation involving the ROS1 ligand-binding site, and an amplification can be of a ROS1 gene.

In some embodiments, the dysregulation of a ROS1 gene, a ROS1 kinase, or expression or activity or level of any of the same, includes overexpression of wild-type ROS1 kinase (e.g., leading to autocrine activation). In some embodiments, the dysregulation of a ROS1 gene, a ROS1 kinase protein, or expression or activity or level of any of the same, includes overexpression, activation, amplification, or mutation in a chromosomal segment comprising the ROS1 gene or a portion thereof, including, for example, the kinase domain portion, or a portion capable of exhibiting kinase activity.

In some embodiments, the dysregulation of a ROS1 gene, a ROS1 kinase protein, or expression or activity or level of any of the same, includes one or more chromosome translocations or inversions resulting in a ROS1 gene fusion. In some embodiments, the dysregulation of a ROS1 gene, a ROS1 kinase protein, or expression or activity or level of any of the same, is a result of genetic translocations in which the expressed protein is a fusion protein containing residues from a non-ROS1 partner protein, and includes a minimum of a functional ROS1 kinase domain.

Non-limiting examples of ROS1 fusion proteins are shown in Table 2.

TABLE 2

Exemplary ROS1 Fusion Proteins

| | |
|---|---|
| CD74 | Non-small-cell lung cancer[1] |
| SLC34A2 including SLC34A2-ROS(S)[28], SLC34A2-ROS(L)[28], and SLC34A2-ROS(VS)[28], SLC34A2-ROS (with a breakpoint at chr6: 117653720, chr4: 25678781)[24] | Non-small-cell lung cancer[1], Colorectal cancer[14], Gastric cancer[15], Lung adenocarcinoma[24] |
| TPM3 | Non-small-cell lung cancer[1] |
| SDC4 | Non-small-cell lung cancer[1], Adenocarcinoma[10] |
| EZR | Non-small-cell lung cancer[1] |
| LRIG3 | Non-small-cell lung cancer[1] |
| KDELR2 | Non-small-cell lung cancer[1] |
| CCDC6 | Non-small-cell lung cancer[1] |
| FIG (GOPC, PIST) including FIG-ROS1(L)[29], FIG-ROS1(S)[29], and FIG-ROS1(VL)[29], FIG-ROS1 (XL)[30] | Non-small-cell lung cancer[2], Cholangiocarcinoma[5], Glioblastoma[8], Ovarian cancer[16], Small bowel adenocarcinomas (SBAs)[22], Acral lentiginous melanoma (ALM)[25] |
| TPD52L1 | Non-small-cell lung cancer[3] |
| CEP85L | Angiosarcoma[4] Pediatric gliomas[31] |
| ZCCHC8 | Congenital gliobastoma multiforme[6] |
| CCDC30 | Papillary thyroid carcinoma[7] |
| TFG | Inflammatory myofibroblastic tumour[9], Sarcomas[26] |
| TMEM106B | Adenocarcinoma[11] |
| YWHAE | Inflammatory myofibroblastic tumor[12] |
| MSN | Lung cancer[13] |
| PWWP2A | Spitzoid neoplasm[17] |
| FYN | Non-small-cell lung cancer[18] |
| MKX | Non-small-cell lung cancer[18] |
| PPFIBP1 | Spitzoid neoplasm[19] |
| ERC1 | Spitzoid neoplasm[19] |
| MY05A | Spitzoid neoplasm[19] |
| CLIP1 | Spitzoid neoplasm[19] |
| HLA-A | Spitzoid neoplasm[19] |
| KIAA1598 (SHTN1) | Spitzoid neoplasm[19] |
| ZCCHC8 | Spitzoid neoplasm[19] |
| CLTC | Non-small-cell lung cancer[20] |
| LIMA1 | Non-small-cell lung cancer[20] |
| NFkB32 | Anaplastic Large Cell Lymphoma[21] |
| NCOR2 | Anaplastic Large Cell Lymphoma[21] |
| KLC1 | Pediatric low-grade glioma[24] |
| TBL1XR1 | Juvenile myelomonocytic leukemia (JMML)[27] |

[1]Davies and Dobele, *Clin. Cancer Res*, 19(15): 4040-5, 2013.
[2]Rimkunas et al., *Clin. Cancer Res.*, 18: 4449-58, 2012.
[3]Zhu et al., *Lung Cancer*, 97:48-50, doi: 10.1016/j.lungcan.2016.04.013, 2012.
[4]Giacomini et al., *PLoS Gene.t*, 9(4): e1003464, 2013.
[5]Saborowski et al., *Proc. Natl. Acad. Sci. U.S.A.*, 110(48): 19513-19518, 2013.
[6]Cocce et al., *Genes Chromosomes Cancer*, 55(9): 677-87, 2016.
[7]Ritterhouse et al., *Thyroid*, 26(6): 794-7, 2016.
[8]Das etal., *Cancer Growth Metastasis*, 8:51-60, doi: 10.4137/CGM.S32801, 2015.
[9]Yamamoto et al., *Histopathology*, 69(1): 72-83, 2016.
[10]Fu et al., *PLoS One*, 10(4): e0124354, 2015.
[11]Ou et al., *Lung Cancer*, 88(3): 352-4, 2015.
[12]Hornick et al., *Mod. Pathol.*, 28(5): 732-9, 2015.
[13]Zheng et al., *Nat Med.*, (12): 1479-84, 2014.
[14]Aisner et al., *Mol. Cancer Res.*, 12(1): 111-8, 2014.

TABLE 2-continued

Exemplary ROS1 Fusion Proteins

| | |
|---|---|
| CD74 | Non-small-cell lung cancer[1] |

[15]Lee et al., *Cancer*, 119(9): 1627-1635, 2013.
[16]Birch et al., *PLoS One*, 6(12): e28250, 2011.
[17]Weisner et al., *Nature Comm.*, 5:3116, doi: 10.1038/ncomms4116, 2014.
[18]U.S. Pat. Application Publication No. 2016/0032396A1.
[19]PCT Patent Application Publication No. WO 2014/130975A1.
[20]Australian Patent Application Publication No. AU 2015/101722A4
[21]Crescenzo et al., *Cancer Cell.*, 27(4): 516-32, 2015.
[22]Schrock et al., *Annals of Oncology*. Vol. 27, Supp_6, 613O, 2016.
[24]Nakano etal. *Pediatr Blood Cancer*. Vol. 64, S54-S55 Suppe. 4. O13-1-7, 2017.
[25]Couts et al. *Pigment Cell Melanoma Res.* Vol. 30, No. 5, pp. e61, 2017.
[26]Ikeda et al. *Annals of Oncology*. Vol. 28 (suppl_10): x1-x6.10.1093/annonc/mdx652, 2017.
[27]Murakami et al. *Blood*, blood-2017-07-798157; DOI: 10.1182/blood-2017-07-798157, 2018.
[28]EP Patent Application Publication No. EP3266795A1
[29]U.S. Pat. Publication No. US9782400B2
[30]PCT Patent Application Publication No. WO 2010/093928
[31]Johnson et al., *Oncologist.* 22(12): 1478-1490, doi: 10.1634/theoncologist.2017-0242, 2017.

In some embodiments, the dysregulation of a ROS1 gene, a ROS1 kinase, or expression or activity or level of any of the same, includes one or more deletions, insertions, or point mutation(s) in a ROS1 kinase. In some embodiments, the dysregulation of a ROS1 gene, a ROS1 kinase, or expression or activity or level of any of the same, includes a deletion of one or more residues from the ROS1 kinase, resulting in constitutive activity of the ROS1 kinase domain.

In some embodiments, the dysregulation of a ROS1 gene, a ROS1 kinase, or expression or activity or level of any of the same, includes at least one point mutation in a ROS1 gene that results in the production of a ROS1 kinase that has one or more amino acid substitutions, insertions, or deletions as compared to the wild-type ROS1 kinase (see, for example, the point mutations listed in Table 3).

TABLE 3

Exemplary ROS1 Point Mutations

| ROS1 Mutation | ROS1-Associated Cancer |
|---|---|
| Amino acid position 15 (e.g., A15G) | Diffuse large B cell lymphoma[1] |
| Amino acid position 118 (e.g., R118N) | B-cell acute lymphoblastic leukemia[2] |
| Amino acid position 122 (e.g., A122T) | Gastrointestinal stromal tumors (GISTs)[3] |
| Amino acid position 245 (e.g., R245I) | Uterine Corpus Endometrioid Carcinoma[4] |
| Amino acid position 1025 (e.g., G1025R) | B-cell acute lymphoblastic leukemia[2] |
| Amino acid position 1186 (e.g., S1186F) | Non-Small-Cell Lung Cancer[5] |
| Amino acid position 1539 (e.g., P1539S) | Skin Cutaneous Melanoma[7] |
| Amino acid position 1735 (e.g., T1735M) | B-cell acute lymphoblastic leukemia[2] |
| Amino acid position 1948 (e.g., R1948H) | Diffuse large B cell lymphoma[1] |
| Amino acid position 2033 (e.g., D2033Y) | Colorectal adenocarcinoma[6] |
| Amino acid position 2072 (e.g., R2072N) | B-cell acute lymphoblastic leukemia[2] |
| Amino acid position 2126 (e.g., R2126W, R2126Q, R2126L) | Breast, melanoma[6] |
| Amino acid position 2308 (e.g., E2308, E2308Q) | Kidney renal clear cell carcinoma, Skin cutaneous melanoma, Head and neck squamous cell carcinoma[7] |

[1]U.S. Pat. Application Publication No. 2016/0032404A1.
[2]de Smith et al., *Oncotarget.*, doi: 10.18632/oncotarget.12238, 2016.
3Qiu et al., *J. Clin. Oncol.* 35:15_suppl, e22507-e22507, 2017.
[4]PCT Patent Application Publication No. WO 2016/187508A2
[5]Gainor et al., *JCO Precis Oncol.* 10.1200/PO.17.00063, 2017.
[6]The Cancer Genome Atlas: http://cancergenome.nih.gov/
[7]Wang, University of Hong Kong, Pokfulam, Hong Kong SAR (Thesis). Retrieved from http://dx.doi.org/10.5353/th_b5659723.

Additional exemplary ROS1 mutations are provided in Table 3a.

TABLE 3a

Exemplary ROS1 Mutations

Amino acid position 1186 (e.g., S1186F[11])
Amino acid position 1935 (e.g., E1935G[10])
Amino acid position 1945 (e.g., L1945Q[7])
Amino acid position 1946 (e.g., T1946S[7])
Amino acid position 1947 (e.g., L1947R[6,10], L1947M[7])
Amino acid position 1948 (e.g., R1948S[7])
Amino acid position 1951 (e.g., L1951R[5], L1951V[7])
Amino acid position 1958 (e.g., E1958V[7])
Amino acid position 1959 (e.g., V1959E[7])
Amino acid position 1961 (e.g., E1961K[7])
Amino acid position 1962 (e.g., G1962E[7])
Amino acid position 1971 (e.g., G1971E[6,10])
Amino acid position 1974 (e.g., E1974K[9])
Amino acid position 1981 (e.g., T1981M[7])
Amino acid position 1982 (e.g., L1982F[5,10], L1982R[6])
Amino acid position 1986 (e.g., S1986Y[1], S1986F[1])
Amino acid position 1990 (e.g., E1990G[5], E1990L[7])
Amino acid position 1993 (e.g., E1993K[7])
Amino acid position 1994 (e.g., F1994L[5])
Amino acid position 2000 (e.g., L2000V[7])
Amino acid position 2002 (e.g., S2002N[7])
Amino acid position 2004 (e.g., F2004L[7], F2004I[9], F2004V[9], F2004C[9])
Amino acid position 2008 (e.g., N2008H[7])
Amino acid position 2009 (e.g., I2009L[7])
Amino acid position 2010 (e.g., L2010M[7])
Amino acid position 2011 (e.g., K2011N[7])
Amino acid position 2016 (e.g., C2016G[7])
Amino acid position 2019 (e.g., N2019D[7], N2019Y[7])
Amino acid position 2020 (e.g., E2020k[9])
Amino acid position 2022 (e.g., Q2022H[7])
Amino acid position 2026 (e.g., L2026M[3])
Amino acid position 2028 (e.g., L2028M[7])
Amino acid position 2029 (e.g., M2029K[7])

TABLE 3a-continued

Exemplary ROS1 Mutations

Amino acid position 2030 (e.g., E2030K[7])
Amino acid position 2032 (e.g., G2032R[2])
Amino acid position 2033 (e.g., D2033G[7], D2033N[8])
Amino acid position 2035 (e.g., L2035I[7])
Amino acid position 2036 (e.g., T2036I[7], T2036N[7])
Amino acid position 2039 (e.g., R2039G[7], R2039H[7], R2039M[7], R2039N[7], R2039S[7])
Amino acid position 2040 (e.g., K2040E[7], K2040Q[7])
Amino acid position 2052 (e.g., T2052S[7])
Amino acid position 2059 (e.g., L2059P[7])
Amino acid position 2060 (e.g., C2060G[6,10])
Amino acid position 2075 (e.g., F2075C[9], F2075I[9], F2075V[9])
Amino acid position 2077 (e.g., H2077P[7])
Amino acid position 2078 (e.g., R2078W[7])
Amino acid position 2087 (e.g., V2087I[7])
Amino acid position 2091 (e.g., D2091N[7])
Amino acid position 2092 (e.g., Y2092N[7])
Amino acid position 2094 (e.g., S2094N[7])
Amino acid position 2098 (e.g., V2098I[6,10])
Amino acid position 2099 (e.g., K2099N[7])
Amino acid position 2100 (e.g., I2100V[7])
Amino acid position 2101 (e.g., G2101A[7])
Amino acid position 2106 (e.g., A2106P[7])
Amino acid position 2107 (e.g., R2107T[7])
Amino acid position 2112 (e.g., N2112K[9])
Amino acid position 2113 (e.g., D2113N[9] D2113G[9])
Amino acid position 2116 (e.g., R2116T[7], R2116K[9])
Amino acid position 2125 (e.g., V2125G[7], V2125L[7])
Amino acid position 2127 (e.g., W2127G[7], W2127[9])
Amino acid position 2128 (e.g., M2128T[9])
Amino acid position 2131 (e.g., E2131D[7], E2131K[7])
Amino acid position 2134 (e.g., M2134I[7])
Amino acid position 2139 (e.g., T2139I[7], T2139S[7])
Amino acid position 2141 (e.g., Q2141H[7])
Amino acid position 2142 (e.g., S2142Y[7])
Amino acid position 2148 (e.g., G2148E[7])
Amino acid position 2151 (e.g., I2151N[7])
Amino acid position 2154 (e.g., I2154M[7])
Amino acid position 2155 (e.g., L2155S[4])
Amino acid position 2160 (e.g., Q2160H[7])
Amino acid position 2165 (e.g., H2165D[7])
Amino acid position 2181 (e.g., E2181D[7])
Amino acid position 2184 (e.g., R2184T[7])
Amino acid position 2201 (e.g., E2201D[7])
Amino acid position 2205 (e.g., R2205I[7])
Amino acid position 2207 (e.g., T2207I[7])
Amino acid position 2209 (e.g., H2209P[7])
Amino acid position 2212 (e.g., Q2212H[7], Q2212P[7])
Amino acid position 2223 (e.g., L2223[9])
Amino acid position 2224 (e.g., N2224K[9])

[1]Facchinetti et al., Clin. Cancer Res., DOI: 10.1158/1078-0432.CCR-16-0917, 2016.
[2]Awad et al., N. Engl. J. Med., 368(25): 2395-401, 2013.
[3]Zou et al., Proc. Natl. Acad. Sci. U.S.A., 112(11): 3493-8, 2015.
[4]Song et al., Clin. Cancer Res., 21(10): 2379-87, 2015.
[5]Katayama et al., Clin. Cancer Res., 21(1): 166-74, 2015.
[6]PCT Patent Application Publication No. WO 2014/134096A1.
[7]PCT Patent Application Publication No. WO 2014/152777A2.
[8]Drilon et al., Clin. Cancer Res., 22(10): 2351-8, 2016.
[9]Davare et al., Proc. Natl. Acad. Sci. U.S.A., 112(39): E5381-90, 2015.
[10]Davare et al., Proc. Natl. Acad. Sci. U.S.A., 110(48): 19519-24, 2013.
[11]Gainor et al., JCO Precis Oncol. 10.1200/PO.17.00063, 2017.

In some embodiments, the dysregulation of a ROS1 gene, a ROS1 kinase, or expression or activity or level of any of the same, includes a splice variation in a ROS1 mRNA which results in an expressed protein that is an alternatively spliced variant of ROS1 having at least one residue deleted (as compared to the wild-type ROS1 kinase) resulting in a constitutive activity of a ROS1 kinase domain. In some embodiments, the dysregulation of a ROS1 gene, a ROS1 kinase, or expression or activity or level of any of the same, includes a splice variation in a ROS1 mRNA which results in an expressed protein that is an alternatively spliced variant of ROS1 having at least one residue added (as compared to the wild-type ROS1 kinase) resulting in a constitutive activity of a ROS1 kinase domain.

A "ROS1 kinase inhibitor" as defined herein includes any compound exhibiting ROS1 inhibition activity. In some embodiments, a ROS1 kinase inhibitor is selective for a wild type and/or mutant ROS1 kinase. In some embodiments, ROS1 kinase inhibitors can exhibit inhibition activity ($IC_{50}$) against a ROS1 kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a ROS1 kinase inhibitors can exhibit inhibition activity ($IC_{50}$) against a ROS1 kinase of less than about 25 nM, less than about 10 nM, less than about 5 nM, or less than about 1 nM as measured in an assay as provided herein. In some embodiments, the ROS1 kinase inhibitor is a compound of Formula I.

As used herein, a "first ROS1 kinase inhibitor" or "first ROS1 inhibitor" is a ROS1 kinase inhibitor as defined herein, but which does not include a compound of Formula I or a pharmaceutically acceptable salt or solvate thereof as defined herein. As used herein, a "second ROS1 kinase inhibitor" or a "second ROS1 inhibitor" is a ROS1 kinase inhibitor as defined herein. In some embodiments, a second ROS1 inhibitor does not include a compound of Formula I or a pharmaceutically acceptable salt or solvate thereof as defined herein. When more than one ROS1 inhibitor is present in a method provided herein (e.g., both a first and a second ROS1 inhibitor are present in a method provided herein), the two ROS1 inhibitors are different (e.g., the first and second ROS1 kinase inhibitor are different). As provided herein, different ROS1 inhibitors are structurally distinct from one another.

In some embodiments, the dysregulation of a ROS1 gene, a ROS1 kinase, or expression or activity or level of any of the same, includes at least one point mutation in a ROS1 gene that results in the production of a ROS1 kinase that has one or more amino acid substitutions or insertions or deletions as compared to the wild-type ROS1 kinase. In some cases, the resulting ROS1 kinase is more resistant to inhibition of its phosphotransferase activity by one or more first ROS1 kinase inhibitor(s), as compared to a wildtype ROS1 kinase or a ROS1 kinase not including the same mutation. Such mutations, optionally, do not decrease the sensitivity of the cancer cell or tumor having the ROS1 kinase to treatment with a compound of Formula I or a pharmaceutically acceptable salt or solvate thereof (e.g., as compared to a cancer cell or a tumor that does not include the particular ROS1 inhibitor resistance mutation). In such embodiments, a ROS1 inhibitor resistance mutation can result in a ROS1 kinase that has one or more of an increased $V_{max}$, a decreased $K_m$ for ATP, and an increased $K_D$ for a first ROS1 kinase inhibitor, when in the presence of a first ROS1 kinase inhibitor, as compared to a wildtype ROS1 kinase or a ROS1 kinase not having the same mutation in the presence of the same first ROS1 kinase inhibitor.

In other embodiments, the dysregulation of a ROS1 gene, a ROS1 kinase, or expression or activity or level of any of the same, includes at least one point mutation in a ROS1 gene that results in the production of a ROS1 kinase that has one or more amino acid substitutions as compared to the wild-type ROS1 kinase, and which has increased resistance to a compound of Formula I or a pharmaceutically acceptable salt or solvate thereof, as compared to a wildtype ROS1 kinase or a ROS1 kinase not including the same mutation. In such embodiments, a ROS1 inhibitor resistance mutation can result in a ROS1 kinase that has one or more of an increased $V_{max}$, a decreased $K_m$, and a decreased $K_D$ in the presence of a compound of Formula I or a pharmaceutically acceptable salt or solvate thereof, as compared to a wildtype ROS1 kinase or a ROS1 kinase not having the same mutation in the presence of the same compound of Formula I or a pharmaceutically acceptable salt or solvate thereof.

Examples of ROS1 inhibitor resistance mutations can, e.g., include point mutations, insertions, or deletions in and near the ATP binding site in the tertiary structure of ROS1 kinase, including but not limited to the gatekeeper residue, P-loop residues, residues in or near the DFG motif, and ATP cleft solvent front amino acid residues. Additional examples of these types of mutations include changes in residues that may affect enzyme activity and/or drug binding including but are not limited to residues in the activation loop, residues near or interacting with the activation loop, residues contributing to active or inactive enzyme conformations, changes including mutations, deletions, and insertions in the loop proceeding the C-helix and in the C-helix. Specific residues or residue regions that may be changed (e.g., ROS1 inhibitor resistance mutations) include but are not limited to those listed in Table 4 based on the human wildtype ROS1 protein sequence (e.g., SEQ ID NO: 1). Changes to these residues may include single or multiple amino acid changes, insertions within or flanking the sequences, and deletions within or flanking the sequences.

In some embodiments, compounds of Formula I and pharmaceutically acceptable salts and solvates are useful in treating patients that develop cancers with ROS1 inhibitor resistance mutations (e.g., that result in an increased resistance to a first ROS1 inhibitor, e.g., a substitution at amino acid position 2032 (e.g., G2032R), amino acid position 2026 (e.g., L2026M), amino acid position 2033 (e.g., D2033N), and/or one or more ROS1 inhibitor resistance mutations listed in Table 4) by either dosing in combination or as a follow-up therapy to existing drug treatments (e.g., ALK kinase inhibitors, TRK kinase inhibitors, other ROS1 kinase inhibitors, e.g., first and/or second ROS1 kinase inhibitors). Exemplary ALK kinase inhibitors are described herein. Exemplary TRK kinase inhibitors are described herein. Exemplary first and second ROS1 kinase inhibitors are described herein. In some embodiments, a first or second ROS1 kinase inhibitor can be selected from the group consisting of alectinib, brigatinib, cabozantinib, ceritinib, crizotinib, entrectinib, foretinib, lorlatinib, and mesestinib.

In some embodiments, compounds of Formula I or pharmaceutically acceptable salts and solvates thereof are useful for treating a cancer that has been identified as having one or more ROS1 inhibitor resistance mutations (that result in an increased resistance to a first or second ROS1 inhibitor, e.g., a substitution at amino acid position 2032 (e.g., G2032R), amino acid position 2026 (e.g., L2026M), amino acid position 2033 (e.g., D2033N)). Non-limiting examples of ROS1 inhibitor resistance mutations are listed in Table 4.

TABLE 4

Exemplary ROS1 Mutations

Amino acid position 1186 (e.g., S1186F[11])
Amino acid position 1935 (e.g., E1935G6[10])
Amino acid position 1945 (e.g., L1945Q[7])
Amino acid position 1946 (e.g., T1946S[7])
Amino acid position 1947 (e.g., L1947R[6,10], L1947M[7])
Amino acid position 1948 (e.g., R1948S[7])
Amino acid position 1951 (e.g., L1951R[5], L1951V[7])
Amino acid position 1958 (e.g., E1958V[7])

TABLE 4-continued

Exemplary ROS1 Mutations

Amino acid position 1959 (e.g., V1959E[7])
Amino acid position 1961 (e.g., E1961K[7])
Amino acid position 1962 (e.g., G1962E[7])
Amino acid position 1971 (e.g., G1971E[6,10])
Amino acid position 1974 (e.g., E1974K[9])
Amino acid position 1981 (e.g., T1981M[7])
Amino acid position 1982 (e.g., L1982F[5,10], L1982R[6])
Amino acid position 1986 (e.g., S1986Y[1], S1986F[1])
Amino acid position 1990 (e.g., E1990G[5], E1990L[7])
Amino acid position 1993 (e.g., E1993K[7])
Amino acid position 1994 (e.g., F1994L[5])
Amino acid position 2000 (e.g., L2000V[7])
Amino acid position 2002 (e.g., S2002N[7])
Amino acid position 2004 (e.g., F2004L[7], F2004I[9], F2004V[9], F2004C[9])
Amino acid position 2008 (e.g., N2008H[7])
Amino acid position 2009 (e.g., I2009L[7])
Amino acid position 2010 (e.g., L2010M[7])
Amino acid position 2011 (e.g., K2011N[7])
Amino acid position 2016 (e.g., C2016G[7])
Amino acid position 2019 (e.g., N2019D[7], N2019Y[7])
Amino acid position 2020 (e.g., E2020k[9])
Amino acid position 2022 (e.g., Q2022H[7])
Amino acid position 2026 (e.g., L2026M[3])
Amino acid position 2028 (e.g., L2028M[7])
Amino acid position 2029 (e.g., M2029K[7])
Amino acid position 2030 (e.g., E2030K[7])
Amino acid position 2032 (e.g., G2032R[2])
Amino acid position 2033 (e.g., D2033G[7], D2033N[8])
Amino acid position 2035 (e.g., L2035I[7])
Amino acid position 2036 (e.g., T2036I[7], T2036N[7])
Amino acid position 2039 (e.g., R2039G[7], R2039H[7], R2039M[7], R2039N[7], R2039S[7])
Amino acid position 2040 (e.g., K2040E[7], K2040Q[7])
Amino acid position 2052 (e.g., T2052S[7])
Amino acid position 2059 (e.g., L2059P[7])
Amino acid position 2060 (e.g., C2060G[6,10])
Amino acid position 2075 (e.g., F2075C[9], F2075I[9], F2075V[9])
Amino acid position 2077 (e.g., H2077P[7])
Amino acid position 2078 (e.g., R2078W[7])
Amino acid position 2087 (e.g., V2087I[7])
Amino acid position 2091 (e.g., D2091N[7])
Amino acid position 2092 (e.g., Y2092N[7])
Amino acid position 2094 (e.g., S2094N[7])
Amino acid position 2098 (e.g., V2098I[6,10])
Amino acid position 2099 (e.g., K2099N[7])
Amino acid position 2100 (e.g., I2100V[7])
Amino acid position 2101 (e.g., G2101A[7])
Amino acid position 2106 (e.g., A2106P[7])
Amino acid position 2107 (e.g., R2107T[7])
Amino acid position 2112 (e.g., N2112K[9])
Amino acid position 2113 (e.g., D2113N[9] D2113G[9])
Amino acid position 2116 (e.g., R2116T[7], R2116K[9])
Amino acid position 2125 (e.g., V2125G[7], V2125L[7])
Amino acid position 2127 (e.g., W2127G[7], W2127[9])
Amino acid position 2128 (e.g., M2128T[9])
Amino acid position 2131 (e.g., E2131D[7], E2131K[7])
Amino acid position 2134 (e.g., M2134I[7])
Amino acid position 2139 (e.g., T2139I[7], T2139S[7])
Amino acid position 2141 (e.g., Q2141H[7])
Amino acid position 2142 (e.g., S2142Y[7])
Amino acid position 2148 (e.g., G2148E[7])
Amino acid position 2151 (e.g., I2151N[7])
Amino acid position 2154 (e.g., I2154M[7])
Amino acid position 2155 (e.g., L2155S[4])
Amino acid position 2160 (e.g., Q2160H[7])
Amino acid position 2165 (e.g., H2165D[7])
Amino acid position 2181 (e.g., E2181D[7])
Amino acid position 2184 (e.g., R2184T[7])
Amino acid position 2201 (e.g., E2201D[7])
Amino acid position 2205 (e.g., R2205I[7])
Amino acid position 2207 (e.g., T2207I[7])
Amino acid position 2209 (e.g., H2209P[7])

TABLE 4-continued

Exemplary ROS1 Mutations

Amino acid position 2212 (e.g., Q2212H[7], Q2212P[7])
Amino acid position 2223 (e.g., L2223[9])
Amino acid position 2224 (e.g., N2224K[9])

[1]Facchinetti et al., *Clin. Cancer Res.*, DOI: 10.1158/1078-0432.CCR-16-0917, 2016.
[2]Awad et al., *N. Engl. J. Med.*, 368(25): 2395-401, 2013.
[3]Zou et al., *Proc. Natl. Acad. Sci. U.S.A.*, 112(11): 3493-8, 2015.
[4]Song et al., *Clin. Cancer Res.*, 21(10): 2379-87, 2015.
[5]Katayama et al., *Clin. Cancer Res.*, 21(1): 166-74, 2015.
[6]PCT Patent Application Publication No. WO 2014/134096A1.
[7]PCT Patent Application Publication No. WO 2014/152777A2.
[8]Drilon et al., *Clin. Cancer Res.*, 22(10): 2351-8, 2016.
[9]Davare et al., *Proc. Natl. Acad. Sci. U.S.A.*, 112(39): E5381-90, 2015.
[10]Davare et al., *Proc. Natl. Acad. Sci. U.S.A.*, 110(48): 19519-24, 2013.
[11]Gainor et al., *JCO Precis Oncol.* 10.1200/PO.17.00063, 2017.

The ROS1 proto-oncogene is expressed in a variety of tumor types, and belongs to the sevenless subfamily of tyrosine kinase insulin receptor genes. The protein encoded by this gene is a type I integral membrane protein with tyrosine kinase activity. ROS1 shares structural similarity with the anaplastic lymphoma kinase (ALK) protein. Gene rearrangements involving ROS1 have been identified in a variety of cancers. The small molecule tyrosine kinase inhibitor, crizotinib, has been approved for the treatment of patients with metastatic NSCLC whose tumors are ROS1-positive or ALK-positive. Although the most preclinical and clinical studies of ROS1 gene fusions have been performed in lung cancer, ROS1 fusions have been detected in multiple other tumor histologies, including ovarian carcinoma, sarcoma, cholangiocarcinomas and others.

ALK is a receptor tyrosine kinase that belongs to the insulin growth factor receptor superfamily. ALK is believed to play a role in the development of the nervous system. A variety of ALK gene fusions have been described, such as EML4, KIF5B, KLC1, and TRK-fused gene (TFG). Such fusion products result in kinase activation and oncogenesis. Non-small-cell lung cancer (NSCLC) harboring the anaplastic lymphoma kinase gene (ALK) rearrangement is sensitive to the small molecule tyrosine kinase inhibitor crizotinib, which is an inhibitor of ALK and ROS1.

In some embodiments, the additional therapeutic agent(s) includes any one of the above listed therapies or therapeutic agents which are standards of care in cancers wherein the cancer has a dysregulation of a ROS1 gene, a ROS1 protein, or expression or activity, or level of any of the same. In some embodiments, the additional therapeutic agent(s) includes any one of the above listed therapies or therapeutic agents which are standards of care in cancers wherein the cancer has a dysregulation of an ALK gene, an ALK protein, or expression or activity, or level of any of the same (e.g., an ALK-associated cancer). In some embodiments, the additional therapeutic agent(s) includes any one of the above listed therapies or therapeutic agents which are standards of care in cancers wherein the cancer has a dysregulation of a TRK gene, a TRK protein, or expression or activity, or level of any of the same (e.g., a TRK-associated cancer).

The term "ALK-associated cancer" as used herein refers to cancers associated with or having a dysregulation of an ALK gene, an ALK protein, or expression or activity, or level of any of the same. Exemplary ALK-associated cancers are provided herein.

The phrase "dysregulation of an ALK gene, an ALK kinase, or the expression or activity or level of any of the same" refers to a genetic mutation (e.g., an ALK gene translocation that results in the expression of a fusion protein, a deletion in an ALK gene that results in the expression of an ALK protein that includes a deletion of at least one amino acid as compared to the wild-type ALK protein, a mutation in an ALK gene that results in the expression of an ALK protein with one or more point mutations, or an alternative spliced version of an ALK mRNA that results in an ALK protein having a deletion of at least one amino acid in the ALK protein as compared to the wild-type ALK protein) or an ALK gene amplification that results in overexpression of an ALK protein or an autocrine activity resulting from the overexpression of an ALK gene in a cell that results in a pathogenic increase in the activity of a kinase domain of an ALK protein (e.g., a constitutively active kinase domain of an ALK protein) in a cell. As another example, a dysregulation of an ALK gene, an ALK protein, or expression or activity, or level of any of the same, can be a mutation in an ALK gene that encodes an ALK protein that is constitutively active or has increased activity as compared to a protein encoded by an ALK gene that does not include the mutation. For example, a dysregulation of an ALK gene, an ALK protein, or expression or activity, or level of any of the same, can be the result of a gene or chromosome translocation which results in the expression of a fusion protein that contains a first portion of ALK that includes a functional kinase domain, and a second portion of a partner protein that is not ALK. In some examples, dysregulation of an ALK gene, an ALK protein, or expression or activity or level of any of the same can be a result of a gene translocation of one ALK gene with another non-ALK gene. Non-limiting examples of fusion proteins are described in Table 5. Additional examples of ALK kinase protein mutations (e.g., point mutations) are ALK inhibitor resistance mutations.

The term "wildtype" or "wild-type" when referring to an ALK nucleic acid or protein describes a nucleic acid (e.g., an ALK gene or an ALK mRNA) or protein (e.g., an ALK protein) that is found in a subject that does not have an ALK-associated disease, e.g., an ALK-associated cancer (and optionally also does not have an increased risk of developing an ALK-associated disease and/or is not suspected of having an ALK-associated disease), or is found in a cell or tissue from a subject that does not have an ALK-associated disease, e.g., an ALK-associated cancer (and optionally also does not have an increased risk of developing an ALK-associated disease and/or is not suspected of having an ALK-associated disease).

In some embodiments, the dysregulation of an ALK gene, an ALK kinase protein, or expression or activity or level of any of the same, includes one or more chromosome translocations or inversions resulting in an ALK gene fusion. In some embodiments, the dysregulation of an ALK gene, an ALK kinase protein, or expression or activity or level of any of the same, is a result of genetic translocations in which the expressed protein is a fusion protein containing residues from a non-ALK partner protein, and includes a minimum of a functional ALK kinase domain.

Non-limiting examples of ALK fusion proteins are shown in Table 5.

TABLE 5

Exemplary ALK Fusion Proteins

| ALK Partner | ALK-Associated Cancer |
| --- | --- |
| NPM/NPM1 | Anaplastic large cell lymphoma[1], Diffuse large B-cell lymphoma[1], Neuroblastoma[8], Lung adenocarcinoma[9] |

TABLE 5-continued

Exemplary ALK Fusion Proteins

| ALK Partner | ALK-Associated Cancer |
|---|---|
| ALO17/RNF213 | Anaplastic large cell lymphoma[1] |
| TFG (e.g., TFGs, TFG$_L$, TFG$_{XL}$)[38] | Anaplastic large cell lymphoma[1], Non-small cell lung cancer[1], Anaplastic thyroid carcinoma[1] |
| MSN (e.g., MSNa and MSNb)[38] | Anaplastic large cell lymphoma[1] |
| TPM3 | Anaplastic large cell lymphoma[1], Inflammatory myofibroblastic tumour[1], Renal medulla carcinoma/renal cell carcinoma[1], Spitzoid neoplasm[5] |
| TPM4 (e.g., type 1 and type 2)[38] | Anaplastic large cell lymphoma[1], Inflammatory myofibroblastic tumour[1], Oesophageal squamous cell carcinoma[1] |
| ATIC | Anaplastic large cell lymphoma[1], Inflammatory myofibroblastic tumour[1] |
| MYH9 | Anaplastic large cell lymphoma[1] |
| CLTC | Anaplastic large cell lymphoma[1], Inflammatory myofibroblastic tumour[1], Diffuse large B-cell lymphoma[1] |
| TRAF1 | Anaplastic large cell lymphoma[1] |
| EML4* | Non-small cell lung cancer[1], Renal medulla carcinoma/renal cell carcinoma[1], Breast cancer[1], Colon cancer[1], Anaplastic thyroid carcinoma[1], Squamous cell carcinoma[14], Lung adenocarcinoma[18], Colorectal Adenocarcinoma[19] |
| KIF5B | Non-small cell lung cancer[1] |
| KLC1 | Non-small cell lung cancer[1] |
| PTPN3 | Non-small cell lung cancer[1] |
| HIP1 | Non-small cell lung cancer[1] |
| TPR | Non-small cell lung cancer[1] |
| STRN | Non-small cell lung cancer[1], Anaplastic thyroid carcinoma[1], Colorectal Adenocarcinoma[19], Renal Cell Carcinoma[20] |
| SEC31A/ SEC31L1[38] (e.g., type 1 and type2)[38] | Inflammatory myofibroblastic tumour[1], Diffuse large B-cell lymphoma[1], Lung adenocarcinoma[21] |
| RANBP2 | Inflammatory myofibroblastic tumour[1], Pediatric acute myeloid leukemia[11] |
| PPFIBP1 | Inflammatory myofibroblastic tumour[1] |
| CARS | Inflammatory myofibroblastic tumour[1] |
| SQSTM1 | Diffuse large B-cell lymphoma[1] |
| VCL | Renal medulla carcinoma/renal cell carcinoma[1] |
| C2orf44 | Colon cancer[1] |
| FN1 | Serous ovarian carcinoma[1], Gastrointestinal leiomyoma[36] |
| GFPT1 | Anaplastic thyroid carcinoma[1] |
| KIAA1618 | Blood Cancer[2] |
| MEL4 | Unspecified[3] |
| ROS1 | Unspecified[4] |
| DCTN1 | Spitzoid neoplasm[5], Sarcoma[26] |
| MDCF2 | Lung adenocarcinoma[6] |
| STK32B | Breast cancer[6] |
| TPM1 | Unspecified[7] |
| PRKAR1A | Unspecified[7] |
| NCOA1 | Unspecified[7] |
| GTF2IRD1 | Unspecified[7] |
| CLTCL1 | Neuroblastoma[8] |
| LMNA | Neuroblastoma[8] |
| PRKAR1A | Neuroblastom[8], Non-small cell lung cancer[15], Colorectal Adenocarcinoma[19] |
| SPTBN1 | Lung adenocarcinoma[10] |
| EIF2AK3 | Lung adenocarincoma[12], Non-small cell lung cancer[15] |
| EML4-EXOC6B | Lung adenocarincoma[13] |
| PPM1B | Non-small cell lung cancer[15] |
| MALAT1 (lncRNA gene fusion) | Triple-negative breast cancer[16] |
| HOOK1 | Renal cell carcinoma[17] |
| CAD | Colorectal Adenocarcinoma[19] |
| PPP1T21 | Colorectal Adenocarcinoma[19] |
| SENPF | Colorectal Adenocarcinoma[19] |
| MAPRE3 | Colorectal Adenocarcinoma[19] |
| SPDYA | Non-small cell lung cancer[22] |
| ASXL2 | Non-small cell lung cancer[22] |
| IGL@ | Diffuse large B-cell lymphoma[23] |
| PPP1R21 | Colorectal Adenocarcinoma[24] |
| PRKAP1B | Colorectal Adenocarcinoma[24] |
| BIRC6 | Non-small cell lung cancer[25] |
| PICALM | Non-small cell lung cancer[25] |
| KCL | Lung adenocarcinoma[27] |
| CRIM1 | Non-small cell lung cancer[28] |
| EEF1G | Anaplastic large cell lymphoma[29] |
| DCTN1 | Advanced Sarcoma[30], Inflammatory myofibroblastic tumor[33], Spitzoid tumors[33] |
| GTF2IRD1 | Pediatric, adolescent and young adult (PAYA) thyroid carcinoma[31] |
| BEND5 | Neuroblastoma[32] |
| PPP1CB | Astrocytoma[32] |
| CUX | Non-small-cell Lung cancer[34] |
| FAM179A | Non-small-cell Lung cancer[35] |
| COL25A1 | Non-small-cell Lung cancer[35] |
| BIRC6 | Non-small-cell Lung Cancer[37] |
| PICALM | Non-small-cell Lung Cancer[37] |
| GTF3C2 | Spitz tumor[39] |
| IGFBP5 | Soft Tissue Sarcoma[40] |
| MYO18A | Adenosarcoma[41] |

*There are a number of different ALK-EML4 fusion variants: 1, 2, 3a, 3b, 4, 5a, 5b, 6, 7, 8a, 8b, 4', 5' (Ann. Oncol., 27(3): iii6-iii24, 2016)
[1]Hallberg and Palmer, Ann. Oncology, 27 (Suppl 3): iii4-iii15. doi: 10.1093/annonc/mdw301, 2016.
[2]U.S. Pat. Publication No. 9,469,876B2.
[3]U.S. Pat. Application Publication No. 2016/0145237A1.
[4]U.S. Pat. Application Publication No. 2016/0108123A1.
[5]U.S. Pat. Application Publication No. 2016/0010068A1.
[6]U.S. Pat. Application Publication No. 2016/00009785A1.
[7]European Patent Application Publication No. 2986736A2.
[8]Katayama, et al. Clin Cancer Res, 21(10):2227-35, May 2015.
[9]Dacic et al., Oncotarget, 2016: doi: 10.18632/oncotarget.12705.
[10]Gu et al., J Hematol Oncol, 9(1): 66, 2016.
[11]Hayashi et al., Blood Cancer J, 6(8): e456, 2016.
[12]Won et al., BMC Cancer, 16:568, 2016.
[13]Ma et al., Oncotarget, 2016, doi: 10.18632/oncotarget.10560.
[14]Yamamoto et al., Mol Clin. Oncol. 5(1): 61-63, 2016.
[15]Ali et al., Oncologist, 21(6): 762-70, 2016.
[16]Shaver et al., Cancer Res, 76(16): 4850-60, 2016.
[17]Cajaiba et al., Genes Chromosomes Cancer, 55(10): 814-7, 2016.
[18]Hainsworth et al., Drugs Real World Outcomes, 3:115-120, 2016.
[19]Yakirevich et al., Clin Cancer Res, 22(15): 3831-40, 2016.
[20]Kusano, Am J. Surg Pathol. 40(6): 761-9, 2016.
[21]Kim et al., Cancer Res Treat, 48(1): 298-402, 2016.
[22]Rosenbaum et al.,Laboratory Investigation, Vol. 96, Supp. SUPPL. 1, pp. 481A-482A, Abstract Number: 1914, 105th Annual Meeting of the United States and Canadian Academy of Pathology, Seattle, WA, 2016.
[23]Pan et al., Laboratory Investigation, Vol. 96, Supp. SUPPL. 1, pp. 367A, Abstract Number: 1450, 105th Annual Meeting of the United States and Canadian Academy of Pathology, Seattle, WA, 2016.
[24]Yakirevich et al., Laboratory Investigation, Vol. 96, Supp. SUPPL. 1, pp. 209A, Abstract Number: 827, 105th Annual Meeting of the United States and Academy of Pathology, Seattle, WA, 2016.
[25]Ying et al., J. Clin. Oncology, Vol. 34, Supp. Supplement 15, Abstract Number: e20506, 2016 Annual Meeting of the American Society of Clinical Oncology, Chicago, IL, 2016.
[26]Groisberg et al., J. Clin. Oncology, Vol. 34, Supp. Supplement 15, Abstract Number: 11046, 2016 Annual Meeting of the American Society of Clinical Oncology, Chicago, IL, 2016.
[27]Ihuegby et al., J. Clin. Oncology, Vol. 34, Supp. Supplement 15, Abstract Number: e20643, 2016 Annual Meeting of the American Society of Clinical Oncology, Chicago, IL, 2016.
[28]Tan et al., J. Clin. Oncology, Vol. 34, Supp. Supplement 15, Abstract Number: 9064, 2016 Annual Meeting of the American Society of Clinical Oncology, Chicago, IL, 2016.

TABLE 5-continued

Exemplary ALK Fusion Proteins

| ALK Partner | ALK-Associated Cancer |
|---|---|

[29]Wlodarska et al., *Blood*, Vol. 126(23): 3654, 57th Annual Meeting of the American Society of Hematology, San Diego, CA, 2015.
[30]Groisberg et al., *Journal of Clinical Oncology*, Vol. 34, Supp. Supplement 15; Abstract Number: 11046; 2016 Annual Meeting of the American Society of Clinical Oncology, ASCO 2016, Chicago, IL. 3-7 June 2016.
[31]Vanden et al., *Annals of Oncology*, Vol. 27, Supp. Supplement 6. Abstract Number: 427PD' 41st European Society for Medical Oncology Congress, ESMO 2016; Copenhagen, Denmark; 7-11 October 2016.
[32]Chmielecki et al., *Cancer Research*, 2017 Jan. 9. doi: 10.1158/0008-5472.CAN-16-1106.
[33]Holla et al., Cold Spring Harb Mol Case Stud, 2017 Jan;3(1): a001115. doi: 10.1101/mcs.a001115.
[34]Yu et al., *Oncotarget*, 2016 Dec. 10. doi: 10.18632/oncotarget.13886.
[35]Cui et al., *Oncotarget*. 2016 Dec. 1. doi: 10.18632/oncotarget.13741.
[36]Panagopoulos et al., *Modern Pathology* 29: 1415-1423, 2016
[37]Li et al., *J. Thorac. Oncol.* 2017 Jan;12(1): 94-101. doi: 10.1016/j.jtho.2016.08.145.
[38]European Patent Application Number EP2558490B1.
[39]PCT Application No. WO2017001491A2.
[40]Chmielecki et al., *Cancer Research*, Vol. 76, No. 14, Supp. Supplement. Abstract Number: LB-178. 107th Annual meeting of the American Association for Cancer Research, AACR. New Orleans, LA. April 16-20 2016.
[41]Majweska et al., *Cancer Research*, Vol. 76, No. 14, Supp. Supplement. Abstract Number: 3190. 107th Annual meeting of the American Association for Cancer Research, AACR. New Orleans, LA. April 16-20 2016.

In some embodiments, the dysregulation of an ALK gene, an ALK kinase, or expression or activity or level of any of the same, includes at least one point mutation in an ALK gene that results in the production of an ALK kinase that has one or more amino acid substitutions, insertions, or deletions as compared to the wild-type ALK kinase.

In some embodiments, an ALK-associated cancer has been identified as having one or more ALK inhibitor resistance mutations (that result in an increased resistance to an ALK inhibitor.

Tropomyosin-related kinase (TRK) is a receptor tyrosine kinase family of neurotrophin receptors that are found in multiple tissues types. Three members of the TRK proto-oncogene family have been described: TrkA, TrkB, and TrkC, encoded by the NTRK1, NTRK2, and NTRK3 genes, respectively. The TRK receptor family is involved in neuronal development, including the growth and function of neuronal synapses, memory development, and maintenance, and the protection of neurons after ischemia or other types of injury (Nakagawara, *Cancer Lett.* 169:107-114, 2001).

TRK was originally identified from a colorectal cancer cell line as an oncogene fusion containing 5' sequences from tropomyosin-3 (TPM3) gene and the kinase domain encoded by the 3' region of the neurotrophic tyrosine kinase, receptor, type 1 gene (NTRK1) (Pulciani et al., *Nature* 300:539-542, 1982; Martin-Zanca et al., *Nature* 319:743-748, 1986). TRK gene fusions follow the well-established paradigm of other oncogenic fusions, such as those involving ALK and ROS1, which have been shown to drive the growth of tumors and can be successfully inhibited in the clinic by targeted drugs (Shaw et al., *New Engl. J. Med.* 371:1963-1971, 2014; Shaw et al., *New Engl. J. Med.* 370:1189-1197, 2014). Oncogenic TRK fusions induce cancer cell proliferation and engage critical cancer-related downstream signaling pathways such as mitogen activated protein kinase (MAPK) and AKT (Vaishnavi et al., *Cancer Discov.* 5:25-34, 2015). Numerous oncogenic rearrangements involving NTRK1 and its related TRK family members NTRK2 and NTRK3 have been described (Vaishnavi et al., *Cancer Disc.* 5:25-34, 2015; Vaishnavi et al., *Nature Med.* 19:1469-1472, 2013). Although there are numerous different 5' gene fusion partners identified, all share an in-frame, intact TRK kinase domain. A variety of different Trk inhibitors have been developed to treat cancer (see, e.g., U.S. Patent Application Publication No. 62/080,374, International Application Publication Nos. WO 11/006074, WO 11/146336, WO 10/033941, and WO 10/048314, and U.S. Pat. Nos. 8,933,084, 8,791,123, 8,637,516, 8,513,263, 8,450,322, 7,615,383, 7,384,632, 6,153,189, 6,027,927, 6,025,166, 5,910,574, 5,877,016, and 5,844,092).

The term "TRK-associated cancer" as used herein refers to cancers associated with or having a dysregulation of a TRK gene, a TRK protein, or expression or activity, or level of any of the same. Exemplary TRK-associated cancers are provided herein.

The phrase "dysregulation of a TRK gene, a TRK kinase, or the expression or activity or level of any of the same" refers to a genetic mutation (e.g., a TRK gene translocation that results in the expression of a fusion protein, a deletion in a TRK gene that results in the expression of a TRK protein that includes a deletion of at least one amino acid as compared to the wild-type TRK protein, a mutation in a TRK gene that results in the expression of a TRK protein with one or more point mutations, or an alternative spliced version of a TRK mRNA that results in a TRK protein having a deletion of at least one amino acid in the TRK protein as compared to the wild-type TRK protein) or a TRK gene amplification that results in overexpression of a TRK protein or an autocrine activity resulting from the overexpression of a TRK gene in a cell that results in a pathogenic increase in the activity of a kinase domain of a TRK protein (e.g., a constitutively active kinase domain of a TRK protein) in a cell. As another example, a dysregulation of a TRK gene, a TRK protein, or expression or activity, or level of any of the same, can be a mutation in a TRK gene that encodes a TRK protein that is constitutively active or has increased activity as compared to a protein encoded by a TRK gene that does not include the mutation. For example, a dysregulation of a TRK gene, a TRK protein, or expression or activity, or level of any of the same, can be the result of a gene or chromosome translocation which results in the expression of a fusion protein that contains a first portion of TRK that includes a functional kinase domain, and a second portion of a partner protein that is not TRK. In some examples, dysregulation of a TRK gene, a TRK protein, or expression or activity or level of any of the same can be a result of a gene translocation of one TRK gene with another non-TRK gene. Non-limiting examples of fusion proteins are described in Tables 6-8. Additional examples of TRK kinase protein mutations (e.g., point mutations) are TRK inhibitor resistance mutations.

The term "wildtype" or "wild-type" when referring to a TRK nucleic acid or protein describes a nucleic acid (e.g., a TRK gene or a TRK mRNA) or protein (e.g., a TRK protein) that is found in a subject that does not have a TRK-associated disease, e.g., a TRK-associated cancer (and optionally also does not have an increased risk of developing a TRK-associated disease and/or is not suspected of having a TRK-associated disease), or is found in a cell or tissue from a subject that does not have a TRK-associated disease, e.g., a TRK-associated cancer (and optionally also does not have an increased risk of developing a TRK-associated disease and/or is not suspected of having a TRK-associated disease).

In some embodiments, the dysregulation of a TRK gene, a TRK kinase protein, or expression or activity or level of any of the same, includes one or more chromosome translocations or inversions resulting in a TRK gene fusion. In some embodiments, the dysregulation of a TRK gene, a TRK kinase protein, or expression or activity or level of any of the same, is a result of genetic translocations in which the expressed protein is a fusion protein containing residues from a non-TRK partner protein, and includes a minimum of a functional TRK kinase domain. See, for example, Tables 6-8.

TABLE 6

Exemplary TrkA Fusion Proteins and Cancers

| Fusion Protein | Non-TrkA Fusion Partner | Non-limiting Exemplary Trk- and Synonyms of Associated Cancer(s) |
|---|---|---|
| TP53-TrkA[1,11] | Tumor Protein P53 | Spitzoid Melanoma, Spitz tumors |
| LMNA-TrkA[1,12] | Lamin A/C | Spitzoid Melanoma, Spitz tumors, Undifferentiated Sarcoma, Adult Soft Tissue Sarcoma (e.g., Soft Tissue Sarcoma Metastatic to Lung), Soft Tissue Fibrosarcoma, Spindle Cell Sarcoma[G], Congenital Infantile Fibrosarcoma[H], Pediatric haemangiopericytoma-like sarcoma[I], Colorectal Cancer[K] |
| CD74-TrkA[2] | MHC class II invariant chain | Non-Small Cell Lung Cancer (NSCLC) Lung adenocarcimona |
| TFG-TrkA (TRK-T3)[3] | TRK-Fused Gene | Papillary Thyroid Carcinoma (PTC), Soft Tissue Solitary Fibrous Tumor |
| TPM3-TrkA[3] | Tropomyosin 3 | Lung Cancer, Papillary Thyroid Carcinoma (PTC), Acute Myeloid Leukemia (AML), Sarcoma, Pediatric Gliomas, Colorectal Cancer (CRC), Soft Tissue Schwannoma, Spitzoid melanocytic tumors[J] |
| NFASC-TrkA[4] | Neurofascin | Gliobastoma multiforme (GBM); Glioblastoma |
| BCAN-TrkA[4] | Brevican | Glioblastoma multiforme (GBM) |
| MPRIP-TrkA[5,E] | Myosin Phosphatase Rho Interacting Protein or Rho Interacting Protein 3 | Non-small cell lung cancer (NSCLC), Lung adenocarcinoma |
| TPR-TrkA (TRK-T1 or TRK-T2)[3] | Translocated Promoter Region, Nuclear Basket Protein | Papillary Thyroid Carcinoma (PTC), Colorectal Cancer (CRC)[4], Non-small cell lung cancer (NSCLC) |
| RFWD2-TrkA[6] | Ring Finger and WD Repeat Domain 2 | Large Cell Neuroendrocine Cancer (LCNEC); NSCLC |
| IRF2BP2-TrkA[7] | Interferon Regulatory Factor 2 Binding Protein 2 | Thyroid Cancer; Thyroid Gland Carcinoma |
| SQSTM1-TrkA[7] | Sequestosome 1 | Thyroid Cancer (e.g., Papillary Thyroid Cancer), Thyroid Gland Carcinoma, Soft TissueFibrosarcoma, Non-small-cell lung cancer[L] |
| SSBP2-TrkA[7] | Single-Stranded DNA Binding Protein 2 | Thyroid Cancer (e.g., Papillary Thyroid Cancer); Thyroid Gland Carcinoma |
| RABGAP1L-TrkA[8] | RAB GTPase Activating Protein 1-Like | Intrahepatic Cholangicarcinoma (ICC) |
| C18ORF8-TrkA[9] | Chromosome 18 Open Reading Frame 8 | Non-Small Cell Lung Cancer (NSCLC) |
| RNF213-TrkA[9] | Ring Finger Protein 213 | Non-Small Cell Lung Cancer (NSCLC) |
| TBC1D22A-TrkA[9] | TBC1 Domain Family, Member 22A | Non-Small Cell Lung Cancer (NSCLC) |
| C20ORF112-TrkA[9] | Chromosome 20 Open Reading Frame 112 | Non-Small Cell Lung Cancer (NSCLC) |
| DNER-TrkA[9] | Delta/Notch-Like EGF Repeat Containing | Non-Small Cell Lung Cancer (NSCLC) |
| ARHGEF2-TrkA[13] | Rho Guanine Nucleotide Exchange Factor 2 | Glioblastoma |
| CHTOP-TrkA[13] | Chromatin Target of PRMT1 | Glioblastoma |
| PPL-TrkA[13] | Periplakin | Thyroid Carcinoma |
| PLEKHA6-TrkA | Pleckstrin Homology Domain-Containing Family A Member 6 | |
| PEAR1-TrkA | Platelet Endothelial Aggregation Receptor 1 | |
| MRPL24-TrkA | 39S Ribosomal Protein L24, Mitochondrial | |
| MDM4-TrkA | Human Homolg of Mouse Double Minute 4 | |
| LRRC71-TrkA | Leucine Rich Repeat Containing 71 | |

TABLE 6-continued

Exemplary TrkA Fusion Proteins and Cancers

| Fusion Protein | Non-TrkA Fusion Partner | Non-limiting Exemplary Trk- and Synonyms of Associated Cancer(s) |
|---|---|---|
| GRIPAP1-TrkA | GRIP1 Associated Protein 1 | |
| EPS15-TrkA | Epidermal Growth Factor Receptor Substrate 15 | |
| DYNC2H1-TrkA[B] | Dynein, Cytoplasmic 2, Heavy Chain 1 | Sarcoma |
| CEL-TrkA | Carboxyl Ester Lipase | Pancreatic adenocarcinoma sample[D] |
| EPHB2-TrkA[B] | EPH Receptor B2 | Lower GradeGlioma |
| TGF-TrkA[C] | Transforming Growth Factor | Papillary Thyroid Cancer |
| NELL1-TrkA[F] | Cytoplasmic Protein That Contains Epidermal Growth Factor (Egf)-Like Repeats | Non-Small Cell Lung Cancer (NSCLC) |
| EPL4-TrkA[F] | EPH-Related Receptor Tyrosine Kinase Ligand 4/ Ephrin-A4 Protein | Non-Small Cell Lung Cancer (NSCLC) |
| CTNND2-TrkA[F] | Catenin (Cadherin-Associated Protein), Delta 2 | Non-Small Cell Lung Cancer (NSCLC) |
| TCEANC2-TrkA[F] | Transcription Elongation Factor A (Sll) N-Terminal And Central Domain | Non-Small Cell Lung Cancer (NSCLC) |

[A]Créancier et al., *Cancer Lett.* 365(1): 107-111, 2015.J
[B]U.S. Pat. Application Publication No. 2015/0315657.
[C]U.S. Pat. Application Publication No. 2015/0283132.
[D]Egren et al., *Cancer Res.* 75(15 Supplement): 4793, 2015.
[E]U.S. Pat. Application Publication No. 2015/0073036.
[F]P.C.T. Patent Application Publication No. WO2015184443A1.
[G]Haller et al., The Journal of pathology 238.5 (2016): 700-710.
[H]Wong et al., *J Natl Cancer Inst* 2016;108: djv307.
[I]Haller et al., J. Pathol. 238(5): 700-10.
[J]Gang et al., Mod Pathol. 2016 Apr; 29(4): 359-69.
[K]Konicek et al., *Cancer research*, Vol. 76, No. 14, Supp. Supplement. Abstract Number: 2647; 107th Annual Meeting of the American Association for Cancer Research, AACR 2016. New Orleans, LA; 16-20 April 2016.
[L]Dtilon et al., *Cancer research*, Vol. 76, No. 14, Supp. Supplement. Abstract 16-20 Apr 2016. Number: CT007; 107th Annual Meeting of the American Association for Cancer Research, AACR 2016. New Orleans, LA; 16-20 April 2016.

TABLE 7

Exemplary TrkB Fusion Proteins and Cancers

| Fusion Protein | Non-TrkB Fusion Partner | Non-limiting Exemplary Trk- and Synonyms of Associated Cancer(s) |
|---|---|---|
| NACC2-TrkB[10] | NACC Family Member 2, BEN and BTB (POZ) Domain Containing | Pilocytic Astrocytoma |
| QKI-TrkB[10] | QKI, KH Domain Containing, RNA Binding | Pilocytic Astrocytoma |
| AFAP1-TrkB[7] | Actin Filament Associated Protein 1 | Lower-grade Glioma, In vitro (murine Ba/F3 cells)[B], Pilocytic astrocytoma with anaplasia (PAA)[E] |
| PAN3-TrkB[7] | PAN3 Poly(A) Specific Ribonuclease Subunit | Head and Neck Squamous Cell Carcinoma |
| SQSTM1-TrkB[7] | Sequestosome 1 | Lower-Grade Glioma |
| TRIM24-TrkB[7] | Tripartite Motif Containing 24 | Lung adenocarcinoma |
| VCL-TrkB[11] | Vinculin | Pediatric gliomas |
| AGBL4-TrkB[11] | ATP/GTP Binding Protein-Like 4 | Pediatric gliomas |
| DAB2IP-TrkB | Disabled Homolog 2-Interacting Protein | |
| NTRK2-TERT[A] | Telomerase Reverse Transcriptase | Thyroid Cancer |
| TEL-TrkB[C] (ETV6) | ETS Variant 6 | In vitro (murine Ba/F3 cells) |
| QKI-TrkB[D] | Protein Quaking | Astrocytoma |

[A]PCT Patent Application Publication No. WO 2015/183836A1
[B]Drilon et al., *Ann Oncol.* 2016 May;27(5): 920-6.
[C]Yuzugullu et al., *Cell Discov.* 2: 16030, 2016.
[D]Ni et al., *Neuro Oncol.* 2017 January;19(1):22-30.
[E]Lin et al., *Neuro-Oncol*, Vol. 18, Supp. Supplement 3, pp. iii58, Abstract Number: HG-48; 17th International Symposium on Pediatric Neuro-Oncology, ISPNO 2016. Liverpool, UK, 12 Jun. 2016-15 Jun. 2016.

TABLE 8

Exemplary TrkC Fusion Proteins and Cancers

| Fusion Protein | Non-TrkB Fusion Partner | Non-limiting Exemplary Trk- and Synonyms of Associated Cancer(s) |
|---|---|---|
| ETV6-TrkC[11] (TEL; or chromosomal translocation t(12; 15) (p 13; q25))[J] | ETS Variant 6 | Salivary Gland Cancer, Secretory Breast Carcinoma, Acute Myeloid Leukemia, Fibrosarcoma, Nephroma, Melanoma, Colorectal Cancer (CRC), Breast Cancer, Pediatric Gliomas, Thyroid Cancer (e.g., Papillary Thyroid Cancer), Infantile Fibrosarcoma, Soft Tissue Hemangioma, Gastrointestinal Stromal Tumor (GIST) (e.g., c-kit-negative GIST), Mammary Carcinoma (e.g., Mammary Analogue Secretory Carcinoma, Secretory Breast Carcinoma (SBSC)[K], Congenital Fibrosarcoma, Acute Myelogenous Leukemia, Polymorphous low-grade adenocarcinom[D], ALK-negative inflammatory myofibroblastic tumors (IMT)[E], Infantile Fibrosarcoma (IFS)[F], Acinic cell carcinoma (AcCC)[G], Cellular mesoblastic nephroma[H], Promyelocytic leukemia[I], Burkitt Lymphoma[I], B-cell lymphoma[I], multiple myeloma[I], medulloblastoma[I], neuroblastoma[I], ovarian cancer[I], intestinal cancer[I] |
| BTBD1-TrkC[11] | BTB (POZ) Domain Containing 1 | Pediatric Gliomas |
| LYN-TrkC[7] | V-Yes-1 Yamaguchi Sarcoma Viral Related Oncogene Homolog (also known as Lck/Yes-Related Novel Protein Tyrosine Kinase) | Head and Neck Squamous Cell Carcinoma |
| RBPMS-TrkC[7] | RNA Binding Protein with Multiple Splicing | Thyroid Cancer (e.g., Papillary Thyroid Cancer) |
| EML4-TrkC[A] | Echinoderm Microtubule-Associated Protein-Like 4 | Fibrosarcoma (e.g., Pediatric Fibrosarcoma) |
| HOMER2-TrkC | Homer Protein Homolog 2 | Soft Tissue Sarcoma |
| TFG-TrkC | TRK-Fused Gene | Soft Tissue Solitary Fibrous Tumor |
| FAT1-TrkC | FAT Atypical Cadherin 1 | Cervical Squamous Cell Carcinoma[B] |
| MYO5A-TrkC | Myosin VA | Spitz tumor[C] |
| MYH9-TrkC | Myosin Heavy Chain 9 | Spitz tumor[C] |

[A]Tannenbaum et al., *Cold Spring Harb. Mol. Case Stud.* 1: a000471, 2015.
[B]U.S. Pat. Application Publication No. 2015/0315657.
[C]Yeh et al., *J Pathol.* 240(3): 282-90, 2016
[D]Montalli et al., *J Oral Pathol Med.* doi: 10.1111/jop.12491, 2016
[E]Alassiri et al., *Am J Surg Pathol.* 2016 August;40(8):1051-61.
[F]Nagasubramanian et al., *Pediatr Blood Cancer.* 2016 August; 63(8):1468-70.
[G]Chintakuntlawar et al., *Oral Surg Oral Med Oral Pathol Oral Radiol.* 2016 May; 121(5): 542-549.e1.
[H]U.S. Pat. Application Publication No. US15030713A.
[I]U.S. Pat. Application Publication No. US9447135B2.
[J]Skalova et al., *Modern Pathology* 30, S27-S43, 2017.
[K]Hyrcza et al., Vol. 469, Supp. Supplement 1, pp. S17. Abstract Number: OFP-1997-7; 31st International Congress of the International Academy of Pathology and the 28th Congress of the European Society of Pathology, Cologne, Germany. 25-29 September 2016.
[L]Sims et al., *Journal of Immunotherapy of Cancer*, Vol. 4, Supp. Supplement 1; Abstract Number: P280; 31st Annual Meeting and Associated Programs of the Society for Immunotherapy of Cancer, SITC 2016. National Harbor, MD; 9-13 November 2016.

In some embodiments, the dysregulation of a TRK gene, a TRK kinase, or expression or activity or level of any of the same, includes at least one point mutation in a TRK gene that results in the production of a TRK kinase that has one or more amino acid substitutions, insertions, or deletions as compared to the wild-type TRK kinase.

In some embodiments, a TRK-associated cancer has been identified as having one or more TRK inhibitor resistance mutations (that result in an increased resistance to a TRK inhibitor.

Accordingly, provided herein are methods for treating a patient diagnosed with (or identified as having) a cancer that include administering to the patient a therapeutically effective amount of a compound of Formula I or a pharmaceutically acceptable salt or solvate thereof. Also provided herein are methods for treating a patient identified or diagnosed as having a ROS1-associated cancer that include administering to the patient a therapeutically effective amount of a compound of Formula I or a pharmaceutically acceptable salt or solvate thereof or a pharmaceutical composition thereof. In some embodiments, the patient that has been identified or diagnosed as having a ROS1-associated cancer through the use of a regulatory agency-approved, e.g., FDA-approved test or assay for identifying dysregulation of a ROS1 gene, a ROS1 kinase, or expression or activity or level of any of the same, in a patient or a biopsy sample from the patient or by performing any of the non-limiting examples of assays described herein. In some embodiments, the test or assay is provided as a kit. In some embodiments, the assay is a liquid biopsy. In some embodiments, the cancer is a ROS1-associated cancer. For example, the ROS1-associated cancer can be a cancer that includes one or more ROS1 inhibitor resistance mutations.

Also provided are methods for treating cancer in a patient in need thereof, the method comprising: (a) determining if the cancer in the patient is associated with a dysregulation of a ROS1 gene, a ROS1 kinase, or expression or activity or level of any of the same; and (b) if the cancer is determined to be associated with a dysregulation of a ROS1 gene, a ROS1 kinase, or expression or activity or level of any of the same, administering to the patient a therapeutically effective amount of a compound of Formula I or a pharmaceutically acceptable salt or solvate thereof or a pharmaceutical composition thereof. Some embodiments of these methods further include administering to the subject one or more additional anticancer agents (e.g., a second ROS1 inhibitor, a second compound of Formula I or a pharmaceutically acceptable salt or solvate thereof, an ALK inhibitor, and/or a TRK inhibitor). In some embodiments, one or more additional anticancer agents (e.g., a second ROS1 inhibitor, a second compound of Formula I or a pharmaceutically acceptable salt or solvate thereof, an ALK inhibitor, and/or a TRK inhibitor) are administered before a compound of Formula I or a pharmaceutically acceptable salt or solvate thereof. In some embodiments, one or more additional anticancer agents (e.g., a second ROS1 inhibitor, a second compound of Formula I or a pharmaceutically acceptable salt or solvate thereof, an ALK inhibitor, and/or a TRK inhibitor) are administered after a compound of Formula I or a pharmaceutically acceptable salt or solvate thereof. In some embodiments, one or more additional anticancer agents (e.g., a second ROS1 inhibitor, a second compound of Formula I or a pharmaceutically acceptable salt or solvate thereof, an ALK inhibitor, and/or a TRK inhibitor) are administered with a compound of Formula I or a pharmaceutically acceptable salt or solvate thereof. In some embodiments, the subject was previously treated with a first ROS1 inhibitor or previously treated with another anticancer treatment, e.g., treatment with another anticancer agent, resection of the tumor or radiation therapy. In some embodiments, the subject was previously treated with an ALK inhibitor, a TRK inhibitor, or both. In some embodiments, the patient is determined to have a ROS1-associated cancer through the use of a regulatory agency-approved, e.g., FDA-approved test or assay for identifying dysregulation of a ROS1 gene, a ROS1 kinase, or expression or activity or level of any of the same, in a patient or a biopsy sample from the patient or by performing any of the non-limiting examples of assays described herein. In some embodiments, the test or assay is provided as a kit. In some embodiments, the assay is a liquid biopsy. In some embodiments, the cancer is a ROS1-associated cancer. For example, the ROS1-associated cancer can be a cancer that includes one or more ROS1 inhibitor resistance mutations.

Also provided are methods of treating a patient that include performing an assay on a sample obtained from the patient to determine whether the patient has a dysregulation of a ROS1 gene, a ROS1 kinase, or expression or activity or level of any of the same, and administering (e.g., specifically or selectively administering) a therapeutically effective amount of a compound of Formula I or a pharmaceutically acceptable salt or solvate thereof or a pharmaceutical composition thereof to the patient determined to have a dysregulation of a ROS1 gene, a ROS1 kinase, or expression or activity or level of any of the same. Some embodiments of these methods further include administering to the subject one or more additional anticancer agents (e.g., a second ROS1 inhibitor, a second compound of Formula I or a pharmaceutically acceptable salt or solvate thereof, an ALK inhibitor, and/or a TRK inhibitor). In some embodiments, one or more additional anticancer agents (e.g., a second ROS1 inhibitor, a second compound of Formula I or a pharmaceutically acceptable salt or solvate thereof, an ALK inhibitor, and/or a TRK inhibitor) are administered before a compound of Formula I or a pharmaceutically acceptable salt or solvate thereof. In some embodiments, one or more additional anticancer agents (e.g., a second ROS1 inhibitor (e.g., a second compound of Formula I or a pharmaceutically acceptable salt or solvate thereof), an ALK inhibitor, and/or a TRK inhibitor) are administered after a compound of Formula I or a pharmaceutically acceptable salt or solvate thereof. In some embodiments, one or more additional anticancer agents (e.g., a second ROS1 inhibitor, a second compound of Formula I or a pharmaceutically acceptable salt or solvate thereof, an ALK inhibitor, and/or a TRK inhibitor) are administered with a compound of Formula I or a pharmaceutically acceptable salt or solvate thereof. In some embodiments of these methods, the subject was previously treated with a first ROS1 inhibitor or previously treated with another anticancer treatment, e.g., treatment with another anticancer agent, resection of a tumor or radiation therapy. In some embodiments, the subject was previously treated with an ALK inhibitor, a TRK inhibitor, or both. In some embodiments, the patient is a patient suspected of having a ROS1-associated cancer, a patient presenting with one or more symptoms of a ROS1-associated cancer, or a patient having an elevated risk of developing a ROS1-associated cancer. In some embodiments, the assay utilizes next generation sequencing, pyrosequencing, immunohistochemistry, an enzyme-linked immunosorbent assay, and/or fluorescence in situ hybridization (FISH) (e.g., break apart FISH or dual-fusion FISH). In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a ROS1 gene, a ROS1 kinase, or expression or activity or level of any of the same includes one or more ROS1 inhibitor resistance mutations.

Also provided is a compound of Formula I or a pharmaceutically acceptable salt or solvate thereof or a pharmaceutical composition thereof for use in treating a ROS1-associated cancer in a patient identified or diagnosed as having a ROS1-associated cancer through a step of performing an assay (e.g., an in vitro assay) on a sample obtained from the patient to determine whether the patient has a dysregulation of a ROS1 gene, a ROS1 kinase, or expression or activity or level of any of the same, where the presence of a dysregulation of a ROS1 gene, a ROS1 kinase, or expression or activity or level of any of the same, identifies that the patient has a ROS1-associated cancer. Also provided is the use of a compound of Formula I or a pharmaceutically acceptable salt or solvate thereof for the manufacture of a medicament for treating a ROS1-associated cancer in a patient identified or diagnosed as having a ROS1-associated cancer through a step of performing an assay on a sample obtained from the patient to determine whether the patient has a dysregulation of a ROS1 gene, a ROS1 kinase, or expression or activity or level of any of the same where the presence of dysregulation of a ROS1 gene, a ROS1 kinase, or expression or activity or level of any of the same, identifies that the patient has a ROS1-associated cancer. Some embodiments of any of the methods or uses described herein further include recording in the patient's clinical record (e.g., a computer readable medium) that the patient is determined to have a dysregulation of a ROS1 gene, a ROS1 kinase, or expression or activity or level of any of the same, through the performance of the assay, should be administered a compound of Formula I or a pharmaceutically acceptable salt or solvate thereof or a pharmaceutical composition thereof. In some embodiments, the assay utilizes next generation sequencing, pyrosequencing, immunohistochemistry, an enzyme-linked immunosorbent assay, and/or fluorescence in situ hybridization (FISH) (e.g., break apart FISH or dual-fusion FISH). In some embodiments, the assay is a regulatory agency-approved assay, e.g., FDA-approved kit. In some embodiments, the assay is a liquid biopsy. In some embodiments, the dysregulation of a ROS1 gene, a ROS1 kinase, or expression or activity or level of any of the same includes one or more ROS1 inhibitor resistance mutations.

Also provided is a compound of Formula I or a pharmaceutically acceptable salt or solvate thereof, for use in the treatment of a cancer in a patient in need thereof or a patient identified or diagnosed as having a ROS1-associated cancer. Also provided is the use of a compound of Formula I or a pharmaceutically acceptable salt or solvate thereof for the manufacture of a medicament for treating a cancer in a patient identified or diagnosed as having a ROS1-associated cancer. In some embodiments, the cancer is a ROS1-associated cancer, for example, a ROS1-associated cancer having one or more ROS1 inhibitor resistance mutations. In some embodiments, a patient is identified or diagnosed as having a ROS1-associated cancer through the use of a regulatory agency-approved, e.g., FDA-approved, kit for identifying dysregulation of a ROS1 gene, a ROS1 kinase, or expression or activity or level of any of the same, in a patient or a biopsy sample from the sample. As provided herein, a ROS1-associated cancer includes those described herein and known in the art.

In some embodiments of any of the methods or uses described herein, the patient has been identified or diagnosed as having a cancer with a dysregulation of a ROS1 gene, a ROS1 kinase, or expression or activity or level of any of the same. In some embodiments of any of the methods or uses described herein, the patient has a tumor that is positive for a dysregulation of a ROS1 gene, a ROS1 kinase, or expression or activity or level of any of the same. In some embodiments of any of the methods or uses described herein, the patient can be a patient with a tumor(s) that is positive for a dysregulation of a ROS1 gene, a ROS1 kinase, or expression or activity or level of any of the same. In some embodiments of any of the methods or uses described herein, the patient can be a patient whose tumors have a dysregulation of a ROS1 gene, a ROS1 kinase, or expression or activity or level of any of the same. In some embodiments of any of the methods or uses described herein, the patient is suspected of having a ROS1-associated cancer (e.g., a cancer having one or more ROS1 inhibitor resistance mutations). In some embodiments, provided herein are methods for treating a ROS1-associated cancer in a patient in need of such treatment, the method comprising a) detecting a dysregulation of a ROS1 gene, a ROS1 kinase, or the expression or activity or level of any of the same in a sample from the patient; and b) administering a therapeutically effective amount of a compound of Formula I or a pharmaceutically acceptable salt or solvate thereof. In some embodiments, the dysregulation of a ROS1 gene, a ROS1 kinase, or the expression or activity or level of any of the same includes one or more fusion proteins. Non-limiting examples of ROS1 gene fusion proteins are described in Table 2. In some embodiments, the fusion protein is SLC34A2-ROS1, CD74-ROS1, EZR-ROS1, TPM3-ROS1, or SDC4-ROS1. In some embodiments, the dysregulation of a ROS1 gene, a ROS1 kinase, or the expression or activity or level of any of the same includes one or more ROS1 kinase protein point mutations, insertions, and/or deletions. Non-limiting examples of ROS1 kinase protein point mutations are described in Table 3 and Table 3a. In some embodiments, the dysregulation of a ROS1 gene, a ROS1 kinase, or the expression or activity or level of any of the same includes one or more ROS1 inhibitor resistance mutations. Non-limiting examples of ROS1 inhibitor resistance mutations are described in Table 4. In some embodiments, the ROS1 inhibitor resistance mutation is selected from the group consisting of L2026M, G2032R, and D2033N. In some embodiments, the cancer with a dysregulation of a ROS1 gene, a ROS1 kinase, or expression or activity or level of any of the same is determined using a regulatory agency-approved, e.g., FDA-approved, assay or kit. In some embodiments, the assay is a liquid biopsy. In some embodiments, the tumor that is positive for a dysregulation of a ROS1 gene, a ROS1 kinase, or expression or activity or level of any of the same is a tumor positive for one or more ROS1 inhibitor resistance mutations. In some embodiments, the tumor with a dysregulation of a ROS1 gene, a ROS1 kinase, or expression or activity or level of any of the same is determined using a regulatory agency-approved, e.g., FDA-approved, assay or kit. In some embodiments, the assay is a liquid biopsy.

In some embodiments of any of the methods or uses described herein, the patient has a clinical record indicating that the patient has a tumor that has a dysregulation of a ROS1 gene, a ROS1 kinase, or expression or activity or level of any of the same (e.g., a tumor having one or more ROS1 inhibitor resistance mutations). In some embodiments, the clinical record indicates that the patient should be treated with one or more of the compounds of Formula I or a pharmaceutically acceptable salts or solvates thereof or compositions provided herein. In some embodiments, the cancer with a dysregulation of a ROS1 gene, a ROS1 kinase, or expression or activity or level of any of the same is a cancer having one or more ROS1 inhibitor resistance mutations. In some embodiments, the cancer with a dysregulation of a ROS1 gene, a ROS1 kinase, or expression or activity or level of any of the same is determined using a regulatory agency-approved, e.g., FDA-approved, assay or kit. In some embodiments, the assay is a liquid biopsy. In some embodiments, the tumor that is positive for a dysregulation of a ROS1 gene, a ROS1 kinase, or expression or activity or level of any of the same is a tumor positive for one or more ROS1 inhibitor resistance mutations. In some embodiments, the tumor with a dysregulation of a ROS1 gene, a ROS1 kinase, or expression or activity or level of any of the same is determined using a regulatory agency-approved, e.g., FDA-approved, assay or kit. In some embodiments, the assay is a liquid biopsy.

Also provided are methods of treating a patient that include administering a therapeutically effective amount of a compound of Formula I or a pharmaceutically acceptable salt or solvate thereof to a patient having a clinical record that indicates that the patient has a dysregulation of a ROS1 gene, a ROS1 kinase, or expression or activity or level of any of the same. Also provided is the use of a compound of Formula I or a pharmaceutically acceptable salt or solvate thereof for the manufacture of a medicament for treating a ROS1-associated cancer in a patient having a clinical record that indicates that the patient has a dysregulation of a ROS1 gene, a ROS1 kinase, or expression or activity or level of any of the same. Some embodiments of these methods and uses can further include: a step of performing an on a sample obtained from the patient to determine whether the patient has a dysregulation of a ROS1 gene, a ROS1 kinase, or expression or activity or level of any of the same, and recording the information in a patient's clinical file (e.g., a computer readable medium) that the patient has been identified to have a dysregulation of a ROS1 gene, a ROS1 kinase, or expression or activity or level of any of the same. In some embodiments, the assay is an in vitro assay. For example, an assay that utilizes next generation sequencing, pyrosequencing, immunohistochemistry, an enzyme-linked immunosorbent assay, and/or fluorescence in situ hybridization (FISH) (e.g., break apart FISH or dual-fusion FISH). In some embodiments, the assay is a regulatory agency-approved, e.g., FDA-approved, kit. In some embodiments, the assay is a liquid biopsy. In some embodiments, the dysregulation of a ROS1 gene, ROS1 kinase, or expression or activity or level of any of the same includes one or more ROS1 inhibitor resistance mutations.

Also provided herein is a method of treating a subject. The method includes performing an assay on a sample obtained from the subject to determine whether the subject has a dysregulation of a ROS1 gene, a ROS1 protein, or expression or level of any of the same. The method also includes administering to a subject determined to have a dysregulation of a ROS1 gene, a ROS1 protein, or expression or activity, or level of any of the same a therapeutically effective amount of a compound of Formula I or a pharmaceutically acceptable salt or solvate thereof. In some embodiments, the dysregulation in a ROS1 gene, a ROS1 kinase protein, or expression or activity of the same is a gene or chromosome translocation that results in the expression of a ROS1 fusion protein (e.g., any of the ROS1 fusion proteins described herein). In some embodiments, the ROS1 fusion can be selected from a SLC34A2 fusion, a CD74 fusion, a EZR fusion, a TPM3 fusion, or a SDC4 fusion. In some embodiments, the dysregulation in a ROS1 gene, a ROS1 kinase protein, or expression or activity or level of any of the same is one or more point mutation in the ROS1 gene (e.g., any of the one or more of the ROS1 point mutations described herein). The one or more point mutations in a ROS1 gene can result, e.g., in the translation of a ROS1 protein having one or more of the following amino acid substitutions: A15G, R118N, G1025R, T1735M, R1948H, and R2072N. In some embodiments, the dysregulation in a ROS1 gene, a ROS1 kinase protein, or expression or activity or level of any of the same is one or more ROS1 inhibitor resistance mutations (e.g., any combination of the one or more ROS1 inhibitor resistance mutations described herein). The one or more point mutations in a ROS1 gene can result, e.g., in the translation of a ROS1 protein having one or more of the following amino acid substitutions: L2026M, G2032R, and D2033N. Some embodiments of these methods further include administering to the subject another anticancer agent (e.g., a second ROS1 inhibitor, a second compound of Formula I or a pharmaceutically acceptable salt or solvate thereof, an ALK inhibitor, and/or a TRK inhibitor).

Also provided are methods (e.g., in vitro methods) of selecting a treatment for a patient identified or diagnosed as having a ROS1-associated cancer. Some embodiments can further include administering the selected treatment to the patient identified or diagnosed as having a ROS1-associated cancer. For example, the selected treatment can include administration of a therapeutically effective amount of a compound of Formula I or a pharmaceutically acceptable salt or solvate thereof. Some embodiments can further include a step of performing an assay on a sample obtained from the patient to determine whether the patient has a dysregulation of a ROS1 gene, a ROS1 kinase, or expression or activity or level of any of the same, and identifying and diagnosing a patient determined to have a dysregulation of a ROS1 gene, a ROS1 kinase, or expression or activity or level of any of the same, as having a ROS1-associated cancer. In some embodiments, the cancer is a ROS1-associated cancer having one or more ROS1 inhibitor resistance mutations. In some embodiments, the patient has been identified or diagnosed as having a ROS1-associated cancer through the use of a regulatory agency-approved, e.g., FDA-approved, kit for identifying dysregulation of a ROS1 gene, a ROS1 kinase, or expression or activity or level of any of the same, in a patient or a biopsy sample from the patient. In some embodiments, the assay is a liquid biopsy. In some embodiments, the ROS1-associated cancers is a cancer described herein or known in the art. In some embodiments, the assay is an in vitro assay. For example, an assay that utilizes next generation sequencing, pyrosequencing, immunohistochemistry, an enzyme-linked immunosorbent assay, and/or fluorescence in situ hybridization (FISH) (e.g., break apart FISH or dual-fusion FISH). In some embodiments, the assay is a regulatory agency-approved, e.g., FDA-approved, kit. In some embodiments, the assay is a liquid biopsy.

Also provided herein are methods of selecting a treatment for a patient, wherein the methods include a step of performing an assay on a sample obtained from the patient to determine whether the patient has a dysregulation of a ROS1 gene, a ROS1 kinase, or expression or activity or level of any of the same (e.g., one or more ROS1 inhibitor resistance mutations), and identifying or diagnosing a patient determined to have a dysregulation of a ROS1 gene, a ROS1 kinase, or expression or activity or level of any of the same, as having a ROS1-associated cancer. Some embodiments further include administering the selected treatment to the patient identified or diagnosed as having a ROS1-associated cancer. For example, the selected treatment can include administration of a therapeutically effective amount of a compound of Formula I or a pharmaceutically acceptable salt or solvate thereof to the patient identified or diagnosed as having a ROS1-associated cancer. In some embodiments, the assay is an in vitro assay. For example, an assay that utilizes next generation sequencing, pyrosequencing, immunohistochemistry, an enzyme-linked immunosorbent assay, and/or fluorescence in situ hybridization (FISH) (e.g., break apart FISH or dual-fusion FISH). In some embodiments, the assay is a regulatory agency-approved, e.g., FDA-approved, kit. In some embodiments, the assay is a liquid biopsy.

Also provided are methods of selecting a patient for treatment, wherein the methods include selecting, identifying, or diagnosing a patient having a ROS1-associated cancer, and selecting the patient for treatment including administration of a therapeutically-effective amount of a compound of Formula I or a pharmaceutically acceptable salt or solvate thereof. In some embodiments, identifying or diagnosing a patient as having a ROS1-associated cancer can include a step of performing an assay on a sample obtained from the patient to determine whether the patient has a dysregulation of a ROS1 gene, a ROS1 kinase, or expression or activity or level of any of the same, and identifying or diagnosing a patient determined to have a dysregulation of a ROS1 gene, a ROS1 kinase, or expression or activity or level of any of the same, as having a ROS1-associated cancer. In some embodiments, the method of selecting a treatment can be used as a part of a clinical study that includes administration of various treatments of a ROS1-associated cancer. In some embodiments, a ROS1-associated cancer is a cancer having one or more ROS1 inhibitor resistance mutations. In some embodiments, the assay is an in vitro assay. For example, an assay that utilizes next generation sequencing, pyrosequencing, immunohistochemistry, an enzyme-linked immunosorbent assay, and/or fluorescence in situ hybridization (FISH) (e.g., break apart FISH or dual-fusion FISH). In some embodiments, the assay is a regulatory agency-approved, e.g., FDA-approved, kit. In some embodiments, the assay is a liquid biopsy. In some embodiments, the dysregulation of the ROS1 gene, the ROS1 kinase, or expression or activity or level of any of the same includes one or more ROS1 inhibitor resistance mutations.

In some embodiments of any of the methods or uses described herein, an assay used to determine whether the patient has a dysregulation of a ROS1 gene, or a ROS1 kinase, or expression or activity or level of any of the same, using a sample from a patient can include, for example, next generation sequencing, pyrosequencing, immunohistochemistry, an enzyme-linked immunosorbent assay, and/or fluorescence in situ hybridization (FISH) (e.g., break apart FISH or dual-fusion FISH), fluorescence microscopy, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a ROS1 gene, a ROS1 kinase, or expression or activity or levels of any of the same (see, e.g., the references cited herein). In some embodiments, the dysregulation of the ROS1 gene, the ROS1 kinase, or expression or activity or level of any of the same includes one or more ROS1 inhibitor resistance mutations. In some embodiments, the sample is a biological sample or a biopsy sample (e.g., a paraffin-embedded biopsy sample) from the patient. In some embodiments, the patient is a patient suspected of having a ROS1-associated cancer, a patient having one or more symptoms of a ROS1-associated cancer, and/or a patient that has an increased risk of developing a ROS1-associated cancer).

In some embodiments, dysregulation of a ROS1 gene, a ROS1 kinase, or the expression or activity or level of any of the same can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.,* 3(3):36, 2016. Liquid biopsy methods can be used to detect total tumor burden and/or the dysregulation of a ROS1 gene, a ROS1 kinase, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a ROS1 gene, a ROS1 kinase, or the expression or activity or level of any of the same. In some embodiments, liquid biopsies can be used to detect the presence of dysregulation of a ROS1 gene, a ROS1 kinase, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a RET gene, a RET kinase, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a ROS1 gene, a ROS1 kinase, or the expression or activity or level of any of the same ). Liquid biopsies can be used to detect dysregulation of a ROS1 gene, a ROS1 kinase, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a liquid biopsy can be used to detect a genetic mutation that develops after development of the primary genetic mutation (e.g., a resistance mutation that arises in response to a treatment administered to a subject). In some embodiments, a dysregulation of a ROS1 gene, a ROS1 kinase, or the expression or activity or level of any of the same identified using a liquid biopsy is also present in a cancer cell that is present in the subject (e.g., in a tumor). In some embodiments, any of the types of dysregulation of a ROS1 gene, a ROS1 kinase, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a ROS1 gene, a ROS1 kinase, or the expression or activity or level of any of the same in the subject can indicate that the subject will be responsive to a treatment that includes administration of a compound of Formula I or a pharmaceutically acceptable salt thereof.

Liquid biopsies can be performed at multiple times during a course of diagnosis, a course of monitoring, and/or a course of treatment to determine one or more clinically relevant parameters including, without limitation, progression of the disease, efficacy of a treatment, or development of resistance mutations after administering a treatment to the subject. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable) or to determine the presence of a resistance mutation that has arisen as a result of the treatment. In some embodiments, a treatment to be administered to a subject can include a compound of Formula I or a pharmaceutically acceptable salt thereof.

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as kinase inhibitors, signal transduction inhibitors and/or monoclonal antibodies. Compounds of Formula I therefore may also be useful as adjuvants to cancer treatment, that is, they can be used in combination with one or more additional therapies or therapeutic agents, for example a chemotherapeutic agent that works by the same or by a different mechanism of action.

In some embodiments of any the methods described herein, the compound of Formula I (or a pharmaceutically acceptable salt or solvate thereof) is administered in combination with a therapeutically effective amount of at least one additional therapeutic agent selected from one or more additional therapies or therapeutic (e.g., chemotherapeutic) agents.

Non-limiting examples of additional therapeutic agents include: other ROS1-targeted therapeutic agents (i.e. a first or second ROS1 kinase inhibitor), ALK-targeted therapeutic agents (e.g., ALK kinase inhibitors), receptor tyrosine kinase-targeted therapeutic agents (e.g., TRK kinase inhibitors), kinase targeted therapeutics, signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

In some embodiments, the other ROS1-targeted therapeutic is a multikinase inhibitor exhibiting ROS1 inhibition activity. In some embodiments, the other ROS1-targeted therapeutic inhibitor is selective for a ROS1 kinase. Exemplary ROS1 kinase inhibitors can exhibit inhibition activity ($IC_{50}$) against a ROS1 kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a ROS1 kinase inhibitor can exhibit inhibition activity ($IC_{50}$) against a ROS1 kinase of less than about 25 nM, less than about 10 nM, less than about 5 nM, or less than about 1 nM as measured in an assay as provided herein.

Non-limiting examples of ROS1-targeted therapeutic agents include (E)-5-chloro-2-(2-(1-(4-fluorophenyl)ethylidene)hydrazinyl)-N-(2-(isopropylsulfonyl)phenyl)pyrimidin-4-amine (*Eur. J. Org. Chem.* 2016, 123, 80-89); alectinib; brigatinib; cabozantinib; ceritinib; crizotinib; entrectinib; foretinib; herbimycin A; lorlatinib; lorlatinib des-methyl analogs; merestinib; ASP3026 (NCT01284192; Astellas Pharma); AZD3634 (AstraZeneca); and ASP3026 (Astrellas Pharma).

In some embodiments, an ALK-targeted therapeutic is a multikinase inhibitor exhibiting ALK inhibition activity. In some embodiments, the ALK-targeted therapeutic inhibitor is selective for an ALK kinase. Exemplary ALK kinase inhibitors can exhibit inhibition activity ($IC_{50}$) against an ALK kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, an ALK kinase inhibitor can exhibit inhibition activity ($IC_{50}$) against an ALK kinase of less than about 25 nM, less than about 10 nM, less than about 5 nM, or less than about 1 nM as measured in an assay.

Non-limiting examples of ALK-targeted therapeutic agents include "Amgen 36"; "Amgen 49"; "Cephalon 30"; "Chugai 13d"; 4-arylaminopyrimidine derivatives (see, e.g., *Eur. J. Med. Chem.* 2016, 123, 80-99); alectinib; anti-ALK monoclonal antibodies; brigatinib; ceritinib; crizotinib; dorsomorphin; ensartinib; entrectinib; ganetespib; lorlatinib; PF-02341066 (Pfizer); IPI-504 (Infinity); TSR-011 (Tesaro, Inc.); CT-707 (Centaurus Biopharma); AUY922; TEW-7197 (Medpacto); CEP-28122 (Teva Pharmaceuticals); CEP-37440 (Teva Pharmaceuticals); ASP3026 (Astellas Pharma); 17-AAG; IPI-504; GSK 1838705 (GlaxoSmithKline); KRCA 0008; AZD3463 (AstraZeneca); NVP-TAE684 (Novartis); "3-39" (Novartis); LDN193189; SB 525334; SB 505124; and TAE684.

In some embodiments, a receptor tyrosine kinase targeted therapeutic is a multikinase inhibitor (e.g., TRK-targeted therapeutic inhibitor) exhibiting TRK inhibition activity. In some embodiments, the TRK-targeted therapeutic inhibitor is selective for a TRK kinase. Exemplary TRK kinase inhibitors can exhibit inhibition activity ($IC_{50}$) against a TRK kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a TRK kinase inhibitor can exhibit inhibition activity ($IC_{50}$) against a TRK kinase of less than about 25 nM, less than about 10 nM, less than about 5 nM, or less than about 1 nM as measured in an assay. For example, a TRK inhibitor assay can be any of those provided in U.S. Pat. No. 8,933,084 (e.g., Example A or B).

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3 S,4R)-4-(3-fluorophenyl)-1-(2-methoxyethyl) pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in *Cancer Chemother. Pharmacol.* 75(1):131-141, 2015; and GNF-5837 (N-[3-[[2,3-dihydro-2-oxo-3-(1H-pyrrol-2-ylmethylene)-1H-indol-6-yl] amino]-4-methylphenyl]-N'-[2-fluoro-5-(trifluoromethyl) phenyl]-urea), described in *ACS Med. Chem. Lett.* 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in *Cancer* 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl) ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in *Int. J. Cancer* 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl) imidazo[1,2-b]pyridazin-3-yl)-[2,4'-bipyridin]-2'-yl)piperidin-4-ol as described in *ACS Med. Chem. Lett.* 6(5):562-567, 2015; GTx-186 and others, as described in *PLoS One* 8(12):e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo [3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J Med. Chem.* 51(15): 4672-4684, 2008; PHA-739358 (danusertib), as described in *Mol. Cancer Ther.* 6:3158, 2007; Go 6976 (5,6,7,13-tetrahydro-13-methyl-5-oxo-12H-indolo[2,3-a]pyrrolo[3,4-c] carbazole-12-propanenitrile), as described in J. Neurochem. 72:919-924, 1999; GW441756 ((3Z)-3-[(1-methylindol-3-yl)methylidene]-1H-pyrrolo[3,2-b]pyridin-2-one), as described in *IJAE* 115:117, 2010; milciclib (PHA-848125AC), described in *J. Carcinog.* 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5 S,6S,8R)-6-Hydroxy-6-(hydroxymethyl)-5-methyl-7,8,14,15-tetrahydro-5H-16-oxa-4b,8a, 14-triaza-5, 8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2 (1H)-one mono 2-hydroxypropanoate hydrate); sitravatinib (N-(3-fluoro-4-((2-(5-(((2-methoxyethyl)amino)methyl) pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl) phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3] benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is *bacillus* Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224, all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

In some embodiments, a kinase inhibitor as provided herein may have activity against more than one kinase (i.e. may be a multikinase inhibitor). When more than one mechanism of action is recited in a method herein (e.g., ROS1, ALK, or TRK kinase inhibition), each of the compounds recited are structurally distinct from one another (e.g., the ROS1 inhibitor and the TRK inhibitor are not the same compound).

Accordingly, also provided herein is a method of treating cancer, comprising administering to a patient in need thereof a pharmaceutical combination for treating cancer which comprises (a) a compound of Formula I or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or a pharmaceutically acceptable salt or solvate thereof and the additional therapeutic agent are together effective in treating the cancer.

These additional therapeutic agents may be administered with one or more doses of the compound of Formula I, or a pharmaceutically acceptable salt or solvate thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer in a patient in need thereof, which comprises (a) a compound of Formula I or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula I or pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a patient in need thereof. In some embodiments the patient is a human. In some embodiments, the cancer is a ROS1-associated cancer, e.g., a ROS1-associated cancer having one or more ROS1 inhibitor resistance mutations.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., a chemotherapeutic agent), are both administered to a patient simultaneously in the form of a single composition or dosage. The term "non-fixed combination" means that a compound of Formula I or a pharmaceutically acceptable salt or solvate thereof and at least one additional therapeutic agent (e.g., chemotherapeutic agent) are formulated as separate compositions or dosages such that they may be administered to a patient in need thereof simultaneously, concurrently or sequentially with variable intervening time limits (e.g., 1 hour, 1 day, 1 week, 2 weeks, 3 weeks, 1 month, 2 months, 3 months), wherein such administration provides effective levels of the two or more compounds in the body of the patient. These also apply to cocktail therapies, e.g. the administration of three or more active ingredients Accordingly, also provided herein is a method of treating a cancer, comprising administering to a patient in need thereof a pharmaceutical combination for treating cancer which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or pharmaceutically acceptable salt or solvate thereof and the additional therapeutic agent are together effective in treating the cancer. In some embodiments, the compound of Formula I or pharmaceutically acceptable salt or solvate thereof, and the additional therapeutic agent are administered simultaneously as separate dosages. In some embodiments, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In some embodiments, the compound of Formula I or pharmaceutically acceptable salt or solvate thereof, and the additional therapeutic agent are administered simultaneously as a combined dosage. In some embodiments, the cancer is a ROS1-associated cancer. For example, a ROS1-associated cancer having one or more ROS1 inhibitor resistance mutations.

Also provided herein is a method of treating a disease or disorder mediated by ROS1 in a patient in need of such treatment, the method comprising administering to the patient a therapeutically effective amount of a compound of Formula I or a pharmaceutically acceptable salt or solvate thereof or a pharmaceutical composition thereof. In some embodiments, the disease or disorder mediated by ROS1 is a dysregulation of ROS1 gene, a ROS1 kinase, or expression or activity or level of any of the same. For example, the dysregulation of a ROS1 gene, a ROS1 kinase, or expression or activity or level of any of the same includes one or more ROS1 inhibitor resistance mutations. A disease or disorder mediated by ROS1 can include any disease, disorder or condition that is directly or indirectly linked to expression or activity of ROS1, including overexpression and/or abnormal activity levels. In some embodiments, the disease is cancer (e.g., a ROS1-associated cancer). In some embodiments, the cancer is any of the cancers or ROS1-associated cancers described herein.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis.

Accordingly, also provided herein are methods for inhibiting, preventing, aiding in the prevention, or decreasing the symptoms of metastasis of a cancer in a patient in need thereof, the method comprising administering to the patient a therapeutically effective amount of a compound of Formula I or a pharmaceutically acceptable salt or solvate thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. In some embodiments, the cancer is a ROS1-associated cancer. In some embodiments, the compound of Formula I or a pharmaceutically acceptable salt or solvate thereof is used in combination with an additional therapy or another therapeutic agent, including a chemotherapeutic agent, such as a kinase inhibitor, for example, a first or second ROS1 kinase inhibitor.

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a ROS1-associated cancer that include: selecting, identifying, or diagnosing a patient as having a ROS1-associated cancer, and administering a therapeutically effective amount of a compound of Formula I or a pharmaceutically acceptable salt or solvate thereof to the patient selected, identified, or diagnosed as having a ROS1-associated cancer. Also provided are methods of decreasing the risk of developing a metastasis or an additional metastasis in a patient having a ROS1-associated cancer that includes administering a therapeutically effective amount of a compound of Formula I or a pharmaceutically acceptable salt or solvent thereof to a patient having a ROS1-associated cancer. The decrease in the risk of developing a metastasis or an additional metastasis in a patient having a ROS1-associated cancer can be compared to the risk of developing a metastasis or an additional metastasis in the patient prior to treatment, or as compared to a patient or a population of patients having a similar or the same ROS1-associated cancer that has received no treatment or a different treatment. In some embodiments, the ROS1-associated cancer is a ROS1-associated cancer having one or more ROS1 inhibitor resistance mutations.

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

In some embodiments, the presence of one or more ROS1 inhibitor resistance mutations in a tumor causes the tumor to be more resistant to treatment with a first ROS1 inhibitor. Methods useful when a ROS1 inhibitor resistance mutation causes the tumor to be more resistant to treatment with a first ROS1 inhibitor are described below. For example, provided herein are methods of treating a subject having a cancer that include: identifying a subject having a cancer cell that has one or more ROS1 inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the first ROS1 inhibitor. Also provided are methods of treating a subject identified as having a cancer cell that has one or more ROS1 inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the first ROS1 inhibitor. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at amino acid positions 2026, 2032, or 2033, e.g., L2026M, G2032R, or D2033N.

For example, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a first ROS1 inhibitor. In some embodiments, the methods further comprise (after (b)) (c) determining whether a cancer cell in a sample obtained from the subject has one or more ROS1 inhibitor resistance mutations; and (d) administering a compound of Formula I, or a pharmaceutically acceptable salt of solvate thereof as a monotherapy or in conjunction with another anticancer agent to the subject if the subject has a cancer cell that has one or more ROS1 inhibitor resistance mutations; or (e) administering additional doses of the first ROS1 inhibitor of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a first ROS1 inhibitor. In some embodiments, the methods further comprise (after (b)) (c) determining whether a cancer cell in a sample obtained from the subject has one or more ROS1 inhibitor resistance mutations; and (d) administering a compound of Formula I selected from Example No. 2, 3, 7, 9, 14, 19, 20, 22, 33-A, 33-B, 35, 36, and 45, or a pharmaceutically acceptable salt or solvate thereof as a monotherapy or in conjunction with another anticancer agent to the subject if the subject has a cancer cell that has one or more ROS1 inhibitor resistance mutations; or (e) administering additional doses of the first ROS1 inhibitor of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting one or more fusion proteins of Table 2 and/or one or more ROS1 kinase protein point mutations, insertions, and/or deletions (e.g., one or more point mutations of Table 3 or Table 3a) in a sample from the subject; and (b) administering to the subject a therapeutically effective amount of a first ROS1 inhibitor. In some embodiments, the methods further comprise (after (b)) (c) determining whether a cancer cell in a sample obtained from the subject has one or more ROS1 inhibitor resistance mutations of Table 4; and (d) administering a compound of Formula I selected from Example No. 2, 3, 7, 9, 14, 19, 20, 22, 33-A, 33-B, 35, 36, and 45, or a pharmaceutically acceptable salt or solvate thereof as a monotherapy or in conjunction with another anticancer agent to the subject if the subject has a cancer cell that has one or more ROS1 inhibitor resistance mutations; or (e) administering additional doses of the first ROS1 inhibitor of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting one or more of the fusion proteins SLC34A2-ROS1, CD74-ROS1, EZR-ROS1, TPM3-ROS1, or SDC4-ROS1 in a sample from the subject; and (b) administering to the subject a therapeutically effective amount of a first ROS1 inhibitor. In some embodiments, the methods further comprise (after (b)) (c) determining whether a cancer cell in a sample obtained from the subject has one or more of the ROS1 inhibitor resistance mutations L2026M, G2032R, or D2033N; and (d) administering a compound of Formula I or a pharmaceutically acceptable salt or solvate thereof selected from the group consisting of a compound of Formula I selected from Example No. 2, 3, 7, 9, 14, 19, 20, 22, 33-A, 33-B, 35, 36, and 45, or a pharmaceutically acceptable salt or solvate thereof as a monotherapy or in conjunction with another anticancer agent to the subject if the subject has a cancer cell that has one or more ROS1 inhibitor resistance mutations; or (e) administering additional doses of the first ROS1 inhibitor of step (b) to the subject if the subject has a cancer cell that does not have one or more ROS1 inhibitor resistance mutations.

For example, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a first ROS1 inhibitor, wherein the first ROS1 inhibitor is selected from the group consisting of alectinib, brigatinib, cabozantinib, ceritinib, crizotinib, entrectinib, foretinib, lorlatinib, and mesestinib. In some embodiments, the methods further comprise (after (b)) (c) determining whether a cancer cell in a sample obtained from the subject has one or more ROS1 inhibitor resistance mutations; and (d) administering a compound of Formula I, or a pharmaceutically acceptable salt of solvate thereof as a monotherapy or in conjunction with another anticancer agent to the subject if the subject has a cancer cell that has one or more ROS1 inhibitor resistance mutations; or (e) administering additional doses of the first ROS1 inhibitor of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a first ROS1 inhibitor, wherein the first ROS1 inhibitor is selected from the group consisting of alectinib, brigatinib, cabozantinib, ceritinib, crizotinib, entrectinib, foretinib, lorlatinib, and mesestinib. In some embodiments, the methods further comprise (after (b)) (c) determining whether a cancer cell in a sample obtained from the subject has one or more ROS1 inhibitor resistance mutations; and (d) administering a compound of Formula I selected from Example No. 2, 3, 7, 9, 14, 19, 20, 22, 33-A, 33-B, 35, 36, and 45, or a pharmaceutically acceptable salt or solvate thereof as a monotherapy or in conjunction with another anticancer agent to the subject if the subject has a cancer cell that has one or more ROS1 inhibitor resistance mutations; or (e) administering additional doses of the first ROS1 inhibitor of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting one or more fusion proteins of Table 2 and/or one or more ROS1 kinase protein point mutations, insertions, and/or deletions (e.g., one or more point mutations of Table 3 or Table 3a) in a sample from the subject; and (b) administering to the subject a therapeutically effective amount of a first ROS1 inhibitor, wherein the first ROS1 inhibitor is selected from the group consisting of alectinib, brigatinib, cabozantinib, ceritinib, crizotinib, entrectinib, foretinib, lorlatinib, and mesestinib. In some embodiments, the methods further comprise (after (b)) (c) determining whether a cancer cell in a sample obtained from the subject has one or more ROS1 inhibitor resistance mutations of Table 4; and (d) administering a compound of Formula I selected from Example No. 2, 3, 7, 9, 14, 19, 20, 22, 33-A, 33-B, 35, 36, and 45, or a pharmaceutically acceptable salt or solvate thereof as a monotherapy or in conjunction with another anticancer agent to the subject if the subject has a cancer cell that has one or more ROS1 inhibitor resistance mutations; or (e) administering additional doses of the first ROS1 inhibitor of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting one or more of the fusion proteins SLC34A2-ROS1, CD74-ROS1, EZR-ROS1, TPM3-ROS1, or SDC4-ROS1 in a sample from the subject; and (b) administering to the subject a therapeutically effective amount of a first ROS1 inhibitor, wherein the first ROS1 inhibitor is selected from the group consisting of alectinib, brigatinib, cabozantinib, ceritinib, crizotinib, entrectinib, foretinib, lorlatinib, and mesestinib. In some embodiments, the methods further comprise (after (b)) (c) determining whether a cancer cell in a sample obtained from the subject has one or more of the ROS1 inhibitor resistance mutations L2026M, G2032R, or D2033N; and (d) administering a compound of Formula I or a pharmaceutically acceptable salt or solvate thereof selected from the group consisting of a compound of Formula I selected from Example No. 2, 3, 7, 9, 14, 19, 20, 22, 33-A, 33-B, 35, 36, and 45, or a pharmaceutically acceptable salt or solvate thereof as a monotherapy or in conjunction with another anticancer agent to the subject if the subject has a cancer cell that has one or more ROS1 inhibitor resistance mutations; or (e) administering additional doses of the first ROS1 inhibitor of step (b) to the subject if the subject has a cancer cell that does not have one or more ROS1 inhibitor resistance mutations.

As another example, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a compound of Formula I, or a pharmaceutically acceptable salt of solvate thereof. In some embodiments, the methods further comprise (after (b)) (c) determining whether a cancer cell in a sample obtained from the subject has one or more ROS1 inhibitor resistance mutations; and (d) administering a second ROS1 inhibitor, as a monotherapy or in conjunction with another anticancer agent to the subject if the subject has a cancer cell that has one or more ROS1 inhibitor resistance mutations; or (e) administering additional doses of the compound of Formula I or a pharmaceutically acceptable salt or solvate thereof of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a compound of Formula I selected from Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more ROS1 inhibitor resistance mutations; and (d) administering a second ROS1 inhibitor, as a monotherapy or in conjunction with another anticancer agent to the subject if the subject has a cancer cell that has one or more ROS1 inhibitor resistance mutations; or (e) administering additional doses of the compound of Formula I or a pharmaceutically acceptable salt or solvate thereof of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting one or more fusion proteins of Table 2 and/or one or more ROS1 kinase protein point mutations, insertions, and/or deletions (e.g., one or more of the point mutations of Table 3 or Table 3a) in a sample from the subject; and (b) administering to the subject a therapeutically effective amount of a compound of Formula I selected from Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more ROS1 inhibitor resistance mutations of Table 4; and (d) administering a second ROS1 inhibitor, as a monotherapy or in conjunction with another anticancer agent to the subject if the subject has a cancer cell that has one or more ROS1 inhibitor resistance mutations; or (e) administering additional doses of the compound of Formula I or a pharmaceutically acceptable salt or solvate thereof of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting one or more of the fusion proteins SLC34A2-ROS1, CD74-ROS1, EZR-ROS1, TPM3-ROS1, or SDC4-ROS1 in a sample from the subject; and (b) administering to the subject a therapeutically effective amount of a compound of Formula I selected Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more of the ROS1 inhibitor resistance mutations L2026M, G2032R, or D2033N; and (d) administering a second ROS1 inhibitor, as a monotherapy or in conjunction with another anticancer agent to the subject if the subject has a cancer cell that has one or more ROS1 inhibitor resistance mutations; or (e) administering additional doses of the compound of Formula I or a pharmaceutically acceptable salt or solvate thereof of step (b) to the subject if the subject has a cancer cell that does not have one or more ROS1 inhibitor resistance mutations.

In some embodiments, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a compound of Formula I, or a pharmaceutically acceptable salt of solvate thereof. In some embodiments, the methods further comprise (after (b)) (c) determining whether a cancer cell in a sample obtained from the subject has one or more ROS1 inhibitor resistance mutations; and (d) administering a second ROS1 inhibitor, wherein the second ROS1 inhibitor is selected from the group consisting of alectinib, brigatinib, cabozantinib, ceritinib, crizotinib, entrectinib, foretinib, lorlatinib, and mesestinib, as a monotherapy or in conjunction with another anticancer agent to the subject if the subject has a cancer cell that has one or more ROS1 inhibitor resistance mutations; or (e) administering additional doses of the compound of Formula I or a pharmaceutically acceptable salt or solvate thereof of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a compound of Formula I selected from Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more ROS1 inhibitor resistance mutations; and (d) administering a second ROS1 inhibitor, wherein the second ROS1 inhibitor is selected from the group consisting of alectinib, brigatinib, cabozantinib, ceritinib, crizotinib, entrectinib, foretinib, lorlatinib, and mesestinib, as a monotherapy or in conjunction with another anticancer agent to the subject if the subject has a cancer cell that has one or more ROS1 inhibitor resistance mutations; or (e) administering additional doses of the compound of Formula I or a pharmaceutically acceptable salt or solvate thereof of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting one or more fusion proteins of Table 2 and/or one or more ROS1 kinase protein point mutations, insertions, and/or deletions (e.g., one or more of the point mutations of Table 3 or Table 3a) in a sample from the subject; and (b) administering to the subject a therapeutically effective amount of a compound of Formula I selected from Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more ROS1 inhibitor resistance mutations of Table 4; and (d) administering a second ROS1 inhibitor, wherein the second ROS1 inhibitor is selected from the group consisting of alectinib, brigatinib, cabozantinib, ceritinib, crizotinib, entrectinib, foretinib, lorlatinib, and mesestinib, as a monotherapy or in conjunction with another anticancer agent to the subject if the subject has a cancer cell that has one or more ROS1 inhibitor resistance mutations; or (e) administering additional doses of the compound of Formula I or a pharmaceutically acceptable salt or solvate thereof of step (b) to the subject if the subject has a cancer cell that does not have one or more ROS1 inhibitor resistance mutations. In some embodiments, provided herein are methods for treating a ROS1-associated cancer in a subject in need of such treatment, the method comprising (a) detecting one or more of the fusion proteins SLC34A2-ROS1, CD74-ROS1, EZR-ROS1, TPM3-ROS1, or SDC4-ROS1 in a sample from the subject; and (b) administering to the subject a therapeutically effective amount of a compound of Formula I selected Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more of the ROS1 inhibitor resistance mutations L2026M, G2032R, or D2033N; and (d) administering a second ROS1 inhibitor, wherein the second ROS1 inhibitor is selected from the group consisting of alectinib, brigatinib, cabozantinib, ceritinib, crizotinib, entrectinib, foretinib, lorlatinib, and mesestinib, as a monotherapy or in conjunction with another anticancer agent to the subject if the subject has a cancer cell that has one or more ROS1 inhibitor resistance mutations; or (e) administering additional doses of the compound of Formula I or a pharmaceutically acceptable salt or solvate thereof of step (b) to the subject if the subject has a cancer cell that does not have one or more ROS1 inhibitor resistance mutations.

Also, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has one or more ROS1 inhibitor resistance mutations; and (d) administering additional doses of the compound of Formula I or a pharmaceutically acceptable salt or solvate thereof of step (b) to the subject as a monotherapy or in conjunction with another anticancer agent (e.g., a second ROS1 inhibitor, a second compound of Formula I, an ALK inhibitor, a TRK inhibitor, or a pharmaceutically acceptable salt thereof) or anticancer therapy (e.g., surgery or radiation) if the subject has a cancer cell that has one or more ROS1 inhibitor resistance mutations. In some embodiments, provided herein are methods for treating a ROS1-associated cancer in a subject in need of such treatment, the method comprising (a) detecting a dysregulation of a ROS1 gene, a ROS1 kinase, or the expression or activity or level of any of the same in a sample from the subject; and (b) administering to the subject a therapeutically effective amount of a compound of Formula I selected from Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more ROS1 inhibitor resistance mutations; and (d) administering additional doses of the compound of Formula I or a pharmaceutically acceptable salt or solvate thereof of step (b) to the subject as a monotherapy or in conjunction with another anticancer agent (e.g., a second ROS1 inhibitor, a second compound of Formula I, an ALK inhibitor, a TRK inhibitor, or a pharmaceutically acceptable salt thereof) or anticancer therapy (e.g., surgery or radiation) if the subject has a cancer cell that has one or more ROS1 inhibitor resistance mutations.

In some embodiments, provided herein are methods for treating a ROS1-associated cancer in a subject in need of such treatment, the method comprising (a) detecting one or more ROS1 fusion proteins of Table 2 and/or one or more ROS1 kinase protein point mutations, insertions, and/or deletions (e.g., one or more of the point mutations of Table 3 or Table 3a) in a sample from the subject; and (b) administering to the subject a therapeutically effective amount of a compound of Formula I or a pharmaceutically acceptable salt or solvate thereof selected from the group consisting of a compound of Formula I selected from Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more ROS1 inhibitor resistance mutations of Table 4; and (d) administering additional doses of the compound of Formula I or a pharmaceutically acceptable salt or solvate thereof of step (b) to the subject as a monotherapy or in conjunction with another anticancer agent (e.g., a second ROS1 inhibitor, a second compound of Formula I, an ALK inhibitor, a TRK inhibitor, or a pharmaceutically acceptable salt thereof) or anticancer therapy (e.g., surgery or radiation) if the subject has a cancer cell that has one or more ROS1 inhibitor resistance mutations. In some embodiments, a second ROS1 inhibitor selected from the group consisting of alectinib, brigatinib, cabozantinib, ceritinib, crizotinib, entrectinib, foretinib, lorlatinib, and mesestinib is administered in step (d). In some embodiments, provided herein are methods for treating a ROS1-associated cancer in a subject in need of such treatment, the method comprising (a) detecting one or more of the fusion proteins SLC34A2-ROS1, CD74-ROS1, EZR-ROS1, TPM3-ROS1, or SDC4-ROS1 in a sample from the subject; and (b) administering to the subject a therapeutically effective amount of a compound of Formula I selected Example No. 2, 3, 7, 9, 14, 19, 20, 22, 33-A, 33-B, 35, 36, and 45, or a pharmaceutically acceptable salt or solvate thereof. In some embodiments, the methods further comprise (after (b)) (c) determining whether a cancer cell in a sample obtained from the subject has one or more of the ROS1 inhibitor resistance mutations L2026M, G2032R, or D2033N; and (d) administering additional doses of the compound of Formula I or a pharmaceutically acceptable salt or solvate thereof of step (b) to the subject as a monotherapy or in conjunction with another anticancer agent (e.g., a second ROS1 inhibitor, a second compound of Formula I, an ALK inhibitor, a TRK inhibitor, or a pharmaceutically acceptable salt thereof) or anticancer therapy (e.g., surgery or radiation) if the subject has a cancer cell that has one or more ROS1 inhibitor resistance mutations. In some embodiments, a second ROS1 inhibitor selected from the group consisting of alectinib, brigatinib, cabozantinib, ceritinib, crizotinib, entrectinib, foretinib, lorlatinib, and mesestinib is administered in step (d).

Also provided are methods of selecting a treatment for a subject having a cancer that include: identifying a subject having a cancer cell that has one or more ROS1 inhibitor resistance mutations; and selecting a treatment that includes administration of a compound of Formula I or a pharmaceutically acceptable salt or solvate thereof. In some embodiments, the one or more ROS1 inhibitor resistance mutations confer increased resistance to a cancer cell or tumor to treatment with a first ROS1 inhibitor. In some embodiments, the compound of Formula I or a pharmaceutically acceptable salt or solvate thereof is administered in combination with the first ROS1 inhibitor. Also provided are methods of selecting a treatment for a subject having a cancer that include: selecting a treatment that includes administration of a compound of Formula I or a pharmaceutically acceptable salt or solvate thereof for a subject identified as having a cancer cell that has one or more ROS1 inhibitor resistance mutations. Also provided are methods of selecting a subject having a cancer for a treatment that does not include a first ROS1 inhibitor as a monotherapy that include: identifying a subject having a cancer cell that has one or more ROS1 inhibitor resistance mutations; and selecting the identified subject for a treatment that includes a compound of Formula I or a pharmaceutically acceptable salt or solvate thereof. Also provided are methods of selecting a subject having a cancer for a treatment that does not include a first ROS1 inhibitor as a monotherapy that include: selecting a subject identified as having a cancer cell that has one or more ROS1 inhibitor resistance mutations for a treatment that includes administration of a compound of Formula I or a pharmaceutically acceptable salt or solvate thereof. In some embodiments, the one or more ROS1 inhibitor resistance mutations include one or more ROS1 inhibitor resistance mutations listed in Table 4. In some embodiments, the one or more ROS1 inhibitor resistance mutations can include a substitution at one or more of amino acid positions 2026, 2032, or 2033, e.g., L2026M, G2032R, or D2033N.

Also provided are methods of determining the likelihood that a subject having a cancer (e.g., a ROS1-associated cancer) will have a positive response to treatment with a first ROS1 inhibitor as a monotherapy that include: determining whether a cancer cell in a sample obtained from the subject has one or more ROS1 inhibitor resistance mutations; and determining that a subject having a cancer cell that has one or more ROS1 inhibitor resistance mutations has a decreased likelihood of having a positive response (i.e. an increased likelihood of having a negative response) to treatment with a first ROS1 inhibitor as a monotherapy. Also provided are methods of determining the likelihood that a subject having a cancer (e.g., a ROS1-associated cancer) will have a positive response to treatment with a first ROS1 inhibitor as a monotherapy that include: determining whether a cancer cell in a sample obtained from the subject has one or more ROS1 inhibitor resistance mutations; and determining that a subject not having a cancer cell that has one or more ROS1 inhibitor resistance mutations has an increased likelihood of having a positive response to treatment with a first ROS1 inhibitor as a monotherapy as compared to a subject having a cancer cell that has one or more ROS1 inhibitor resistance mutations. Also provided are methods of predicting the efficacy of treatment with a first ROS1 inhibitor as a monotherapy in a subject having cancer that include: determining whether a cancer cell in a sample obtained from the subject has one or more ROS1 inhibitor resistance mutations; and determining that treatment with a first ROS1 inhibitor as a monotherapy is less likely to be effective in a subject having a cancer cell in a sample obtained from the subject that has one or more ROS1 inhibitor resistance mutations. Also provided are methods of predicting the efficacy of treatment with a first ROS1 inhibitor as a monotherapy in a subject having cancer that include: determining that treatment with a first ROS1 inhibitor as a monotherapy is less likely to be effective in a subject having a cancer cell in a sample obtained from the subject that has one or more ROS1 inhibitor resistance mutations. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N.

Also provided are methods of treating a subject having a cancer that include: (a) administering a first ROS1 inhibitor to the subject for a period of time (e.g., 1 month, 2 months, 3 months, 6 months, 9 months, 1 year); (b) after (a), determining whether a cancer cell in a sample obtained from the subject has one or more ROS1 inhibitor resistance mutations; and (c) administering a compound of Formula I or a pharmaceutically acceptable salt or solvate thereof as a monotherapy or in conjunction with another anticancer agent to the subject if the subject has a cancer cell that has one or more ROS1 inhibitor resistance mutations; or (d) administering additional doses of the first ROS1 inhibitor of step (a) to the subject if the subject has a cancer cell that does not have one or more ROS1 inhibitor resistance mutations. In some embodiments, where the subject is administered additional doses of the first ROS1 inhibitor of step (a), the subject can also be administered another anticancer agent (e.g., a second ROS1 inhibitor, an ALK inhibitor, a TRK inhibitor, or a compound of Formula I or a pharmaceutically acceptable salt or solvate thereof). In some embodiments, another anticancer agent is any anticancer agent known in the art. For example, another anticancer agent can be another ROS1 inhibitor (e.g., a second ROS1 inhibitor). In some embodiments of step (c), another anticancer agent can be the first ROS1 inhibitor administered in step (a). In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2032, e.g., L2026M, G2032R, or D2033N.

Also provided are methods of treating a subject having a cancer that include: (a) administering a first ALK inhibitor to the subject for a period of time (e.g., 1 month, 2 months, 3 months, 6 months, 9 months, 1 year); (b) after (a), determining whether a cancer cell in a sample obtained from the subject has one or more ROS1 inhibitor resistance mutations; and (c) administering a compound of Formula I or a pharmaceutically acceptable salt or solvate thereof as a monotherapy or in conjunction with another anticancer agent to the subject if the subject has one or more ROS1 inhibitor resistance mutations; or (d) administering additional doses of the first ALK inhibitor of step (a) to the subject if the subject has a cancer cell that does not have one or more ROS1 inhibitor resistance mutations. In some embodiments, where the subject is administered additional doses of the first ALK inhibitor of step (a), the subject can also be administered another anticancer agent (e.g., a second ALK inhibitor, a first ROS1 inhibitor, a TRK inhibitor, or a compound of Formula I or a pharmaceutically acceptable salt or solvate thereof). In some embodiments, another anticancer agent is any anticancer agent known in the art. For example, another anticancer agent can be another ALK inhibitor (e.g., a second ALK inhibitor). In some embodiments of step (c), another anticancer agent can be the first ALK inhibitor administered in step (a). In some embodiments of step (c), another anticancer agent can be another ROS1 inhibitor. In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N.

Also provided are methods of treating a subject having a cancer that include: (a) administering a first TRK inhibitor to the subject for a period of time (e.g., 1 month, 2 months, 3 months, 6 months, 9 months, 1 year); (b) after (a), determining whether a cancer cell in a sample obtained from the subject has one or more ROS1 inhibitor resistance mutations; and (c) administering a compound of Formula I or a pharmaceutically acceptable salt or solvate thereof as a monotherapy or in conjunction with another anticancer agent to the subject if the subject has one or more ROS1 inhibitor resistance mutations; or (d) administering additional doses of the first TRK inhibitor of step (a) to the subject if the subject has a cancer cell that does not have one or more ROS1 inhibitor resistance mutations. In some embodiments, where the subject is administered additional doses of the first TRK inhibitor of step (a), the subject can also be administered another anticancer agent (e.g., a second TRK inhibitor, a first ROS1 inhibitor, an ALK inhibitor, or a compound of Formula I or a pharmaceutically acceptable salt or solvate thereof). In some embodiments, another anticancer agent is any anticancer agent known in the art. For example, another anticancer agent can be another TRK inhibitor (e.g., a second TRK inhibitor). In some embodiments of step (c), another anticancer agent can be the first TRK inhibitor administered in step (a). In some embodiments of step (c), another anticancer agent can be another ROS1 inhibitor. In some embodiments, the dysregulation of a ROS1 gene, a ROS1 kinase, or expression or activity or level of any of the same confers increased resistance to a cancer cell or tumor to treatment with the first TRK inhibitor. In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N.

Also provided are methods of treating a subject having a cancer that include: (a) administering a first ROS1 inhibitor to the subject for a period of time (e.g., 1 month, 2 months, 3 months, 6 months, 9 months, 1 year); (b) after (a), determining whether a cancer cell in a sample obtained from the subject has one or more ROS1 inhibitor resistance mutations; and (c) administering a second ROS1 inhibitor as a monotherapy or in conjunction with another anticancer agent to the subject if the subject has a cancer cell that has one or more ROS1 inhibitor resistance mutations; or (d) administering additional doses of the first ROS1 inhibitor step (a) to the subject if the subject has a cancer cell that does not have one or more ROS1 inhibitor resistance mutations. In some embodiments, where the subject is administered additional doses of the first ROS1 inhibitor of step (a), the subject can also be administered another anticancer agent. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N. In some embodiments, another anticancer agent is any anticancer agent known in the art. For example, another anticancer agent can be another ROS1 inhibitor (e.g., a compound of Formula I or a pharmaceutically acceptable salt or solvate thereof).

Also provided are methods of treating a subject having a cancer (e.g., a ROS1-associated cancer) that include: (a) determining whether a cancer cell in a sample obtained from a subject having a cancer and previously administered a first ROS1 inhibitor, has one or more ROS1 inhibitor resistance mutations; and (b) administering a compound of Formula I or a pharmaceutically acceptable salt or solvate thereof as a monotherapy or in conjunction with another anticancer agent to the subject if the subject has a cancer cell that has one or more ROS1 inhibitor resistance mutations; or (c) administering additional doses of the first ROS1 inhibitor previously administered to the subject if the subject has a cancer cell that does not have one or more ROS1 inhibitor resistance mutations. In some embodiments, where the subject is administered additional doses of the first ROS1 inhibitor previously administered to the subject, the subject can also be administered another anticancer agent (e.g., a second ROS1 inhibitor, an ALK inhibitor, a TRK inhibitor, or a compound of Formula I or a pharmaceutically acceptable salt or solvate thereof). In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N. In some embodiments, another anticancer agent is any anticancer agent known in the art. For example, another anticancer agent can be another ROS1 inhibitor (e.g., a second ROS1 inhibitor). In some embodiments of step (b), another anticancer agent can be the first ROS1 inhibitor administered in step (a).

Also provided are methods of treating a subject having a cancer (e.g., a ROS1-associated cancer) that include: (a) determining whether a cancer cell in a sample obtained from a subject having a cancer and previously administered a first ALK inhibitor has one or more ROS1 inhibitor resistance mutations; and (b) administering a compound of Formula I or a pharmaceutically acceptable salt or solvate thereof as a monotherapy or in conjunction with another anticancer agent to the subject if the subject has a cancer cell having one or more ROS1 inhibitor resistance mutations; or (c) administering additional doses of the first ALK inhibitor previously administered to the subject if the subject has a cancer cell that does not have one or more ROS1 inhibitor resistance mutations. In some embodiments, where the subject is administered additional doses of the first ALK inhibitor previously administered to the subject, the subject can also be administered another anticancer agent (e.g., a second ALK inhibitor, a TRK inhibitor, a first ROS1 inhibitor, or a compound of Formula I or a pharmaceutically acceptable salt or solvate thereof). In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N. In some embodiment, another anticancer agent is any anticancer agent known in the art. For example, another anticancer agent is can be another ALK inhibitor (e.g., a second ALK inhibitor). In some embodiments of step (b), another anticancer agent can be the first ALK inhibitor administered in step (a). In some embodiments of step (b), another anticancer agent can be another ROS1 inhibitor.

Also provided are methods of treating a subject having a cancer (e.g., a ROS1-associated cancer) that include: (a) determining whether a cancer cell in a sample obtained from a subject having a cancer and previously administered a first TRK inhibitor is associated with a dysregulation of a ROS1 gene, a ROS1 kinase, or expression or activity or level of any of the same; and (b) administering a compound of Formula I or a pharmaceutically acceptable salt or solvate thereof as a monotherapy or in conjunction with another anticancer agent to the subject if the subject has a cancer cell that has one or more ROS1 inhibitor resistance mutations; or (c) administering additional doses of the first TRK inhibitor previously administered to the subject if the subject has a cancer cell that does not have one or more ROS1 inhibitor resistance mutations. In some embodiments, where the subject is administered additional doses of the first TRK inhibitor previously administered to the subject, the subject can also be administered another anticancer agent (e.g., a second TRK inhibitor, an ALK inhibitor, a first ROS1 inhibitor, or a compound of Formula I or a pharmaceutically acceptable salt or solvate thereof). In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N. In some embodiments, another anticancer agent is any anticancer agent known in the art. For example, another anticancer agent is can be another TRK inhibitor (e.g., a second TRK inhibitor). In some embodiments of step (b), another anticancer agent can be the first TRK inhibitor administered in step (a). In some embodiments of step (b), another anticancer agent can be another ROS1 inhibitor.

Also provided are methods of treating a subject having a cancer that include: (a) determining whether a cancer cell in a sample obtained from a subject having a cancer and previously administered a first ROS1 inhibitor has one or more ROS1 inhibitor resistance mutations; and (b) administering a second ROS1 inhibitor as a monotherapy or in conjunction with another anticancer agent to the subject if the subject has a cancer cell that has one or more ROS1 inhibitor resistance mutations; or (c) administering additional doses of the first ROS1 inhibitor previously administered to the subject if the subject has a cancer cell that does not have one or more ROS1 inhibitor resistance mutations. In some embodiments, where the subject is administered additional doses of the first ROS1 inhibitor previously administered to the subject, the subject can also be administered another anticancer agent. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N. In some embodiments, another anticancer agent is any anticancer agent known in the art. For example, another anticancer agent can be another ROS1 inhibitor (e.g., a compound of Formula I or a pharmaceutically acceptable salt or solvate thereof). In some embodiments of (b), another anticancer agent can be the first ROS1 inhibitor administered in step (a).

Also provided are methods of treating a subject having a cancer that include: (a) determining whether a cancer cell in a sample obtained from a subject having a cancer and previously administered a first ALK inhibitor has one or more ROS1 inhibitor resistance mutations; and (b) administering a ROS1 inhibitor as a monotherapy or in conjunction with another anticancer agent to the subject if the subject has a cancer cell that has one or more ROS1 inhibitor resistance mutations; or (c) administering additional doses of the first ALK inhibitor previously administered to the subject if the subject has a cancer cell that does not have one or more ROS1 inhibitor resistance mutations. In some embodiments, where the subject is administered additional doses of the first ALK inhibitor previously administered to the subject, the subject can also be administered another anticancer agent. In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N. In some embodiments, another anticancer agent is any anticancer agent known in the art. For example, another anticancer agent can be a ROS1 inhibitor (e.g., a compound of Formula I or a pharmaceutically acceptable salt or solvate thereof). In some embodiments of (b), another anticancer agent can be the first ALK inhibitor administered in step (a).

Also provided are methods of treating a subject having a cancer that include: (a) determining whether a cancer cell in a sample obtained from a subject having a cancer and previously administered a first TRK inhibitor is associated with a dysregulation of a ROS1 gene, a ROS1 kinase, or expression or activity or level of any of the same; and (b) administering a ROS1 inhibitor as a monotherapy or in conjunction with another anticancer agent to the subject if the subject has a cancer cell that has one or more ROS1 inhibitor resistance mutations; or (c) administering additional doses of the first TRK inhibitor previously administered to the subject if the subject has a cancer cell that does not have one or more ROS1 inhibitor resistance mutations. In some embodiments, where the subject is administered additional doses of the first TRK inhibitor previously administered to the subject, the subject can also be administered another anticancer agent. In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N. In some embodiments, another anticancer agent is any anticancer agent known in the art. For example, another anticancer agent can be a ROS1 inhibitor (e.g., a compound of Formula I or a pharmaceutically acceptable salt or solvate thereof). In some embodiments of (b), another anticancer agent can be the first TRK inhibitor administered in step (a).

Also provided are methods of selecting a treatment for a subject having a cancer that include (a) administering a first ROS1 inhibitor to the subject for a period of time (e.g., 1 month, 2 months, 3 months, 6 months, 9 months, 1 year); (b) after (a), determining whether a cancer cell in a sample obtained from the subject has one or more ROS1 inhibitor resistance mutations; and (c) selecting a compound of Formula I or a pharmaceutically acceptable salt or solvate thereof as a monotherapy or in conjunction with another anticancer agent for the subject if the subject has a cancer cell that has one or more ROS1 inhibitor resistance mutations; or (d) selecting additional doses of the first ROS1 inhibitor of step (a) for the subject if the subject has a cancer cell that does not have one or more ROS1 inhibitor resistance mutations. In some embodiments, when additional doses of the first ROS1 inhibitor of step (a) are selected for the subject, the method can further include selecting doses of another anticancer agent for the subject. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N. In some embodiments, another anticancer agent is any anticancer agent known in the art. For example, another anticancer agent can be another ROS1 inhibitor (e.g., a second ROS1 inhibitor). In some embodiments of step (c), another ROS1 inhibitor can be the first ROS1 inhibitor administered in step (a).

Also provided are methods of selecting a treatment for a subject having a cancer that include (a) administering a first ALK inhibitor to the subject for a period of time (e.g., 1 month, 2 months, 3 months, 6 months, 9 months, 1 year); (b) after (a), determining whether a cancer cell in a sample obtained from the subject has one or more ROS1 inhibitor resistance mutations; and (c) selecting a compound of Formula I or a pharmaceutically acceptable salt or solvate thereof as a monotherapy or in conjunction with another anticancer agent for the subject if the subject has a cancer cell that has one or more ROS1 inhibitor resistance mutations; or (d) selecting additional doses of the first ALK inhibitor of step (a) for the subject if the subject has a cancer cell that does not have has one or more ROS1 inhibitor resistance mutations. In some embodiments, when additional doses of the first ALK inhibitor of step (a) are selected for the subject, the method can further include selecting doses of another anticancer agent for the subject. In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N. In some embodiments of step (c), another anticancer agent is any anticancer agent known in the art. For example, another anticancer agent can be another ROS1 inhibitor. In some embodiments of step (c), another anticancer agent is the first ALK inhibitor administered in step (a).

Also provided are methods of selecting a treatment for a subject having a cancer that include (a) administering one or more doses of a first TRK inhibitor to the subject for a period of time (e.g., 1 month, 2 months, 3 months, 6 months, 9 months, 1 year); (b) after (a), determining whether a cancer cell in a sample obtained from the subject has one or more ROS1 inhibitor resistance mutations; and (c) selecting a compound of Formula I or a pharmaceutically acceptable salt or solvate thereof as a monotherapy or in conjunction with another anticancer agent for the subject if the subject has a cancer cell that has one or more ROS1 inhibitor resistance mutations; or (d) selecting additional doses of the first TRK inhibitor of step (a) for the subject if the subject has a cancer cell that does not have one or more ROS1 inhibitor resistance mutations. In some embodiments, when additional doses of the first TRK inhibitor of step (a) are selected for the subject, the method can further include selecting doses of another anticancer agent for the subject. In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N. In some embodiments of step (c), another anticancer agent is any anticancer agent known in the art. For example, another anticancer agent can be another ROS1 inhibitor. In some embodiments of step (c), another anticancer agent is the first TRK inhibitor administered in step (a).

Also provided are methods of selecting a treatment for a subject having a cancer that include (a) administering a first ROS1 inhibitor to the subject for a period of time (e.g., 1 month, 2 months, 3 months, 6 months, 9 months, 1 year); (b) after (a), determining whether a cancer cell in a sample obtained from the subject has one or more ROS1 inhibitor resistance mutations; and (c) selecting a second ROS1 inhibitor as a monotherapy or in conjunction with another anticancer agent if the subject has a cancer cell that has one or more ROS1 inhibitor resistance mutations; or (d) selecting additional doses of the first ROS1 inhibitor of step (a) for the subject if the subject has a cancer cell that does not have one or more ROS1 inhibitor resistance mutations. In some embodiments, when additional doses of the first ROS1 inhibitor of step (a) are selected for the subject, the method can further include selecting doses of another anticancer agent for the subject. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N. In some embodiments, another anticancer agent is any anticancer agent known in the art. For example, another anticancer agent is another ROS1 inhibitor (e.g., a compound of Formula I or a pharmaceutically acceptable salt or solvate thereof). In some embodiments, another ROS1 can be the first ROS1 inhibitor administered in step (a).

Also provided are methods of selecting a treatment for a subject having a cancer that include (a) determining whether a cancer cell in a sample obtained from a subject having a cancer and previously administered a first ROS1 inhibitor has one or more ROS1 inhibitor resistance mutations; (b) selecting a compound of Formula I or a pharmaceutically acceptable salt or solvate thereof as a monotherapy or in conjunction with another anticancer agent for the subject if the subject has a cancer cell that has one or more ROS1 inhibitor resistance mutations; or (c) selecting additional doses of the first ROS1 inhibitor previously administered to the subject if the subject has a cancer cell that does not have one or more ROS1 inhibitor resistance mutations. In some embodiments, when additional doses of the first ROS1 inhibitor previously administered to the subject are selected for the subject, the method can further include selecting doses of another anticancer agent (e.g., a compound of Formula I or a pharmaceutically acceptable salt or solvate thereof) for the subject. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N. In some embodiments, another anticancer agent is any anticancer agent known in the art. For example, another anticancer agent is another ROS1 inhibitor (e.g., a second ROS1 inhibitor). In some embodiments of step (c), another ROS1 inhibitor can be the first ROS1 inhibitor administered in step (a).

Also provided are methods of selecting a treatment for a subject having a cancer (e.g., a ROS1-associated cancer) that include: (a) determining whether a cancer cell in a sample obtained from a subject having a cancer and previously administered a first ALK inhibitor has one or more ROS1 inhibitor resistance mutations; and (b) selecting a compound of Formula I or a pharmaceutically acceptable salt or solvate thereof as a monotherapy or in conjunction with another anticancer agent for the subject if the subject has a cancer cell that has one or more ROS1 inhibitor resistance mutations; or (c) selecting additional doses of the first ALK inhibitor previously administered to the subject if the subject has a cancer cell that does not have one or more ROS1 inhibitor resistance mutations. In some embodiments, where additional doses of the first ALK inhibitor previously administered to the subject are selected for the subject, the method can further include selecting doses of another anticancer agent (e.g., a second ALK inhibitor, a TRK inhibitor, a first ROS1 inhibitor, or a compound of Formula I or a pharmaceutically acceptable salt or solvate thereof). In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N. In some embodiments, another anticancer agent is any anticancer agent known in the art. For example, another anticancer agent is can be another ALK inhibitor (e.g., a second ALK inhibitor). In some embodiments of step (b), another anticancer agent can be the first ALK inhibitor administered in step (a). In some embodiments of step (b), another anticancer agent can be another ROS1 inhibitor.

Also provided are methods of selecting a treatment for a subject having a cancer (e.g., a ROS1-associated cancer) that include: (a) determining whether a cancer cell in a sample obtained from a subject having a cancer and previously administered a first TRK inhibitor has one or more ROS1 inhibitor resistance mutations; and (b) selecting a compound of Formula I or a pharmaceutically acceptable salt or solvate thereof as a monotherapy or in conjunction with another anticancer agent for the subject if the subject has a cancer cell that has one or more ROS1 inhibitor resistance mutations; or (c) selecting additional doses of the first TRK inhibitor previously administered to the subject if the subject has a cancer cell that does not have one or more ROS1 inhibitor resistance mutations. In some embodiments, where additional doses of the first TRK inhibitor previously administered to the subject are selected for the subject, the method can further include selecting doses of another anticancer agent (e.g., a second TRK inhibitor, an ALK inhibitor, a first ROS1 inhibitor, or a compound of Formula I or a pharmaceutically acceptable salt or solvate thereof). In some embodiments, the ROS1 inhibitor resistance mutation includes one or more ROS1 inhibitor resistance mutations listed in Table 4. For example, a ROS1 inhibitor resistance mutation can include a substitution at one or more of amino acid positions 2026, 2032, or 2033, e.g., L2026M, G2032R, or D2033N. In some embodiments, another anticancer agent is any anticancer agent known in the art. For example, another anticancer agent is can be another TRK inhibitor (e.g., a second TRK inhibitor). In some embodiments of step (b), another anticancer agent can be the first TRK inhibitor administered in step (a). In some embodiments of step (b), another anticancer agent can be another ROS1 inhibitor.

Also provided are methods of selecting a treatment for a subject having a cancer that include (a) determining whether a cancer cell in a sample obtained from a subject having a cancer and previously administered a first ROS1 inhibitor has one or more ROS1 inhibitor resistance mutations; (b) selecting a second ROS1 inhibitor as a monotherapy or in conjunction with another anticancer agent for the subject if the subject has a cancer cell that has one or more ROS1 inhibitor resistance mutations; or (c) selecting additional doses of the first ROS1 inhibitor previously administered to the subject if the subject has a cancer cell that does not have one or more ROS1 inhibitor resistance mutations. In some embodiments, when additional doses of the first ROS1 inhibitor previously administered to the subject are selected for the subject, the method can further include selecting doses of another anticancer agent (e.g., a compound of Formula I or a pharmaceutically acceptable salt or solvate thereof) for the subject. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N. In some embodiments, another anticancer agent is any anticancer agent known in the art. For example, another anticancer agent is another ROS1 inhibitor (e.g., a compound of Formula I or a pharmaceutically acceptable salt or solvate thereof). In some embodiments, another ROS1 can be the first ROS1 inhibitor administered in step (a).

Also provided are methods of determining a subject's risk for developing a cancer that has some resistance to a first ROS1 inhibitor that include: determining whether a cell in a sample obtained from the subject has one or more ROS1 inhibitor resistance mutations; and identifying a subject having a cell that has one or more ROS1 inhibitor resistance mutations as having an increased likelihood of developing a cancer that has some resistance to the first ROS1 inhibitor. Also provided are methods of determining a subject's risk for developing a cancer that has some resistance to a first ROS1 inhibitor that include: identifying a subject having a cell that has one or more ROS1 inhibitor resistance mutations as having an increased likelihood of developing a cancer that has some resistance to the first ROS1 inhibitor. Also provided are methods of determining the presence of a cancer that has some resistance to a first ROS1 inhibitor that include: determining whether a cancer cell in a sample obtained from the subject has one or more ROS1 inhibitor resistance mutations; and determining that the subject having a cancer cell that has one or more ROS1 inhibitor resistance mutations has a cancer that has some resistance to the first ROS1 inhibitor. Also provided are methods of determining the presence of a cancer that has some resistance to a first ROS1 inhibitor in a subject that include: determining that a subject having a cancer cell that has one or more ROS1 inhibitor resistance mutations has a cancer that has some resistance to the first ROS1 inhibitor. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations listed in Table 4. For example, the one or more ROS1 inhibitor resistance mutations can include a substitution at one or more of amino acid positions 2026, 2032, or 2033, e.g., L2026M, G2032R, or D2033N.

In some embodiments of any of the methods described herein, a ROS1 inhibitor resistance mutation that confers increased resistance to a cancer cell or tumor to treatment with a first ROS1 inhibitor can be any of the ROS1 inhibitor resistance mutations listed in Table 4 (e.g., a substitution at one or more of amino acid positions 2026, 2032, or 2033, e.g., L2026M, G2032R, or D2033N).

Also provided are methods of determining the likelihood that a subject having a cancer will have a positive response to treatment with a compound of Formula I or a pharmaceutically acceptable salt or solvate thereof as a monotherapy that include: determining whether a cancer cell in a sample obtained from the subject has one or more ROS1 inhibitor resistance mutations; and determining that the subject having the cancer cell that has one or more ROS1 inhibitor resistance mutations has an increased likelihood of having a positive response to treatment with a compound of Formula I or a pharmaceutically acceptable salt or solvate thereof as a monotherapy. Also provided are methods of determining the likelihood that a subject having cancer will have a positive response to treatment with a compound of Formula I or a pharmaceutically acceptable salt or solvate thereof as a monotherapy that include: determining that a subject having a cancer cell that has one or more ROS1 inhibitor resistance mutations has an increased likelihood of having a positive response to treatment with a compound of Formula I or a pharmaceutically acceptable salt or solvate thereof as a monotherapy. Also provided are methods of predicting the efficacy of treatment with a compound of Formula I or a pharmaceutically acceptable salt or solvate thereof as a monotherapy in a subject having cancer that include: determining whether a cancer cell in a sample obtained from the subject has one or more ROS1 inhibitor resistance mutations; and determining that treatment with a compound of Formula I or a pharmaceutically acceptable salt or solvate thereof as a monotherapy is likely to be effective in a subject having a cancer cell in a sample obtained from the subject that has one or more ROS1 inhibitor resistance mutations. Also provided are methods of predicting the efficacy of treatment with a compound of Formula I or a pharmaceutically acceptable salt or solvate thereof as a monotherapy in a subject having cancer that include: determining that treatment with a compound of Formula I or a pharmaceutically acceptable salt or solvate thereof as a monotherapy is likely to be effective in a subject having a cancer cell in a sample obtained from the subject that has one or more ROS1 inhibitor resistance mutations.

Methods of determining the level of resistance of a cancer cell or a tumor to a ROS1 inhibitor (e.g., any of the ROS1 inhibitors described herein or known in the art) can be determined using methods known in the art. For example, the level of resistance of a cancer cell to a ROS1 inhibitor can be assessed by determining the $IC_{50}$ of a ROS1 inhibitor (e.g., any of the ROS1 inhibitors described herein or known in the art) on the viability of a cancer cell. In other examples, the level of resistance of a cancer cell to a ROS1 inhibitor can be assessed by determining the growth rate of the cancer cell in the presence of a ROS1 inhibitor (e.g., any of the ROS1 inhibitors described herein). In other examples, the level of resistance of a tumor to a ROS1 inhibitor can be assessed by determining the mass or size of one or more tumors in a subject over time during treatment with a ROS1 inhibitor (e.g., any of the ROS1 inhibitors described herein). In other examples, the level of resistance of a cancer cell or a tumor to a ROS1 inhibitor can be indirectly assessed by determining the activity of a ROS1 kinase including one or more of the ROS1 inhibitor resistance mutations (i.e., the same ROS1 kinase expressed in a cancer cell or a tumor in a subject). The level of resistance of a cancer cell or tumor having one or more ROS1 inhibitor resistance mutations to a ROS1 inhibitor is relative to the level of resistance in a cancer cell or tumor that does not have one or more ROS1 inhibitor resistance mutations (e.g., a cancer cell or tumor that does not have the same ROS1 inhibitor resistance mutations, a cancer cell or a tumor that does not have any ROS1 inhibitor resistance mutations, or a cancer cell or a tumor that expresses a wildtype ROS1 protein). For example, the determined level of resistance of a cancer cell or a tumor having one or more ROS1 inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have one or more ROS1 inhibitor resistance mutations (e.g., a cancer cell or tumor that does not have the same ROS1 inhibitor resistance mutations, a cancer cell or a tumor that does not have any ROS1 inhibitor resistance mutations, or a cancer cell or a tumor that expresses a wildtype ROS1 protein).

Also provided is a method for inhibiting ROS1 kinase activity in a cell, comprising contacting the cell with a compound of Formula I. In some embodiments, the contacting is in vitro. In some embodiments, the contacting is in vivo. In some embodiments, the contacting is in vivo, wherein the method comprises administering an effective amount of a compound of Formula I or a pharmaceutically acceptable salt or solvate thereof to a subject having a cell having ROS1 kinase activity. In some embodiments, the cell is a cancer cell. In some embodiments, the cancer cell is any cancer as described herein. In some embodiments, the cancer cell is a ROS1-associated cancer cell.

Also provided is a method for inhibiting ROS1 kinase activity in a mammalian cell, comprising contacting the cell with a compound of Formula I. In some embodiments, the contacting is in vitro. In some embodiments, the contacting is in vivo. In some embodiments, the contacting is in vivo, wherein the method comprises administering an effective amount of a compound of Formula I or a pharmaceutically acceptable salt or solvate thereof to a mammal having a cell having ROS1 kinase activity. In some embodiments, the mammalian cell is a mammalian cancer cell. In some embodiments, the mammalian cancer cell is any cancer as described herein. In some embodiments, the mammalian cancer cell is a ROS1-associated cancer cell.

As used herein, the term "contacting" refers to the bringing together of indicated moieties in an in vitro system or an in vivo system. For example, "contacting" a ROS1 kinase with a compound provided herein includes the administration of a compound provided herein to an individual or patient, such as a human, having a ROS1 kinase, as well as, for example, introducing a compound provided herein into a sample containing a cellular or purified preparation containing the ROS1 kinase.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein The phrase "effective amount" means an amount of compound that, when administered to a patient in need of such treatment, is sufficient to (i) treat a ROS1 kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the patient in need of treatment, but can nevertheless be routinely determined by one skilled in the art.

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable Also provided herein are pharmaceutical compositions which contain, as the active ingredient, a compound of Formula I or a pharmaceutically acceptable salt or solvate thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is formulated as a tablet or capsule.

The compositions comprising a compound of Formula I or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound for Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

Provided herein are pharmaceutical kits useful, for example, in the treatment of RET-associated diseases or disorders, such as cancer or irritable bowel syndrome (IBS), which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

Example A. Inhibition of ROS1 Kinase

The potency of a compound inhibiting wild type and exemplary mutant ROS1 kinases was determined using CisBio's HTRF Kinease-TK assay technology. The assays contained 5 nM wild type ROS1 (SignalChem—Cat. No. R14-11G), 5 nM G2032R ROS1 (SignalChem—Cat. No. R14-12BG), 5 nM L2026M ROS1 (Array Biopharma, p 1965), or 5 nM D2033N ROS1 (Array Biopharma, p 1994). Each kinase is incubated with 250 nM TK-substrate biotin (CisBio, Cat. No. 62TK0PEC) and 1 mM ATP along with test compound in a buffer consisting of 25 mM MOPS [pH 7.4], 5 mM $MgCl_2$, 0.005% Triton X-100, and 2% DMSO in a volume of 8 µL. Compounds were prepared in a four-fold serial dilution in DMSO and added to the assay to give the appropriate final concentration. After a 120-minute incubation at 22° C., the reaction was quenched by adding 8 µL of quench solution containing 31.3 nM Sa-XL665 and 1×TK-Ab-Cryptate in HTRF detection buffer (CisBio, Cat. No. 62TK0PEC). After a 1 hour incubation at 22° C., the extent of reaction was determined using a PerkinElmer EnVision multimode plate reader via HTRF dual wavelength detection, and the percent of control (POC) was calculated using a ratiometric emission factor. 100 POC is determined using no test compound and 0 POC is determined in the absence of enzyme. The POC values are fit to a 4-parameter logistic curve and the $IC_{50}$ value is calculated based on the point at which the curve crosses 50 POC.

Table 9 provides averaged $IC_{50}$ values for compounds tested in this assay.

TABLE 9

| Compound No. | Structure | ROS1 wT $IC_{50}$ (nM) | ROS1 G2032R $IC_{50}$ (nM) | ROS1 L2026M $IC_{50}$ (nM) | ROS1 D2033N $IC_{50}$ (nM) |
|---|---|---|---|---|---|
| 2 | 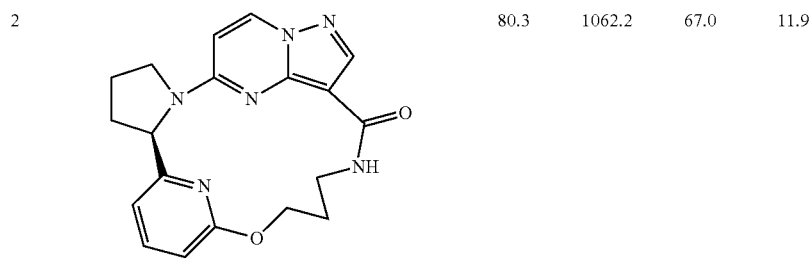 | 80.3 | 1062.2 | 67.0 | 11.9 |

TABLE 9-continued

| Compound No. | Structure | ROS1 wT IC$_{50}$ (nM) | ROS1 G2032R IC$_{50}$ (nM) | ROS1 L2026M IC$_{50}$ (nM) | ROS1 D2033N IC$_{50}$ (nM) |
| --- | --- | --- | --- | --- | --- |
| 3 | 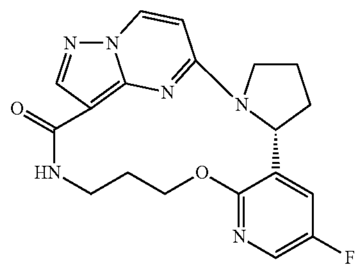 [SMILES: O=C1NCCCOc2ncc(F)cc2[C@H]2CCCN2c2ccn3ncc1c3n2] | 1.2 | 9.4 | 1.2 | 0.3 |
| 7 | 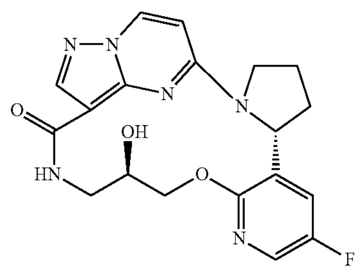 [SMILES: O=C1NC[C@@H](O)COc2ncc(F)cc2[C@H]2CCCN2c2ccn3ncc1c3n2] | 3.1 | 29.2 | 2.9 | 0.6 |
| 9 | 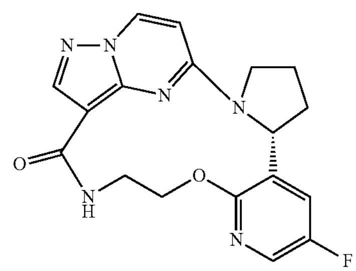 [SMILES: O=C1NCCOc2ncc(F)cc2[C@H]2CCCN2c2ccn3ncc1c3n2] | 9.2 | 98.6 | 10.2 | 1.7 |
| 14 | 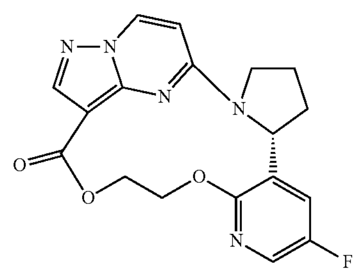 [SMILES: O=C1OCCOc2ncc(F)cc2[C@H]2CCCN2c2ccn3ncc1c3n2] | 28.9 | 107.3 | 30.3 | 7.6 |
| 19 | 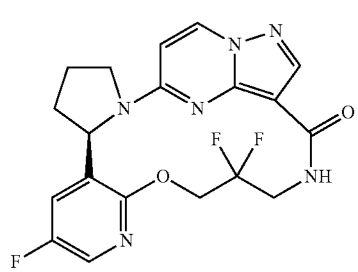 [SMILES: O=C1NCC(F)(F)COc2ncc(F)cc2[C@H]2CCCN2c2ccn3ncc1c3n2] | 2.4 | 14.4 | 2.4 | 1.2 |

TABLE 9-continued

| Compound No. | Structure | ROS1 wT IC$_{50}$ (nM) | ROS1 G2032R IC$_{50}$ (nM) | ROS1 L2026M IC$_{50}$ (nM) | ROS1 D2033N IC$_{50}$ (nM) |
|---|---|---|---|---|---|
| 20 | 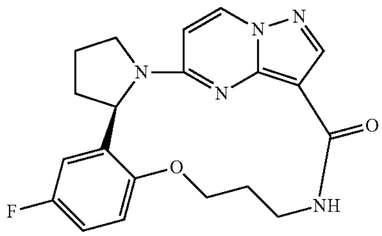 [SMILES: O=C1NCCCOc2ccc(F)cc2[C@H]2CCCN2c2ccn3ncc1c3n2] | 2.5 | 21.6 | 2.2 | 2.8 |
| 22 | 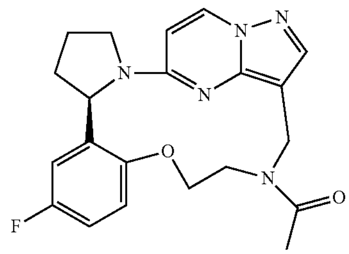 [SMILES: CC(=O)N1CCOc2ccc(F)cc2[C@H]2CCCN2c2ccn3ncc(c3n2)C1] | 330.6 | 3980.2 | 712.9 | 396.9 |
| 33-A | 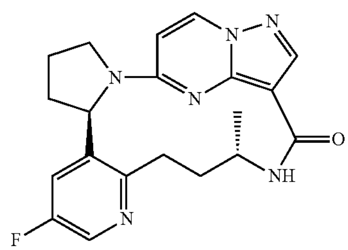 [SMILES: C[C@H]1CCc2ncc(F)cc2[C@H]2CCCN2c2ccn3ncc(c3n2)C(=O)N1] | 19.2 | 157.1 | 19.6 | 14.3 |
| 33-B | 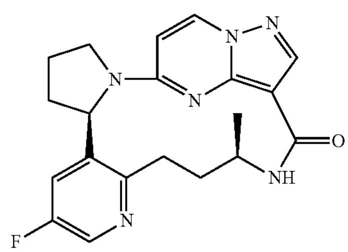 [SMILES: C[C@@H]1CCc2ncc(F)cc2[C@H]2CCCN2c2ccn3ncc(c3n2)C(=O)N1] | 2.7 | 20.4 | 3.6 | 0.5 |
| 35 | 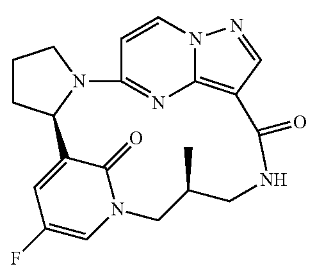 [SMILES: C[C@H]1CNC(=O)c2cnn3ccc(nc23)N2CCC[C@@H]2c2cc(F)cn(c2=O)C1] | 779.1 | 4931.9 | 589.3 | 260.1 |
| 36 | 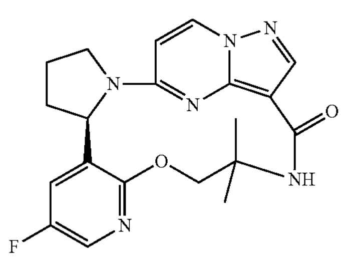 [SMILES: CC1(C)COc2ncc(F)cc2[C@H]2CCCN2c2ccn3ncc(c3n2)C(=O)N1] | 0.7 | 6.5 | 0.5 | 0.2 |

TABLE 9-continued

| Compound No. | Structure | ROS1 wT IC$_{50}$ (nM) | ROS1 G2032R IC$_{50}$ (nM) | ROS1 L2026M IC$_{50}$ (nM) | ROS1 D2033N IC$_{50}$ (nM) |
|---|---|---|---|---|---|
| 45 | 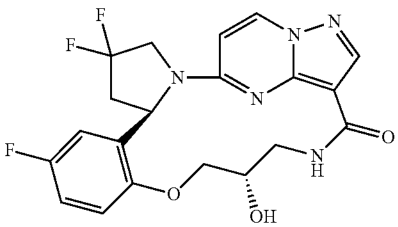 [SMILES: O=C1NC[C@H](O)COc2ccc(F)cc2[C@H]2CC(F)(F)CN2c2ccn3ncc1c3n2] | 6.1 | 113.6 | 4.6 | 16.8 |

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

---

What is claimed is:

1. A method for treating a ROS1-associated cancer in a subject in need thereof, wherein the subject has been administered a first TRK inhibitor that is entrectinib, and the ROS1-associated cancer has developed resistance to the first TRK inhibitor, the method comprising administering (6R,15R)-9-fluoro-15-methyl-2,11,16,20,21,24-hexaazapentacyclo[16.5.2.02,6.07,12.021,25]pentacosa-1(24),7,9,11,18(25),19,22-heptaen-17-one;

or a pharmaceutically acceptable salt thereof;

wherein the ROS1-associated cancer is selected from non-small-cell lung cancer or papillary thyroid carcinoma and has a point mutation in the ROS1 gene results in the production of a ROS1 kinase having one or more amino acid substitutions selected from the group consisting of A15G, R118N, A122T, R245I, G1025R, S1186F, P1539S, T1735M, R1948H, D2033Y, R2072N, R2162W, R2162Q, R2162L, and E2308W.

2. The method of claim 1, wherein the cancer further comprises one or more chromosome translocations or inversions resulting in a ROS1 gene fusion.

3. The method of claim 2, wherein the ROS1 gene fusion is selected from the group consisting of: CD74-ROS1, SLC34A2-ROS1, TPM3-ROS1, SDC4-ROS1, EZR-ROS1, LRIG-ROS1, KDELR2-ROS1, CCDC6-ROS1, FIG-ROS1, TPD52L1-ROS1, CEP85L-ROS1, ZCCHC8-ROS1, CCDC30-ROS1, TFG-ROS1, TMEM106B-ROS1, YWHAE-ROS1, MSN-ROS1, PWWP2A-ROS1, FYN-ROS1, MKX-ROS1, PPFIBP1-ROS1, ERC1-ROS1, MY05A-ROS1, CLIP1-ROS1, HLA-A-ROS1, KIAA1598-ROS1, CLTC-ROS1, LIMA1-ROS1, NFkB2-ROS1, NCOR2-ROS1, KCL1-ROS1, and TBL1XR1-ROS1.

* * * * *

UNITED STATES PATENT AND TRADEMARK OFFICE
CERTIFICATE OF CORRECTION

PATENT NO. : 10,688,100 B2
APPLICATION NO. : 16/199875
DATED : June 23, 2020
INVENTOR(S) : Steven W. Andrews et al.

Page 1 of 1

It is certified that error appears in the above-identified patent and that said Letters Patent is hereby corrected as shown below:

In the Claims

Claim 1, Column 129, Line 38, "gene results" should read --gene that results--.

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 1

<210> SEQ ID NO 1
<211> LENGTH: 2347
<212> TYPE: PRT
<213> ORGANISM: Homo sapiens

<400> SEQUENCE: 1

```
Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Glu Val Leu
                85                  90                  95

Glu Asn Ala Asp Leu Pro Thr Ala Pro Phe Ala Ser Ser Ile Gly Ser
            100                 105                 110

His Asn Met Thr Leu Arg Trp Lys Ser Ala Asn Phe Ser Gly Val Lys
        115                 120                 125

Tyr Ile Ile Gln Trp Lys Tyr Ala Gln Leu Leu Gly Ser Trp Thr Tyr
    130                 135                 140

Thr Lys Thr Val Ser Arg Pro Ser Tyr Val Val Lys Pro Leu His Pro
145                 150                 155                 160

Phe Thr Glu Tyr Ile Phe Arg Val Val Trp Ile Phe Thr Ala Gln Leu
                165                 170                 175

Gln Leu Tyr Ser Pro Pro Ser Pro Ser Tyr Arg Thr His Pro His Gly
            180                 185                 190

Val Pro Glu Thr Ala Pro Leu Ile Arg Asn Ile Glu Ser Ser Ser Pro
        195                 200                 205
```

```
Asp Thr Val Glu Val Ser Trp Asp Pro Pro Gln Phe Pro Gly Gly Pro
    210                 215                 220

Ile Leu Gly Tyr Asn Leu Arg Leu Ile Ser Lys Asn Gln Lys Leu Asp
225                 230                 235                 240

Ala Gly Thr Gln Arg Thr Ser Phe Gln Phe Tyr Ser Thr Leu Pro Asn
                245                 250                 255

Thr Ile Tyr Arg Phe Ser Ile Ala Ala Val Asn Glu Val Gly Glu Gly
                260                 265                 270

Pro Glu Ala Glu Ser Ser Ile Thr Thr Ser Ser Ser Ala Val Gln Gln
                275                 280                 285

Glu Glu Gln Trp Leu Phe Leu Ser Arg Lys Thr Ser Leu Arg Lys Arg
290                 295                 300

Ser Leu Lys His Leu Val Asp Glu Ala His Cys Leu Arg Leu Asp Ala
305                 310                 315                 320

Ile Tyr His Asn Ile Thr Gly Ile Ser Val Asp Val His Gln Gln Ile
                325                 330                 335

Val Tyr Phe Ser Glu Gly Thr Leu Ile Trp Ala Lys Lys Ala Ala Asn
                340                 345                 350

Met Ser Asp Val Ser Asp Leu Arg Ile Phe Tyr Arg Gly Ser Gly Leu
                355                 360                 365

Ile Ser Ser Ile Ser Ile Asp Trp Leu Tyr Gln Arg Met Tyr Phe Ile
370                 375                 380

Met Asp Glu Leu Val Cys Val Cys Asp Leu Glu Asn Cys Ser Asn Ile
385                 390                 395                 400

Glu Glu Ile Thr Pro Pro Ser Ile Ser Ala Pro Gln Lys Ile Val Ala
                405                 410                 415

Asp Ser Tyr Asn Gly Tyr Val Phe Tyr Leu Leu Arg Asp Gly Ile Tyr
                420                 425                 430

Arg Ala Asp Leu Pro Val Pro Ser Gly Arg Cys Ala Glu Ala Val Arg
                435                 440                 445

Ile Val Glu Ser Cys Thr Leu Lys Asp Phe Ala Ile Lys Pro Gln Ala
450                 455                 460

Lys Arg Ile Ile Tyr Phe Asn Asp Thr Ala Gln Val Phe Met Ser Thr
465                 470                 475                 480

Phe Leu Asp Gly Ser Ala Ser His Leu Ile Leu Pro Arg Ile Pro Phe
                485                 490                 495

Ala Asp Val Lys Ser Phe Ala Cys Glu Asn Asn Asp Phe Leu Val Thr
                500                 505                 510

Asp Gly Lys Val Ile Phe Gln Gln Asp Ala Leu Ser Phe Asn Glu Phe
                515                 520                 525

Ile Val Gly Cys Asp Leu Ser His Ile Glu Glu Phe Gly Phe Gly Asn
                530                 535                 540

Leu Val Ile Phe Gly Ser Ser Gln Leu His Pro Leu Pro Gly Arg
545                 550                 555                 560

Pro Gln Glu Leu Ser Val Leu Phe Gly Ser His Gln Ala Leu Val Gln
                565                 570                 575

Trp Lys Pro Pro Ala Leu Ala Ile Gly Ala Asn Val Ile Leu Ile Ser
                580                 585                 590

Asp Ile Ile Glu Leu Phe Glu Leu Gly Pro Ser Ala Trp Gln Asn Trp
                595                 600                 605

Thr Tyr Glu Val Lys Val Ser Thr Gln Asp Pro Pro Glu Val Thr His
                610                 615                 620
```

-continued

```
Ile Phe Leu Asn Ile Ser Gly Thr Met Leu Asn Val Pro Glu Leu Gln
625                 630                 635                 640

Ser Ala Met Lys Tyr Lys Val Ser Val Arg Ala Ser Ser Pro Lys Arg
            645                 650                 655

Pro Gly Pro Trp Ser Glu Pro Ser Val Gly Thr Thr Leu Val Pro Ala
        660                 665                 670

Ser Glu Pro Pro Phe Ile Met Ala Val Lys Glu Asp Gly Leu Trp Ser
    675                 680                 685

Lys Pro Leu Asn Ser Phe Gly Pro Glu Phe Leu Ser Ser Asp Ile
690                 695                 700

Gly Asn Val Ser Asp Met Asp Trp Tyr Asn Asn Ser Leu Tyr Tyr Ser
705                 710                 715                 720

Asp Thr Lys Gly Asp Val Phe Val Trp Leu Leu Asn Gly Thr Asp Ile
                725                 730                 735

Ser Glu Asn Tyr His Leu Pro Ser Ile Ala Gly Ala Gly Ala Leu Ala
                740                 745                 750

Phe Glu Trp Leu Gly His Phe Leu Tyr Trp Ala Gly Lys Thr Tyr Val
            755                 760                 765

Ile Gln Arg Gln Ser Val Leu Thr Gly His Thr Asp Ile Val Thr His
770                 775                 780

Val Lys Leu Leu Val Asn Asp Met Val Val Asp Ser Val Gly Gly Tyr
785                 790                 795                 800

Leu Tyr Trp Thr Thr Leu Tyr Ser Val Glu Ser Thr Arg Leu Asn Gly
                805                 810                 815

Glu Ser Ser Leu Val Leu Gln Thr Gln Pro Trp Phe Ser Gly Lys Lys
            820                 825                 830

Val Ile Ala Leu Thr Leu Asp Leu Ser Asp Gly Leu Leu Tyr Trp Leu
            835                 840                 845

Val Gln Asp Ser Gln Cys Ile His Leu Tyr Thr Ala Val Leu Arg Gly
850                 855                 860

Gln Ser Thr Gly Asp Thr Thr Ile Thr Glu Phe Ala Ala Trp Ser Thr
865                 870                 875                 880

Ser Glu Ile Ser Gln Asn Ala Leu Met Tyr Tyr Ser Gly Arg Leu Phe
            885                 890                 895

Trp Ile Asn Gly Phe Arg Ile Ile Thr Thr Gln Glu Ile Gly Gln Lys
        900                 905                 910

Thr Ser Val Ser Val Leu Glu Pro Ala Arg Phe Asn Gln Phe Thr Ile
    915                 920                 925

Ile Gln Thr Ser Leu Lys Pro Leu Pro Gly Asn Phe Ser Phe Thr Pro
930                 935                 940

Lys Val Ile Pro Asp Ser Val Gln Glu Ser Ser Phe Arg Ile Glu Gly
945                 950                 955                 960

Asn Ala Ser Ser Phe Gln Ile Leu Trp Asn Gly Pro Pro Ala Val Asp
            965                 970                 975

Trp Gly Val Val Phe Tyr Ser Val Glu Phe Ser Ala His Ser Lys Phe
        980                 985                 990

Leu Ala Ser Glu Gln His Ser Leu Pro Val Phe Thr Val Glu Gly Leu
    995                 1000                1005

Glu Pro Tyr Ala Leu Phe Asn Leu Ser Val Thr Pro Tyr Thr Tyr
    1010                1015                1020

Trp Gly Lys Gly Pro Lys Thr Ser Leu Ser Leu Arg Ala Pro Glu
    1025                1030                1035

Thr Val Pro Ser Ala Pro Glu Asn Pro Arg Ile Phe Ile Leu Pro
```

-continued

```
                1040                1045                1050
Ser Gly Lys Cys Cys Asn Lys Asn Glu Val Val Glu Phe Arg
            1055                1060                1065
Trp Asn Lys Pro Lys His Glu Asn Gly Val Leu Thr Lys Phe Glu
            1070                1075                1080
Ile Phe Tyr Asn Ile Ser Asn Gln Ser Ile Thr Asn Lys Thr Cys
            1085                1090                1095
Glu Asp Trp Ile Ala Val Asn Val Thr Pro Ser Val Met Ser Phe
            1100                1105                1110
Gln Leu Glu Gly Met Ser Pro Arg Cys Phe Ile Ala Phe Gln Val
            1115                1120                1125
Arg Ala Phe Thr Ser Lys Gly Pro Gly Pro Tyr Ala Asp Val Val
            1130                1135                1140
Lys Ser Thr Thr Ser Glu Ile Asn Pro Phe Pro His Leu Ile Thr
            1145                1150                1155
Leu Leu Gly Asn Lys Ile Val Phe Leu Asp Met Asp Gln Asn Gln
            1160                1165                1170
Val Val Trp Thr Phe Ser Ala Glu Arg Val Ile Ser Ala Val Cys
            1175                1180                1185
Tyr Thr Ala Asp Asn Glu Met Gly Tyr Tyr Ala Glu Gly Asp Ser
            1190                1195                1200
Leu Phe Leu Leu His Leu His Asn Arg Ser Ser Ser Glu Leu Phe
            1205                1210                1215
Gln Asp Ser Leu Val Phe Asp Ile Thr Val Ile Thr Ile Asp Trp
            1220                1225                1230
Ile Ser Arg His Leu Tyr Phe Ala Leu Lys Glu Ser Gln Asn Gly
            1235                1240                1245
Met Gln Val Phe Asp Val Asp Leu Glu His Lys Val Lys Tyr Pro
            1250                1255                1260
Arg Glu Val Lys Ile His Asn Arg Asn Ser Thr Ile Ile Ser Phe
            1265                1270                1275
Ser Val Tyr Pro Leu Leu Ser Arg Leu Tyr Trp Thr Glu Val Ser
            1280                1285                1290
Asn Phe Gly Tyr Gln Met Phe Tyr Tyr Ser Ile Ile Ser His Thr
            1295                1300                1305
Leu His Arg Ile Leu Gln Pro Thr Ala Thr Asn Gln Gln Asn Lys
            1310                1315                1320
Arg Asn Gln Cys Ser Cys Asn Val Thr Glu Phe Glu Leu Ser Gly
            1325                1330                1335
Ala Met Ala Ile Asp Thr Ser Asn Leu Glu Lys Pro Leu Ile Tyr
            1340                1345                1350
Phe Ala Lys Ala Gln Glu Ile Trp Ala Met Asp Leu Glu Gly Cys
            1355                1360                1365
Gln Cys Trp Arg Val Ile Thr Val Pro Ala Met Leu Ala Gly Lys
            1370                1375                1380
Thr Leu Val Ser Leu Thr Val Asp Gly Asp Leu Ile Tyr Trp Ile
            1385                1390                1395
Ile Thr Ala Lys Asp Ser Thr Gln Ile Tyr Gln Ala Lys Lys Gly
            1400                1405                1410
Asn Gly Ala Ile Val Ser Gln Val Lys Ala Leu Arg Ser Arg His
            1415                1420                1425
Ile Leu Ala Tyr Ser Ser Val Met Gln Pro Phe Pro Asp Lys Ala
            1430                1435                1440
```

```
Phe Leu Ser Leu Ala Ser Asp Thr Val Glu Pro Thr Ile Leu Asn
    1445            1450                1455

Ala Thr Asn Thr Ser Leu Thr Ile Arg Leu Pro Leu Ala Lys Thr
    1460            1465                1470

Asn Leu Thr Trp Tyr Gly Ile Thr Ser Pro Thr Pro Thr Tyr Leu
    1475            1480                1485

Val Tyr Tyr Ala Glu Val Asn Asp Arg Lys Asn Ser Ser Asp Leu
    1490            1495                1500

Lys Tyr Arg Ile Leu Glu Phe Gln Asp Ser Ile Ala Leu Ile Glu
    1505            1510                1515

Asp Leu Gln Pro Phe Ser Thr Tyr Met Ile Gln Ile Ala Val Lys
    1520            1525                1530

Asn Tyr Tyr Ser Asp Pro Leu Glu His Leu Pro Pro Gly Lys Glu
    1535            1540                1545

Ile Trp Gly Lys Thr Lys Asn Gly Val Pro Glu Ala Val Gln Leu
    1550            1555                1560

Ile Asn Thr Thr Val Arg Ser Asp Thr Ser Leu Ile Ile Ser Trp
    1565            1570                1575

Arg Glu Ser His Lys Pro Asn Gly Pro Lys Glu Ser Val Arg Tyr
    1580            1585                1590

Gln Leu Ala Ile Ser His Leu Ala Leu Ile Pro Glu Thr Pro Leu
    1595            1600                1605

Arg Gln Ser Glu Phe Pro Asn Gly Arg Leu Thr Leu Leu Val Thr
    1610            1615                1620

Arg Leu Ser Gly Gly Asn Ile Tyr Val Leu Lys Val Leu Ala Cys
    1625            1630                1635

His Ser Glu Glu Met Trp Cys Thr Glu Ser His Pro Val Thr Val
    1640            1645                1650

Glu Met Phe Asn Thr Pro Glu Lys Pro Tyr Ser Leu Val Pro Glu
    1655            1660                1665

Asn Thr Ser Leu Gln Phe Asn Trp Lys Ala Pro Leu Asn Val Asn
    1670            1675                1680

Leu Ile Arg Phe Trp Val Glu Leu Gln Lys Trp Lys Tyr Asn Glu
    1685            1690                1695

Phe Tyr His Val Lys Thr Ser Cys Ser Gln Gly Pro Ala Tyr Val
    1700            1705                1710

Cys Asn Ile Thr Asn Leu Gln Pro Tyr Thr Ser Tyr Asn Val Arg
    1715            1720                1725

Val Val Val Val Tyr Lys Thr Gly Glu Asn Ser Thr Ser Leu Pro
    1730            1735                1740

Glu Ser Phe Lys Thr Lys Ala Gly Val Pro Asn Lys Pro Gly Ile
    1745            1750                1755

Pro Lys Leu Leu Glu Gly Ser Lys Asn Ser Ile Gln Trp Glu Lys
    1760            1765                1770

Ala Glu Asp Asn Gly Cys Arg Ile Thr Tyr Tyr Ile Leu Glu Ile
    1775            1780                1785

Arg Lys Ser Thr Ser Asn Asn Leu Gln Asn Gln Asn Leu Arg Trp
    1790            1795                1800

Lys Met Thr Phe Asn Gly Ser Cys Ser Ser Val Cys Thr Trp Lys
    1805            1810                1815

Ser Lys Asn Leu Lys Gly Ile Phe Gln Phe Arg Val Val Ala Ala
    1820            1825                1830
```

-continued

| | | | | | | | | | | | |
|---|---|---|---|---|---|---|---|---|---|---|---|
| Asn | Asn | Leu | Gly | Phe | Gly | Glu | Tyr | Ser | Gly | Ile | Ser | Glu | Asn | Ile |
| 1835 | | | | | 1840 | | | | 1845 | | |
| Ile | Leu | Val | Gly | Asp | Asp | Phe | Trp | Ile | Pro | Glu | Thr | Ser | Phe | Ile |
| 1850 | | | | | 1855 | | | | 1860 | | |
| Leu | Thr | Ile | Ile | Val | Gly | Ile | Phe | Leu | Val | Val | Thr | Ile | Pro | Leu |
| 1865 | | | | | 1870 | | | | 1875 | | |
| Thr | Phe | Val | Trp | His | Arg | Arg | Leu | Lys | Asn | Gln | Lys | Ser | Ala | Lys |
| 1880 | | | | | 1885 | | | | 1890 | | |
| Glu | Gly | Val | Thr | Val | Leu | Ile | Asn | Glu | Asp | Lys | Glu | Leu | Ala | Glu |
| 1895 | | | | | 1900 | | | | 1905 | | |
| Leu | Arg | Gly | Leu | Ala | Ala | Gly | Val | Gly | Leu | Ala | Asn | Ala | Cys | Tyr |
| 1910 | | | | | 1915 | | | | 1920 | | |
| Ala | Ile | His | Thr | Leu | Pro | Thr | Gln | Glu | Glu | Ile | Glu | Asn | Leu | Pro |
| 1925 | | | | | 1930 | | | | 1935 | | |
| Ala | Phe | Pro | Arg | Glu | Lys | Leu | Thr | Leu | Arg | Leu | Leu | Leu | Gly | Ser |
| 1940 | | | | | 1945 | | | | 1950 | | |
| Gly | Ala | Phe | Gly | Glu | Val | Tyr | Glu | Gly | Thr | Ala | Val | Asp | Ile | Leu |
| 1955 | | | | | 1960 | | | | 1965 | | |
| Gly | Val | Gly | Ser | Gly | Glu | Ile | Lys | Val | Ala | Val | Lys | Thr | Leu | Lys |
| 1970 | | | | | 1975 | | | | 1980 | | |
| Lys | Gly | Ser | Thr | Asp | Gln | Glu | Lys | Ile | Glu | Phe | Leu | Lys | Glu | Ala |
| 1985 | | | | | 1990 | | | | 1995 | | |
| His | Leu | Met | Ser | Lys | Phe | Asn | His | Pro | Asn | Ile | Leu | Lys | Gln | Leu |
| 2000 | | | | | 2005 | | | | 2010 | | |
| Gly | Val | Cys | Leu | Leu | Asn | Glu | Pro | Gln | Tyr | Ile | Ile | Leu | Glu | Leu |
| 2015 | | | | | 2020 | | | | 2025 | | |
| Met | Glu | Gly | Gly | Asp | Leu | Leu | Thr | Tyr | Leu | Arg | Lys | Ala | Arg | Met |
| 2030 | | | | | 2035 | | | | 2040 | | |
| Ala | Thr | Phe | Tyr | Gly | Pro | Leu | Leu | Thr | Leu | Val | Asp | Leu | Val | Asp |
| 2045 | | | | | 2050 | | | | 2055 | | |
| Leu | Cys | Val | Asp | Ile | Ser | Lys | Gly | Cys | Val | Tyr | Leu | Glu | Arg | Met |
| 2060 | | | | | 2065 | | | | 2070 | | |
| His | Phe | Ile | His | Arg | Asp | Leu | Ala | Ala | Arg | Asn | Cys | Leu | Val | Ser |
| 2075 | | | | | 2080 | | | | 2085 | | |
| Val | Lys | Asp | Tyr | Thr | Ser | Pro | Arg | Ile | Val | Lys | Ile | Gly | Asp | Phe |
| 2090 | | | | | 2095 | | | | 2100 | | |
| Gly | Leu | Ala | Arg | Asp | Ile | Tyr | Lys | Asn | Asp | Tyr | Tyr | Arg | Lys | Arg |
| 2105 | | | | | 2110 | | | | 2115 | | |
| Gly | Glu | Gly | Leu | Leu | Pro | Val | Arg | Trp | Met | Ala | Pro | Glu | Ser | Leu |
| 2120 | | | | | 2125 | | | | 2130 | | |
| Met | Asp | Gly | Ile | Phe | Thr | Thr | Gln | Ser | Asp | Val | Trp | Ser | Phe | Gly |
| 2135 | | | | | 2140 | | | | 2145 | | |
| Ile | Leu | Ile | Trp | Glu | Ile | Leu | Thr | Leu | Gly | His | Gln | Pro | Tyr | Pro |
| 2150 | | | | | 2155 | | | | 2160 | | |
| Ala | His | Ser | Asn | Leu | Asp | Val | Leu | Asn | Tyr | Val | Gln | Thr | Gly | Gly |
| 2165 | | | | | 2170 | | | | 2175 | | |
| Arg | Leu | Glu | Pro | Pro | Arg | Asn | Cys | Pro | Asp | Asp | Leu | Trp | Asn | Leu |
| 2180 | | | | | 2185 | | | | 2190 | | |
| Met | Thr | Gln | Cys | Trp | Ala | Gln | Glu | Pro | Asp | Gln | Arg | Pro | Thr | Phe |
| 2195 | | | | | 2200 | | | | 2205 | | |
| His | Arg | Ile | Gln | Asp | Gln | Leu | Gln | Leu | Phe | Arg | Asn | Phe | Phe | Leu |
| 2210 | | | | | 2215 | | | | 2220 | | |
| Asn | Ser | Ile | Tyr | Lys | Ser | Arg | Asp | Glu | Ala | Asn | Asn | Ser | Gly | Val |

|      |      |      |      |      | 2225 |      |      |      |      | 2230 |      |      |      |      | 2235 |      |      |
|------|------|------|------|------|------|------|------|------|------|------|------|------|------|------|------|------|------|

Ile Asn Glu Ser Phe Glu Gly Glu Asp Gly Asp Val Ile Cys Leu
    2240                    2245                2250

Asn Ser Asp Asp Ile Met Pro Val Ala Leu Met Glu Thr Lys Asn
    2255                2260                2265

Arg Glu Gly Leu Asn Tyr Met Val Leu Ala Thr Glu Cys Gly Gln
    2270                2275                2280

Gly Glu Glu Lys Ser Glu Gly Pro Leu Gly Ser Gln Glu Ser Glu
    2285                2290                2295

Ser Cys Gly Leu Arg Lys Glu Glu Lys Glu Pro His Ala Asp Lys
    2300                2305                2310

Asp Phe Cys Gln Glu Lys Gln Val Ala Tyr Cys Pro Ser Gly Lys
    2315                2320                2325

Pro Glu Gly Leu Asn Tyr Ala Cys Leu Thr His Ser Gly Tyr Gly
    2330                2335                2340

Asp Gly Ser Asp
    2345